US007122306B2

(12) United States Patent
Maertens et al.

(10) Patent No.: US 7,122,306 B2
(45) Date of Patent: Oct. 17, 2006

(54) SEQUENCES OF HEPATITIS C VIRUS GENOTYPES AND THEIR USE AS THERAPEUTIC AND DIAGNOSTIC AGENTS

(75) Inventors: Geert Maertens, Brugge (BE); Lieven Stuyver, Lede (BE)

(73) Assignee: N.V. Innogenetics S.A., Ghent (BE)

( * ) Notice: Subject to any disclaimer, the term of this patent is extended or adjusted under 35 U.S.C. 154(b) by 804 days.

(21) Appl. No.: 09/873,224

(22) Filed: Jun. 5, 2001

(65) Prior Publication Data

US 2003/0064360 A1 Apr. 3, 2003

Related U.S. Application Data

(60) Division of application No. 09/638,693, filed on Aug. 15, 2000, which is a continuation of application No. 08/362,455, filed as application No. PCT/EP94/01323 on Apr. 27, 1994.

(30) Foreign Application Priority Data

Apr. 27, 1993 (EP) ............................. 93 401 099
Aug. 5, 1993 (EP) ............................. 93 402 019

(51) Int. Cl.
*C12Q 1/68* (2006.01)
(52) U.S. Cl. .................... 435/6; 536/23.7; 536/23.72
(58) Field of Classification Search ............... 536/23.1, 536/257, 23.7; 435/5, 6; 702/20
See application file for complete search history.

(56) References Cited

U.S. PATENT DOCUMENTS

| 5,514,539 A | 5/1996 | Bukh et al. ............... 435/5 |
| 5,846,704 A | 12/1998 | Maertens et al. ............ 435/5 |
| 5,882,852 A | 3/1999 | Bukh et al. ............... 435/5 |
| 6,548,244 B1 | 4/2003 | Maertens et al. ............ 435/5 |
| 6,762,024 B1 | 7/2004 | Maertens et al. ............ 435/6 |

FOREIGN PATENT DOCUMENTS

| EP | 0 532 167 | 3/1987 |
| EP | 0419182 | 3/1991 |
| EP | 0 463 848 A2 | 1/1992 |
| GB | 2 239 245 A | 6/1991 |
| WO | WO 92/19743 | 11/1992 |
| WO | WO 93/06126 | 4/1993 |
| WO | WO 93/10239 | 5/1993 |
| WO | WO 94/25601 | 1/1995 |

OTHER PUBLICATIONS

Liu et al, Gene 114:245 (1992).*
Van Doorn et al, J. Hepatology 21:122 (1994).*
Bukh et al, Proc. Natl. Acad. Sci. USA 90:8234 (1993).*
Tokita et al, Natl. Acad. Sci. USA 11022 (1994).*
Stuyver et al, Virus Res. 38:137 (1995).*
Qu et al, J. Gen. Virology 75:1063 (1994).*
Kennell, Progr. Nucl. Acid Res. Mol. Biol. 11:259-301 (1971).*

S.W. Chan et al., "Analysis of a new hepatitis C type and its phylogenetic relationship to existing variants", J. of General Virology (1992), vol. 73, pp. 1131-1141.

S. Mori et al., "A new type of hepatitis C in patients in Thailand", Biochemical and Biophysical Research Communications, vol. 183, No. 1, 1992, pp. 334-342.

T.A. Cha et al., "At least five related but distinct genotypes of hepatitis C virus exist", Proc. National Acad. Sci., USA, vol. 89, pp. 7144-7148, Aug. 1992.

A. Weiner et al., "Variable and hypervariable regions are found in the regions of HCV corresponding to the flavivirus envelope and NS1 proteins", Virology, 180, (1991) pp. 842-848.

K. Chayama et al., "Genotypic subtyping of hepatitis C virus", Journal of Gastronenterology and Hepatology, vol. 8, (1993) pp. 150-156.

L. Stuyver et al., "Analysis of the putative E1 envelope and NS4a epitope regions of HCV type 3", Biochemical and Biophysical Research Communications, vol. 192, No. 2, 1993, pp. 635-641.

L. Stuyver et al., "Typing of hepatitis C virus isolates and characterization of new subtypes using a line probe assay", Journal of General Virology, vol. 74, 1993, pp. 1093-1102.

P. Simmonds et al., Mapping of serotype-specific immunodominant epitopes in the NS4 region of hepatitis C virus, Journal of Clinical Microbiology, vol. 31, 1993, pp. 1493-1503.

George et al., in Macromolecular Sequencing and synthesis, Selected Methods and Applications, Schlesinger (ed.), 1988, Alan R. Liss, Inc., New York, pp. 127-149.

Chen et al. Virology, 188: 102 (1992).

Wallace et al., Methods Enzymol. 152:432 (1987).

Bukh, PNAS 89: 4942 (1992).

Innis et al., PCR Protocols: A Guide to Methods and Applications, 1990, (Innis et al. (ed.), Academic Press, New York, pp. 3-11.

Kato et al, "Molecular Cloning of the Human Hepatitis C Virus Genome Form Japanese Patients with Non-A Non-B Hepatitis", Proc. Natl. Acad, Sci. USA, vol. 87, 1990, pp. 9254-9258.

Van Doorn et al, :Sequence Analysis of Hepatitis C Virus Genotypes 1 to 5, Database Genban 'Online' Accession No. X78863, May 20, 1994, XP002017147.

Hotta et al, "Subtype Analysis of Hepatitis C Virus in Indonesia", Database Genban 'Online' Accession No. D26387, Feb. 4, 1994, XP002017146.

(Continued)

*Primary Examiner*—James Martinell
(74) *Attorney, Agent, or Firm*—Nixon & Vanderhye.P.C.

(57) ABSTRACT

The present application provides polynucleic acid sequences of 8 or more contiguous nucleotides selected from an HCV subtype 3c genomic sequence selected from the region spanning positions 1 to 957 of the Core of Core/E1 region of HCV subtype 3c, wherein said polynucleic acid sequence is capable of hybridizing to HCV type 3c, but not another type or subtype of HCV; or the complement of the polynucleic acid, wherein the polynucleic acid contains at least one genotype-specific nucleotide. Methods and means of using and making the described sequences are also provided.

14 Claims, 111 Drawing Sheets

OTHER PUBLICATIONS

Stuyver et al, "Classification of hepatitis C viruses based on phylogenetic analysis . . . ", Proceedings of the National Academy of Sciences of USA, vol. 91, No. 21, pp. 10134-10138 (1994).

Enomoto et al, "There are two major types of hepatitis C virus in Japan", Biochem. Biophys. Res. Commun., vol. 170, No. 3, 1990, pp. 1021-1025, XP002017145.

Driesel et al, "Hepatitis C Virus (HCV) Genotype . . . ", Arch Virol (1994) 139:379-388.

Majzoub et al., "Vasopressin and Oxytocin mRNA Regulation in the Rat Assessed by Hybridization with Synthetic Oligonucleotides", 1983, PNAS 258, 14061-14064.

Chan et al., "Construction and selection of recombinant plasmids containing full-length complementary DNAs corresponding to rat insulins 1 and II", 1979, PNAS 76, 5036-504 (copy of abstract).

Meyerhans et al, Nucleic Acids Research, vol. 20, No. 3, pp. 521-523.

* cited by examiner

Figure 1

| | 7932 | | | | | | 7981 |
|---|---|---|---|---|---|---|---|
| HCV-1    | CTCCACAGTCACTGAGAGGAGGCGACATCCGTACGGAGGAGGCAATCTACCAAT |
| HCV-J    | ---A--G------------AT------------T-----AT--T--------- |
| BE90     | ---A---------------------------T--T------------------ |
| 2TY4     | ---A-------C------A---------GTT-------T-------------- |
| 4TY4     | -----------------------------------A-------A--------- |
| 1c       | -------------------A--------A-G-T-----T-C--A--T-GGG-- |
| HC-J6    | ---A--C-----------------G---AA-A--A--A-AT-C--A--T--GG |
| HC-J8    | ---A--C-----------------G---AA-A--A--A--A--AT-C--A--T---G |
| NE91     | ---A--C-----------------G---T---AA-A--A--A--AT-C--A--T---G |
| EB12     | -------------------------------------------A--T--GG |
| ARG6     | -----------------------------------------T--TG-- |
| ARG8     | --------------------------------------------G-- |
| I10      | --------------------------------------------T--TG-- |
| T983     | -----------------------------------------------GG |
| NE92     | ---A--G-------G---------G-----A-A--T---T-C--A---TTG |
| CHR20    | ---T--T------------ACAG----A-GGT---A----AG--A--G-- |
| CHR21    | ---G--T------------ACAG----A-GGT---A----AG--A------ |
| CHR22    | ---A--T------------ACAG----A-GGT---A----AG--A------ |
| T1       | ---A--T------------ACAG----A-GGT---A----AG--A------ |
| T7       | ---A--T------------ACAG----A-GGT---A----AG--A------ |
| NE93     | ---G--T------------ACAG----A-GGT---A----AG--A--T--- |
| NZL13    | ---A--T------------ACAG----A-GGT---A----AG--A------ |
| EB1      | ---------------------------------------A---------- |
| EB2      | ---------------------------------------A---------- |
| EB3      | ---------------------------------------A---------- |
| EB7      | ---------------------------------------A--T------- |
| T9       | ---T--T------------ACAT----A-G-----A-G---------- |
| T10      | ---T--T------------ACAG----A-G-----A-G--A-------- |
| BE98     | -------------------------------------------GG |

Figure 1 - Continued 1

```
                    7932                                                              7981
GB48      4c      ----T--A--C---A-AG-----------A-GGTC--------AGG------T--G-
GB116     4c      ----T--A--C---A-AG-----------A-GGTC--------AGG-A----T--G-
GB215     4c      ----T--A--C---A-AA-----------A-GGTC--------AGG-A----T--G-
GB358     4c      ----T--A--C---A-AG-----------A-GGTC--------AGG-A----T--G-
GB809     4e      ----T--G------A--------------AAGGTC--A--A-A-G-------T--G-
CAM600    4e      ----T--G--------A-------------A-GGTC--A--A-A-G------T--G-
CAMG22    4f      -----------G---A---------A----A-GGTC--A--A-AGG------T--G-
GB549     4g      ----G--C---A--G--T------------A-G--C---A-AG---------T--G-
GB438     4h      ----G--C---A--G---------------TA-GGTC---A-AG--------T--G-
CAR4/1205 4i      -C--C--G--N----G--------------N--A-GGTC----A-AGG----T--G-
CAR1/501  4j      ---G--T--GN-C------G----------A-G--A-----GA-AGG-----T--G-
EG-13     4k                                                          G----T--G-
EG-19     4k                                                          G----T--G-
BE95      5a      ---G--C--T---C--ACAT--------AATG--C--A-----T-C--T---
BE96      5a      ---A--C--C---C--ACAT--------ATTG--T--A-----T-C--A---
CHR18     5a      ---G--C--T---C--ACAT--------AATG--T--A-----T-T--T---
CHR19     5a      ---G--C--T---C--ACAT--------AATG--T--A-----T-C--T---
```

Figure 1 - Continued 2

| | SEQ ID | 7982 | | | | | | | | | | 8031 |
|---|---|---|---|---|---|---|---|---|---|---|---|---|
| HCV-1 | | GTTGTGACCTTCGACCCCCAAGCCCGCGGTGGCCATCAAGTCCCTCACCGAG |
| HCV-J | | --------------T--G-C-----G-----A-GCA---------A-G---A--- |
| BE90 | 213 | --------------T--G-C-----G-----A-ACA---------A-----G---A--- |
| 2TY4 | | --------------GC----A-----T-----------------AAAT-----T--- |
| 4TY4 | | --------------GC----A----CT-----------------AAAT-----T--- |
| HC-J6 | | C----TC-T-GCC-GAGG-G----A-ACT------AC-C--A---G--T--- |
| HC-J8 | | C----TCT--GCCT-AAG-------A-AACT-T----AC-C--G---T--- |
| NE91 | 215 | C----TC---GCC--AAG-G----A-AACT-T----AC-C--G------- |
| EB12 | | C----TC---GCCT-AAG-G----A-AACT-T----AC-C--G---T--- |
| ARG6 | | CC---TCA--GCCTGAGG-G--T--A-AACT------AC-C--A---G---T--- |
| ARG8 | | CC---TCA--GCC-GAGG-G--T--A-AACT-T----AC-C--A---G---T--- |
| I10 | | CC---TCA--GCCTGAGG-G-----A-AACT-T----AC-C--A---G---T--- |
| T983 | | C----TCA--GCCT-AGG-G--T--A-GACT--T----AC-C--AT-G---T--- |
| NE92 | 145 | C----CTCTT-ACC-GAG------A-GACT------AC-C--A---G---T--- |
| 2d | | -C------A---T-A---GG-G----A-GAAA-TG---TCC---------G--- |
| CHR20 | | -C------A---T-A---GG-G----A-GAAA-TG---TCC---------G--- |
| CHR21 | | -C------A---T-A---GG-G----A-GAAA-TG---TCC---------G--A |
| CHR22 | | -C------A---T-A---GG-G----A-GAAA-TG---TCC---------G--- |
| T1 | | -C------A---T-A---GG-G----A-GAGA-TG---TCC---------G--- |
| T7 | | -C------A---T-G---GG-G----A-GAAA-TG---TCC---------G--- |
| NE93 | 217 | -C---CA-----T-A---GG-G----A-GAAA-TG---TCC---------G--- |
| NZL13 | | -C------A---T-A---GG-G----A-GAAA-TG---TCC---------G--- |
| EB1 | | -C------A---T-A---GG-G----A-GAAA-TG---TCC---------G--A |
| EB2 | | -C------A---T-A---GG-G----A-GAAA-TG---TCC---------G--- |
| EB3 | | -C------A---T-A---GG-G----A-AAAA-TG---TCC---------G--- |
| EB7 | | -C------A---T-A---GG-G----A-GAA--TG---TCC---------G--- |
| BR33 | 9,11 | | | | | | | | | | | G--A |
| BR34 | 1,3 | | | | | | | | | | | G--- |
| BR36 | 5,7 | ----------T--G--AG-G--T--GAA---G---GCG-T-----A--- |
| T9 | | -C-------------T--G--AG-G--T--GAA---G---GCG-T-----A--- |

Figure 1 - Continued 3

| | | SEQ ID | 7982 | | | | | 8031 |
|---|---|---|---|---|---|---|---|---|
| T10 | 3b | 149 | -C----- | ---T--G--AG-G--T--GAA---G----GCG-T-----A--- | | | | |
| BE98 | 3c | | CC----- | ---A-GGA-G-G--TA-GAG--TG--A-CT--A-----G--- | | | | |
| GB48 | 4c | 106 | ------- | ------G------G-----AA---A---T-CCG-----A--A--- | | | | |
| GB116 | 4c | 108 | ------- | ------G------G-----AGA--A---T-CCG-----A--A--- | | | | |
| GB215 | 4c | 110 | ------- | ------G------G-----AA--TA---T-CCG-----A--A--- | | | | |
| GB358 | 4c | 112 | ------- | ------G------G-----AA---A---T-CTG-----A--A--- | | | | |
| GB809 | 4c | 116 | ------- | ------G------G-----AA--TA---AGCCG-----G--- | | | | |
| CAM600 | 4e | 201 | ---T--- | ------G------G-----AA--TA---A-CCG-----G--- | | | | |
| CAMG22 | 4f | 203 | ------- | ------G--TG--A-----AA--TA---ATCTG--------T--A | | | | |
| GB549 | 4g | 205 | --C--C- | ------G------G-----AA--TG---ATCCG-----A--G--A | | | | |
| GB438 | 4h | 207 | --C---- | ------G------G--A--AA--TG---ATCCG-T-----A--A | | | | |
| CAR4/1205 | 4i | 209 | --C---- | --A-T--G--GN--G-T-N----AA--T-----CG-----A--- | | | | |
| CAR1/501 | 4j | 211 | ------- | ------G--A--GG-----AA--TA------CCG--------T--- | | | | |
| EG-13 | 4k | | ------- | ----A----G----G----T-----AA---T--T-CTG-----A--A | | | | |
| EG-19 | 4k | | ------- | ----AGT--G--G-T-G-G----AA--TT--T-CTG-----G--A | | | | |
| BE95 | 5a | 159 | CA----- | ---T-GC-G---G-G--A----CA--A--ACG-----A--C-A | | | | |
| BE96 | 5a | 161 | CA----- | ---TCGC-G---G-C--A----CA--A--ACG-----A--C-A | | | | |
| CHR18 | 5a | | CA-TGT- | --T-GC-G--TG-G--T-----A--A--ACG-----A--C-A | | | | |
| CHR19 | 5a | | CA-TGT- | --T-GC-G--TG-G--A-----C--A--ACG-----A--C-A | | | | |

Figure 1 - Continued 4

```
                8032                                              8081
         AGGCTTTATGTTGGGGCCCCTCTTACCAATTCAAGGGGGAGAACTGCGG
HCV-1 1a  C------------C---T--C--G--T----G-A----C---------
HCV-J 1b  C------------C---T--C--G--T-------A---C--------T-
BE90  1b  C------A-C---T--C--G--C--G-------A---C-----------
2TY4  1c  --AT-G--C---C--A--G--C--G----------A---T--A------
4TY4  1c  --AT-G--C---C--T--G--C--G----------AA--C---------
HC-J6 2a  --A-----C--G--A--G--CA--GTT---CAGC-A---CC----C---
HC-J8 2b  --A-----C--A--A--G--CA-G--A---CAGC-AA---C-ATC----
NE91  2b  --A-----C--C--G--A--CA-G--A---CAGC-AA---C-ATC----
EB1.2 2b  --A-----C--C--A--G--CA-G-TA---CAGC-AA---C-ATC----
ARG6  2c  --A-----G--C--A--G--CA-G--A---CAGC-A----C-ATC----
ARG8  2c  ---------G--C--A-----CA-G--A---CAGC-A----CC-ATC--
I10   2c  --A--A--C--A-----G--CA-G--A---CAGC-A----C-ATC----
T983  2c  --A--G--C--A-----G--CA-G--A---CAGC-A----C--TC----
NE92  2c  --A--A--C--G--A--G--CA-G--A---CAGC-AA---C--TC----
NE93  2d  ----G---A--G--A--G--CA-GCTA---CAGC-AA---C-A-C----
CHR20 3a  C-----CTGC--------A-GTT---CAGC-A---CCC-G---T--
CHR21 3a  C-----CTGC--------A-GTT---AGC-A---CCC-G---T--
CHR22 3a  C-----CTGC--------A-GTT---CAGC-A---CCC-G---T--
T1    3a  C-----CTGC--------A-GTT---CAGC-A---CCC-G---T--
T7    3a  C-----CTGC--------A-GTT---CAGC-A---CCC-A---T--
NE93  3a  C-----CTGC---A----A-GTA---CAGC-A---TCC-G---T--
NZL13 3a  C-----CTGC---A----A-GTTT--CAGC-A---CCC-G---T--
EB1   3a  C-----CTGC--------A-GTT---CAGC-A---CCC-G---T--
EB2   3a  C-----CTGC--------CA-GTT--CAGC-A---CCC-G---T--
EB3   3a  C-----CTGC--------CA-GTT--CAGC-AA--CCC-G---T--
EB7   3a  C-----CTGC--------A-GTT---CAGC-A---CCC-G---T--
BR33  3a  C-----CTGC--------A-GTT---CAGC-A---CCC-G---T--
BR34  3a  C-----CTGC--------A-GTT---CAGC-A---CCC-G---T--
BR36  3a  C-----CTGC--------A-GTTT--CAGC-AA--CCC-G---T--
T9    3b  C----G--CA-C----A--T--CA-GTA---CAGT-A----CTCC-G---
```

Figure 1 - Continued 5

| | | | | | | | | | | |
|---|---|---|---|---|---|---|---|---|---|---|
| T10 | 3b | C----G--CA-C--A--T--CA-GTA----CAGT-A-----CTCC-G--- |
| BE98 | 3c | C-------CTG-------T--T---A-GTT----CAGC-A-----AC-AC--- |
| GB48 | 4c | --A--C----C---G--C--T--CA-GCAT--CAGC--A---A--CCTG--- |
| GB116 | 4c | --A--C----C---G--C--T--CA-GCAT--CAGC--A---A--CCTG--- |
| GB215 | 4c | --A--C----C---G--C--T--CA-GCAT--CAGC--A---A--CCTG--- |
| GB358 | 4c | --A--C----C---G--C--T--CA-GCAT--CAGC--AA--A--CCTG-T- |
| GB809 | 4c | --A--C----C---G--C-----CA-GCAT--CAGC--A---A--CCTT-T- |
| CAM600 | 4e | --A--C----C---G--C-----CA-GCAT--CAGC--A---A--CCTT--- |
| CAMG22 | 4e | --A--C----C---G--C-----A--GTA----AGC--A---A--CCTA--- |
| GB549 | 4f | --A--C----C---G--C--T--CA-GCA----CAGC------A--CCTA--- |
| GB438 | 4g | --A--C----C---G--C--T--CA-GTA----C--C-A------CCTA--- |
| CAR4/1205 | 4h | --A--C--CAAG--C-----CA-GCAT--CAGC--A---A--CCTG-T- |
| CAR1/501 | 4i | --A--C----C---G-----A--GCA-----CAGC--A---A--CCTG--- |
| EG-13 | 4j | --A--C----C---G--C-----CA-GTT----CAGC--A---A--CCTT-T- |
| EG-19 | 4k | --A--C----C---G--C-----CA-GCA----CAGC--A---A--CCTT-T- |
| BE95 | 4k | --A--C----C---G-----A-AGCA----AGC--A---A--CCTT-T- |
| BE96 | 5a | C--C--C--CTG---A-----CA-GTA----CAGC--A-----C-AC-G-T- |
| CHR18 | 5a | C--CT-G-TCTG---A-----CA-GTAT--CAGC--A-----C-AC-A-T- |
| CHR19 | 5a | C--C--G--CTG---A-----CA-GTAT--CAGC--A-----C-AC-A-T- |
| | 5a | C--C--G--CTG---A-----CA-GTAT--CAGC--A-----C-AC-A-T- |

Figure 1 - Continued 6

```
              8082                                                    8131
              CTATCGCAGGTGCCGCGGCGGGCGGAGCGGCGTACTGACAACTAGCTGTGGTAACA
HCV-1    1a   T-------C------------A--T----G-------G------C--C-----
HCV-J    1b   --------C-A----A-------------G--C-----------C-------T-
BE90     1b   --------C-A----------------------C----------C----------
2TY4     1c   ---------------T-------T---------C----------C----------
4TY4     1c   ---------------T-------------C---C----------C----------
HC-J6    2a   G--CA-GC-T-------------C----G--G--T--C------C---ATG--G----
HC-J8    2b   ---CA-GC-T-------------A----T--TT-C--C------C---ATG--G--T-
NE91     2b   T--CA-GC-T-------------A----T--TT-C--C------C---ATG--G--T-
EB12     2b   T--CA-GC-C-------------A----T--TT-C--T------C---ATG--G--T-
ARG6     2b   G--CA-GC-T------------------A--G--C--C------C---ATG-------
ARG8     2c   ---CA-GC-T----------------CA--G--C--C------C---ATG--C----
I10      2c   ---------------------------A--G--C--C------C---ATG--C----
T983     2c   T--CA-GC-T-----------------TG--G--C--C------C---ATG--C----
NE92     2c   A--CA-AC-C-----------C--A--C-T--A--C--T------C---ATG--A--T-
CHR20    2d   T-------C-T----T------T-T--A--C----T--C-T----C-------T-
CHR21    3a   T-------C-T----T------T-T--A--T----C-T--C-T----TC--C----
CHR22    3a   T-------C-T----T------T-C--A--T----C-T--C-T----TC--C----
T1       3a   T-------C--------------T-C--A--C----C-T--C-T----TC--C----
T7       3a   T-------C-C-----------T-C--A--C----C-T--C-T----TC--C----
NE93     3a   T-------C-T----T------T-C--A--T----C-T--C-T----TC--C----
NZL13    3a   T-------C-T----T------T-C--A--T----C-T--C-T----TC--C----
EB1      3a   T-------C-T----T------T-C--A--T----C-T--C-T----TC--C----
EB2      3a   T-------C-T----T------T-C--A--T----C-T--C-T----TC--C----
EB3      3a   T-------C-T----T------T-C--A--T----C-T--C-T----TC--C----
EB7      3a   T-------C-T----T------T-C--A--T----C-T--C-T----TC--C----
BR33     3a   T-------C-C-----------T-C--A--T----C-T--C-T--T-TC--C----
BR34     3a   T-------C-C-----------T-C--A--T----C-T--C-T----TC--C----
BR36     3a   T-------C-C-----------T-C--A--T----C-T--C-T----TC--C----
T9       3b   ---------C-C-----------C----------CT--C-T----TC--C---T-
```

Figure 1 - Continued 7

|       |     | 8082           |              |              |              | 8131         |
|-------|-----|----------------|--------------|--------------|--------------|--------------|
| T10   | 3b  | ----           | --C-C-       | ----         | -C---        | -CT--C-T--C--TC--C--T- |
| BE98  | 3c  | T--C----       | --C-C-       | ----T-       | -T--T--G-    | -AC-C---C------TC--G-- |
| GB48  | 4c  | G-------       | ----A--T-    | ----A-       | ------       | -CTAC---C-------TC--G-- |
| GB116 | 4c  | G-------       | ----A-----T- | ------       | ------       | -CTAC---C-------TC--G-- |
| GB215 | 4c  | G-------       | ----A---     | ----A-       | ------       | -CTAC---C-------TC--G-- |
| GB358 | 4c  | G-------       | ----A---     | ----A-       | ------       | -CTAC---C-------TC--G-- |
| GB809 | 4e  | G-------       | ---T-A-      | ------       | ------       | --TAC---C-------TC--G-- |
| CAM600| 4e  | G-------       | ------       | ----A-       | ------       | --TAT---C-------TC--G-- |
| CAMG22| 4f  | G--C--T--A-    | ------       | ------       | ------       | --TAC---C---A---TC--G-- |
| GB549 | 4g  | GC-A---G-      | ------       | ----A-       | ---G-        | -CTAC---C-------TC--G-- |
| GB438 | 4h  | GCT-----G-     | ------       | ----A-       | ---G-        | --TAC---C---A---TC--G-- |
| CAR4/1205 | 4i | -ATC---T--A-  | ------       | ------       | ------       | -TTAC---C-------TC--A-- |
| CAR1/501 | 4j | AC-A-----C-    | ------       | ----A-       | ------       | --GT-C---C-------TC--G-- |
| EG-13 | 4k  | G-------       | ---G--A--T-  | -G--A-       | ---A-        | --CT-T--G---C-------TC--A-- |
| EG-19 | 4k  | G--C---G-      | ------A-     | -G--A-       | ---A-        | -CTAT---G---C-------TC--A-- |
| BE95  | 5a  | T-------       | ----A---     | ------C-     | ------       | -TT-C---C---C---TATG--C--- |
| BE96  | 5a  | T-------       | ----A---     | ------C-     | ------       | -CT-C---C---C---TATG--C--- |
| CHR18 | 5a  | T---T--        | ---T-A---    | ------C-     | ------       | -CT-C---C---C---TATG--C--- |
| CHR19 | 5a  | T--C--T--A-    | ------       | ------C-     | ------       | -CT-C---C---C---TATG--C--- |

Figure 1 - Continued 8

|        | 8132                                                     | 8181 |
|--------|----------------------------------------------------------|------|
|        | CCCTCACTTGCTACATCAAGGCCCGGGCAGCCTGTCGAGCCGCAGGGCTC       |      |
| HCV-1  | ----------------------------------------                  |      |
| HCV-J  | ----A--T---T-G----ACT--G------T--AA---                   |      |
| BE90   | ---T-A--T---C-A--------TCT--------T--GAA---              |      |
| 2TY4   | --T-------------------TA------------                     |      |
| 4TY4   | --T--------C----------TA------------                     |      |
| 1c     |                                                          |      |
| 1c     |                                                          |      |
| HC-J6  | --A-----------TG-G--A----TTA--G------AAG--T-----A-A      |      |
| HC-J8  | -A-G--A--T--------A----TT----G--AAG--T-----A---          |      |
| NE91   | -A-G--G--T--------A----TT----G--AA---------A---          |      |
| EB12   | -A-G--A-----------A----TT----G--CAA---T--G--A---         |      |
| ARG6   | -A-----G---------G-G--A--TAAA--G--A---AAC----G--CA-T     |      |
| ARG8   | -A-----G-----------G-G--A----A--G--G---AAC----G--CA-T    |      |
| I10    | -G-----G-----------G-G--A--A-A--G--G---AAC----G--CA-T    |      |
| T983   | -A--T--G--T--------G-G--A----AA-----G--CAAC---TG--CA-T   |      |
| NE92   | -A-----------------G-G----A-AA------AAG--T--G--CA-A      |      |
| CHR20  | -AA----T--------------------TA-A--G--T-CGAAG----C---     |      |
| CHR21  | -AA----T---------------------TA-A--G--TGCGAAG-------     |      |
| CHR22  | -AA----T--------------A--TA-A--G--TGCCGA-------C---      |      |
| T1     | -AA----T--------------ACA--G--TGCGAAG---------C---       |      |
| T7     | -AA----T--------------ACA--G--TGCAA-G---------C---       |      |
| NE93   | -GA----T--------------ACAA-G---GCGAAG---------C---       |      |
| NZL1.3 | -AA----T--------------ACA--G--TGC-AAG-------AAC---       |      |
| EB1    | -AA----T------A--TACA--G----CGAG---------C---            |      |
| EB2    | -AA----T--------------ACA--G----CGAG---------C---        |      |
| EB3    | -AA----T--------------ACA--G----CAAG---------C---        |      |
| EB7    | -AA----T--------------ACA--G----CAA-----------C---       |      |
| BR33   | -AA----T--------------ACA--G--TGCAAA----------C---       |      |
| BR34   | -AA----T--------------ACA--G--TGCAA-G---------C---       |      |
| BR36   | -AA----T-----------A--ACA--G---GCAAA----------C---       |      |
| T9     | -AA-A--C--T-----------ACT--------A--CA-G--T--G---T---    |      |
| 3b     |                                                          |      |

Figure 1 - Continued 9

```
                           8132                                              8181
T10       3b    -AA-A--C---T-------------------ACT--G---A-CA-G--T---G--T---
BE98      3c    -AA----C---T----------A--AAA------------TACCAA---T--C--AA-T

GB48      4c    --A--G--G------------C----A----TCA--C--TATCAA---G-------G
GB116     4c    --A--G--G-----------TC----A----TCA--C--TATCA----G-------G
GB215     4c    --A--G--G-----------TC----A----TCA--C--ATCA-G--GT-------G
GB358     4c    --A--G--G------------C----A----TCA--C--TATCA----G-------G
GB809     4c    -AA--G--G------------C----A----TCA-----ATCA-G--T-------A
GB809     4e    --A--G--G----------C-T----A----TCA-----ATCA-G--T-------G
CAM600    4e    --A--G--G----------C-T----A----TCA--------A-G--T-------G
G22       4f    --T--G--G----------T-C---------ACA--G--ACCAA-----T--C--A
GB549     4g    --TG-A--G--T-----TC----------C-GTT--G--TAC-A-G------T--G
GB438     4h    --GG-G--A--------C-T-----A-----ACA--G--ACCA-G--T--------G
CAR4/1205 4i    --G--G--G----------C------A-----ACA--G--ACCA-G---G--CT--G
CAR1/501  4j    --A--G--G----------C-T----A-----ACA--T--TAC-A---A--C--CT-A
EG-13     4k    --A--G--G----------C-T----A-----AC---C--TAT-A---G--------G
EG-19     4k    --G--G--G----------C-A----A-----ACA--C--TAT-A-G--G--A--A
BE95      5a    --G--G--G-----------C-----------TTTA-CT-----A-------A------
BE96      5a    --A-G--G-----------------T-------TTTA-CT-----A--A---T------
CHR18     5a    --A-G--G-----------------T-------TTTA-CT-----A-----AA------
CHR19     5a    --A-G--G---------C-----------TTCA--C-----A---T--AA------
```

| | | 8182 | 8231 |
|---|---|---|---|
| T10 | 3b | A-A---CCAT--T-C--T--C--C--A------T--G---G-G-C--- |
| BE98 | 3c | A--AA-TCCAT-AT-C--T--C--C--A----T-------G---G--TGC--- |
| GB48 | 4c | AGA-------T-G--C------T--------T--C-G--T----C---GC--- |
| GB116 | 4c | AGA-------T-G--C------T--------T--C-G--T----C---TGC--- |
| GB215 | 4c | AGA---T----T-G--C-A---T--------T--C-G-------C---TGCC--- |
| GB358 | 4c | AGA-------T-G--C------T--------T--C-G-------C---GC--- |
| GB809 | 4c | AGA-----------G--C-----T-----C--------C---G---GCC--- |
| CAM600 | 4e | A---T---------G--T-----C--T-----------G----C---GC--- |
| G22 | 4e | A-------------G------T-----T----------------GCC--- |
| GB549 | 4f | A---T--------T-G----------T--A--G-----C------C--- |
| GB438 | 4g | A-A-GT---G-----------G--T-A---------A------- |
| CAR4/1205 | 4h | A-A--T-------T--G--A--C--T---------C----TGCC--- |
| CAR1/501 | 4i | A----T-------G-C--N---T-----------C-G--T--C--TGC--- |
| EG-13 | 4j | A---T---------G--C---C--T---------T--CC--- |
| EG-19 | 4k | AGA-----T--------------------------- |
| BE95 | 4k | A-A---A--T--------------------------- |
| BE96 | 5a | -G-----GC-C---G----------T------TC-T--G-CC-----C--- |
| CHR18 | 5a | -G---A--GC-C---G----------T-----TCAT--G-CC-----C--- |
| CHR19 | 5a | ------GC-C---G----------T--T--TC-T--G-CC--T--C--- |
| | 5a | ------GC-C---G----------T--T--TC-T--G-CC--T--C--- |
| | 5a | ------GC-C---G---------T-TTAC---G--G-CC--T--C--- |

Figure 1 - Continued 12

```
                         8232                                          8271
        HCV-1    1a      AAGCGCGGGGGTCCAGGAGGACGCGGCGAGCCTGAGAGCC
        HCV-J    1b      G---T-----AAC-----------T-----GC---AC---
        BE90     1b      ----------AAC-----A-----------AC---T----
        HC-J6    2a      G---CA----AC-G----------A-CG--A---------
        HC-J8    2b      G---CAA---TAA-G---------A-CGA-A---------
        NE91     2b      G---CA----TAA-G---------A-CGA-A-------T-
        NE92     2d      G---TCA---AC-G----------A-CG--A---AC----
        CHR20    3a      G---T-AT--C---G-C---TAGA--AGC-----------
        CHR21    3a      G---T-AT--C---G-C---TAGAA-AGC---C-------
        CHR22    3a      G---T-AT--C---A-T---TAGA--AGC-----------
        T1       3a      G---T-AT--C---G-T---TAGA--AGC-----G-----
        T7       3a      G---T-AT--C---G-C---TAG-A--GC-----------
        NE93     3a      G---T-AT--C---G-C---TAGA--AGC-----------
        NZL13    3a      G---T-AT--C---G-T---TAGA--AGC-----------
        BR33     3a      G---T-------------------------------
        BR34     3a      G---T-------------------------------
        BR36     3a      G---T-------------------------------
        T9       3b      ----TGC--C---G----------AGA--AGCT---C---
        T10      3b      ----TGC--C---G----------AGA--AGCT---C---
        BE98     3c      G---T---A---G-T---------AGA-----
```

Figure 1 - Continued 13

|  |  | 8232 |  | 8271 |
|---|---|---|---|---|
| GB48 | 4c | G----AT--C---AG- | ----AAACGACC---CG- | ---- |
| GB116 | 4c | -----AT--C---AG- | ----AAACGAGC---CG- | ---- |
| GB215 | 4c | G----AT--C---AG- | ----AAACGAGC---CG- | --T- |
| GB358 | 4c | G----AT--C---TG- | ----AAACGAGC---CG- | ---- |
| GB809 | 4e | G----GT--C---TG- | -----AA-CGAGC---CG- | --T |
| CAM600 | 4e | -----GT--C----G- | -----AA-CGAGC---CG- | --T |
| G22 | 4f | -----AT--T--G-A- | -----CGCCGAGC---CG- | --T |
| GB549 | 4g | G----GC--C---AG- | -----T--AAGAGC---CC- | --- |
| GB438 | 4h | -----GT--C---GG- | ------CCGAGC---CC- | --- |
| CAR4/1205 | 4i | G----ATT--CA-AG-C | ----AA-CAAGC---CC-NA-T | |
| CAR1/501 | 4j | G----C--T--GG--- | ----TC-CANA-C--NNC--C-N | |
| BE95 | 5a | G----CA---ACA--C- | ----T-AA---A---- | |
| BE96 | 5a | G----CA---ACA--C- | ----T-AA---A---- | |
| CHR18 | 5a | G----CA---ACG--C- | ----TAAA------ | |
| CHR19 | 5a | G----CAA---ACG--C- | ----T-AA---T---T- | |

Figure 2

```
              SEQ ID  2645                                            2694
                     STVTESDIRTEEAIYQCCDLDPQARVAIKSLTERLYVGGPLTNSRGENCG
HCV-1    1a
HCV-J    1b                 ----N-----S------A-E--Q--R--------------K-Q---
BE90     1b   214           ----N---V--S------A-E--Q-----I----------K-Q---
2TY4     1c                 ------------------H-D----N--------------K-----
4TY4     1c                 ------------------H-D--A--N--------------------

HC-J6    2a                 ---R------S--RA-S-PEE-HT--H-----MF---K--QT---
HC-J8    2b                 ---R------S--A-S-PQE--TV--H-----M----K--QS---
NE91     2b   216           ---R------S--A-S-PQE--TV--H-----MI---K--QS---
EB12     2b                 ----------A-S-PQE--TV--H-----M----K--QS---
ARG8     2c                 ----------A-S-PEE--T---H-----M----K--QS---
I10      2c                 ----------S-S-PEE--T---H-----M----K--QS---
T983     2c                 ----------LS-S-PEE--T---H-----M----K--QS---
NE92     2c                 ----------A-S-PQE--T---H-----M----K--QS---
         2d   146           ---R------S--LA-S-PE---T---H----ML---K--QT---

CHR20    3a                 ---Q---V--E-------N-E-E---KV-S----C---MF---K--AQ---
CHR21    3a                 ---Q---V--E-------N-E-E---KV-S----C---MF---K--AQ---
CHR22    3a                 ---Q---V--E-------N-E-E---KV-S----C---MF---K--AQ---
T1       3a                 ---Q---V--E-------N-E-E---KV-S----C---MF---K--AQ---
T7       3a                 ---Q---V--E-------N-E-E---KV-S----C---MY---K--VQ---
NE93     3a   218           ---Q---V--E-------N-E-E---RV-S----C---MF---K--AQ---
NZL13    3a                 N--Q---V--E-------N-E-E---KV-S----C---MF---K--AQ---
EB1      3a                 ------------------N-E-E---KV-S----C---MF---K--AQ---
EB2      3a                 ------------------N-E-E---KV-S----C---MF---K--AQ---
EB3      3a                 ------------------N-E-E---KV-S----C---MF---K--AQ---
EB7      3a                 ------------------N-E-E---KV-S----C---MF---K--AQ---
BR33     3a   10,12         ------------------N-E-E---KV-S----C---MF---K--AQ---
BR34     3a   2,4                                              C---MF---K--AQ---
BR36     3a   6,8                 --------------E-E---K--SA---C---MF---K--AQ---
T9       3b                 ----H-----------E-E---K--SA---I---MY---K--LQ---
T10      3b                 ----Q-----------E-E---K--SA---I---MY---K--LQ---
BE98     3c   150           A---KDE--RV-T----C---MF---K--QH---
```

Figure 2 - Continued 1

```
                          2645                                              2694
EG13     4a             ----------------------V----N-E-E---K--TA--------------MH---K-DL--
EG19     4a             ----------------------V----S--ELE-KV-TA--------------MH---K-DL--
GB48     4c      107    ----K---V--EV---------------E-E---K--TA--------------MH---K-DL--
GB116    4c      109    ----K---V--EV---------------E-E---R--TA--------------MH-----DL--
GB215    4c      111    ----K---V--EV---------------E-E---KV-TA--------------MH---K-DL--
GB358    4c      113    ----K---V--EV---------------E-E---K--TA--------------MH---K-DL--
GB809    4e      117    ----R--KV--EV---------------E-E---KV-AA--------------MH---K-DI,--
CAM600   4e      202    ----R---V--EV---------------E-E---KV-TA--------------MY---K-DL--
CAMG22   4f      204    ----R---V--E----------------E-ET--KV-SA--------------MH-----DL--
GB549    4g      115    ----R---V--EV---------------E-E---KV-SA--------------MY---K-DL--
GB438    4h      208    ----R---V--E----------------E-E---KV-SA-----K--------MY---K-DL--
CAR4/1205 4i     210    P---R-X-V--EV---------N-EXDX-KV-NA--------------MH---K-DL--
CAR1/501 4j      212    ---X-R---------GEV----------E-E---KV-TA--------------MF---K-DL--

BE95     5a      160    -------H---M---S------S----Q-E---A---R----Q---C---MY---K-QQ--
BE96     5a      162    --A----H---L---S------S----SQ-D---A---R----Q--FC---MY---K-QQ--
CHR18    5a             -------H---M---S------SLY--Q-E---R----R---Q---C---MY---K-QQ--
CHR19    5a             -------H---M---S------SLY--Q-E---A---R----Q---C---MY---K-QQ--
```

Figure 2 - Continued 2

```
                 2695                                              2744
                 YRRCRASGVLTTSCGNTLTCYIKARAACRAAGLQDCTMLVCGDDLVVICE
HCV-1    1a      --------------------------------------------------
HCV-J    1b      ------------------------L--T----K----------N------
BE90     1b      ------------------------L--S----K-----------------
2TY4     1c      ------------------------L---------R---------------
4TY4     1c      ------------------------L-------------------------
HC-J6    2a      ----------------M---I---V--L---K----IIAP--------S-
HC-J8    2a      ----------F-----M---I---V--L---K----IV-PV--------S-
NE91     2b      ----------F-----M---I---V--L---K----IV-PV--------S-
EB12     2b      ----------F-----M---I---V--L---K----IV-PV----------
ARG8     2c      --------A-------M-------V------N----IVAP-----------
I10      2c      ----------------M-------V------N----IVAP-----------
T983     2c      ----------------M-------V--K--N-V---IVAS-----------
NE92     2d      --------V-------M---I---V--Q---K----IIAP--------S-
CHR20    3a      ----------P-----F---I---------SK----RNPDF-------VA-
CHR21    3a      ----------P-----F---I---------AK----RTPDF-------VA-
CHR22    3a      ----------P-----F---I---------AE----RNPDF-------VA-
T1       3a      ----------P-----F---I------T--AK----RNPDF-------VA-
T7       3a      ----------P-----F---I------T--A-----RNPDF-------VA-
NE93     3a      ----------P-----F---I------TT-AK----RNPDF-------VA-
NZL13    3a      ----------P-----F---I------T--AK--N-RNPDF-------VA-
EB1      3a      ----------P-----F---I------T---E----RNPD--------VA-
EB2      3a      ----------P-----F---I------T---E----RNPD-----------
EB3      3a      ----------P-----F---I------T---K----RNPD-----------
EB7      3a      ----------P-----F---I------T---K----RNPD-----------
BR33     3a      ----------P-----F---I------T--AK----RNPDF-------VA-
BR34     3a      ----------P-----F---I------T--A-----RNPDF-------VA-
BR36     3a      ----------P-----F---I------T--AK----RSPDF-------VA-
T9       3b      ----------P-----F---I------T---S----K-PSF-------VS-
T10      3b      ----------P-----F---I------T---S----K-PSF-------VS-
BE98     3c      ----------P-----F---I---K--TK-------IKNPSF-------A-
```

Figure 2 - Continued 3

| | | 2695 | | | | | | | | | | | | | | | | | | | | | | | | | 2744 |
|---|---|---|---|---|---|---|---|---|---|---|---|---|---|---|---|---|---|---|---|---|---|---|---|---|---|---|---|
| GB48 | 4c | - | - | Y | - | - | F | - | - | - | - | L | - | S | - | - | I | K | - | - | - | R | - | - | - | - | A - |
| GB116 | 4c | - | - | Y | - | - | F | - | - | - | - | L | - | S | - | - | I | - | - | - | - | R | - | - | - | - | A - |
| GB215 | 4c | - | - | Y | - | - | F | - | - | - | - | L | - | S | - | - | I | - | S | - | - | R | - | Y | - | - | A - |
| GB358 | 4c | - | - | Y | - | - | F | - | - | - | - | L | - | S | - | - | I | - | - | - | - | R | - | - | - | - | A - |
| GB809 | 4c | - | - | Y | - | - | F | - | - | M | - | L | - | S | - | - | I | - | - | - | - | K | - | - | - | - | A - |
| CAM600 | 4e | - | - | Y | - | - | F | - | - | - | - | L | - | S | - | - | I | - | - | - | - | K | - | - | - | - | A - |
| CAMG22 | 4e | - | - | Y | - | - | F | - | - | - | - | FL | - | T | - | - | TK | - | - | - | - | K | - | - | - | - | A - |
| GB549 | 4f | Q | - | Y | - | - | F | - | - | V | - | L | - | V | - | - | T | - | - | - | - | KG | - | S | - | - | - - |
| GB438 | 4g | L | - | Y | - | - | F | - | - | V | - | L | - | T | - | - | T | - | - | - | - | K | - | - | - | - | A - |
| CAR4/1205 | 4h | I | - | Y | - | - | F | - | - | - | - | L | - | T | - | - | T | - | - | - | - | K | - | - | - | - | A - |
| CAR1/501 | 4i | Q | - | F | - | - | F | - | - | - | - | L | - | T | - | - | I | - | - | - | - | R | - | - | - | - | S - |
| EG13 | 4j | - | - | F | - | - | F | - | - | - | - | L | - | T | - | - | I | - | - | - | - | K | - | - | - | - | - - |
| EG19 | 4k | - | - | Y | - | - | F | - | - | - | - | L | - | T | - | - | I | - | - | - | - | K | - | S | - | - | - - |
| BE95 | 5a | - | - | - | - | - | F | - | - | M | - | - | - | L | - | S | - | - | - | - | - | R | - | R | - | - | L - - - A - |
| BE96 | 5a | - | - | - | - | - | F | - | - | M | - | - | - | L | - | S | - | - | T | - | - | R | - | Y | - | L | - - - H - A - |
| CHR18 | 5a | - | - | - | - | - | F | - | - | M | - | - | - | L | - | S | - | - | - | - | - | K | - | - | - | L | - - - - A - |
| CHR19 | 5a | - | - | - | - | - | F | - | - | M | - | - | - | - | - | S | - | - | - | - | - | K | - | - | - | L | - V T - - A - |

Figure 2 - Continued 4

```
             2745            2757
             SAGVQEDAASLRA
HCV-1    1a
HCV-J    1b  ---T-----A---
BE90     1b  ---T-------V-

HC-J6    2a  -Q-TE--ERN---
HC-J8    2b  -Q-NE--ERN---
NE91     2b  -Q-NE--ERN---
NE92     2d  -Q-TE--ERN---

CHR20    3a  -D---D--R-A--
CHR21    3a  -D---D--RTA--
CHR22    3a  -D---N--R-A-G
T1       3a  -D---D--R-A--
T7       3a  -D---D--RTA--
NE93     3a  -D---D--R-A--
NZL13    3a  -D---D--R-A--
BR33     3a  -
BR34     3a  -
BR36     3a  -
T9       3b  -C---E--R-A--
T10      3b  -C---E--R-A--
BE98     3c  ---ID---R-
```

Figure 2 - Continued 5

|  | | 2745 | 2757 |
|---|---|---|---|
| GB48 | 4c | -D--E--KRP-G- | |
| GB116 | 4c | -D--E--KRA-G- | |
| GB215 | 4c | -D--E--KRA-GV | |
| GB358 | 4c | -D--E--KRA-G- | |
| GB809 | 4e | -G--E--KRA-G- | |
| CAM600 | 4e | -G--E--KRA-G- | |
| G22 | 4f | -D--E--RRA-G- | |
| GB549 | 4g | -G--E--RA--- | |
| GB438 | 4h | -G--E--RA--- | |
| CAR4/1205 | 4i | -I-ID--KQA--T | |
| CAR1/501 | 4j | ----E--PXTX-P | |
| BE95 | 5a | -Q-TH--E---- | |
| BE96 | 5a | -Q-TH--E-N--- | |
| CHR18 | 5a | -Q-TH--K---- | |
| CHR19 | 5a | -Q-TH--E-C--V | |

Figure 3

```
                        1
              SEQ ID    ATGAGCACGAATCCTAAACCTCAAAAAAAAACAAACGTAACACCAACCG
HCV-1                   ------------------------------------------------
HCV-J                   ---------A--------------G----C-------A-A--------
HC-J6                   ---------A--------------G----C-------A-A--A-----
HC-J8                   ---------A--------------G----C-------A-A--A--T--
NE92          143       ---------A--------------G----C-------A-A-----T--
EB1                     -----------------ACT----G----C-------A-A-----T--
3a                      -----------------ACT----G----C-------A-A---ACT--
NZL1                    -----------------ACT----G----C-------A-A--------
HCV-TR                  -----------A------------G--C-C-------A-A--------
BE98          147       ------------------------G----C-------A-A--------
GB358         191       -------------T----------G----C-------A-A--------
GB809         163       ------------------------G----C-------A-A--------
CAM600        165       ------------------------G----C-------A-A--------
4?            193       ------------------------G----C-------A-A--------
4?                      ------------------------------C-------A-A--------
EG-29                   ------------------------G----C-------A-A--------
BE95          151       ---------A--------------G----C-------A-A-------S

51
              SEQ ID    TCGCCCACAGGACGTCAAGTTCCCGGGTGGCGGTCAGATCGTTGGTGGAG
HCV-1                   ---------------------------------------------
HCV-J                   C------A-----T-----------C--T---C-----------
HC-J6                   -------------T---T-------C--C--------C-------
HC-J8                   C------------T---T-------C--C--------C-------
NE92                    C------------T-----------C--T---C--A---------
EB1                     -------------T-----------C--T---C--A---------
3a                      ----A--------T-----------C--C--------A-------
NZL1                    -------------T-----------C--C--------A-------
HCV-TR                  -------------T-----------C--T-------C--A------
BE98                    C--G---CAT---T-----------C--T--------C-------
GB358                   C------CAT---T-----------C--T---C----C-------
GB809                   C------CAT---T-----------C--C---C----C-------
CAM600                  C------TAT---T-----------C--T---C--A--C-------
4?                      C------TAT---T-----------C--T----------C-------
4?                      C------CAT---T-----------C--T---C-------------
EG-29                   C-----------------------C--T----------C-------
BE95                    C---------------------------------------------
```

Figure 3 - Continued 1

```
        101
        TTTACTTGTTGCCGCGCCAGGGGCCCTAGATTGGGTGTGCCGCGACGAGA
HCV-1   1a  ----------------------------------------------
HCV-J   1b  ----C-------------------------C--G-----------T--G
HC-J6   2a  ---A-------------------------C--G-----------A--G
HC-J8   2b  ------------C----------------C--G-----------A--G
NE92    2d  ---A-------------------------CC-G--------------G
EB1     3a  ---A---G---------------------AC--------T-------
NZL1    3a  ---A---G---------------------AC---------------C-T
HCV-TR  3b  ---A-TG--C-------T-----------AC---------------C-T
BE98    3c  ----G--C-A--A---------------CCAG--------AGTAC-T
GB358   4c  -------------------------------------T--AGT-C--C
GB809   4c  ----------------------------C--G---------------T--G
CAM600  4e  ------------------------------G----------------TC-G
GB724   4?  -----------------------------C--G--------------TC-G
EG-29   4?  -----------------------------CC-G--------------TC-G
BE95    5a  ----------------------------------GA-----------TC-G
                                                    -GA-----------TC-G

151
        AAGACTTCCGAGCGGTCGCAACCTCGAGGTAGACGTCAGCCTATCCCCAA
HCV-1   1a  --------------------------------------------------
HCV-J   1b  ------------G-------------T--A--G--A--A-----------
HC-J6   2a  ------------G--------C--G--A--T--A--G--C-----C----T-
HC-J8   2b  ---------T--------A--C--G--G--T--AC--C--C-----G--
NE92    2d  ---A----------------C--G--A--T--G--G--C-----C----
EB1     3a  ---A--------T--A-----A--G-----C--AC---A----------
NZL1    3a  ---A--------T--A-----T--G-----C--AC---A----------
HCV-TR  3b  ---A--------------------G-----C--AC---A----------
BE98    3c  ----------------------------CAAACAG---C--A--C-----
GB358   4c  ------------G-----------------CA-----G--C--A--C-----G
GB809   4c  ------------G-----------------T--G-----G--C--A-----T-
CAM600  4e  ------------G-----------------T--G-----G--C--A-----
GB724   4?  ------------G--------------------T--C--G-----A-----
EG-29   4?  ------------G-----------------T--G-----C--A--------A--
BE95    5a  ---------G--A-----------------C--T--AC-G------T-----
```

Figure 3 - Continued 2

```
          201
HCV-1    GGCTCGTCGGCCCCGAGGGCAGGACCTGGGCTCAGCCCGGGTACCCTTGGC
HCV-J    ----------C---------------T-------------------------
HC-J6    --A---G---CT--ACT----AAT----GAA-A--A--A----C--------
HC-J8    A-A---G---CT--ACC---A-T-----GAA---A--A--T-----------
NE92     A-A---G---C---ACT---A-T-----GAA-A--A--A-------------
2d       ---G------AG--A-----T-----------------------G-------
EB1      ---G------AG--A---C-T-------------------------------
3a       ------CTC--G------C-T-------------------------------
3a       --G---C--AA-------T-------------------------A-------
NZL1     --A-----AT-T---A---T---------G----------T-----------
3c       --G---C-AT---------AT--------G----------T-----------
BE98     --G---C--AA--------AT--------G----------------------
GB358    --G---C---T---------T-------G--AG-------C-----------
GB809    --G-----AT-----A----T-----A--A--A--A--T--A----------
CAM600   --G---C-A---AC-----C--T-----G----A------------------
4?
4?
5a

251
HCV-1    CCCTCTATGGCAATGAGGGCTGCGGGTGGGCGGGATGGCTCCTGTCTCCC
HCV-J    ---------------C----TATG----A------------A--------
HC-J6    --A---C---G-----ACT---C-----A-----------C---------
HC-J8    --G---C---A--G----T---C-----A-----T---------C-----
NE92     --G---C---G-------T---C-----A--G--------C---------
2d       --G---C---G------CT---C-----A--G--------C---------
EB1      ---------T--C----------------A--G-------C-----C--A
3a       ---------T--C----------------A--G-------C-----C--A
NZL1     --------C--G--A------T----T-A-------T-C-----------
HCV-TR   --------C--G------T-------T-A-------T-C-----------
BE98     ---A------G---------------A-A-------G---C---C--G
GB358    ---T--C---T------------T----A-----A-----C-----C--T
GB809    ---T--C-----------------T---A-----G-----C-----C--T
CAM600   ---T--C-----------------CT--A-----G-----------C--T
GB724    -------------------------------------------------T
4?
4?
5a       --T--C-C--------------CT-------A--G----G--C--C--T
```

Figure 3 - Continued 3

| | 301 | | | | | |
|---|---|---|---|---|---|---|
| HCV-1   | CGTGGCTCTCGGCCTAGCTGGGGCCCCACAGACCCCGGCGTAGGTCGCG |
| HCV-J   | ------------------------T------------------------ |
| HC-J6   | --A--T--C--T--CTCT-----------AT---------A-----C-- |
| HC-J8   | --C--G--T--CT----------------C-----------A--A--A- |
| NE92    | --A--G--C--GTCA--------------A--T--------AC-----A- |
| HC-J8   | --A--G--C--T--ATCT-----------A--T---------A-----C-- |
| EB1     | --C--C--T--ATCT-----------A--AT---------G------C- |
| NZL1    | -----T--C--T-------------A--AT-----------A--C- |
| HCV-TR  | --C--C--GTCG-------------A--AT---------C---A |
| BE98    | --C--G----GTCT-----------T--AT--T--------G-----C- |
| GB809   | --C--N----N-GTCT---------A--AT--T--------N-G--A--C- |
| CAM600  | --C--C--T--ATCT-----------A--AT--T--------G--A-- |
| GB724   |                       --AT-----------A--AA--- |
| BE95    | --A-----AT-------------------------------T----- |

| | 351 | | | | | |
|---|---|---|---|---|---|---|
| HCV-1   | CAATTTGGGTAAGGTCATCGATACCCTTACGTGCGGCTTCGCCGACCTCA |
| HCV-J   | T---------------------------A--------T----------- |
| HC-J6   | --CG---------------------A-----------T--T-------- |
| HC-J8   | --C--GA----------------------A------T--T-------- |
| NE92    | --C---------------A------------------T---------- |
| EB1     | -----------A--------------C---G------------------ |
| NZL1    | --C--T---------------------A------A-------------- |
| HCV-TR  | --CC--------------------A--T--A------------------ |
| GB809   | --C----------------------A--A----------------- |
| CAM600  | --C----------------------A----------------------- |
| GB724   | --------------------------G----A------------------ |
| BE95    | T-------------------------A----A---------T------- |

Figure 3 - Continued 4

```
       401
HCV-1  TGGGGTACATACCGCTCGTCGGCGCCCCTCTTGGAGGCGCTGCCAGGGCC
HCV-J  ----------T--------------------C--A--G------------
HC-J6  ------C--TG--A-----------------G--C--C----TC---A--T
HC-J8  ------C--TG--------------------G--C--C----TC---A--T
NE92   ------C--TG--T-----------------GG---------TC---A--T
HC-J8  ------C--TG--------------AG----AG--T--T-TC----A-A--
NE92   ------C-------------T----------T--G--A----TC--A-A--
NZL1   ------T-------------------------G-G--G----TC---A---
HCV-TR -----A-C----T--A---------------CG-G--T----TC---A---
GB809  -----A-C----T--A---------------CG-G--T----TC---A---
CAM600 -----A-C----------G------------CG-C--G----TC-------
GB724  -------C--------G--------------CA----G-----TC--A---
BE95   ----T-C---------A--------------G--CA---------TC--A--T

451
HCV-1  CTGGCGCATGGGCGTCCGGGTTCTGGAAGACGGCGTGAACTATGCAACAG
HCV-J  ---A--T------G-------------G----------------------
HC-J6  --C-------------------GA-A---C-----G---T--T-T-----
HC-J8  --C-----------A--C--T--GA-A---C-----G--T--C-------
NE92   ---A---C--T-----------TA--C-----GA-A--T--C--------
HC-J8  --C-----------A--A----GA-A------GA-A--------------
NE92   --C---T-------A-------GA--CC--T-GA-A--T-TC--------
NZL1   --C---T-------A-------GA--CA-T-GG-A---------------
HCV-TR --C---A-------T-------TA--C-G-----GA-C--C---------
GB809  --C---A-------T-------TA--C-G-----GA-C--T---------
CAM600 -------A-----------A--C-G-----GA-C--T------N-G----
GB724  --C---A--------------A-----C-G-----GA-T-----------
BE95   --C---A--C----T--GA---C---T--G-----G--A-----------
```

Figure 4

| | | SEQ ID NO | 379 ACGTGCGGGCTTCGCCGACCTCATGGGTACATACCGCTCGTCGGCGCCCC 428 |
|---|---|---|---|
| HCV-1 | 1a | | |
| HCVEC1 | 1a | | |
| HCVHCT18 | 1a | | ----------------------T------------------------- |
| HCVHCT23 | 1a | | ---------------------------------------T-------- |
| HCVHCT27 | 1a | | |
| HCVTH | 1a | | --A----------------------T-------T--------------- |
| HCV-J | 1b | | -------------------------T-------T--------------- |
| HC-J6 | 2a | | -------T-------------------------C--TG----A----- |
| HC-J8 | 2b | | --T--T-T-------------------------C--TG----T----- |
| NE92 | 2d | 143 | -------T-------------------------C--TG---------- |
| HD10 | 3a | 13,15,17 | ------------------------------T------------T----- |
| BR33 | 3a | 23,25,27 | ------------------------------T------------T----- |
| BR36 | 3a | 19,21 | ------------------------------T------------T----- |
| NZL15 | 3a | | ------------------------------C------------T----- |
| HCV-TR | 3b | | ------------------------------T------------------ |
| GB809_4 | 4a | 189 | -------A----------------------A---C---------G---- |
| GB116 | 4c | 183 | --C----------------------------A---C------A------ |
| GB215 | 4c | 185 | --T----------------------------A---C------A------ |
| GB358 | 4c | 118,187 | --T----------------------------A---C------A------ |
| GB809_2 | 4e | 122,169 | --A----------------------------A---C----T--A----- |
| CAM600 | 4e | 167 | --A----------------------------A---C----T--A----- |
| CAMG22 | 4f | 171 | --A----------------------------A---C----T--G----- |
| CAMG27 | 4f | 173 | ---T-C-------------------------A---C-------A----- |
| GB549 | 4g | 120,175 | ----T--------------------------A---C--------G---- |
| GB438 | 4h | 177 | -------G-----------------------A---C--------G---- |
| CAR4/1205 | 4i | 179 | --C----------------------------A---C------A----- |

Figure 4 - Continued 1

| | | | | | | | | | |
|---|---|---|---|---|---|---|---|---|---|
| CAR4/901 | 4? | 181 | G------- | -------- | ----T--- | --A----- | ---C---- | ---A---- | ------- |
| BE95 | 5a | 143 | -------- | ----A--- | ----T--- | -------- | ---C---- | ---A---- | --G---- |
| BE100 | 5a | 195 | -------- | ----A--- | -------- | ---G---- | ---C---- | ---A---- | --G---- |

Figure 4 : Continued 2

```
                   429                                                                    478
                   TCTTGGAGGCGCTGCCAGGGCCCTGGCGCATGGCGTCCGGGTTCTGGAAG
HCV-1         1a   ------------------------------------------------- 
HCVEC1        1a   ------------------------------------------------- 
HCVHCT18      1a   --------------CG------------C-------------------- 
HCVHCT23      1a   ----------------------------------------T-------- 
HCVHCT27      1a   ------G------------------------------------------ 
HCVTH         1a   ------G------------------------------------------ 
HCV-J         1b   C--A--G--------------A---T-------------G---------

HC-J6         2a   G--C--C----TC---A--A--T--C--------GA-A---C-----G- 
HC-J8         2b   GG---------TC---A--A--T-------A--C--TA---C-----G- 
NE92          2d   AG---T-TC---A--A--T--C-----------GA-A------------

HD10          3a   -G-A------TC--A--A----T----------GA-----CC--T---G- 
BR33          3a   CG-A------TC--A--A----T----------GA-----CC--T---G- 
BR36          3a   CG-A------TC--A--A----T----------GA-----CC--T---G- 
NZL15         3a   -G-A------TC--A--A----C----------GA-----CC--T---G- 
HCV-TR        3a   -G-G------TC--A--A----C----T-----GA-----CA--T-GG- 
GB809_4       3b   -G-G--G---TC--A--A----------T------A----C-G-----G- 
GB116         4a   CG----G---TC---------A-AA--C--T--TA---C-G-------G- 
GB215         4c   -G-G--T---TC---------A----AA-----TA---C-G-------G- 
GB358         4c   CG-G--T---TC------------A--C--T--TA---C-G-------G- 
GB809_2       4c   -G-G--T---TC------------A--C--T--TA---C-G-------G- 
GB809_2       4e   CG-G--T---TC------------A--C--T--TA---C-G-------G- 
CAM600        4e   CG-G--T---TC---------A--A--C--T--GA---CA--T-GG--G- 
CAMG22        4e   -G----T---TC---------------------A----C-G-------G- 
CAMG27        4f   -G-G--T---TC------------------T--TA---C-G-------G- 
GB549         4f   -G-G--T---TC---------------T---------A--C-G-------G- 
GB438         4g   -G-G--T---TC----------T----------A----CCG------G-

GB438         4h   AG-A-----TC------A---T-----------A---C-G---G- 
CAR4/1205     4i   CG-G-----TC------AR-T------------A---C-------- 
```

Figure 4 : Continued 3

```
CAR4/901  4?   CG-G--T----TC-----A-----------C--T--TA---C-G-----G-
BE95      5a   CG-----G----TC--A----T--C--A---T--C--T--GA---C--T--G-
BE100     5a   CG-----G----TC--A----T--C--A---T--C--T--GA------T--G-
```

Figure 4 : Continued 4

```
                479                                                528
          ACGGGCGTGAACTATGCAACAGGGAACCTTCCTGGTTGCTCTTTCTCTATC
HCV-1     1a  --------------------------------------------------
HCVEC1    1a  --------------------------------------------------
HCVHCT18  1a  ----------------------------------C---------------
HCVHCT23  1a  --------------------------------------T-----------
HCVHCT27  1a  --------------------------------------------------
HCVTH     1a  --------------------------T-G--C------C-----------
HCV-J     1b  --------------------------------------------------

HC-J6     2a  ---G--T--T-T--------------T-A--C------C--T--------
HC-J8     2b  --GA-A--T--C--------------TT-A--C--------T--------
NE92      2d  --GA-A--------------------T-G--C------C--T--------

HD10      3a  --GA-A--T-TC--------------TT-G--C------C--T--------
BR33      3a  --GA-A----TC--------------TT-G--C------C--T--------T
BR36      3a  --GA-A--T-TC--------------TT-G--C------C--T--------
NZL15     3a  --GA-A--T-TC--------------T-G--C------C--T--------
HCV-TR    3b  --A-----------------------T----------------T-------T

GB809_4   4a  --GA-T--------------G-----T----C------T--T--------
GB116     4c  --TA-T--T-----------------T----C-C----T--T--------
GB215     4c  --A-C--T------------------T----C------T--T--------
GB358     4c  --GA-C--T-----------G-----T----C------T--T--------
GB809_2   4e  --GA-C--C-----C-----------T----C------T--T--------
CAM600    4e  --GA-C--T-----------------T----C------T--T--------

CAMG22    4f  --GA-T--------------------------------C--T--------
CAMG27    4f  --GA-A--------------------------------C--T--------
GB549     4g  --GA-T--T-------------------T---------C--T--------
GB438     4h  --GA-C--T-----C-------------------C---C--T--------
```

Figure 4 - Continued 5

```
CAR4/1205   4i   ----GA--C---T---------------------------T-------------
CAR4/901    4?   ----GA--T---------C-----------------------T-------------
BE95        5a   ----G---A-------C---------------------TT--A---C---------
BE100       5a   ----G-------T---------------------------T---G-----------
```

Figure 4 : Continued 6

```
          529                                                       578
HCV-1     1a  TTCCTTCTGGCCCTGCTCTCTTGCTTTGACTGTGCCCGCTTCGGCCTACCA
HCVEC1    1a  -----T--------------------------------------------
HCVHCT18  1a  -------------------------C-----------------A------
HCVHCT23  1a  ------------A------------C-----------------A------
HCVHCT27  1a  -------T-----------------C--------------A---------
HCVTH     1a  --------------------------TC--------------A-------
HCV-J     1b  --------------------------C------CA--C---A----T--G

HC-J6     2a  ---T-G---------G--C---A-C--CACC---G-TC---C---TGC-G
HC-J8     2b  --TT-G--T--T---T--G--A----G-C---A-----A-TG---T--AGTGG
S83       2c  --------------------------T---------A-TG---T------GTGG-
NE92      2d  --T-AT----------A------TA-C-----------G-TC---C-G--TG--

HD10      3a  -----T--T---T-----------------------A-TCCAT--A--AG-TAGTCTAG-
BR33      3a  -----T--T---T-----------------------A-TCCAT--A--AG-T-GTCTAG-
BR36      3a  -----T--T---T-----------------------A-T-CAT--A--AG-TAGTCTAG-
NZL15     3a  -----T--T---T-----------------------A-T-CAT--A--AG-CAGTCTAG-
HCV-TR    3b  ---C--C--T---CT------C---------TGC------G---T-G--TAG-
```

Figure 4 - Continued 7

|  |  | 529 |  | 578 |
|---|---|---|---|---|
| GB809_4 | 4a | -----C----A--T--T--G---C-C-----C--A--G--A--TG-G-- |
| Z4 | 4a |  |  | G--G-- |
| Z1 | 4b |  |  | GTG-- |
| GB116 | 4c | -C---CT---A---T--T--G---C----T---A-C--A---GT-A- |
| GB215 | 4c | -A---CT---A---T--T--G---C----T---A-C------AT--- |
| GB358 | 4c | -----CT---A---T--T--G---C----T---A-C------GT-A- |
| Z6 | 4c |  |  | GTTA- |
| Z7 | 4c |  |  | GT-A- |
| DK13 | 4d |  |  | ---A- |
| GB809_2 | 4e | -----CT---A---T-----G---C-C--T---G-----G-GTTA- |
| CAM600 | 4e | -----CT---G---C-----G---C-C--T---A-A-----GTTA- |
| G22 | 4f | -----------A---T-----G---C----C---C------TGTG- |
| G27 | 4f | -----------A---T-----G--------C---C--A---TGTG- |
| GB549 | 4g | -----------A---T-----G-----C--C---G-----GC-G-- |
| GB438 | 4h | ----A--A---TA--T-----GC--C-A--C---G--T--TC-G-- |
| CAR4/1205 | 4i | -C---CT--TA--T-----G-----C--T---C--A---AT--- |
| CAR4/901 | 4? | -N-------T-AA--T-----G-----C--C---G-----TC-G-- |
| BE95 | 5a | --TA----T--T--T-----G--TC-----C--T--G--C--T--AGTT-C |
| BE100 | 5a | ---A------T--A--T-----G-----C-----C--T--G--C--T--AGTT-C |
| SA4 | 5a |  |  | GTT-C |

Figure 4 - Continued 8

|  |  | 579 | 628 |
|---|---|---|---|
| HCV-1 | 1a | AGTGCGCAACTCCACGGGGCTTTACCACGTCACCAATGATTGCCCTAACT | |
| HCVEC1 | 1a | ------------------------T------------------------ | |
| HCVHCT18 | 1a | ------------------------T---------------C-------- | |
| HCVHCT23 | 1a | -----------T------------T------------------------ | |
| HCVHCT27 | 1a | ---A------------T----CA-T---------------------T-- | |
| HCVTH | 1a | ----------------------------------------C-------- | |
| HCV-J | 1b | G-----------GTGT-C----A-A----T------G--C---T-C--- | |
| HC-J6 | 2a | ---AAG----AT--GTACCGGC---ATG--G-------C----A-C--TG | |
| HC-J8 | 2b | ---CA-G---ATT-GTTCTAGC----T---C---T-------T-A---A | |
| S83 | 2c | G--CAAGG--A--GGC-ACTCC---ATGCCG-------C-----T-C--- | |
| NE92 | 2d | G--CAAG---A----GCA-CTC-----ATG--A-------C----AG---A | |
| HD10 | 3a | GTG---G---A-GT-T---C--C--TGT-C-T-------C--TT-C--TA | |
| BR33 | 3a | GTG---G--TA-GT-T---C--C--TGT-C-T-------C--TT-C--TA | |
| BR36 | 3a | GTG---G--TA-GT-T---C--C--TGT-C-T-------C--TT-C--TA | |
| NZL15 | 3a | GTG---G--TA-GT-T---C--C--GT-C-T-------C--TT-C--TA | |
| HCV-TR | 3b | GTACACG---A-GT-T---C--A--TGTGC-T-------C----T---TG | |

Figure 4 - Continued 9

```
              579                              628
GB809_4    4a  CTAC--G--TG-TT-----CA-C---T----A------------------
Z4         4a  CTAC--G--TG-TT-----CA-C---T----A------C--T--G---T-
Z1         4b  CTAC--G--TG-TT-----CG-C---T----T-------------T--G--T-
GB116      4c  CTAT-----G--T------CG-C---T---TA------------------A
GB215      4c  CTAT-----TG--T-----CG-C---T---------C--G----T-
GB358      4c  CTAT-----TG--T-----CG-C---T----A------C--G-----
Z6         4c  CTAT-----TG--T-----CA-C---T----A------C--G-----
Z7         4c  CTAT-----TG--T-----CG-C---T------------C--G-----
DK13       4d  CTAT-A---TG--T-----CG-C---T----A------C--G-----
GB809_2    4e  CTAT-----AG-T------TG-C---T-----------C--G-----
CAM600     4e  CTAT-----TG-TT-----CG-----T----A------C--G--TG
G22        4f  CTAT-----TG-TT-----CA-----T----A------C--G--TG
G27        4f  TTAT-A-----T-------CA-C---------C-----C-----
GB549      4g  TTAT-A-----A--T----CA-C---T----A---T--------------
GB438      4h  CTAC--G----AT-T----CA-----T----------------C--G-----
CAR4/1205  4i  CTAC--G--TG-AT-----CA-C---T----T------C--G-----
CAR4/901   4?  CTAT-----TG-TT-----ACGG---TT-TA-------------G-----

BE95       5a  CTAC--A--TG--T-T---A-----T----T-------A--------
BE100      5a  CTAC--A--TG--T-T---A-C---T----T-------A--------
SA4        5a  CTAC--A----G--T----G------T----T-------A-----T-
```

Figure 4 - Continued 10

```
          629                                                            678
          CGAGTATTGTGTACGAGGCGGCCGATGCCATCCTGCACACTCCGGGGTGC
HCV-1   1a ------------------------------------------------T
HCVEC1  1a ---C--------------------C-----------------------T
HCVHCT18 1a ---------A--A-----------------------G-----------T
HCVHCT23 1a ------------------------CA----------T-----------T
HCVHCT27 1a ----------A--------A----------------G-----------T
HCVTH   1a ---------------------------T--------------------T
HCV-J   1b -A-----------T----A--G--CATG--A--------C--------T

HC-J6   2a AT--C---ACC-GGC-ACTCCAG-C--TG-----C--GTC--C-----T
HC-J8   2b AC--C---CACC-GGC--CTCA-T--C--AG-T--C--TCT---T--A-
S83     2c -T---C--T-GGC--CTT-AA-GA--AG-G----T---T-----T--A-
NE92    2d GT--C--C-GGC--CTCAGG-----TG-T--T----GTC--C-----T

HD10    3a GC----------T-----C-AT--C-TT--T--------A--C--C--T
BR33    3a GT----------T-----C-AT--C-TT--T--------G-G--C--T
BR36    3a GC----------------C-AT--C-TT--T--------A--C--C--T
NZL15   3a GC----------T-----C-AT---T--T----------A--C--C--T
HCV-TR  3b G---C-----------C-AA----TG--T-------TTA--C--A----
```

Figure 4 - Continued 11

|  |  | 629 |  |  |  |  |  |  |  |  | 678 |
|---|---|---|---|---|---|---|---|---|---|---|---|
| GB809_4 | 4a | --C--- | -CG- | -A-- | -C-- | -T-- | -AA- | -T- | -A- | -C- | -CCAT- | -AT--- | ---TTG--- | ---- | --- |
| Z4 | 4a | --C--- | ---- | -A-- | -C-- | -T-- | -A-- | -T- | -A- | -C- | ---CA-- | --A--- | ---TTG--- | ---- | --- |
| Z1 | 4b | --C--- | -C-- | -A-- | ---- | ---- | --A- | --- | -AGC- | -CCA- | ------- | --A--- | ---TTG--- | -A-- | -T- |
| GB116 | 4c | --C--- | ---- | -A-- | ---- | ---- | ---- | -T- | -A- | -T- | -CCA-- | --A--- | ---CTC--- | -T-- | --- |
| GB215 | 4c | --C--- | ---- | -A-- | ---- | ---- | ---- | -C- | -A- | -C- | -CCA-- | --A--- | ---CT--- | -A-- | -T- |
| GB358 | 4c | --C--- | ---- | -A-- | ---- | ---- | -A-C- | -AGC- | -CCA- | ------- | --A--- | ---CTC--- | -A-- | --- |
| Z6 | 4c | --C--- | ---- | -A-- | ---- | -T-- | ---- | -C- | -AAC- | -CCAG- | --T-A- | ---CTC--- | -A-- | --- |
| Z7 | 4c | --C--- | -AA- | ---- | ---- | -T-- | ---- | -C- | -AAC- | -CCA-- | ------- | --A--- | ---CTC--- | -A-- | --- |
| DK13 | 4d | --C--- | ---- | -A-- | ---- | -T-- | -AA- | -C- | -ATT- | -CCA-- | --T-A- | ---CTC--- | -A-- | --- |
| GB809_2 | 4e | --A--- | -C-- | -A-- | ---- | ---- | ---- | -A-C- | -A-A- | ---CA-- | --T-A- | ---CTC--- | -A-- | -A- |
| CAM600 | 4e | --C--- | -C-- | -A-- | ---- | ---- | ---- | -A-C- | -AAA- | ---CA-- | --T--- | ---CT--- | -A-- | --- |
| G22 | 4f | --T--- | -C-- | -A-- | -C-- | -TT- | ---- | -A-T- | -C-- | ---CA-- | --T--- | ---CT--- | -A-- | -T- |
| G27 | 4f | --T--- | -C-- | -A-- | -C-- | -TT- | ---- | -A-AGC- | ---CA-- | --T--- | ---TCT--- | -A-- | -A- |
| GB549 | 4g | --T--- | ---- | -A-- | ---- | ---- | -T-- | -A-T- | -A-C- | -CAT-- | --A--- | ---TCTA--- | -A-- | -T- |
| GB438 | 4h | --C--- | ---- | ---- | ---- | ---- | ---- | -A-C- | -A-C- | ---CA-- | ------- | --A--- | ---CTA--- | -C-- | --- |
| CAR4/1205 | 4i | --T--- | -A-- | ---- | ---- | -T-- | ---- | -A-C- | -AGA- | -CCA-- | --T--- | ---CT--- | ---- | --- |
| CAR4/901 | 4? | --C--- | -A-- | ---- | ---- | -T-- | ---- | -A-C- | -ATC- | -CCA-- | --A--- | ---TTA--- | -A-- | --- |
| BE95 | 5a | -TTCC-- | -A-- | -C-- | ---- | -T-- | ---- | ---- | -A-ATA- | -CCTG- | ---A--- | ---G-A- | -T-- | --- |
| BE100 | 5a | -TTCC-- | -A-- | -C-- | ---- | -T-- | ---- | ---- | -A-AT-- | -CTG-- | ---A--- | ---G-A- | -T-- | -C- |
| SA4 | 5a | -TTCC-- | -A-- | -T-- | ---- | ---- | ---- | -T-ATA- | -CCTG- | ---T--- | ---TG-A- | -T-- | --- |

Figure 4 - Continued 12

|  |  | 679 | | | | | 728 |
|---|---|---|---|---|---|---|---|
|  |  | GTCCCTTGCGTTCGTGAGGGCAACGCCCTCGAGGTGTTGGGTGGCGATGAC | | | | | |
| HCV-1 | 1a | ------------------------------------------------- | | | | | |
| HCVEC1 | 1a | ---------AC--------T---------------G------------- | | | | | |
| HCVHCT18 | 1a | ---------AC--------T---------------G------------- | | | | | |
| HCVHCT23 | 1a | ------------C------AT----A------------------------ | | | | | |
| HCVHCT27 | 1a | ------------C------T------AA------C---G-AG------- | | | | | |
| HCVTH | 1a | ------------C------T------------------------------ | | | | | |
| HCV-J | 1b | --G---C-----C--G---A-T--TTT---CC-T----C----A----C-C- | | | | | |
| HC-J6 | 2a | -----G---AGAAA-T---G--TA-A--TC----C----A-AC--G-CT- | | | | | |
| HC-J8 | 2b | -----A---T-AGAA---TAATGG-A---T-CAT---C----A-ACAAG-A-- | | | | | |
| S83 | 2c | -----T-AG---ACC-C----T---TC-A-------C--G-TG- | | | | | |
| NE92 | 2d | -----T-AGGAGA-------ATA---CC-C-------A-AC--G-TT- | | | | | |
| HD10 | 3a | --A----T---AG--C--T---TA-A--TGC---C---ACCC-AG--- | | | | | |
| BR33 | 3a | --A----T---C-AG--C--T---TA-G--T-CA---C---ACCC-AG-A-- | | | | | |
| BR36 | 3a | A-A----T---C-AG--C------TA-A--C-C---C---ACCC-AG--- | | | | | |
| NZL15 | 3a | --A----T---C-AG--C------TA-A--T-C---C---ACCC-AG--- | | | | | |
| HCV-TR | 3b | --G--C----CACAACC------CAA--ATCA--C---ACAA--G-CT- | | | | | |

Figure 4 - Continued 13

```
          679                                                              728
GB809_4   --A--C-------GA-G-CC--G-----TG--TC-T--C---AC-C--G-A---
Z4        --A--C---T---GATGACT--G-----A-A---C-T--C---AC-C--G----
Z1        -----C---T---G--GAC--AG---TA-T--TC-C--C-------C-CT----
GB116     T-A--C-------GA-G-TT--G---TCAG--AC-C--C--------CC-T---
GB215     T-A--C---T---GA-G-TT--G---TCAG--AC-T--C--------CC-CT--
GB358     T-A--C-------GA-G-TT--G---TCAG--AC-C--C--------CC-C---
Z6        T-G--C---T---GA-G-TT--G---TCAG--AC-C--C--------CC-T---
Z7        --A--C---T---GA-G-----G-----CAG--AC-C--C--------CC-T---
DK13      --T----------GA-G--A--G-----AAG--T-CA--C-----T-TC-C---
GB809_2   --A--C---T---GAAGACC--G-----CAG---C----------------CC-C---
CAM600    --A--C---T---GA-GACT--G-----CAG---C----------------CC-C---
G22       -----T---T---AA-AACT--G-----CAG--TC---C-----A---CT----
G27       --C--T-------GA-AACT--G-----CAG--AC-A--C---A--A--CT---
GB549     --G----------GA-AACC--G-----A----C-C--C--------C-C---
GB438     --G--C---T---AA-AACT--G-----T-T---C-T--C---A-TC-TT-A--
CAR4/1205 A-A--C---T---GAAGACC--G-----TCAG---C-------------TC-C---
CAR4/901  A-A--C---T---GA-GACC--G-----TT----C---C-----AT-TC----
BE95      --G------T---CATGACA--T--T-TGAGT--A---C-----CCAA--T---
BE100     --G------T---CA-GA-A-AT--T-TGAGT-------C-----CCAA--T---
SA4       --G------T---CA-GC-A-AT--T-T-AGT-A----C-----CCAA---C--
```

Figure 4 - Continued 14

```
            729                                                              778
HCV-1    1a  CCCTACGGTGGCCACCAGGGATGGCAAACTCCCCGCGACGCAGCTTCGAC
HCVEC1   1a  ---C----------------------------------A-A---------
HCVHCT18 1a  ---C----------------------------------A-A---------
HCVHCT23 1a  ---C-------------------A--------------A-A---------
HCVHCT27 1a  ---C---A----------------C-------------A-----------
HCVTH    1a  ---C--------------------C-------------A-A-------G-
HCV-J    1b  T--C----C--C---GG-----A-CA-----GCA----A-C---ACAA-A-

HC-J6    2a  A--G-AT----GTGCA-C-GCC-GGCGC--T-A--CA-GGCT-A--GA
HC-J8    2b  A--C-AC----TGTG-AAC-CC--GGTGCG-T-A-TCGTAGC-G---A
S83      2c  ---C-ATC-C---TA--TC-ACCTGGGCT-T-A-T-A-GGC-G---C
NE92     2d  G--C-ATA-A---TGTG--CC-ACCTGGTGCG-TTA-C-A-GGC-G--GA

HD10     3a  A------A-----AGT----T-C-T-GG-GCAA--A-CG-TTC-A--CA
BR33     3a  A------A-----AGT----T-C-T-GGGGCAA--A-CG-TTC-A-A-CA
BR36     3a  A------A-----AGT---A-T-C-T-GG-GCAA--A-CG-TTC-A--CA
NZL15    3a  A------A-----AGT----T-C-T-GG-GCAA-TA-TG-TTC-A--CA
HCV-TR   3b  AA-G---------GTT----ACCCTTGGCG-GA--A-CG--TC-A-C--A
```

Figure 4 - Continued 15

```
              729                                                              778
GB809_4       A------   ------   -TG-   --GTATCCATGG-   CGCT-   --GCTCGA-   TCCT-   C---G--
Z4            G------   ----A-   -TGT-  -GCAC-CCCGGGCGT-        --GCTTGA-   TC-T-   C---G--
Z1            ------   ----T-   ----   -G-GCCCT-   --CC-   --CGCA-   --GTTAGA-   TCCA-   G---CA
GB116         T--C---   ---C--   --GG-  -GCCTT-   C-TTGGTGCT-   --GCTAGAATCC-   --C---GA
GB215         T--C---   ---C--   --GG-  -GCCTT-   -CAT-GGTGCT-   --A-TTGAATCCT-  --C---GA
GB358         T--C---   ---C--   --GG-  -GCCTT-   -CAT-GGCGCT-   --GCTTGAATCC-   --C---GA
Z6            T--C---   ---C--   -----  -GGTGTCTT-   --AT-GGTGCT-   --GCTTGACTCC-   --C---GA
Z7            T--C---   ---C--   --GG-  -GCCTT-   ---AT-GGTGCA-   --GCTTGAATCCA-  -C---GA
DK13          ------   ---C--   --TG-  -GCAAC-   --CTG-   --TGCT-   --GCTTGA-   TCTT-GA---
GB809_2       T--C---   ----A-   --GT-  -GCCTT-   -C--T-GGTGCT-   --GCTTGCT-   --CCT-G---G--
CAM600        T--C---   ----A-   -A---  -GT-GCCAT-   -C-C-GGTGCT-   --GCTTGA-   --CCT-G---G--
G22           ------   ---C--   --G---  -GCCAT-   -CCTTGGCGCT-   --ACTCGA-TCCA-   G---G--
G27           ------   -T----   -----  -G-GCCAC-   -CATTGGCGCT-   --ACTTGA-TCCA-   G---G--
GB549         A------   ---C--   -TG-   --CCCT-   ---TTGGCGCG-   --GCTCGAATCCA-  G---G--
GB438         A--C---   -T--A-   ---GT-  -CCCT-   -CCT-GGGGCT-   --ACTT-   ---TCTG-A---G--
CAR4/1205     ---C---   ------   ---GG-  -CCCAC-   -CCTACGTGCT-   --GCTTT-   --TCCT-A---GG
CAR4/901      A------   ------   -TG-   -TCCCT-   -CCT-GGGGCT-   --GCTT-   ----TC---A---G--

BE95          ---------AC-   -T-AG-   --CC-AGCCT-   -GG-GCAGT-   -A---G-T-CT-   ----GA
BE100         -----C---   -T-AG-   --CC-AGCTT-   -GG-GCAGT-   -A---G-T-CC-   ----GA
SA4           -----C---   -T-T-AG-   -CC-A---CT-   -GG-GCGGT-   -A---G-T-CT-   ----GA
```

Figure 4 - Continued 16

```
                     779                                              828
HCV-1       1a   GTCACATCGATCTGCTTGTCGGGAGCGCCACCCTCTGTTCGGCCCTCTAC
HCVEC1      1a   -------------------------------------------C------
HCVHCT18    1a   -------------------------------------------C----T
HCVHCT23    1a   -------------------------------------------C------
HCVHCT27    1a   ---------------------T------------T--------C----T
HCVTH       1a   -------------------------------------------C------
HCV-J       1b   -C----G----T---C--T---GCG--TG-T------C--TA-G------

HC-J6       2a   CG----T--CA--G----GAT-TC-----G---------C---T--T---
HC-J8       2b   CA----G--CA--A-C---AAT-GCA--T--GGC-----C-----T-G--T
S83         2c   CA-------A-CA-C---GAT-TCT--T--GG-------------T----T
NE92        2d   CG--T--T--ACCA-CA-T-CATC---T--GT-T---C---T----G---

HD10        3a   -G---TG-A--CA--T-G--G--CGCG-----GA-G---C---T--T---
BR33        3a   -----TG-G--C---T-A---A---CGCG-----GA-G---C---T--G--T
BR36        3a   ----TG-G--C--AT-A--G---CGCG-----GA-G---C---T--G---
NZL15       3a   ----TG-G--C--AT-A---A---CGCG-----GA-G---C---T--G---
HCV-TR      3b   CC--TG-G--A-----A---CGCACGACAA--G--------G---G---
```

Figure 4 - Continued 17

|  | | 779 | | | | | | | | | | | 828 |
|---|---|---|---|---|---|---|---|---|---|---|---|---|---|
| GB809_4 | 4a | -G--TG-G--- | -C--- | -AA-G- | -A-- | -TGCG- | --- | -G-G | --- | --- | --- | -T-- | -T--- |
| Z4 | 4a | -A--TG-G--- | -CT-- | -AA-G- | -A-- | -CGCG- | --- | -TT-G | --- | -C-- | --- | -T-- | -T--- |
| Z1 | 4b | -G--TG-A--- | -C--- | -A-G-- | -G-- | -TGCG- | -T-- | -TA-G | --- | -C-- | --- | -T-- | --- |
| GB116 | 4c | -G--TG-G--- | --- | -A-G-- | -A-- | -TGCT- | -T-- | -TG-G | --- | -C-- | --- | -T-- | -T--- |
| GB215 | 4c | -A--- | -CA-- | -A-G-- | -G-- | -CGCT- | -T-- | -TG-G | --- | -C-- | --- | -T-- | --- |
| GB358 | 4c | --G-G--- | --- | -A-G-- | -A-- | -TGC-- | -T-- | -TGCG | --- | -C-- | --- | -T-- | -T--- |
| Z6 | 4c | -A--TG-G--- | -C--- | -A-G-- | -G-- | -CGC-- | -T-- | -TG-A | --- | -C-- | --- | -T-- | --- |
| Z7 | 4c | -A--TG-G--- | -C--- | -A-G-- | -A-- | -CGCT- | -T-- | -AG-G | --- | -C-- | --- | -T-- | --- |
| DK13 | 4d | --G-G--- | --- | -A-G-- | -G-- | -CG--- | --- | -T--- | --- | -C-- | --- | --- | --- |
| GB809_2 | 4e | -C--TG-G--- | -C--- | -A-G-- | -A-- | -TGCT- | --- | -G-G | --- | -C-- | --- | -T-- | --- |
| CAM600 | 4e | --- | --- | -A-G-- | -A-- | -TGCT- | --- | -A-G | --- | -C-- | -A-- | -A-- | --- |
| G22 | 4f | --TG-G--- | --- | -A-G-- | -G-- | -C--CT | -T-- | -AT-G | --- | -C-- | -A-- | -A-- | --- |
| G27 | 4f | --G-G--- | -T-- | -A-G-- | -A-- | -C--CT | --- | -AT-G | --- | -C-- | --- | --- | --- |
| GB549 | 4g | --TG-G--- | -T-- | -A-G-- | -A-- | -TGC-- | --- | -G--- | --- | --- | -C-- | --- | -G-- |
| GB438 | 4h | -G--G-G--- | -CT-- | -AA-G- | -G-- | -GCG-- | --- | -T-A- | --- | -C-- | --- | -T-- | --- |
| CAR4/1205 | 4i | AG--TG-G--- | -C--- | -A-G-- | -G-- | -GC--- | --- | -GGCA | --- | -C-- | --- | -TT-T | --- |
| CAR4/901 | 4? | CG--TG-G--- | -C--- | -AA-G- | -G-- | -TGCA- | --- | -T--- | --- | -C-- | --- | -T-- | --- |
| BE95 | 5a | -G--TG-G--- | -AGC-G-T- | -CTAC- | -A-CG- | -AG-G- | -TG- | | | -C-- | -C-- | -GT-A | --- |
| BE100 | 5a | -AGC-G-T- | -TACT-G- | -G-- | -TG- | | | -C-- | -C-- | -GT-A | --- |
| SA4 | 5a | -GGC-G-T- | -CTACT-A-CG- | -AG-G- | -TG- | | | -C-- | -C-- | -A--A | --- |

Figure 4 - Continued 18

```
              829                                                        878
HCV-1      1a GTGGGGGACCTATGCGGGTCTGTCTTTTCTTGTCGGCCAACTGTTCACCTT
HCVEC1     1a ---------------G---------------C-----------------T-
HCVHCT18   1a -----------T-G-----------------------------------T-
HCVHCT23   1a -------------T---CA------------T-----------------T-
HCVHCT27   1a -----------T-G---CA------------T-----------------T-
HCVTH      1a -------------G-----------------T--------------------
HCV-J      1b --T--C-----T-C----A--C--T------C---TC----G----------

HC-J6      2a -----C-----------TGGG--GA-G-----CA-C---GA----TTG---
HC-J8      2a --A--TG-G--------G-C--GA-GA--C-ATCG--GGCT----TGG---
S83        2c --A--G-G--T--CG--GC-GA-G--C--CT--GG-CG--GT-G---
NE92       2d A-A--A-----------CG-G--GA-GT-G-CTTCT--G-C-----T-A---

HD10       3a ---T--TA-G--T----G-C-----C---G--A----GCC-----G-----
BR33       3a ---T--TA-G--T----G-C-----C---G--A----GCC-----G-----
BR36       3a ---T--A-G--T----G--------C---G--A----GCC-----G-----
NZL15      3a ---T--TA-G--T----G-------C---G--A----GCC-----G-----
HCV-TR     3b ---C------GCT-T--G-----G------G--A----GC------------
```

```
              879                                                            928
              CTCTCCCAGGCGCCACTGGACGACGCAAGGTTGCAATTGCTCTATCTATC
HCV-1     1a  --------------------------------------------------
HCVEC1    1a  --------------------------------------------------
HCVHCT18  1a  ------------------------G-AC----T-----------------
HCVHCT23  1a  ------------------------A--C----------------C-----
HCVHCT27  1a  ---C----------A-----------A-----------------------
HCVTH     1a  --------------------------A---------------A-------
HCV-J     1b  ---A--TC-C--GT-TGA----GTA-----A-------------------

HC-J6     2a  ---G--ACA--A------TTTGT---AC-----C---C------------
HC-J8     2b  A--A--ACAA--------AACTTC--C-----AG---C--T---C-----
S83       2c  G--G--ACAA-A------TAC-TTTGTC--G-AA---C--T---C--A--C-
NE92      2d  ---G---CA--AT-----TAA-TTTGTC--G-AC---C--T---C--A--C-

HD10      3a  -AGA--TC-T--------TCAA---GTC--GACC--T---C----AC-G--C-
BR33      3a  -AGA---C-C--------TCAA---GTC--GACC--T---C----GC-G--C-
BR36      3a  -AGA--TC-T--------TCAA---GTC--GACC--T---C----GC-G--C-
S83       3a  -AGA--TC-A--------TCAA---GTC--GACC--T---C----GC-G--C-
NZL15     3a  -AGA--TC-C--------AC---CGT---GACG-------C----G--A--C-
HCV-TR    3b  -AGA--TC-C--------AC---CGT---GACG-------C----G--A--C-
```

Figure 4 - Continued 21

```
                    879                                                      928
GB809_4   4a    -CAG--GC-T----------------C-------G-A---T--------------A
Z4        4a    TCGG--GC-T----------------C-------G-AG-----------T--C--CA
Z1        4b    -CGA--GC-C--G-------------C-----C-G-A---------C--------CG
GB116     4c    -CAG--GC-A----------------C-------G-AC----------T--C--CG
GB215     4c    -CAG--AC-A----------------T-------G-AC----------T--C--CG
GB358     4c    -CAG--GC-----------------T--------G-AC----------T--C--CG
Z6        4c    -CAG--GC-A----------------T-------G-AC----------T--C--CG
Z7        4c    -CAG--GC-A----------------T-------G-AC----------T--C---G
DK13      4d    -CAA--TC-C----------------C-----C-AC------------T--C--CA
GB809_2   4e    -CAA--GC-A----------------C-----C-G-AC--T-------T--C--CG
CAM600    4e    -CAA--GC-A--T-------------C-----C-G-AC----------T--C--CA
G22       4f    -CGG----C-T-------T-------C-----C-G-AG----------T--C-C-
G27       4f    -AGG----C-TG--------------T-------G-AG-------------C---G
GB549     4g    -CGG--GC-C----------T-----T-----C-G-AC----------T--C---G
GB438     4h    -CAA----C-------T---------T-----T-G-A-----------------CT
CAR4/1205 4i    -CGG--AC-CATT--TGAA--C----T-----T-G-AC--------C-----CT
CAR4/901  4?    -CAG--GC-C----------------C-----C-G-AC----------C--T--CG

BE95      5a    TAGG--TC-C-AG----GCT---GT---GAAC-----C--T--C--T---CA
BE100     5a    TAGG--TC-C-AG----TGCT---GT----G-AC---C--T--C------CA
SA4       5a    TAGG--TC-C-AG----ACT---GT-----AC-----------------T--CA
```

Figure 4 - Continued 22

```
                     929                         957
            CCGGCCATATAACGGGTCACCGCATGGCA
HCV-1    1a ----------------------------- 
HCVHCT18 1a -------C-----G--------------- 
HCVHCT23 1a ----------------------------- 
HCVHCT27 1a ----------A------------------ 
HCVTH    1a ----------------------------- 
HCV-J    1b ------CG--T-A---------------T

HC-J6    2a -T--TACC--C---T--A-------G--- 
HC-J8    2b AA---T--C--C---C--T---------- 
S83      2c -G----GC--T---A-------------T 
NE92     2d -A----C---C---A---T--G------G

HD10     3a -A-----C-TT-A--A--T--A----A--T 
BR33     3a -A-----C-TT-A--A--T--A----A--T 
BR36     3a -A-----C-TT-A--A--T--A----A--T 
NZL15    3a -A-----C-TT-A--A--T--A----A--T 
HCV-TR   3b -A-----G-TT-A--A--T--A----T--G 
```

Figure 4 - Continued 23

```
                    929                                957
GB809_4   4a       -T-- ---- ---C -- -C-- ---- A-G-- ---G
Z4        4a       -T-- ---- ---C -- -C-- ---- A-G-- ---G
Z1        4b       -T-- -T-- -CG-CT-- ---- ---- A-G-- ---C
GB116     4c       -G-- -G-- -CG- T-- -C-- T--- A-G-- ----
GB215     4c       -G-- -G-- -CG- --- -C-- ---- G-A-- ----
GB358     4c       -G-- -G-- -CG- T-- -C-- ---- A-G-- ----
Z6        4c       -G-- -G-- -C-- --- -C-- ---- A-G-- ----
Z7        4c       -A-- -G-- -CG- T-- -A-- ---- A-G-- ----
DK13      4d       -G-- -G-- -CG- --- -C-- A--- A-G-- ---T
GB809_2   4e       -A-- -A-- ---- --- -A-- A--- A-A-- ---T
CAM600    4e       -G-- -G-- ---- T-- -C-- ---- T-G-- ---T
G22       4f       -G-- ---- -C-- T-- ---- ---- T-G-- ---G
G27       4f       -G-- ---- -C-- --- ---- ---- TA-A- ---G
GB549     4g       -A-- ---- -C-- --- ---- ---- A-A-- ---T
GB438     4h       AT-- ---- -C-- C-- -C-- ---- TA-A- ---T
CAR4/1205 4i       TG-- ---- -C-- C-- -C-- ---- A-G-- ---C
CAR4/901  4?       -A-- -G-- -C-- A-- -A-- ---- A-A-- ---T

```
                SEQ ID    1
                          MSTNPKPQKKNKRNTNRRPQDVKFPGGGQIVGGVYLLPRRGPRLGVRATR
HCV1     1a               -------------------------------------------------
HCVJ     1b               ------R-T----------------------------------------

HCJ6     2a               ------R-T----------------------------------------
HCJ8     2b               ------R-T----------------------------------------
NE92     2d      144      ------R-T----------------------------------------

EB1      3a               ---L--R-T---I------------------------V-----C-----
NZL1     3a               ---L--R-T---I------------------------V-----------
HCV-TR   3b               ---L--RQT---L---N--------------------V-----------
BE98     3c      148      ---L--R-T----X-----------------------V--Q--V-----

GB358    4c      192      ------R-T----------M-----------------------------
GB809    4e      164      ---L--R-T----------M-----------------------------
CAM600   4e      166      ------R-T----------M-----------------------------
GB724    4?      194      ------R-T----------M-----------------------------
EG-29    4?               ---R--------------M------------------------------
BE95     5a      152      ------R-T--------------------------------M-------
```

|  |  | KTSERSQPRGRRQP | IPKAR | RPEGRTWAQ | PGYPWPLYGNEGCGWAGWLLSP |
|---|---|---|---|---|---|
| HCV1 | 1a | -------------- | ----- | --------- | ---------------------- |
| HCVJ | 1b | -------------- | ----- | --------- | ----M----------------- |
| HCJ6 | 2a | -------------- | --D-- | -ST-KS-GK | -----------L---------- |
| HCJ8 | 2b | -------------- | --D-- | -ST-KS-GK | ---------------------- |
| NE92 | 2d | -------------- | --D-- | ---T-KS-GK | -----------L---------- |
| EB1 | 3a | -------------- | ----- | -S---S--- | ---------------------- |
| NZL1 | 3a | -------------- | ----- | -S---S--- | ---------------------- |
| HCV-TR | 3b | ----KQ-HL----- | ----- | SR----S-- | --------K---L--------- |
| BE98 | 3c | ---S---------- | -S--R | -T----S-- | ---------------------- |
| GB358 | 4c | -------------- | ----- | -S---S--- | ---------------------- |
| GB809 | 4e | -------------- | ----- | -S---S--- | ---------------------- |
| CAM600 | 4e | -------------- | ----- | -T---S--- | ---------------------- |
| GB724 | 4? | -------------- | ----- | -S---S--- | -----A---------------- |
| EG-29 | 4? | -------------- | ----- | -S---S--- | ---------------------- |
| BE95 | 5a | -------------- | ----- | Q-T--S-G- | -----A-----L---------- |

V-core (box around RPEGRTWAQ column)

Figure 5 - Continued 2

```
            101                       126
            RGSRPSWGPTDPRRRSRNLGKVIDTL
HCV1   1a   -------------------------
HCVJ   1b   --------N---H-----V------
HCJ6   2a   ---T----------------R----I
HCJ8   2b   --------------H----------
NE92   2d   --------------H----------

NZL1   3a   ----------N--------------
HCV-TR 3b   ----------N---F----------
BE98   3c   ----------N--------------

GB809  4e   ----------N--------------
CAM600 4e   -X--X-----N--X-----------
GB724  4?  ----------N--------------

```
              127                                                176
HCV-1     1a  TCGFADLMGYIPLVGAPLGGAARALAHGVRVLEDGVNYATGNLPGCSFSI
HCVEC1    1a  -------------------------------------------------
HCVHCT18  1a  -------------------------------------------------
HCVHCT23  1a  ----------------------R--------------------------
HCVHCT27  1a  -------------------------------------------------
HCVTH     1a  ----------------------------------------------L--
HCV-J     1b  -------------------------------------------------

HC-J6     2a  ------------V--V------------------------------F--
HC-J8     2b  ------------V--V--V---------------------------I--
NE92      2d  ------------V--V------------------------------I--

HD10      3a  ------------V--V--------------A---------------I-F-
BR33      3a  ------------V--V--------------A---------------I-F-
BR36      3a  ------------V--V--------------A---------------I-F-
NZL1      3a  ------------V--V--------------A---------------I-F-
HCV-TR    3b  ------------V--V--------------A-G-----------------
```

Figure 5 - Continued 4

|         |      | 127 |  |  |  |  |  | 176 |
|---------|------|-----|--|--|--|--|--|-----|
| GB809_4 | 4a   | ---------- | ---------- | ---------- | --V------- | ---------- | ----AV---I | ---------- |
| GB116   | 4c   | ---------- | ---------- | ---------- | --V------- | ----E----- | ----AV---I | ---------- |
| GB215   | 4c   | ---------- | ---------- | ---------- | --V------- | ----E----- | ----AV---I | ---------- |
| GB358   | 4c   | ---------- | ---------- | ---------- | --V------- | ---------- | ----AV---I | ---------- |
| GB809_2 | 4e   | ---------- | ---------- | ---------- | --V------- | ---------- | ----AV---I | ---------- |
| CAM600  | 4e   | ---------- | ---------- | ---------- | --V------- | ---------- | ----AV---I | ---------- |
| CAMG22  | 4f   | ---------- | ---------- | ---------- | --V------- | ---------- | ----AV---I | ---------- |
| CAMG27  | 4f   | ---S------ | ---------- | ---------- | --V------- | ---------- | ----AV---I | ---------- |
| GB549   | 4g   | ---------- | ---------- | ---------- | --V------- | ---------- | ----AV---I | ---------- |
| GB438   | 4h   | ---------- | ---------- | ---------- | --V------- | ---------- | ----A----I | ---------- |
| CAR4/1205 | 4i | ---------- | ---------- | ---------- | --V------- | ---------- | ----AV---I | ---------- |
| CAR4/901  | 4? | A--------- | ---------- | ---------- | --V------- | ---------- | ----AV---I | ---------- |
| BE95    | 5a   | ---------- | ---------- | ---------- | ---G-V--V- | ---------- | -------P-- | ---------- |
| BE100   | 5a   | ---------- | ----V----- | ---------- | ---G-V--V- | ---------- | ---------- | ---------- |

Figure 5 - Continued 5

```
               177                                                                     226
               FLLALLSCLTVPASA  YQVRNSTGLYHV  TNDCPNSSI  VYEAADAILIT  PGC
                                └─────V1────┘             └────V2───┘
            ┌──────────────────┐┌────────────┐           ┌───────────┐
HCV-1    1a │---------------   ││------------│---------  │-----------│ ---
HCVEC1   1a │---------------   ││-----S------│---------  │-----------│ ---
HCVHCT18 1a │---------------   ││H-----------│---------  │-----------│ ---
HCVHCT23 1a │---------------   ││-----S-I----│---------  │---T-T---S-│ ---
HCVHCT27 1a │---------------   ││---------   │---------  │-------A---│ ---
HCVTH    1a │---------------   ││---         │---------  │---M-M-----│ ---
HCV-J    1b │------I--------   ││-E---VS-I---│----S----  │-----------│ ---

HC-J6    2a │----I-T-V------   ││AE-K-ISTG-M-│---T-D---  │TWQLQA-V--V│ ---
HC-J8    2a │-----V----V----   ││VE---ISSS-YA│---S-N---  │TWQLT--V--L│ ---
S83      2c │---------------   ││VE-KDTGDS-MP│----S----  │-WQLEG-V--V│ ---
NE92     2d │----I---V-G----   ││L--K-TSSS-M-│----Q----  │-WQLR--V--V│ ---

HD10     3a │-F----IH--AS---   ││LEW--TS---VL│----S----  │---D-V----V│ ---
BR33     3a │-F----IH--AG---   ││LEW--TS---VL│----S----  │---D-V----A│ ---
BR36     3a │-F----IH--AS---   ││LEW--TS---VL│----S----  │---D-V-----│ ---
NZL1     3a │-F----IH--AS---   ││LEW--TS---VL│----S----  │---D-V-----│ ---
HCV-TR   3b │-F----C----G---   ││LEYT-TS---VL│----S-G--  │---E-V----L│ ---
            └──────────────────┘└────────────┘           └───────────┘
              E1→
```

Figure 5 - Continued 6

| | | 177 | V1 | | V2 | 226 |
|---|---|---|---|---|---|---|
| GB809_4 | 4a | ---------- | EHY--AS-I--I | -------V | ----TDHH----L | --- |
| Z4 | 4a | ---------- | EHY--AS-I--I | -------- | ----DHH----L | --- |
| Z1 | 4b | ---------- | VHY--AS-V--I | -------- | ----TEHH--M-L | --- |
| GB116 | 4c | S--------- | VNY--AS-V--I | -----T-- | ----DYH----L | --- |
| GB215 | 4c | Y--------- | IHY--AS-V--I | -------- | ----DHH----L | --- |
| GB358 | 4c | ---T------ | VNY--AS-V--I | -------- | ----TEHH----L | --- |
| Z6 | 4c | ---------- | VNY--AS-V--I | -------- | ----DHH----L | --- |
| Z7 | 4c | ---------- | VNYH-AS-V--I | -------- | M---EHH----L | --- |
| DK13 | 4d | ---------- | -NY---S-V--- | -------- | ----TDYH----L | --- |
| GB809_2 | 4e | ------G--- | VNY--AS-V--I | -------A | ----TDNH----L | --- |
| CAM600 | 4e | ---T------ | VNY--AS-I--I | -------A | ----TENH----L | --- |
| CAMG22 | 4f | ---------- | VHYH-TS-I--L | -------- | ----F--VHH----L | --- |
| CAMG27 | 4f | ---------- | VHYH-TS-I--I | -------- | ----F--EHH----L | --- |
| GB549 | 4g | ---------- | QHY--IS-I--- | -------- | ----DHH--M-L | --- |
| GB438 | 4h | ---V--R--- | QHY--AS-I--- | -------- | ----DHH--M-L | --- |
| CAR4/1205 | 4i | S--E------ | IHY--ASDG-YI | -------- | ----ENH----L | --- |
| CAR4/901 | 4? | X--------- | QHY--VS-I--- | -------- | ----DHH--M-L | --- |
| BE95 | 5a | --I------- | VPY--AS-I--- | -------- | ---DNL----A | --- |
| BE100 | 5a | --I------- | VPY--AS-I--- | -------- | ---D-L----A | --- |
| SA4 | 5a | ---------- | VPY--AS-V--- | -------- | ---DNL----A | --- |
| HK2 | 6a | ---------- | LTYG-S----L | -------- | -L--DAM----L | --- |

Figure 5 - Continued 7

|  |  | 227 | V3 |  | V4 |  | 276 PUTATIVE |
|---|---|---|---|---|---|---|---|
|  |  | VPC | VREGNASRCWVAM | TPTVA | TRDGKLPATQ | LRRHID | LLVGSATLCSALY |
| HCV-1 | 1a | VPC | VREGNASRCWVAM | TPTVA | TRDGKLPATQ | LRRHID | LLVGSATLCSALY |
| HCVEC1 | 1a | --- | -H----V------ | ----- | ---------- | ------ | ------------- |
| HCVHCT18 | 1a | --- | -H----V------ | ----- | ---T------ | ------ | ------------- |
| HCVHCT23 | 1a | --- | ---D-V------- | ----- | ---T------ | ------ | ------------- |
| HCVHCT27 | 1a | --- | ------K---PV- | A---- | --K------- | ------ | ------------- |
| HCVTH | 1a | --- | ------------- | ----- | ---N------ | ------ | ------------- |
| HCV-J | 1b | --- | ---S-F------L | ----L | A-NSSI-T-T | I---V | ---A-A----M-- |
| HC-J6 | 2a | --- | EKV-T----IPV | S-N-- | VQQPGALTQG | --T-- | MV-M--------- |
| HC-J8 | 2b | --- | ENDNGTLH--IQV | ---N-- | VKHRGALTRS | --T-V | MI-MA---A---- |
| s83 | 2c | --- | E-TA-V----PV | A-NL- | ISQPGALTKG | --A--- | II-M---V----- |
| NE92 | 2d | --- | EEK--I----IPV | S-NI- | VSQPGALTKG | --T--- | TIIA---F----- |
| HD10 | 3a | --- | -QD--T-A-TPV | ----- | V-YVGATTAS | I---V | M----A---M--- |
| BR33 | 3a | --- | -QD--T-T-TPV | ----- | V-YVGATTAS | I-S-V | -----A---M--- |
| BR36 | 3a | I-- | -QD--T-T-TPV | ----- | VKYVGATTAS | I-S-V | -----A---M--- |
| NZL1 | 3a | --- | -QD--T-T-TPV | ----- | V-YVGATTAS | I-S-V | -----A---M--- |
| HCV-TR | 3b | --- | TT--Q-S--TTV | ST--- | V-TLGVTTAS | I-T-V | M---ARQ------ |

Figure 5 - Continued 8

| | | 227 | V3 | | V4 | | PUTATIVE 276 |
|---|---|---|---|---|---|---|---|
| GB809_4 | 4a | --- | --A--V----TPV | --- | AVSMDA-LES | F----V- | --M--A---V-- |
| Z4 | 4a | --- | -MT--T----TPV | --- | VAHPGA-LES | F----V- | --M--A------ |
| Z1 | 4b | --- | --TE-T----PL- | --- | APYPNA-LES | M----V- | --M--A--M--F |
| GB116 | 4c | L-- | --V--Q------L | --- | APYVGA-LES | --S--V- | --M--A--V--- |
| GB215 | 4c | L-- | --V--Q------L | S-- | APYIGA-VES | F----V- | --M--A--V--- |
| GB358 | 4c | L-- | --V--Q------L | --- | APYIGA-LES | --S--V- | MM--A--A--- |
| Z6 | 4c | L-- | --V--Q------L | --- | VSYIGA-LDS | -----V- | --M--A--A--- |
| Z7 | 4c | --- | --V--Q------L | --- | APYIGA-LES | -----V- | --M--A--V--- |
| DK13 | 4d | --- | --KT--------L | --- | AQHLNA-LES | I----V- | --M--A--V--- |
| GB809_2 | 4e | --- | --T--Q------L | --- | SPYVGA-LEP | -----V- | --M--G------ |
| CAM600 | 4e | --- | --T--Q------L | --- | SPYAGA-LEP | -----V- | --M--A--M--- |
| CAMG22 | 4f | --- | --T--Q----I-L | -L- | APYLGA-LES | M----V- | --M--T------ |
| CAMG27 | 4f | --- | --T--T----I-L | -L- | APHIGA-LES | M----V- | --M--T------ |
| GB549 | 4g | --- | --T--T----PL- | --- | APYVGA-LES | M----V- | --M--A--V--- |
| GB438 | 4h | --- | --T--V----IPL | --- | VPYLGA-L-S | V-q-V- | --M--A--V--- |
| CAR4/1205 | 4i | I-- | --KT--Q------L | -L- | APHLRA-LSS | --A-V- | --M--A--A--F |
| CAR4/901 | 4? | I-- | --T--V------SL | --- | APYLGA-L-S | -----V- | --M--A------ |
| BE95 | 5a | --- | -MT--V-----QI | --LS | APSLGAVTAP | --AV- | Y--A--G--A-- |
| BE100 | 5a | --- | --KD-V-----QI | --LS | APSFGAVTAP | --AV- | Y--G--A----- |
| SA4 | 5a | --- | --QD-V-K----QI | --LS | APNLGAVTAP | --AV- | Y--A--G--A-- |
| HK2 | 6a | L-- | ---VDDR-T---H-V | ---L- | IPNAST----G | F----V- | --A--A--VV--S-- |

Figure 5 - Continued 9

|  | | 277 TRANSMEMBRANE DOMAIN | | V5 | | 319 |
|---|---|---|---|---|---|---|
|  | | VGDLCGSVFLVGQLFTF | SPRRHWTTQG | CNCSIYPGHITGHRMA | | |
| HCV-1 | 1a | ----------------- | ---------- | ---------------- | | |
| HCVEC1 | 1a | ----------------- | ---------- | ---------------- | | |
| HCVHCT18 | 1a | ----I------------ | ---------- | ---------------- | | |
| HCVHCT23 | 1a | ----------------- | -------D-- | ---------------- | | |
| HCVHCT27 | 1a | ----I------------ | -------D-- | ---------------- | | |
| HCVTH | 1a | ----------------- | ---------- | ---------------- | | |
| HCV-J | 1b | ---S------------- | ---YE-V-D- | -------VS------- | | |
| HC-J6 | 2a | ---G-M--AA-M-IV-- | --QH--FV-D | -------T-------- | | |
| HC-J8 | 2b | ---V--A-MILS-A-MV | --Q---NF--E | -------Q-------- | | |
| S83 | 2c | ---V--ALM-AA-VVVV | --QH-TFV-E | ---------------- | | |
| NE92 | 2d | I-----A-M-AS-V-II | --QH-KFV-D | ----------R----- | | |
| HD10 | 3a | ---M--A-------A-- | R----Q-V-T | -------L----LS-- | | |
| BR33 | 3a | ---M--A-------A-- | R----Q-V-T | -------L----LS-- | | |
| BR36 | 3a | ---M--A-------A-- | R----Q-V-T | -------L----LS-- | | |
| NZL1 | 3a | ---M--A-------A-- | R----Q-V-T | -------L----LS-- | | |
| HCV-TR | 3b | --AF-A--------A-- | R----T-V-T | -------VS------- | | |

Figure 5 - Continued 10

|  |  | 277 TRANSMEMBRANE DOMAIN |  | V5 |  | 319 |
|---|---|---|---|---|---|---|
| GB809_4 | 4a | -----GA-----M- | - | Q------D | ----T----- | - |
| Z4 | 4a | -----GA--M--MI | - | R------E | ----T----- | - |
| Z1 | 4b | ------G------- | D | R------D | ----VS---- | - |
| GB116 | 4c | ------G-----M- | S | Q------D | ----A--V-- | - |
| GD215 | 4c | ------G-----M- | S | R------D | ----A----G | - |
| GB358 | 4c | ------G-----M- | S | Q------D | ----A--V-- | - |
| Z6 | 4c | -----GA-----M- | S | Q------D | ----A----- | - |
| Z7 | 4c | ------G------- | - | Q------D | ----A--V-- | - |
| DK13 | 4d | ----V-G------- | - | Q------D | ----T----- | - |
| GB809_2 | 4e | ------GL----M- | - | Q------D | ----A----- | - |
| CAM600 | 4e | ------GL------ | - | Q------D | ----T----- | - |
| CAM622 | 4f | -----GI--A--M- | - | R--L---E | -T-------- | - |
| CAM627 | 4f | -----GI-----M- | N | R--L---E | ----D----- | - |
| GB549 | 4g | ------G-----M- | - | R------D | ----V----- | - |
| GB438 | 4h | -----II-G--A-MV | S | Q------D | ----S----- | - |
| CAR4/1205 | 4i | -----I-G---A-- | I | R--I-E--D | ----V----- | - |
| CAR4/901 | 4? | ------G-----M- | - | Q------D | ----V----- | - |
| BE95 | 5a | ---A--AL----M- | Y | R--Q-A-V-N | ----S--V-- | - |
| BE100 | 5a | ---A--AL----M- | Y | R--Q-A-V-D | ----S--V--Q | - |
| SA4 | 5a | ---A--A-----M- | Y | R--Q-T-V-D | ----S----- | - |
| HK2 | 6a | I-----L--A---- | - | Q------V-D | ----T--V-- | - |

Figure 6

```
            4648                                                      4698
HCV-1    GTGTGCCAGGACCATCTTGAATTTTGGGAGGGCGTCTTTACAGGCCTCACT
HCV-J    --C-------------C--A--G--C------A-----C-------C
HC-J6    -------A------------G-------------CA--T--C--C-------A
HC-J8    --A--T--A------C--G--G--C------A-CG------T--A
HCCL53                                   -A--C---------A-------C--T--A--A---
EB1                                                          ↑
EB2                                                        4664
EB6
EB7

4699                                                      4750
HCV-1    CATATAGATGCCCCACTTTCTATCCCAGAACAAAGCAGAGTGGGGAGAACCTT
HCV-J    --C-------------CT-G------C--A---GCA--A--C-----C
HC-J6    --C-------------C--T----A-------ATCG-----A--TT-C
HC-J8    --C--T--C-------C--C-------G-----AG-A--A--A--T--
HCCL53   --C-------------G--A---T------CAG--ACTC---T-C
EB1                                         ----CAG--ACTC---T-C
EB2                                         ----CAG--ACTC---T-C
EB6                                         A----CAG--ACTC---T-C
EB7                                         A----CAG--ACTC---T-C
                                                 ↑
                                                4731
```

Figure 6 - continued 1

```
        4751                                              4800
HCV-1   CCTTACCTGGTAGGCGTACCAAGCCACCGTGTGCGCTAGGGCTCAAGCCCC
HCV-J   --C------------A-------A------C--------G--T--
HC-J6   G-A---T-AAC---C-----G--T--A--------CA---------
HC-J8   G-G--T--AACG--C------G----A--A---C----AA-G---:--
HCCL53  T-G-T----ACT--C-----------T------------C-C--G-G--T--
EB1     T-G-----AACT--C-----------T------------CC-C--G--G--T--T
EB2     T-G-----AACT--C-----------T------------CC-C--G--G--T--
EB6     T-G-----AACT--C-----------T------------CC-C--G--G--T--
EB7     T-G-----AACT--C-----------T------------CC-C--G--G--T--

4801                                              4849
HCV-1   TCCCCCATCGTGGGACCAGATGTGGAAGTGTTGATTCGCCCTCAAGCCCA
HCV-J   A--T-------------A---------------C-C--A-G--A-----
HC-J6   C-----G--C------GTC-------------C--A-----------
HC-J8   ---T--T-----GT------------------C-A-C-A-G-----A--T--
HCCL53  ------AGT-------G----------------C-CG-A--G--T----A-
EB1     ------AGT-------G------C--------A---C-CG-G--G--T----A-
EB2     ------AGT-------G------C--------A---C-CG-G--A-------A-
EB6     ------AGT-------G---------------A---C-CG-G--G-------A-
EB7     ------AGT-------G---------------A---C-CG-G--G-------A-
```

Figure 6 - continued 2

```
             SEQ ID NO    4850                                                4900
                          CCCTCCATGGGCCAACACCCCTGCTATACAGACTGGGGGCTGTTCAGAAT
HCV-1         29          -A--G-------------G-------G-----G--A--A--C----A---
HCV-J         31          -A---GTG--C--C----T--C--G---C-CT----T-----ACC--C
HC-J6         33          -A--GAC---T--C----C--G---C-CT----T--C--GACC---
HC-J8         35          -A--------A----T--G--T--T------TC----GT---GC---A---
HCCL53        37                                ↑
HD10-1-25     39                              4863
HD10-1-3
BR36-20-164                                                              -C--A---
BR36-20-166                                                              -C--A---
BR36-20-165                                                              -C--A---
EB1                       -A--A--C--A---T--G------T-----TC                -C--A---
EB2                       -A--A-----A---T--G------T-----TC                -C--A---
EB6                       -AT-A-----A--C--G------T-----TC                 ↑
EB7                       -AT-A-----A--C--G------T-----TC                 4892
                                  ↑
                                4878
```

Figure 6 - continued 3

```
              4901                                               4949
         GAAATCACCCTGACGCACCCAGTCACCAAATACATCATGACATGCATGTC
HCV-1
HCV-J    --GG----T--C--A-----CA-A-----------------G--------
HC-J6    --GG-------C----T----T--G--G--------GCC--C-----CA
HC-J8    --GG--------T-------C--G--G---------GCC---G-----CA
HCCL53   -----------TG-T-----A----CA----A-------------G----
HD10-1-25 ----------TG-T-----A----C-----A------T--G--------
HD10-1-3 -----------TG-T-----A----C-----A------T--G--------
BR36-20-164 --------TG-T-----A----CA-----A------T---G--------
BR36-20-166 --------TG-T-----A----CA-----A----------G--------
BR36-20-165 --------TG-T-----A----CA-----A----------G--------

4950                                              4990
         GGCCGACCTGGAGGTCGTCACGAGCACCTGGGTGCTCGTTG
HCV-1
HCV-J    -----T---------------T---------------A--A-
HC-J6    ---------------A-G--C-----G-----CT-A-C--
HC-J8    -------C-------A-G--A---T-A-------C--G-CG-
HCCL53   A
HD10-1-25 A--T---T-----A--AAC---C-----------T-GC---
HD10-1-3  A--T---T-----A--AAC---C-----------T-GC---
BR36-20-164 A--T---T-----A--AAC---C---------TT-GC---
BR36-20-166 A--T---T-----A--AAC---C---------TT-GC---
BR36-20-165 A--T---T-----A--AAC---C---------TT-GC---
```

Figure 6 - continued 4

```
                              4991                                            5040
HCV-1         GCGGCGTCCTGGCTGCTTTGGGCCGGCGTATTGCCTGTCAACAGGCTGCGTG
HCV-J         ----A----T--G----C--------C----A-G-----A--------
HC-J6         -G--G----T--G--CG-C---------C--------G-G--C--G--T--T
HC-J8         -G--G----G--A--C--CG----A--T--C------G-G--T-----A-T
HD10-1-25     -G--G--G--A--C--CC--A--C----T----GTC---------T
HD10-1-3      -A--G------C--G--CC--A--G--C----T----GTC---------T
BR36-20-164   -A--G------C--G--CC--A--G--C----T-----GTC--T--T--T
BR36-20-166   -A--G------C--G--CC--A--G--C----T-----GTC--T--T--T
BR36-20-165   -A--G------C--G--CC--A--G--C----T-----GTC--T--T--T 5041                                            5090
HCV-1         GTCATAGTGGGCAGGGTCGTCTTGTCCGGGAAGCCGGGCAATCATACCTGA
HCV-J         -----T-----A--A-----------G----A--TG-T--T--C--
HC-J6         TG---CA-C---C-CT-GCA-G-TAA-CA-CGAG-C-TCG-TGC---G--
HC-J8         TC---CA-T---C-CC-ACA-C--AAT-ATCG-GT--TTG-GGCC--C--
HD10-1-25     --A--C------TCATA---AGC---GGG--C--------C--G-T--A--
HD10-1-3      --A--C------TCATA---AGC---GGG--C--------C--G-T--A--
BR36-20-164   --G--T------TCATA---AGC---GGG--C--------C--G-T--A--
BR36-20-166   --G--T------TCATA---AGC---GGG--C--------G-T--A--
BR36-20-165   --G--T------TCATA---AGC---GGG--C--------G-T--A--
```

Figure 6 - continued 5

```
                5091                                                        5140
HCV-1        CAGGGAAGTCCTCTACCGAGAGTTCGATGAGATGGAAGAGTGCTCTCAGC
HCV-J        ------------------AG-----------------------TG--TCA-
HC-J6        --A---G-------TGAG-CT--T------G--A--TG-CTCTA
HC-J8        --A----A--T-A--TGAG-CC--T---------A---G-CTCCA
HD10-1-25    --A---G--GT-G--T-A-C---A-----------G--AG
HD10-1-3     --A---G--GT-G--T-A-C---A------G-------G--AG
BR36-20-164  --AA--G--GT-G--T-A-C-A-A-------------A--AG
BR36-20-166  --AA--G--GT-G--T-A-C-A-A-------------A--AG
BR36-20-165  --AA--G--GT-G--T-A-C-A-A-------------A--AG 5141                                                        5190
HCV-1        ACTTACCGTACATCGAGCAAGGGATGATGCTCGCCGAGCAGTTCAAGCAG
HCV-J        --C-C--T-------------A---CA-----A-----A-
HC-J6        GAGCGG-TCT--T--AG-G---CA-CG-A-A-----AT-C-G---TCC
HC-J8        -AGCCG-CCT--T---G-----CA-CG-A-G---AT-C----ATCT
HD10-1-25    C-GCC--A-----A----CTCA-G-AA-A---C-C-------G--
HD10-1-3     C-GCC--A-----A----CTCA-G-AA-A---C-C-------G--
BR36-20-164  CTGCC--A--T--A----CTCA-G-AA-A--TC-C-------GGA
BR36-20-166  CTGCC--A--T--A----CTCA-G--A-A--TC-C-------G-A
BR36-20-165  CTGCC--A---T-A----CTCA-G-AA-A--TC-C-------G-A
```

Figure 6 - Continued 6

```
             5191                                                5240
HCV-1        AAGGCCCTCGGCCCTCCTGCAGACCGGGTCCCGTCAGGCAGAGGTTATCGC
HCV-J        ----G----AT-G-----A--A--CA---AAG--A---G----C-GCT--
HC-J6        ---AT--AA---T-AT-----CAA---T---AAA--A---TC-A-AC--ACA
HC-J8        ---ATA-AA-----A---ACAG--CA-AA--G--A---TC-A-AC--ACA
HD10-1-25    --AAT---T--A--G-------CGA----CA---AA---ACA---CT---C---T-A
HD10-1-3     --AAT---T--A--G-------CGA----CA---AA---ACA---CT---C---T-A
BR36-20-164  --A-T---T--AT-G-------CGA----CA---AA---ACA---CT---C---T-A
BR36-20-166  --A-T---T--AT-G-------CGA----CA---AA---ACA---CT---C---T-A
BR36-20-165  --A-T---T--AT-G-------CGA----CA---AA---ACA---CT---C---T-A 5241                                                5290
HCV-1        CCCTGCTGTCCAGACCAACTGGCAAAAACTCGAGACCTTCTGGGGCGAAGC
HCV-J        T--C-TG--GG--T----G----G-GCC--T---GT------A-
HC-J6        A--C-----G--G-TTCT----CC--GG-A--CAA-------C-A-
HC-J8        G--A---A--T-ATCA----CC--G--T-ACAA--T----C-A-
HD10-1-25    G--C-TAA-AGCTT----------G--T--A-------CAC---
HD10-1-3     G--C-TAA-AGCTT----------G--T--A-------CAC---
BR36-20-164  G--CATA--AACT-----------G--T--G---T---CAC---
BR36-20-166  G--CATA--AACT-----------G--T--G---T---CAC---
BR36-20-165  G--CATA--AACT-----------G--T--G---T---CAC---
```

Figure 6 - continued 7

| | 5292 |
|---|---|
| HCV-1 | AT |
| HCV-J | -C |
| HC-J6 | -C |
| HC-J8 | -C |
| HD10-1-25 | -- |
| HD10-1-3 | -- |
| BR36-20-164 | -- |
| BR36-20-166 | -- |
| BR36-20-165 | -- |

Figure 7

```
                SEQ ID NO       1290      1300      1310      1320      1330
                            ITTGSPITYSTYGKFLADGGCSGGAYDIIICDECHSTDATSILGIG
HCV-1                       ----G---------C-------------------S-T--------
HCV-J                       V---A--------------------A--------AV-S-T-----
HC-J6                       V---DS-------------I------AA-------V---T-----
HC-J8                       --------------------------------V---Q---T----
BE95            270         ----AS----------------------------V----------

1340      1350      1360      1370      1380
                            TVLDQAETAGARLVVLATATPPGSVTVPHPNIEEVALSTTGEIPFYGKAI
HCV-1                       ---------------------------------I----N----------
HCV-J                       ----------------V--T---------T-----------GQE----R--
HC-J6                       ----------------V---------T--T-S---------GHE-------
HC-J8                       ----------------------------T----T-S---------GHE-------
BE95                        -----------------------------T-----------PQE--V---R--
```

Figure 7 - Continued 1

|  | | 1390 | 1400 | 1410 | 1420 | 1430 |
|---|---|---|---|---|---|---|
| HCV-1 | 1a | PLEVIKGGRHLIFCHSKKKCDELAAKLVALGINAVAYYRGLDVSVIPTSG |
| HCV-J | 1b | --I-A-------------------------TG--L------------- |
| HC-J6 | 2a | --SY----------------------A-RGM-L----------Q---- |
| HC-J8 | 2b | --AF----------------------A-RGM-V----------Q---- |
| BE95  | 5a | --AF------------------KQ-TS--V-------A-----A---- |

|  | | 1440 | 1450 | 1460 | 1470 | 1480 |
|---|---|---|---|---|---|---|
| HCV-1 | 1a | DVVVVATDALMTGYTGDFDSVIDCNTCVTQTVDFSLDPTFTIETITLPQD |
| HCV-J | 1b | --------------F------------------------T-------- |
| HC-J6 | 2a | --------------F-----------VA---V--------T-Q-V--- |
| HC-J8 | 2b | ---------------------------VA-S-I-------T-Q-V--- |
| BE95  | 5a | ----CS--------F-----------SA------------T-V----- |

Figure 7 - Continued 2

```
              1490      1500      1510      1520      1530
         AVSRTQRRGRTGRGKPGIYRFVAPGERPSGMFDSSVLCECYDAGCAWYEL
HCV-1    --------------------------------------------------
HCV-J    ----A-------RS-----T--------------------A---------
HC-J6    ----S-------RL---Y-ST---A-----V---------A---------
HC-J8    ----S-------RL-V-Y-SS---------V---------A---------
BE95     ----S-------RH---Y-SA---D-----V-------------D-----

1540      1550      1560      1570      1580
         TPAFTTVRLRAYMNTPGLPVCQDILEFWEGVFTGLTHIDAHFLSQTKQSG
HCV-1    --------------------------------------------------
HCV-J    ----S----L-----------------S--------------A-------
HC-J6    ---------F-----------------A----------------G-----
HC-J8    ---------F-----------------A------------N--M-G----
BE95     ---------I-----------------------------------G----
BR36     -----------------------D---S-------------------Q-
```

SEQ ID NO
HCV-1    1a
HCV-J    1b
HC-J6    2a
HC-J8    2b
BE95     5a
BR36     3a    223

Figure 7 - Continued 3

|       | 1590       1600       1610       1620       1630 |
|-------|---------------------------------------------------|
| HCV-1 | ENLPYLVAYQATVCARAQAPPPSWDQMWKCLIRLKPTLHGPTPLLYRLGA |
| HCV-J | D------------------------------------------------ |
| HC-J6 | --FA--T--------K--------V---T-----V--------S      |
| HC-J8 | --FA--T--------K--------V---T-----T               |
| BE95  | --F---------V--K--------T-----ML------T           |
| BR36  | L-FST-T-------------------E------V-----------P    |

|       | 1640       1650       1660       1670       1680 |
|-------|---------------------------------------------------|
| HCV-1 | VQNEITLTHPVTKYIMTCMSADLEVVTSTWVLVGGVLAALAAYCLSTGCV |
| HCV-J | ----V-----A-----------------------------T--S-     |
| HC-J6 | --T-V-----A---Q---M----A----V---A-         |
| HC-J8 | --T-V-----A---Q---IM-S---A----V---A---I    |
| BE95  | ------I---A---------I-------V------TV-S-          |
| BR36  | ------I---A-C-----------T---L-----V--            |

Figure 7 - Continued 4

```
                  1690       1700       1710       1720       1730
                   |          |          |          |          |
                           NS4-1                 NS4-5
         VIVGRVV LSGKPAIIPDREVLYREFDE MEEC  SQHLPYIEQGMM LAEQFKQ
HCV-1    VIVGRVV LSGKPAIIPDREVLYREFDE MEEC  SQHLPYIEQGMM LAEQFKQ
HCV-J    ------- ---II----R--V------ ----  AS-------Q-- -------
HC-J6    ------- C-I--LH VNQRAVVA--K---EA-- ----  ASRAAL--E-QR I--ML-S
HC-J8    ------- S-I--LH NDRVVVA--K-I--EA-- ----  ASKAAL--E-QR M--ML-S
BR36     ------- ---G----V--K-----QQY-- ----  --AA----AQV I--H---E
BE95     ------- A-----II ---------A--QQ--- ----  -AS---MDETRA I-G----E 1740       1750       1760
                   |          |          |
                        NS4-7
         KALGLLQTASRQA EVIAPAVQTNWQKLETFWAKH
HCV-1    KALGLLQTASRQA EVIAPAVQTNWQKLETFWAKH
HCV-J    ------TK-- -AA--V-ESK-RA--V-----
HC-J6    IQ----Q-K-- QD-Q---AS-P-V-Q-----
HC-J8    IQ----Q-T-- QD-Q--I-SS-P---Q-----
BR36     V----R-TQ-Q A--E-I-T----A--H---
BE95     V--FIS-TGQK- -TLK--ATSV-N-A-Q--XTY
```

Figure 9

| | SEQ ID NO | 1 ATGAGCACGAATCCTAAACCTCAAAGAAAAACCAAAGAAACACCAACCG 50 |
|---|---|---|
| PC-3-4 | 49 | |
| PC-3-8 | 51 | ---------------------------------------------- |
| PC-2-1 | 41 | ---------------------------------------------- |
| PC-2-6 | 43 | ---------------------------------------------- |
| PC C/E1 | 53 | ---------------------------------------------- |

| | 51 TCGCCCACAGGACGTCAAGTTCCCCGGGCGGTGGTCAGATCGTTGGCGGAG 100 |
|---|---|
| PC-3-4 | |
| PC-3-8 | ---------------------------------------------- |
| PC-2-1 | ---------------------------------------------- |
| PC-2-6 | ---------------------------------------------- |
| PC C/E1 | ---------------------------------------------- |

Figure 9 - Continued 1

```
          101                                              150
PC-3-4    TTTACTTGTTGCCGGCGCAGGGGCCCTAGGATGGGTGTGCGCGGACTCGG
PC-3-8    --------------------------------------------------
PC-2-1    --------------------------------------------------
PC-2-6    --------------------------------------------------
PC C/E1   --------------------------------------------------

151                                              200
PC-3-4    AAGACTTCGGAACGGTCGCAACCCCGTGGACGGCGTCAGCCTATTCCCAA
PC-3-8    --------------------------------------------------
PC-2-1    --------------------------------------------------
PC-2-6    --------------------------------------------------
PC C/E1   --------------------------------------------------
```

Figure 9 - Continued 2

```
       201                                                 250
PC-3-4  GGCGCGGCCAGCCCACGGGCCGGTCCTGGGGTCAACCCGGGTACCCTTGGC
PC-3-8  --------------------------------------------------
PC-2-1  --------------------------------------------------
PC-2-6  --------------------------------------------------
PC C/E1 --------------------------------------------------

251                                                 300
PC-3-4  CCCTTTACGCCAATGAGGGCCTCGGGTGGGCAGGGTGGCTGCTCTCCCCT
PC-3-8  --------------------------------------------------
PC-2-1  --------------------------------------------------
PC-2-6  --------------------------------------------------
PC C/E1 --------------------------------------------------
```

Figure 9 - Continued 3

```
        301                                              350
PC-3-4  CGAGGCTCTCGGCCCTAATTGGGGCCCCAATGACCCCCGGGGAAAATCGCG
PC-3-8  --------------------------------------------------
PC-2-1  --------------------------------------------------
PC-2-6  --------------------------------------------------
PC C/E1 --------------------------------------------------

351                                              400
PC-3-4  TAATTTGGGTAAGGTCATCGATACCCTAACGTGCGGATTCGCCGATCTCA
PC-3-8  --------------------------------------------------
PC-2-1  --------------------------------------------------
PC-2-6  --------------------------------------------------
PC C/E1 --------------------------------------------------
```

Figure 9 - Continued 4

```
           401                                            450
PC-3-4    TGGGGTATATCCCGCTCGTAGGCGGGCCCCATTGGGGGCGTCGCAAGGGCT
PC-3-8    ----------C---------------------------------------
PC-2-1    --------------------------------G-----------------
PC-2-6    --------------------------------------------------
PC-4-1    --------------------------------------------------
PC-4-6    --------------------------------------------------
PC C/E1   -----------C-----------Y--------R-----------------

SEQ ID NO    451                                            500
                       CTCGCACACGGTGTGAGGGTCCTTGAGGACGGGGTAAACTATGCAACAGG
PC-3-4        45       --------------------------------------------------
PC-3-8        46       --------------------------------------------------
PC-2-1                 --------------------------------------------------
PC-2-6                 ---------------------------------C----------------
PC-4-1                 --------------------------------------------------
PC-4-6                 --------------------------------------------------
PC C/E1                ----------------------------------------S---------
```

Figure 9 - Continued 5

```
        501                                                  550
PC-3-4  GAATTTACCCGGGTTGCTCTTTCTCTATCTTTATTCTTGCTCTTCTCGT
PC-3-8  ------------------------------------------------
PC-2-1  ------------------------------------------------
PC-2-6  ------------------------------------------------
PC-4-1  ------------------------------------------------
PC-4-6  ------------------------------------------------
PC C/E1 ------------------------------------------------

551                                                  600
PC-3-4  GTCTGACCGTTCCGGCCCTCTGCAGTTCCCTACCGAAATGCCTCTGGGATT
PC-3-8  -------------------------------------------------
PC-2-1  -------------------------------------------------
PC-2-6  -------------------------------------------------
PC-4-1  -------------------------------------------------
PC-4-6  -------------------------------------------------
PC C/E1 -------------------------------------------------
```

Figure 9 - Continued 6

```
        601                                              650
PC-3-4  TATCATGTTACCAATGATTGCCCAAACTCTTCCATAGTCTATGAGGCAGA
PC-3-8  --------------------------------------------------
PC-4-1  --------------------------------------------------
PC-4-6  --------------------------------------------------
PC C/E1 --------------------------------------------------

651                                              700
PC-3-4  TAACCTGATCCCTACACGGCACCTGGTTGCCGTGCCTTGTGTCATGACAGGTA
PC-3-8  ----------------------------------------------------
PC-4-1  ----------------------------------------------------
PC-4-6  ----------------------------------------------------
PC C/E1 ----------------------------------------------------
```

Figure 9 - Continued 7

```
        701                                              750
PC-3-4  ATGTGAGTAGATGCTGGGGTCCAAATTACCCCTACACTGTCAGCCCCGAGC
PC-3-8  -------------------------------------------------
PC-4-1  -------------------------------------------------
PC-4-6  -------------------------------------------------
PC C/E1 -------------------------------------------------

751                                              800
PC-3-4  CTCGGAGCAGTCACGGGCTCCTCTTCGGAGAGCCGTTGACTACCTAGCGGG
PC-3-8  -------------------------------------------------
PC-4-1  -------------------------------------------------
PC-4-6  -------------------------------------------------
PC C/E1 -------------------------------------------------
```

Figure 9 - Continued 8

```
       801                                              850
PC-3-4 AGGGGCTGCCCTCTGCTCCGGCGTTATACGTAGGAGACGGCGTGTGGGGCA
PC-3-8 --------------------------------------------------
PC-4-1 --------------------------------------------------
PC-4-6 --------------------------------------------------
PC C/E1 --------------------------------------------------

851                                              900
PC-3-4 CTATTCTTGGTAGGCCAAAATGTTCACCTATAGGCCTCGCCAGCACGCTACG
PC-3-8 --------------------------------------------------
PC-4-1 --------------------------------------------------
PC-4-6 --------------------------------------------------
PC C/E1 --------------------------------------------------
```

Figure 9 - Continued 9

```
         901                                                 950
PC-3-4   GTGCAGAACTGCAACTGTTCCATTTACAGTGGCCATGTTACCGGCCACG
PC-3-8   ------------------------------------------------
PC-4-1   ------------------------------------------------
PC-4-6   ------------------------------------------------
PC C/E1  ------------------------------------------------

951
PC-3-4   GATGGCA
PC-3-8   -------
PC-4-1   -------
PC-4-6   -------
PC C/E1  -------
```

Figure 10

```
         SEQ ID NO              3856                                                   3890
HCV-1       197        ACCACTGGCAGCCCCATCACGTACTCCACCTACGG----TT-
HCV-J       199        ------G--G-----------------------------TT-
HC-J6                  --G--C--GGCG----------------------A--T----
HC-J8                  -----C--GGA-T--------------T-----T---T----
PC1_37                 -----C--AGCTT-T-----------A------T--------
C1_48                  -----C--AGCTT-T-----------A------T--------
BR36        222        ------------------------------------------

3891                                                          3940
HCV-1                  CAAGTTCCTTGCCGACGGCGGGTGCTCGGGGCGCTTATGACATAATAA
HCV-J                  -----------------------T--A---C------C---
HC-J6                  ----A-----C----T--G--C----G-A--C-----C---
HC-J8                  -----------------TA-C--A-T--A--C--TG-A-CC--T--C---
PC1_37                 -------------------T--A--T---T---A--C----GC---
C1_48                  -------------------T--T--A-------T---A--C---G---
BR36                   -----------------------T--T--A-------T---A--C---

3941                                                          3990
HCV-1                  TTTGTGACGAGTGCCACTCCACGGATGCCACATCCATCTTGGGCATCGGC
HCV-J                  -A----T--A------T--A----CT-G--TA---
HC-J6                  -A--C--T--A------TG--GT--CT-T--CA----TC-C------A
HC-J8                  -A--C--T--A------T--AGT--C--T--TA---C-T----T--A
PC1_37                 -A--C-----A------T---CA--C------CA-----TC-T--G--A-
C1_48                  -A--C-----C------T---CA--C------CA-----TC-T--G--A-
BR36                   -A--C-----C------T---CA--C------CA-----TC-T--G--A-
```

Figure 10 - Continued 1

```
         3991
HCV-1    ACTGTCCTTGACCAAGCAGAGACTGCCGGGGCGAGACTGGTTGTGCTCGC        4040
HCV-J    ----A---G--T--G--------------G--T--A---C-G--C--C--
HC-J6    ---A---G--T--G--------------A--C---TC--G--AAC---A--G--
HC-J8    ---A---C--T--------------T----C--A--C-TC--G--A--G--TT-G--
PC1_37   ---A--------------------T-----C--A--T--G--C---C---CT-G--
PC1_48   -------------------G---------G--T--A--T--G--C---C---CT-G--
5a       -------------------G---------G--T--A--T--G--C---C---CT-G--
BR36     -------------------G---------G--T--A--T--G--C---C---CT-G--

4041
HCV-1    CACCGGCCACCCCTCCGGGCTCCGTCACTGTGCCCCATCCCAACATCGAGG       4090
HCV-J    -------------G--------A--GA---C---A---C-----------
HC-J6    T--G--T--G--C--C--G--A--G--AACC---C-----------A---
HC-J8    ---G---------------C--TA-G--G--AACT---CAGT------A--
PC1_37   ---A-----------------C---AGT--G--AAC---C-----------
PC1_48   ---G----------------C----AGT--G--AAC---C-----------
5a       ---G----------------C----AGT--G--AAC---C-----------
BR36     ---G----------------C----AGT--G--AAC---C-----------

4091
HCV-1    AGGTTGCTCTGTCCACCACCGGAGAGATCCCTTTTTACGGCAAGGCTATC        4140
HCV-J    --A--G--C------A--T-----T--C--C--T---A--C-----
HC-J6    ---G--C---CGGGCAGGAG--T-----C--C--T--G---G--T
HC-J8    ---G--C---TGGTCA-GAG--C--------T----A---T
PC1_37   --A--G--C---TCAGGAG--G-----G--T--C-----GA--C--T
PC1_48   --A--G--C---TCAGGAG--G-----G--T--C-----GA--C--T
5a       --A--G--C---TCAGGAG--G-----G--T--C-----GA--C--T
BR36     --A--G--C---TCAGGAG--G--------T--C-----GA--C--T
```

Figure 10 - Continued 2

```
        4141                                                    4190
HCV-1   CCCCTCGAAGTAATCAAGGGGGGAGACATCTCATCTTCTGTCATTCAAA
HCV-J   ---A-T--G-CC-------------A--G---------------C-----
HC-J6   ------GTC-TAC------------A--A----CT-G--------C----
HC-J8   ------GTC-TAC------------A--A----CT-G--------C----
PC1_37  -----A-CTT-C-------------C-------CT-G----T---C----
PC1_48  ------T-CTT-T--A---------T--T--G-------------C----
PC1_48  ------T-CTT-T--A---------T--T--G-------------C----
BR36    ------T-CTT-T--A---------T--T--G-------------C----

4191                                                    4240
HCV-1   GAAGAAGTGCGACGAACTCGCCCGCAAAGCTGGTCGCATTGGGCATCAATG
HCV-J   --------------T-----G--------------ACA-GCC-C--AC--
HC-J6   --------------T----------G--------G--GGCC--TCGG-GTA-----T-G--C-
HC-J8   --------------T----------G--------A--GGCC--CCGG-GCA------TG----
PC1_37  -------------A-----------T--T--------AAGC-A----AC-AGCC-----G--G--C-
PC1_48  ----------------------------T--------AAGC-A----AC-AGCC-----G--G--C-
PC1_48  -------------A-----T--T--------------AAGC-A----AC-AGCC-----G--G--C-
BR36    -------------A-----T--T--------------AAGC-A----AC-AGCC-----G--G--C-

4241                                                    4290
HCV-1   CCGTGGCCTACTACCCGCGGTCTTGACGTGTCCGTCATCCCGACCAGCGGC
HCV-J   -T--A--G--T-----G---T-----C--T-----A----T-----A
-A-------A-----A-A--G--G-----C----A--A--A--TCAG--A
HC-J6   ---T---A-----TA-G--------C-------T--A--A--TCAA--A
HC-J8   ---T---A-----TA-A--------C----------A--C--A--CA--A
PC1_37  ---A---T--TA-A-----------A----CG------A--C--A--CA--A
PC1_48  ---A---T--TA-A-----------A----CG------C--AGCA--A
BR36    ---A---T--TA-A-----------A----CG------C--AGCA--A
```

Figure 10 - Continued 3

```
          4291                                              4340
HCV-1   GATGTTGTCGTCGTGGCAACCGATGCCCTCATGACCGGCTATACCGGCGA
HCV-J   --C--C--T-------A--C--T--------G--T--T---------- 
HC-J6   --C--A--G-----C--C--C-----------G--G--T---T--A---
HC-J8   --C--G--G--T--C--C--T-----A-----T--G--C---------- 
PC1_37  --C--G--G--T--C--C--T--------------T--C---------- 
PC1_48  --C--G-----GTGCAGC-----C--G--------G--A--TC------
PC1_48  --C--G-----GTGCAGC--------G--------G--A--TC------
BR36    --C--G-----GTGCAGC--------G--------G--A--TC------

4341                                              4390
HCV-1   CTTCGACTCGGTGATAGACTGCAATACGTGTGTCACCCAGACAGTCGATT
HCV-J   ---T-----A--C--------C--A-------------------------
HC-J6   ---T-----C--------C--------CGTAGCG----T---AGTT--A--C-
HC-J8   ---T-----C--C--C-----T-------GTTGCA---T--T----TT--T--C-
PC1_37  ---T-----C--C--C-----T--------CT-CGCC---T-------G--G--C-
PC1_48  ---T--T--T--C---------T-------CT-CGCC---T-------G--G--C-
PC1_48  ---T--T--T--C---------T-------CT-CGCC---T-------G--G--C-
BR36    ---T--T--T--C---------T-------CT-CGCC---T-------G--G--C-

4391                                              4440
HCV-1   TCAGCCTTGACCCTACCTTCACCATTGAGACAATCACGCTCCCCCAGGAT
HCV-J   ---T-G--T--C-------------------G-CA---G----A--C
HC-J6   ---T-G-----C--A-------------AACC--CAG--TG---T--A--C
HC-J8   --------C--A---------------CACC--TCAA--CG---T-----C
PC1_37  ---A--G--T--C--T--T-------------T--C---AG-G-------C
PC1_48  ---T-G--T--C--T--T--------------T--C---AG-G-------C
PC1_48  ---T-G--T--C--T--T--------------T--C---AG-G-------C
BR36    ---T-G--T--C--T--T--------------T--C---AG-G-------C
```

Figure 10 - Continued 4

```
          4441
HCV-1     GCTGTCTCCCGCACTCAACGTCGGGGCAGGACTGGCAGGGGGAAGCCAGG                      4490
HCV-J     --G--G--TG-G--G--G--A--T-------------C-G-AGT--
HC-J6     -----A--T-GC--G--C-----C-C--G-----A-GA-TG--
HC-J8     ----------------T-G-----A-A--G--A--G------CGATTG-
HC-J8     -------------T-G----------A-A--G-----G-----CGATTG-
PC1_37    --A--G---A-AGC--G--T----C-C--G--A--T-G--AC-
PC1_48    --A--G---A-AGC--G----A-----C-C--G--A--T-G--AC-
BR36      --A--G---A-AGC--G-------A-----G--G--A--T-G--AC- 4491                                                                  4550
HCV-1     CATCTACAGATTTGTGGCACCGGGGAGCGCCCCTCCGGCATGTTCGACT
HCV-J     -----G-----A-T--A--G-----A---
HC-J6     T--T--T--G-A---TT-CA-T--T----AG---A--A---T--A
HC-J6     -G-T-----G-A---TT-GT-A--C-----A-G--G--T---A
HC-J8     -----A----C-G-A----CT-GG--T-----A-A--G--T--
PC1_37    -----A----C-G-A----CT-GG-T--A----A-A--N--T-A--
PC1_48    -----A----C-G-A----CT-GG-T--A----A-A--N--T-A--
BR36      -----A----C-G-A----CT-GG-T--A----A-A--N--T-A--

4551                                                                  4590
HCV-1     CGTCCGTCCTCTGTGAGTGCTATGACGCAGGCTGTGCTTGGTATGAGCTC
HCV-J     -C--G--G-----------C-----
HC-J6     GTGTA--G-----C------C--T---GGCC--A-------T
HC-J6     GCGTA--G-----C------C--T---GGCA--C-------C
HC-J8     -CGTG--G-----------C--T---A-----C--T-G
PC1_37    -CGTG--G-----------C--T---A-----C--T-G
PC1_48    -CGTG--G-----------C--T---A-----G--T-G
BR36      -CGTG--G-----------C--T---A-----G--T-G
```

Figure 10 - Continued 5

```
        4591                                                       4640
        ACGCCCGCCGAGACTACACAGTTAGGCTACGAGCGTACATGAACACCCCGGG
HCV-1   ----------------------T---CT-G-----T-G--G---C-A--T--A--
HCV-J   ----A--A--G--------C---C---C----CA----A--TT-C----A--T--
HC-J6   ----A--T--T------------G--G--A--C--G---T--TT-C----G--C--
HC-J8   ---------------------G-------C--G---T---TT-C----G--C--
PC1_37  ---T---T--------------C------C--G---T--C--T----N-A------C--
PC1_48  ---T---T--------------C------C--G---T--C--T------A------C--
BR36    ---T------------------C------C--G---T--G--C--T----A------C--

4641                                                       4690
        GCTTCCCGTGTGCCAGGACCATCTTGAATTTTGGGAGGGGTCTTTACAG
HCV-1   -T-G-----C----------------C--A---G--C-----A---C---
HCV-J   TT-G----T-----A--------G------------CA--T--C---C--
HC-J6   TT-G-----A--T-A--------C--G--G---C----A-CG-------C--
HC-J8   ---C---T--T------------------T-G----G---G--C--G--
PC1_37  ---C---T--C--T---------------T-G----G---G--C--G--
PC1_48  ---C---T---------------------T-G----G---G--C--G--
BR36    -----------------------------A---C---------A---T--

4691                                                       4740
        GCCCTCACTTCATATAGATGCCCACTTTCTATCCCAGACAAAGCAGAGTGGG
HCV-1   ------C--C--------------CT-G-----C--A----GCA--A
HCV-J   ------A--C------------C--T---A-------ATCG--
HC-J6   -------------T--C-----C---C---------G-----AG-A--A
HC-J8   -T---A--C--C--T--C---------G-----A--G---
PC1_37  -G------A-C--C--C---T--A-G---A------C--A---G----
PC1_48  -G------A-C--C--C---T--A-G---G--A---C--A---G----
BR36    -A--A---C----------------A---------G--A-----CAG--A
```

|          |
|----------|
| HCV-1    |
| HCV-J    |
| HC-J6    |
| HC-J8    |
| PC1_37   |
| PC1_48   |
| BR36     |

Figure 10 - Continued 6

```
        4741                                              4790
HCV-1   GAGAACCTTCCTTACCTGGTAGCGTACCAAGCCCACCGTGTGCGCTAGGGC
HCV-J   --C----------C--C---------A-----------A-----C-----
HC-J6   --A---TT-CG-A---T-AAC----C---G--T--A-----------C--
HC-J8   --A---T--G-G---T--AACG--C---G---A--A--C-----------
PC1_37  --A---T--C--A-----T--------------A--A--C--T-T-C-C-
PC1_48  ------TT-C--A-----T----------------A--C---T-T-C-C-
BR36    ------TT-N--A-----T------------------T-----C-C----
        CTC---T-CT-G-T----ACT--C---------------------

4791                                              4840
HCV-1   TCAAGCCCCCTCCCCCATCGTGGGACCAGATGTGGAAGTGTTTGATTCGCC
HCV-J   --G--T--A--T------------A--------------C-C---A--G-
HC-J6   CA--------C-----G---C---GTC------------------C---A
HC-J8   AA-G-----------T-----T-----GT---------C-A-C--A-G-
PC1_37  GA----G--C------------CAGC-------A---CA--C-C----T-
PC1_48  GA----G--C------------CAGC------A---CA--C-C----T-
BR36    G--G--T----------------AGT------G---------C-CG-A--G-

4841                                              4890
HCV-1   TCAAGCCCCACCCCTCCATGGGCCAACACCCCTGCTATACAGACTGGGCGCT
HCV-J   -A---------A-G---------------G-----G---G--A--A--C-
HC-J6   ------A---GTG--C--C---T---C-G---C-CT---T--C
HC-J8   -------A---GAC----C--T--T------C-CT---T--C
PC1_37  -------A---NT-AAC------C--T--T---CT-G------G------GC-C
PC1_48  -------A---TT-AAC------C--T--T---CT-G------G------GC-C
BR36    -T-----A--A------A---T--G--T-------TC-GT-----GC--
```

Figure 10 - Continued 7

```
         4891                                                  4940
       GTTCAGAATGAAATCACCCTGACGGCACCCAGTCACCAAATACATCATGAC
HCV-1  ----------------------------------------------------
HCV-J  ----A---GG---T--C--A----CA-A------------------G----
HC-J6  ---ACC--C--GG---C-----T--T--G--------T--G------GCC-
HC-J8  ---GACC-----GG---------T---------C--G--G-------GCC-
PC1_37 ---C--------------------A--------CA------G----T--G-
PC1_48 ---C--------N---G-------A--------CA------G----T--G-
BR36   ---C--A-----------------TG-T----A-CA------A----G---

4941                                                  4990
       ATGCATGTCGGCCGACCTGGAGGTCGTCACGAGCACCTGGGTGCTCGTTG
HCV-1  ----------------------------------------------------
HCV-J  ---------T-------------T---------T-----------A--A--
HC-J6  ---C----CAA-----T-----A-G--C---G------CT-A-C------
HC-J8  ---G----CAA-----T-----A--A-G--T-A-----C--G-CG-----
PC1_37 T-------------T--T--G--T-----A-T-C-----T----T-G--G-
PC1_48 T-------------T--T--G--T-----A-T-C-N---T----T-G--G-
BR36   --------A---T--T--------A--T----AAC----C----TT-GC--

4991                                                  5040
       GCGGGCGTCCTGGCTGCTTTGGCCCGGTATTGCCTGTCAACAGGCTGCGTG
HCV-1  ----------------------------------------------------
HCV-J  --A-------T--G--C-------C-------A-G---A-----------
HC-J6  -G--G----T---G--CG-C----C-------G-G--C--G--T-----
HC-J8  -G--G--A--C--CG----A--T-C-------G-G--T------A-T---
PC1_37 -G-----TG---G--CC--G--C---T---A-GGTG--T-CG--A-----
PC1_48 -G-----TG---G--CC--G--C---T---A-GGTG--T-CG--A-----
BR36   -A--G----C---G--CC-A--G--C---T-------GTC---T--T--T
```

Figure 10 - Continued 8

```
           5041                                              5090
HCV-1   GTCATAGTGGGCAGGGTCGTCTCTTGTCCGGGAAGCCGGCAATCATACCTGA
HCV-J   ----T------------A---A---------G---A--TG-T--T--C---
HC-J6   TG---CA-C----C-CT-GCA-G-TAA-CA-CGAG-C-TCG-TGC---G--
HC-J8   TC---CA-T----C-CC-ACA-C--AAT-ATCG-GT--TTG-GGCC--C--
PC1_37  --C--------C--T--A--C-C--T----A--T------T--C------
PC1_48  --C--------C--T--A--A-C-C--T----A--T--C------T--C-
BR36    --G--T-----TCATA---AGC--GGG--C-----------G-T--A---

5091                                              5140
HCV-1   CAGGGAAGTCCTCTACCGAGAGTTCGATGAGATGGAAGAGTGCTCTCAGC
HCV-J   -------------------AG-----------------TG--TCA----
HC-J6   --A---G------TGAG-CT--T------------G--A--TG-CTCTA
HC-J8   --A---A--T-A--TGAG-CC--T-------------A--G-CTCCA--
PC1_37  T----G--AT-A---AGC-A--T-----G------------GGCCT---
PC1_48  T----G--CAT-A---AGC-A--T-----G------------GGCCT---
BR36    --AA--G--GT-G--T-A-C-A-A---------------A--AG-----

5141                                              5190
HCV-1   ACTTACCGTACATCGAGCAAGGGATGATGCTCGCCGAGCAGTTCAAGCAG
HCV-J   --C--C--T-------------A--CA-----------A-----A----
HC-J6   GAGCGG-TCT----T--AG-G--CA-CG-A----AT-C-G---TCC---
HC-J8   -AGCCG-CCT----T----G----CA-CG-A-G--G---AT-C---ATCT
PC1_37  CG--G--C---T--G---CG---ACACGTGCCA-T---GA--A----AG-
PC1_48  CG--G--C---T--G---CG--GACACGTGCCA-T---GA--A----AG-
BR36    CTGCC--A----T-----A----CTCA-G-AA--A---TC-C-----G-A
```

Figure 10 – Continued 9

```
        5191                                                    5240
HCV-1   AAGGCCCTCGGCCCTCCTGCAGACCGGCGTCCCGTCAGGCAGAGGTTATCGC
HCV-J   ----G----AT-G-----A--CA--AAG--A--G---C-GCT--
HC-J6   ---AT--AA---T-AT-----CAA--T---AAA--A--TC-A-AC--ACA
HC-J8   ---ATA-AA-----------A--ACAG--CA-AA-G--A--TC-A-AC--ACA
PC1_37  --A-TG------T--A-CAGC--GA-CGG--AGA----T---AAC-C-GAA
PC1_48  --A-TG------T--A-CAGC--GA-CGG--AGA----T---AAC-C-GAA
BR36    --A-T---T--AT-G------CGA--CA---AA--ACA--CT--C---T-A 5241                                                    5290
HCV-1   CCCTGCTGTCCAGACCAACTGGCAAAAACTCGAGACCTTCTGGGCGAAGC
HCV-J   T--C-TG--GG--T---G----G-GCC--T---GT-------A--
HC-J6   A--C-----G---G-TTCT----CC--GG-A---CAA------C--A--
HC-J8   G---------G--T-ATCA----CC--G-T--ACAA--T---C--A--
PC1_37  G--A---A-A--T-TGTG---A-C--GGCT--CAG-----N-C-CAT
PC1_48  G--G-A-C-AC-T-TGTG---A-C--GGCT--CAG-----C-CAT
BR36    G--CATA--AACT------------G--T---G----T---CAC--

5291
HCV-1   AT
HCV-J   -C
HC-J6   -C
HC-J8   -C
PC1_37  -C
PC1_48  -C
BR36    --
```

Figure 11

```
         1286
HCV-1    TTGSPITYSTYGKFLADGGCSGGAYDIIICDECHSTDATSILGIGTVLDQAETAGARLVV    SEQ ID NO
HCV-J    ---G--------C----------------------S-T----------------------
HC-J6    ---A------------------A----------AV-S-T---------------V--T--
HC-J8    ---DS----------I--------------AA-----T-----------------V--T--
PC-1-48  ---AS----------------------------------T---------------------  56
PC-1-37  ---AS-----------------------H-V--------Q-T-------------------  58

1346
HCV-1    LATATPPGSVTVPHPNIEEVALSTTGEIPFYGKAIPLEVIKGGRHLIFCHSKKKCDELAA
HCV-J    -------------I------------------N------------I-A------------
HC-J6    -----------T------------T--------GQE-----R---SY-------------
HC-J8    -------T--T--S-----------------GHE-----------AF-------------
PC-1-48  --X-X-----T------------------------PQE---V---XR----AF-------
PC-1-37  ---X------T------------------------PQE---V---R-----AF---N---
```

Figure 11 - Continued 1

```
       1406
HCV-1  KLVALGINAVAYYRGLDVSVIPTSGDVVVVATDALMTGYTGDFDSVIDCNTCVTQTVDFS
HCV-J  --TG--L-----------------------F-----------------------------
HC-J6  A-RGM-L------------------Q----F------------------VA---V----
HC-J8  A-RGM-V------------------Q-----------------------VA-S-I----

1466
HCV-1  LDPTFTIETITLPQDAVSRTQRRGRTGRGKPGIYRFVAPGERPSGMFDSSVLCECYDAGC
HCV-J  -------------T-----A--------RS---T--------------------------
HC-J6  -----T-Q-V---------S--------RL--Y-ST---A------V------------A
HC-J8  -----T-Q-V---------S--------RL-V--Y-SS-------V-------------A

1526
HCV-1  AWYELTPAETTVRLRAYMNTPGLPVCQDHLEFWEGVFTGLTIIDAHFLSQTKQSGENLPY
HCV-J  ------S------L---------------S---------------------A-D---FA
HC-J6  -----------F---A-----A---------A---------------------------FA
HC-J8  -----------F---A---------------A---------------G-----------FA
```

Figure 11 - Continued 2

```
        1586
HCV-1   LVAYQATVCARAQAPPPSWDQMWKCLIRLKPTLHGPTPLLYRLGAVQNEITLTHPVTKYI
HCV-J   ----------------------------------------------------V---I--
HC-J6   -T-----------K--------V---T-----V------S-T--V--------------
HC-J8   -T-----------K--------V---T-----V---------T--V-------------

1646
HCV-1   MTCMSADLEVVTSTWVLVGGVLAALAAYCLSTGCVVIVGRVVLSGKPAIIPDREVLYREF
HCV-J   -A----------------------------------T--S---II---R--V----Q--
HC-J6   A---Q--------A------V-----A----C-I--LHVNQRAVVA--K----EA----
HC-J8   A---Q----IM--S------A------V---A--IS-I--LH--NDRVVVA--K-I--EA-
PC-1-48 -A---------------I--X---------------TV-S-A---II--------A-XQ--
PC-1-37 -AF--P-------L-X-----------V-T-XX---TV-S-A---II--------X---QQ- 1706                                                    1764
HCV-1   DEMEECSQHLPYIEQGMMLAEQFKQKALGLLQTASRQAEVIAPAVQTNWQKLETFWAKH
HCV-J   ----AS----------------Q----------------TK---AA--V-ESK-RA--V---
HC-J6   ----ASRAAL--E-QRI--ML-S-IQ----Q--K--QD-Q----AS--P-V-Q------
HC-J8   ----ASKAAL--E-QRM--ML-S-IQ----Q--T---QD-Q--I-SS-P---Q------
PC-1-48 ----AS---MDETRAI-G---E-V--FIS-TGQK--TLK--ATSV-N-AXQ---TY---
PC-1-37 ----AS---MDETRXI-G---E-V--FIS-TGQK--TLK--ATSV-N-ADQ---XTY--
```

Figure 12

```
                330        340        350        360        370
                 |          |          |          |          |
HCV1    PTTALVMAQLLRIPQAILDMIAGAHWGVLAGIAYFSMVGNWAKVLVVLLL
HCVJ    -------VS---------VV--V----------L--Y-------I-M---
HCJ6    --ATMIL-YAM-V-EV-I-I-G-------MF-L----Q-A-----V-I--
HCJ8    --LTMIL-YAA-V-ELV-EI-F-G-----VF-L----Q-A-----IAI--
NZL1    -AVGM-V-HV--L---TLF-IM-------I---L---Y----AIIMVM
HCVTR   --IG--ISH-M-L---TLF-LVS-T----M-L---------VI--IM
BE95    -------LV----------VVI--I---S--------FAA--YAS-A---T---VL--F---

380        390        400        410        420
                 |          |          |          |   *       * |
        E2
HCV1    FAGVDA|ETHVTGGSAGHTVSGFVSLLAPGAKQNVQLINTNGSWHLNSTAL
HCVJ    ------|---G-------RVASSTQSL--W-SQ-PS-KI--V------I-R---
HCJ6    A-----|Q---TV--TA-NARTLTGMFSL--R-KI--------I-R---
HCJ8    V-----|T-YSS-QE--R--A--AG-FTT----LY--------I-R---
NZL1    -S----|H-YT---T-SRHTQA-AG-FDI-PQ-KL---V---I----
HCVTR   -S----|N-YT-A--MAQSIYRLTDIFST-PS-KL---V-S---
BE95    ------|T-QIS---SAQ-TY-IA-FITR--Q-KL------I-R---
```

Figure 12 - Continued 1

```
               430       440       450       460       470
                -*                  *                    *
HCV1     NCNDSLNTGWLAGLFYHHKFNSSGCPERLASCRPLTDFDQGWGPISY AN
HCVJ     ----Q--FI-A----A-R--A------M----IDE-A----TH DM
HCJ6     ----H--F-S----T-S----------MSA--SIEA-RV--ALQ-ED-
HCJ8     ----Q--F-S----T-----------S---G-D--RI----TLE-ET-
NZL1     ---E-I--FI----Y-----T---Q--S---K-I-F-R----LTD --
HCVTR    ----Q--FI----Y---------------D-M----A-AT-----T---
BE95

480       490       500       510       520
HCV1     GSGP/DQRPYCWHYPPKPCGIVPAKSVGPVYCFTPSPVVVGTTDRSGAP
HCVJ     PESS/---------------A-R----SQ--------------F---
HCJ6     VTN-E-M-------RQ--V-S-S--------L---
HCJ8     VTNDG-M-------R-----RT-------------KQ-V-
NZL1     IT--S-D-------A-R--D----S--
HCVTR
BE95     I---S-DK------R----V---QE-----------SK-H--
```

Figure 12 - Continued 2

```
              530            540
              |              *
HCV1    1a    TYSWGENDTDVFVLNNTRPPL
HCVJ    1b    -----E----LL--TRP-QG
HCJ6    2a    --T--E----L--S----Q
HCJ8    2b    --T--E----L--S----R
NZL1    3a
HCVTR   3b
BE95    5a    ---N--S-V--F-LM-----I
```

Figure 13

| | SEQ ID | 980<br>CCCCTACGACGACGGGCGTTGGTAATGGCTCAGCTGCTCCGGATCCCACAAGCC |
|---|---|---|
| HCV-1 | 1a | ----------------------------------------------------------- |
| IICH-H | 1a | ---------------G-A-----GG-A--------A---------------------- |
| HC-J1 | 1a | ---------------G------------------------------------------- |
| HCV-J | 1b | -A-----------A----CC-A--GG-AT-G-----A---------------------- |
| HCV-BK | 1b | -G---C--A--A---CC-A--GG---T-G-------T---------------------- |
| HC-J4.83 | 1b | -A-----A--A---CC-A--GG---T-G-------T---------------------- |
| HC-J4.91 | 1b | -A-----A--A---CC-A--GG---T-G-------T---------------------- |
| HCV-JTA | 1b | -G-----A--A---CC-A--GG---T-G-------T-A--------------------- |
| HCV-JTB | 1b | -G-----A--A---CC-A--GG---T-G-------T-A--------------------- |
| HCV-CHINA | 1b | -G-----A--A---TC-A--GG---T-G-------T-A---T----------------- |
| HCV-T | 1b | -G-----A--C---A---GG---T-G-------T-A--------------------- |
| HCV-JK1 | 1b | -A-----A--A---CC-A--GG-AT-G-------A---T----------------- |
| HCUNK | 1b | -G-----A--A---CC-C---G---T-G-------T-A--------------------- |
| IICV-N | 1b | -A-----A--A---CC--A--CC----GT-CGC-A-G----CG---CG-G-T--- |
| HC-J6 | 2a | -G---C---G-TA-CA--A--CC----CT-CGCCGCT-TG-T--CG--CTG |
| HC-J8 | 2b | -T---A--TCTTA-CA--A--CC-C---CT-CGCCGCT-TG-T--CG--CTG |
| HC-J5 | 2a | -A---C---G-CA-CA--A--CC----GT-CGC-A-G----CG---CG-G-TT |
| HC-J7 | 2b | -A---A--TCTTA-CA--A--CC-C---CT-TGCCGCT-TG-T--TG-GCTA |
| NZL1 | 3a | ----CG-TGT--GTA-----GG-----G-TG-C--G--TT-A--C--GA-- |
| HEM26 | 3a | ----CG-TGT--GTA-----GG-----G--CG-C--G--TT-G--C--GA-- |
| TH85 | 3a | ----CG-CGT--GTA-----GG-A--G--TG-C--G--TT-G--C--GA-- |
| US114 | 3a | ----CG-CGT--GTA-----GG-----G----G--CG-T--G--TC-G--C--GA-- |
| BE95 | 5a | -A---------A--TC--C-GG-----C------T-A--G----T--C---TG |

```
                     1030
              ATCTTGGACATGATCGCTGGTGCTCACTGGGAGTCCTGGCGGGCATAGC
HCV-1    1a   ---------------------------------------------AA
HCII-H   1a   ---A--------T--------C--C-----------------------
HC-J1    1a   ------------T-----------------------------------
HCV-J    1b   ---G--------------G--G---C--C--------T---A---C-T
HCV-BK   1b   ---G--------------G--G---C--C----------------C-T
HC-J4.83 1b   ---G--------------G--G---C--C------------------C
HC-J4.91 1b   ---G--------------G--G---C--C------------------C
HCV-JTA  1b   ---G-----T--------G--G---C--C----------------C-T
HCV-JTB  1b   ---G-----T--------G--G---C--C------------A---C-T
HCV-CHINA 1b  ---G--------------G--G---C--C------------A---C-T
HCV-T    1b   ---G--------------G--G-TG-C--C--------A------C-T
HCV-JK1  1b   ---G-----T--------G--GGG-C--C----------------C-C
HCUNK    1b   ---G--------------G--GA-A--GT-C--------------C-T
IICV-N   1b   ---G-----A--------G--G---C--C----------------C-T
HC-J6    2a   ---A--A-----C--T-GC--G-------T------C----A--TTC-T--
HC-J8    2b   ---G--C--C--A--T--TTTC--C-GC--T--------T--GG--TTT-G-
HC-J5    2a   ---A--A-----C--TAGC--G-------C------C----A--TTC-C--
HC-J7    2b   ---G--C--T--GG-TG--TTC--C-GC--T--------C--GG--TTT-G-
NZL1     3a   T--G--C-----A--C-----G---C--C--T-----CA--T------C-G
HEM26    3a   T--G--C-----A--A-----C---G--C--T-----CA--T------C--
TH85     3a   T--G--C-----A--A-----C---G--C--T-----CA--T------C--
US114    3a   T--G--C--T--AG-A-----C---G--C--T-----CA--T------C--
BE95     5a   G--A-T-------C-----A---GAGC----G-----G---T--TTT-C-GCC--
```

Figure 13 - Continued 2

| | | 1080 | | | | | | |
|---|---|---|---|---|---|---|---|---|
| HCV-1 | 1a | GTATTTCTCCATGGTGGGAACTGGGCGAAGGTCCTGTAGTGCTGCTGC | | | | | | |
| HCH-H | 1a | ---------------------------------------------- | | | | | | |
| HC-J1 | 1a | ---------------------------------------T------ | | | | | | |
| HCV-J | 1b | C---C-AT-------------------T-----T--A-T----A---A- | | | | | | |
| HCV-BK | 1b | C---C-AT-------C-----------T-----T--A-T----A---A- | | | | | | |
| HC-J4.83 | 1b | C---C-AT----------A--------T-----T--A-T---GC---A- | | | | | | |
| HC-J4.91 | 1b | C---C-AT----------A--------T-----T--A-T---GC---A- | | | | | | |
| HCV-JTA | 1b | C---C-AT------------------T-----T--A-T----A-T-A- | | | | | | |
| HCV-JTB | 1b | C---C-AT-------------------T-----T--A-T----A---A- | | | | | | |
| HCV-CHINA | 1b | C---C-ATG------------------T-----T--A-T----A---A- | | | | | | |
| HCV-T | 1b | C---C-AT---------------T---T-----TT--A-T----A---A- | | | | | | |
| HCV-JK1 | 1b | C---C-AT-------------------T-----T--AA-T----A---A- | | | | | | |
| HCUNK | 1b | C---C-AT-------------------T-----T--A-T----A---A- | | | | | | |
| HCV-N | 1b | C---C-AT------C------------T-----T--AA-T-C-A----A- | | | | | | |
| HC-J6 | 2a | C---C----T---CA---AGCG-----A---A---G-T--CA-T--TT- | | | | | | |
| HC-J8 | 2b | C---C--------CAA--AGCG-------C--A---A-C-CCA--C--C--T- | | | | | | |
| HC-J5 | 2a | C---C----T---CA---AGCG-----------T--G-T--CA-C---T- | | | | | | |
| HC-J7 | 2b | C---C--------CA---AGCG-------C--A---A-T-CCA--C---C- | | | | | | |
| NZL1 | 3a | C----A-------CA----C-------C-----GCAA-CA-CA--G-TA | | | | | | |
| HEM26 | 3a | C----A-------CA----C----T--C-----GCTA-CA-CG--G-TA | | | | | | |
| TH85 | 3a | C----A-------CAA---C-------C-----GCTA-CA-CA--G-TA | | | | | | |
| US114 | 3a | C----A-------CA----C-------C-----GCTA-CA-CA--G-TA | | | | | | |
| BE95 | 5a | A---C-ATG-ATC-----CT----A-C-----G--C-G---CT--T-T- | | | | | | |

Figure 13 - Continued 3

```
          1130
          TATTTGCCGGGCGTCGACGCGGAAACCCACGTCACCGGGGGAAGTGCCGGC
HCV-1     --------------------------------------------------
HCH-H     -------------------------------AT--T-------A------
HC-J1     -G-------------------------------------------CAA--C-
HCV-J     -C----T--------G-C-C-------G--A-------------G-TA-C-
HCV-BK    ------T--------G--T--------G--A-------------GGGCAA-C-
HCV-J4.83 -T----T--------G---G-------T-ACGT-G---------GGCG---A-
HC-J4.91  -C---C---------G--CG------T-ACGT-G---------GGTG-----
HCV-JTA   -C-------------G--TC--TT---T-ACG--A--------GTCGCAA-CT
HCV-JTB   -C-------------G--TC--TT---T-ACG--A--------GTCGCAA-CT
HCV-CHINA -C-------------G---T-------T--CGT-T--------GGCGCAG--
HCV-T     -T----T--------G-AGT--AT---T--GT-A--A--G-CA-TG-C-
HCV-JK1   -C-------------G-ACT--T----T--GT-A-T-------GCA--AA--
HCUNK     -C----T--------GAACC-------G--A------------GGCGCAA--T
HCV-N     -C----T--------G-C-C---T-ACA--G------------GCAC--T-C-
HC-J6     -GGCC-----G----C--------TAC-GTT------------TTC-A---CG
HC-J8     -TG---A--G----T-AACC---T-TTC--G--CCAGGAA--G--T
HC-J5     -GGCC--T--A----G--T----A-C-G-AC-GTT-C------TTC---T-CG
HC-J7     -TG-C-A--A----G--T---AGC----A---T---C---CAA--G-C-
NZL1      -G---CT-A--G----T--CC-C-AT-TAC-------T--C-C---ATCT
HEM26     -C---T-A--G----T----C---AT-TAC-------T--C---TG-CT
TH85      -C------G----T--C--G--A-G-A--------------C--C---A-CT
US114     -C---T-A--G----T-CAGC--A--TA-----T--CTC-ATG-CT
BE95      -G-----A--G----T--T---TACT----GA-TT-G--C--CTCCAG--C-
```

Figure 13 - Continued 4

```
              1180
HCV-1     1a  CACACTGTGTCTGGATTTGTTAGCCTCCTCGCACCAGGGCGCCAAGCAGAA
HCH-H     1a  -G---CAC-G---GC----G-T---TA------------------------
HC-J1     1a  -G-G-CA------C-----T---A-----T---------------------
HC-J      1b  TC--GCACCCAGA-CC-C--GTC-TGG---T----A---C-ATCT------
HCV-BK    1b  A-A--CACCAACA-GC-C--GTC-A-GT-----AGT--GC-GTCT------
HCV-J     1b  -----CACC--CACGC-C-CGTC----T---T------T--G--GTCT---G
HC-J4.83  1b  -G---CACC--C---G--CACGTC---T---T------T--T--GTCT---G
HC-J4.91  1b  -G-CACACCCAGA-CG--CACGTC-T---T---A-C-A---GC-GGCC---G
HCV-JTA   1b  -G-CACACCCAG--GG-C-CGTC-T---T---A-C------GC-GGCC---G
HCV-JTB   1b  -G---CACCCTC---G--CACGTC-------T--TA-----G--TCT-----
HCV-CHINA 1b  -G-T-CACCCTC---G--CACGTC-------T--TA-----G--GTCC----
HCV-T     1b  -G---CACCCACA-TC-C-CGTCT---T--TA---A---G--T-GGCT----
HCV-JK1   1b  -G---CACCCGGC-CG---CGTC-T---T--AGT---T----T-GGCT----
HCUNK     1b  GGG-C-CTAGCTCGC-AACGTC-----T--TAGC--T--GC-GGTT---C
HCV-N     1b  -----CTCACCAGC---G--C-CGG-----T--TA----T--GC-GTCT---G
HC-J6     2a  --T-AC-CCAGGACCC-CACCG--A-GT---T--C-TT---T--G------
HC-J8     2b  -GT--C--CG-G--G--C-C-G------T--TA-TA-T--T----------
HC-J5     2a  GCA--CACCAGG--C--CACC---A-GT--T-CT--T---T-G--------
HC-J7     2b  --T--C--TAGA--G-C-CC---A--T--AGC--T----T---CG-----G
NZL1      3a  -GTCA-ACCCAA-CG----C-G-T--TT-T-ACAT---C--C-A-------
HEM26     3a  -TG--ACCAGA--GA-A-C--T--TT-TA-TGTG----------CGC----
TH85      3a  -TGA---C-ACA-G---C------TT---AAT-GG----CGA--A------
US114     3a  -GTGA---C-ACA-G--CAC-G--T-TT----C-GG----C---GT-----
BE95      5a  --A--GAC--A---CA-C-CCTCAT-TA--A-C-GC----GC---------
```

Figure 13 - Continued 5

```
                      1230
                      CGTCCAGCTGATCAACACCAACGGCAGTTGGCACCTCAATAGCACGGCCC
HCV-1       1a        --------------------------------------------------
HCH-H       1a        -A----A-----------------------------A-----------T-
HC-J1       1a        -A------------------------------------------------
HCV-J       1a        -A------------------------------------------------
HCV-BK      1b        AA---A--CG-G------------C-------A-------C--G--T---
HCV-J       1b        AA-----T-A--------T-G-------------------C--G--T---
HC-J4.83    1b        AA----TG-G--T-----------C-------A-------C--G--T---
HC-J4.91    1b        AA----TG-G--T-----------C-------A-------C--G--T---
HCV-JTA     1b        AA-----C-A--------T-----C-------A-------C--G--T---
HCV-JTB     1b        AA-----C-A--------T-----C-------A-------C--G--T---
HCV-CHINA   1b        GA-----T-A--T-----T-T---C---------TA----C--G--T---
HCV-T       1b        AA-----T-A--------T-----C-------A-------C--G--T--T
HCV-JK1     1b        AA---A--TG-T------T-----C---------TA----C--G--T---
HCUNK       1b        -C-----C-A--------T-------------A-------C--G--C---
HCV-N       1b        AA-----T-A--------T-----C-------A-------C--G--T---
HC-J6       2a        AA-----C----------T-------------A-------CC-G--T---
HC-J8       2b        -C--T-TT-A--------T-----C----A--A-A----CC-G--T---
HC-J5       2a        -C-T---C--T-----T-------C-------A-------CC-G--C---
HC-J7       2b        -C-G---G------------------------A-A----CC-G--C---
NZL1        3a        TA--AGT-A---------T-----TCG-----A-------C--T--T---
HEM26       3a        AC-G---G--------------T-TCG-----A-------C--T--T---
TH85        3a        AC-G---G--------------T-TCG-----A----A--T---
US114       3a        -C-G---T-G------------T-TCG----TA-------CC--T---
BE95        5a        AC-G---C--A--T----A---C-------A-------C--G--C---
```

Figure 13 - Continued 6

```
        1280
        TGAACTGCAATGATAGCCTCAACACCGGCTGGTTGGCAGGGCTTTTCTAT
HCV-1   --------------------------------------------------
HCH-H   -----------------A---T-----------------A---------
HC-J1   -----------------A---T-----------------A--C------
HCV-J   ---T-------------CTC-------C-A---T---G-TCA-T--T--C---G------C
HCV-BK  -----------------CTCT------C-G---T---G-TTC-T--C--C---G------C
HC-J4.83 -A---------------CTC-------C-----T---G-TCC-T--C--C---G------C
HC-J4.91 -A--T------------CTC-------C-----T---G-TCC-T--C--C---G------,--C
HCV-JTA ------------------ATC------------T---G-TC--T--C--CA--G------C
HCV-JTB ------------------ATC----------------G-TC--T--C--CA--G------C
HCV-CHINA----------------CTC---------T-T---T---G-TTC-T--C--C---G------C
HCV-T   -A---------------C--CTC----C-G---T---G-TTC-T--CTC-C---G------C
HCV-JK1 ---T-------------C--GTC-A----------T-G-TC--T--C--C---G------C
HCUNK   --G--------------CTC-------------T---G-TTG-T--C--C---G------C
HCV-N   -----------------CTC-----C-G---T-G-TCC-T--C--CC--G-C--C
HC-J6   -----------------CTCTT-GC-----------TCC-C--GTCA--G------C
HC-J8   -C--T------------C---T-AC-G--G---T-TCC-C--TTCCT-G--T--C
HC-J5   ---T-------------CTC-T-G-------------TTA-C--GTCC--G------C
HC-J7   -C--T------------C---T-GC-A---A--T-TC-C--T-CC--G--T--C
NZL1    -A--T------------GTC-A-A-------------G-TTA-A--T---T-G--T--C
HEM26   --------T--------GTC-A-A-------------G-TCA-A--T---T-A--T--C
TH85    -----------------TC-A-A--------------G-TCA-A--TA--T-G--T--C
US114   -----------------GTC-A-A----------T--G-TCA-A--T---T-GC-T--C
BE95    -T--T--T------------C----C-G--T------G-TCA-A--C---C--C---C
```

| | | 1380 | | | | |
|---|---|---|---|---|---|---|
| HCV-1 | 1a | ACCCCTTACCGATTTTGACCAGGGCTGGGGCCCTATCAGTTAT | | | | GCCA |
| HCH-H | 1a | --G--------------------------------------- | | | | ---- |
| HC-J1 | 1a | --G--------------------------------------- | | | | ---- |
| HCV-J | 1a | ------------------------------C----------- | | | | -AT- |
| HCV-BK | 1b | C----A-CGAT--G---C-CT-----G-----T--C--C-C- | | | | ---- |
| HC-J4.83 | 1b | CA---A--GA-A-G--C--------A------T--C--T-C- | | | | --TG |
| HC-J4.91 | 1b | C----A--GA-TGG--C-C---------A---C-----CC-- | | | | A-TG |
| HCV-JTA | 1b | C----A--GA--GG--C-C---------A---C-----CC-- | | | | A-TG |
| HCV-JTB | 1b | C----A--GA---G--C-CT--------A---C-----CC-- | | | | A--G |
| HCV-CHINA | 1b | CT---A-CGA-A-G--C-CT--------A---C-----CC-- | | | | A--G |
| HCV-T | 1b | CT---A--GA-A-G--C-CT--------A---T-----CC-- | | | | A-TG |
| HCV-JK1 | 1b | C----A--GATACA--C--T--------A---T-----CC-- | | | | A-TG |
| HCUNK | 1b | TT---A--GA-A-G--C--T-----A--G---T-----CCC- | | | | --TG |
| HCV-N | 1b | T----A--GA-AGG--C-CT--A--G------T-----C--- | | | | A-TG |
| HC-J6 | 2a | C----A--GATACA--C--CG-------G---T-----C--- | | | | ---- |
| HC-J8 | 2b | CT---A--GA-A-G--C-------A-------T-----C--C | | | | ---- |
| HC-J5 | 2a | CAGTA-CGAG-CC---CGGGT----A------G-CT-ACAA- | | | | -GAG-A |
| HC-J7 | 2b | CGGG--GGA-------CG-ATC----------AA-CT-GGAA | | | | -CGAAA |
| NZL1 | 3a | CAG-A-CGAG-C---CCGGATA--G-------A-CT-GCAA- | | | | -CGAG-AT |
| HEM26 | 3a | TAAG--GGAT------CG-ATC--G-------AA-CT-GGAA | | | | -GAGA- |
| TH85 | 3a | G----A-C--TTTC--CAGG----A-------CT-A-CAG-- | | | | --T- |
| US114 | 3a | G----A-C--TTCC--CAGG----G-------T-CT-G-CAG | | | | --T- |
| BE95 | 5a | G----A-C---TCC--CA-T------------CT-G-CAG-- | | | | -AA- |
| | | G----A-C--TTCC--CAGG-----------T-CT-G-CAG | | | | --T- |
| | | GG---AC-------------------------AA------C | | | | ---- |

Figure 13 - Continued 9

|  |  | 1430 |  |
|---|---|---|---|
|  |  | ACGGAAGCGGCCCC | GACCAGCGCCCCTACTGCTGGCACTACCCCCA |
| HCV-1 | 1a | -------------- | -------------------------------- |
| HCH-H | 1a | ------T------- | ---G-A----------------------T--- |
| HC-J1 | 1a | -------------- | ----A-----------T--------------- |
| HCV-J | 1b | TGCCTGAGA--T-G | ---A-G--A----T-----------G-G--T- |
| HCV-BK | 1b | -GTCT---A-AT-A | ---A-G--A--T-------------------- |
| HC-J4.83 | 1b | -GCCTGA-A---G | ---A-G--A--T-------------A--T- |
| HC-J4.91 | 1b | -GCCT-A-A---G | ---A-G--A--T--------T----G-G--T- |
| HCV-JTA | 1b | -GCCT--G-A--TG | ---A-G--T--T-------------G-G--T- |
| HCV-JTB | 1b | -GCCTG-G-A-TTG | ---A-G--T--T--------T----G-A--T- |
| HCV-CHINA | 1b | -GCCTGATA--T-G | ---A-G--T--T-------------G-G--T- |
| HCV-T | 1b | -G-CTGA-AT--AG | ---A-G--T-----------T----G-A--C |
| HCV-JK1 | 1b | -GTCTC--A--T-G | ---AA-G--T--T------------G-G--T- |
| HCUNK | 1b | -GCCTCAT-ATTTG | ---A-G--T-----------T----G-A--T- |
| HCV-N | 1b | TCCT-AA-A---G | ---A-G--T--T--------T-------A--- |
| HC-J6 | 2a | T-TC-C-AAT--AGAG | TAT-A-A--G---------T----------- |
| HC-J8 | 2b | -TC-C-AA-GATGGG | -AT-A-G--G---------T----------G |
| HC-J5 | 2a | T-TC-C-AAT--AGAA | TAT-A-A--A---------------A----- |
| HC-J7 | 2b | T-TT-C-AA-GAGAG | -AT-A-A--G---------T----T--G |
| NZL1 | 3a | --ATC-C---T--TTCT | -TG-CA-A--A---------------G-A--T |
| HEM26 | 3a | -ATCTC---TT-GTCC | -AG-CAAA--G---------------G-A--T |
| TH85 | 3a | -ATC-C---T--TCT | -TG-CAAA--A---------------G-A--T |
| US114 | 3a | -ATC-C--ATT-TTCT | -TG-CAAA--G---------------G-A--T |
| BE95 | 5a | -AT-TCG--T--AGT | -TG-CAAA--A----T----------G-A--T |

Figure 13 - Continued 10

```
                    1480
HCV-1      1a  AAACCTTGCGGGTATTGTGCCCGCGAAGAGTGTG
HCH-H      1a  -G-------T--C-------------A----C---
HC-J1      1a  -----------------C---------A----C--A
HCV-J      1b  CG----G----G---C------T---TC-CAG---
HCV-BK     1b  CC---AA-TACC---C---A---T---TC-GAG---
HC-J4.83   1b  CG----G--T-----C---A-------TC-CAG---
HC-J4.91   1b  CG----G--T-----C---A---T---TC-CAG---
HCV-JTA    1b  CG----G--T-----C---A---T---TC-CAG---
HCV-JTB    1b  CGG-AG--T-----C---A---T---TC-CAG---
HCV-CHINA  1b  CGG-AG--T-----C---A---T---TC-GAG---
HCV-T      1b  CG-AAG------C------A---T---TC-CAG---
HCV-JK1    1b  CGG--G--T-----C---A--------TT-CAG---
HCUNK      1b  C----G--T---------------A--TT-CAG---
HCV-N      1b  C----G--T---------------A--TT-CAG---
HC-J6      2a  C---AG--T-----CA-A--CT-----CG-TCCGAG-C-
HC-J8      2b  -G-AG--T----G-A--CT-------GCTC-----
HC-J5      2a  -GG-----C---C---C--G---T-G---CG--T-
HC-J7      2b  -----G--T---C---A--C------G--TC-----
NZL1       3a  ---G----T-AC---C--G--ATCA-------C
HEM26      3a  -G----TACCG--C---A--ATCA-------C
TH85       3a  -G---TAAA-G--C---A--ATCA-------C
US114      3a  -G---T-A-CC---G--ATCA-------C
BE95       5a  CGG--G----AG-G---A--CC-AGAG--C
```

SEQUENCES OF HEPATITIS C VIRUS GENOTYPES AND THEIR USE AS THERAPEUTIC AND DIAGNOSTIC AGENTS

This is a divisional of application Ser. No. 09/638,693, filed Aug. 15, 2000, which is a Continuation of application Ser. No. 08/362,455, filed Jan. 11, 1995, allowed, which was a 371 application of PCT/EP94/01323, filed Apr. 27, 1994, the entire content of which is hereby incorporated by reference in this application.

The invention relates to new sequences of hepatitis C virus (HCV) genotypes and their use as therapeutic and diagnostic agents.

The present invention relates to new nucleotide and amino aced sequences corresponding to the coding region of a new type 2 subtype 2d, type-specific sequences corresponding to HCV type 3a, to new sequences corresponding to the coding region of a new subtype 3c, and to new sequences corresponding to the coding region of HCV type 4 and type 5 subtype 5a: a process for preparing them, and their use for diagnosis, prophylaxis and therapy.

The technical problem underlying the present invention is to provide new type-specific sequences of the Core, the E1, the E2, the NS3, the NS4 and the NS5 regions of HCV type 4 and type 5, as well as of new variants of HCV types 2 and 3. These new HCV sequences are useful to diagnose the presence of type 2 and/or type 3 and/or type 4 and/or type 5 HCV genotypes in a biological sample. Moreover, the availability of these new type-specific sequences can increase the overall sensitivity of HCV detection and should also prove to be useful for therapeutic purposes.

Hepatitis C viruses (HCV) have been found to be the major cause of non-A, non-B hepatitis. The sequences of cDNA clones covering the complete genome of several prototype isolates have been determined (Kato et al., 1990; Choo et al., 1991; Okamoto et al., 1991: Okamoto et al., 1992). Comparison of these isolates shows that the variability in nucleotide sequences can be used to distinguish at least 2 different genotypes, type 1 (HCV-1and HCV-J) and type 2 (HC-J6 and HC-J8), with an average homology of about 68%. Within (each type, at least two subtypes exist (e.g. represented by HCV-1 and HCV-J), having an average homology of about 79%. HCV genomes belonging to the same subtype show average homologies of more than 90% (Okamoto et al., 1992). However, the partial nucleotide sequence of the NS5 region of the HCV-T isolates showed at most 67% homology with the previously published sequences, indicating the existence of a yet another HCV type (Mori et al., 1992). Parts of the 5' untranslated region (UR), core, NS3, and NS5 regions or this type 3 have been published, further establishing the similar evolutionary distances between the 3 major genotypes and their subtypes (Chan et al., 1992).

The identification of type 3 genotypes in clinical samples can be achieved by means of PCR with type-specific primers for the NS5 region. However, the degree to which this will be successful is largely dependent on sequence variability and on the virus titer present in the serum. Therefore, routine PCR in the open reading frame, especially for type 3 and the new type 4 and 5 described in the present invention and/or group V (Cha et al., 1992) genotypes can be predicted to be unsuccessful. A new typing system (LiPA), based on variation in the highly conserved 5' UR, proved so be more useful because the 5 major HCV genotypes and their subtypes can be determined (Stuyver et al., 1993). The selection of high-titer isolates enables to obtain PCR fragments for cloning with only 2 primers, while nested PCR requires that 4 primers match the unknown sequences of the new type 3, 4 and 5 genotypes.

New sequences of the 5' untranslated region (5' UR) have been listed by Bukh et al. (1992). For some of these, the E1 region has recently been described (Bukh et al., 1993). Isolates with similar sequences in the 5' UR to a group of isolates including DK12 and HK10 described by Bukh et al. (1992) and E-b1 to E-b8 described and classified as type 3 by Chan et al. (1991), have been reported and described in the 5' UR, the carboxyterminal part of E1, and in the NS5 region as group IV by Cha et al. (1992; WO 92/19743), and have also been described in the 5' UR for isolate BR56 and classified as type 3 by the inventors of this application (Stuyver et al., 1993).

The aim of the present invention is to provide new HCV nucleotide and amino acid sequences enabling the detection of HCV infection.

Another aim of the present infection is to provide new nucleotide and amino acid HCV sequences enabling the classification of infected biological fluids into different serological groups unambiguously linked to types and subtypes at the genome level.

Another aim of the present invention is to provide new nucleotide and amino acid HCV sequences ameliorating the overall HCV detection rate.

Another aim of the present invention is to provide new HCV sequences, useful for the design of HCV vaccine compositions.

Another aim of the present invention is to provide a pharmaceutical composition consisting of antibodies raised against the polypeptides encoded by these new HCV sequences, for therapy or diagnosis.

The present invention relates more particularly to a composition comprising or consisting of at least one polynucleic acid containing at least 5, and preferably 8 or more contiguous nucleotides selected from at least one of the following HCV sequences:

an HCV type 3 genomic sequence, more particularly in any of the following regions:
  the region spanning positions 417 to 957 of the Core/E1 region of HCV subtype 3a,
  the region spanning positions 4664 to 4730 of the NS3 region of HCV type 3,
  the region spanning positions 4892 to 5292 of the NS3/4 region of HCV type 3,
  the region spanning positions 8023 to 8235 of the NS5 region of the BR36 subgroup of HCV subtype 3a,
an HCV subtype 3c genomic sequence, more particularly the coding regions of the above-specified regions;
an HCV subtype 2d genomic sequence, more particularly the coding region of HCV subtype 2d;
an HCV type 4 genomic sequence, more particularly the coding region, more particularly the coding region of subtypes 4a, 4e, 4f, 4g, 4h, 4i, and 4j.
an HCV type 5 genomic sequence, more particularly the coding region of HCV type 5, more particularly the regions encoding Core, E1, E2, NS3, and NS4
with said nucleotide numbering being with respect to the numbering of HCV nucleic acids as shown in Table 1, and with said polynucleic acids containing at least one nucleotide difference with known HCV (type 1, type 2, and type 3) polynucleic acid sequences in the above-indicated regions, or the complement thereof.

It is to be noted that the nucleotide difference in the polynucleic acids of the invention may involve or not an amino acid difference in the corresponding amino acid sequences coded by said polynucleic acids.

According to a preferred embodiment, the present invention relates to a composition comprising or containing at least one polynucleic acid encoding an HCV polyprotein, with said polynucleic acid containing at least 5, preferably at least 8 nucleotides corresponding to at least part of an HCV nucleotide sequence encoding an HCV polyprotein, and with said HCV polyprotein containing in its sequence at least one of the following amino acid residues: L7, Q43, M44, S60, R67, Q70, T71, A79, A87, N106, K115, A127, A190, S130, V134, G142, I144, E152, A157, V158, P165, S177 or Y177, I178, V180 or E180 or F182, R184, I186, H187, T189, A190, S191 or G191, Q192 or L192 or L192 or V192 or E192, N193 or H193 or P193, W194 or Y194, H195, A197 or I197 or V197 or T197, V202, I203 or L203, Q208, A210, V212, F214, T216, R217 or D217 or E217 or V217, H218 or N218, H219 or V219 or L219, L227 or I227, M231 or E231 or Q231, T232 or D232 or A232 or K232, Q235 or I235, A-237 or T237, I242, I246, S247, S248, V249, S250 or Y250, I251 or V251 or M251 or F251, D252, T254 or V254, L255 or V255, E256 or A256, M258 or F258 or V258, A260 or Q260 or S260, A261, T264 or Y264, M265, I266 or A266, A267, G268 or T268, F271 or M271 or V271, I277, M280 or H280, I284 or A284 or L84, V274, V291, N292 or S292, R293 or I293 or Y293, Q294 or R294, L297 or I297 or Q297, A299 or K299 or Q299, N303 or T303, T308 or L308, T310 or F310 or A310 or D310 or V310, L313, G317 or Q317, L333, S351, A358, A359, A363, S364, A366, T369, L373, F376, Q386, I387, S392, I399, F402, I403, R405, D454, A461, A463, T464, K484, Q500, E501, S521, K522, H524, N528, S531, S532, V534, F536, F537, M539, I546, C1282, A1283, H1310, V1312, Q1321, P1368, V1372, V1373, K1405, Q1406, S1409, A1424, A1429, C1435, S1436, S1456, H1496, A1504, D1510, D1529, I1543, N1567, D1556, N1567, M1572, Q1579, L1581, S1583, F1585, V1595, E1606 or T1606, M1611, V1612 or L1612, P1630, C1636, P1651, T1656 or I1656, L1663, V1667, V1677, A1681, H1685, E1687, G1689, V1695, A1700, Q1704, Y1705, A1713, A1714or S1714, M1718, D1719, A1721, or T1721, R1722, A1723 or V1723, H1726 or G1726, E1730, V1732, F1735, I1736, S1737, R1738, T1739, G1740, Q1741, K1742, Q1743, A1744, T1745, L1746, E1747 or K1747, I1749, A1750, T1751 or A1751, V1753, N1755, K1756, A1757, P1758, A1759, H1762, T1763, Y1764, P2645, A2647, K2650, K2653 or L2653, S2664, N2673, F2680, K2681, L2686, H2692, Q2695 or L2695 or I2695, V2712, F2715, V2719 or Q2719, T2722, T2724, S2725, R2726, G2729, Y2735, H2739, I2748, G2746 or I2746, I2748, P2752 or K2752, P2754 or T2754, T2757 or P2757, with said notation being composed of a letter representing the amino acid residue by its one letter code, and a number representing the amino acid numbering according to Kato et al., 1990.

Each of the above-mentioned residues can be found in any of FIGS. 2, 5, 7, 11 or 11 or 12 showing the new amino acid sequences of the present invention aligned with known sequences of other types or subtypes of HCV for the Core, E1, E2, NS3, NS4, and NS5 regions.

More particularly, a polynucleic acid contained in the composition according to the present invention contains at least 5, preferably 8, or more contiguous nucleotides corresponding to a sequence of contiguous nucleotides selected from at least one of HCV sequences encoding the following new HCV amino acid sequences:

new sequences spanning amino acid positions 1 to 319 of the Core/E1 region of HCV subtype 2d, type 3 (more particularly new sequences for subtypes 3a and 3c), new type 4 subtypes (more particularly new sequences for subtypes 4a, 4e, 4f, 4g, 4h, 4i and 4j) and type 5a, as shown in FIG. 5;

new sequences spanning amino acid positions 328 to 546 of the E1/E2 region of HCV subtype 5a as shown in FIG. 12;

new sequences spanning amino acid positions 1556 to 1764 of the NS3/NS4 region of HCV type 3 (more particularly for new subtypes 3a sequences), and subtype 5a, as shown in FIG. 7 or 11;

new sequences spanning amino acid positions 2645 to 2757 of the NS5B region of HCV subtype 2d, type 3 (more particularly for new subtypes 3a and 3c), new type 4 subtypes (more particularly subtypes 4a, 4e, 4f, 4g, 4h, 4i and 4j) and subtype 5a, as shown in FIG. 2, Using the LiPA system mentioned above, Brazilian blood donors with high titer type 3 hepatitis C virus, Gabonese patients with high-titer type 4 hepatitis C virus, and a Belgian patient with high-titer HCV type 5 infection were selected. Nucleotide sequences in the core, E1, NS5 and NS4 regions which have not yet been reported before, were analyzed in the frame of the invention. Coding sequences (with the exception of the core region) of any type 4 isolate are reported for the first time in the present invention. The NS5b region was also analyzed for the new tone 3 isolates. After having determined the NS5b sequences, comparison with the Ta and Tb subtypes described by Mori et al. (1992) was possible, and the type 3 sequences could be identified as type 3a genotypes. The new type 4 isolates segregated into 10 subtypes, based on homologies obtained in the NS5 and E1 regions. New type 2 and 3 sequences could also be distinguished from previously described type 2 or 3 subtypes from sera collected in Belgium and the Netherlands.

The term “polynucleic acid” refers to a single stranded or double stranded nucleic acid sequence which may contain at least 5 contiguous nucleotides to the complete nucleotide sequence (f.i. at least 6, 7, 8, 9, 10, 11, 12, 13, 14, 15 or more contiguous nucleotides). A polynucleic acid which is up till about 100 nucleotides in length is often also referred to as an oligonucleotide. A polynucleic acid may consist of deoxyribonucleotides or ribonucleotides, nucleotide analogues or modified nucleotides, or may have been adapted for therapeutic purposes. A polynucleic acid may also comprise a double stranded cDNA clone which can be used for cloning purposes, or for in vivo therapy, or prophylaxis.

The term “polynucleic acid composition” refers to any kind of composition comprising essentially said polynucleic acids. Said composition may be of a diagnostic or a therapeutic nature.

The expression “nucleotides corresponding to” refers to nucleotides which are homologous or complementary to an indicated nucleotide sequence or region within a specific HCV sequence.

The term "coding region" corresponds to the region of the HCV genome that encodes the HCV polyprotein. In fact, it comprises the complete genome with the exception or the 5' untranslated region and 3' untranslated region.

The term "HCV polyprotein" refers to the HCV polyprotein of the HCV-J isolate (Kato et al., 1990). The adenine residue at position 330 (Kato et al., 1990) is the first residue of the ATG codon that initiates the long HCV polyprotein of 3010 amino acids in HCV-J and other type 1b isolates, and of 3011 amino acids in HCV-1 and other type 1a isolates, and of 3033 amino acids in type 2 isolates HC-J6 and HC-J8 (Okamoto et al., 1992).

This adenine is designated as position 1 at the nucleic acid level, and this methionine is designated as position 1 at the amino acid level, in the present invention. As type 1a isolates contain 1 extra amino acid in the NS5a region, coding sequences of type 1a and 1b have identical numbering in the Core, E1, NS3, and NS4 region, but will differ in the NS5b region as indicated in Table 1. Type 2 isolates have 4 extra amino acids in the E2 region, and 17 or 18 extra amino acids in the NS5 region compared to type 1 isolates, and will differ in numbering from type 1 isolates in the NS3/4 region and NS5b regions as indicated in Table 1.

TABLE 1

| | Region | Positions described in the present invention* | Positions described for HCV-J (Kato et al., 1990) | Positions described for HCV-1 (Choo et al., 1991) | Positions described for HC-J6, HC-J8 (Okamoto et al., 1992) |
|---|---|---|---|---|---|
| Nucleo-tides | NS5b | 8023/8235 | 8352/8564 | 8026/8238 | 8433/8645 |
| | | 7932/8271 | 8261/8600 | 7935/8274 | 8342/8681 |
| | NS3/4 | 4664/5292 | 4993/5621 | 4664/5292 | 5017/5645 |
| | | 4664/4730 | 4993/5059 | 4664/4730 | 5017/5083 |
| | | 4892/5292 | 5221/5621 | 4892/5292 | 5245/5645 |
| | | 3856/4209 | 4185/4528 | 3856/4209 | 4209/4762 |
| | | 4936/5292 | 5265/5621 | 4936/5292 | 5289/5645 |
| | | coding region of present invention | 330/9359 | 1/9033 | 342/9439 |
| Amino Acids | NS5b | 2675/2745 | 2675/2745 | 2676/2746 | 2698/2768 |
| | | 2645/2757 | 2645/2757 | 2646/2758 | 2668/2780 |
| | NS3/4 | 1556/1764 | 1556/1764 | 1556/1764 | 1560/1768 |
| | | 1286/1403 | 1286/1403 | 1286/1403 | 1290/1407 |
| | | 1646/1764 | 1646/1764 | 1646/1764 | 1650/1768 |

Table 1.

Comparison of the HCV nucleotide and amino acid numbering system used in the present invention (*) with the numbering used for other prototype isolates For example, 8352/8564 indicates the region designated by the numbering from nucleotide 8352 to nucleotide 8564 as described by Kato et al. (1990). Since the numbering system of the present invention starts at the polyprotein initiation site, the 329 nucleotides of the 5' untranslated region described by Kato et al (1990) have to be substracted, and the corresponding region is numbered from nucleotide 8023 ("8352–329") to 8235 ("8564–329")

the term "HCV type" corresponds to a group of HCV isolates of which the complete genome shows more than 74% homology at the nucleic acid level, or of which the NS5 region between nucleotide positions 7932 and 8271 shows more than 74% homology at the nucleic acid level, or of which the complete HCV polyprotein shows more than 78% homology at the amino acid level, or of which the NS5 region between amino acids at positions 2645 and 2757 shows more than 80% homology at the amino acid level, to polyproteins of the other isolates of the group, with said numbering beginning at the first ATG codon or first methionine of the long HCV polyprotein of the HCV-J isolate (Kato et al., 1990). Isolates belonging to different types of HCV exhibit homologies, over the complete genome, of less than 74% at the nucleic acid level and less than 78% at the amino acid level. Isolates belonging to the same type usually show homologies of about 92 to 95% at the nucleic acid level and 95 to 96% at the amino acid level when belonging to the same subtype, and those belonging to the same type but different subtypes preferably show homologies of about 79% at the nucleic acid level and 85–86% at the amino acid level.

More preferably the definition of HCV types is concluded from the classification of HCV isolates according to their nucleotide distances calculated as detailed below.

(1) based on phylogenetic analysis of nucleic acid sequences in the NS5b region between nucleotides 7935 and 8274 (Choo et al., 1991) or 8261 and 8600 (Kato et al., 1990) or 8342 and 8681 (Okamoto et al., 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34, usually ranging from 0.1384 to 0.2477, and more usually ranging from 0.15 to 0.32, and isolates belonging to different HCV types show nucleotide distances greater than 0.34, usually greater that 0.35, and more usually of greater than 0.358, more usually ranging from 0.1384 to 0.2977.

(2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.364, and isolates belonging to the same subtype show nucleotide distances of less than 0.17, usually of less than 0.16, and more usually of less than 0.15, more usually less than 0.135, more usually less than 0.134, and consequently isolates belonging to the same type but different subtypes show nucleotide distances ranging from 0.15 to 0.38, usually ranging from 0.16 to 0.37, and more usually ranging from 0.17 to 0.36, more usually ranging from 0.133 to 0.379, and isolates belonging to different HCV types show nucleotide distances greater than 0.34, 0.35, 0.36, usually more than 0.365, and more usually of greater than 0.37, (3) based on phylogenetic analysis of nucleic acid sequences in the NS3/NS4 region between nucleotides 4664 and 5292 (Choo et al., 1991) or between nucleotides 4993 and 5621 (Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

TABLE 2

Molecular evolutionary distances

| Region | Core/E1<br>579 bp | E1<br>384 bp | NS5B<br>340 bp | NS5B<br>222 bp |
|---|---|---|---|---|
| Isolates* | 0.0017–0.1347<br>(0.0750 ± 0.0245) | 0.0026–0.2031<br>(0.0969 ± 0.0289) | 0.0003–0.1151<br>(0.0637 ± 0.0229) | 0.000–0.1323<br>(0.0607 ± 0.0205) |
| Subtypes* | 0.1330–0.3794<br>(0.2786 ± 0.0363) | 0.1645–0.4869<br>(0.3761 ± 0.0433) | 0.1384–0.2977<br>(0.2219 ± 0.0341) | 0.117–0.3538<br>(0.2391 ± 0.0399) |
| Types* | 0.3479–0.6306<br>(0.4703 ± 0.0525) | 0.4309–0.9561<br>(0.6308 ± 0.0928) | 0.3581–0.6670<br>(0.4994 ± 0.0495) | 0.3457–0.7471<br>(0.5295 ± 0.0627) |

*Figures created by the PHYLIP program DNADIST are expressed as minimum to maximum (average ± standard deviation). Phylogenetic distances for isolates belonging to the same subtype ('isolates'), to different subtypes of the same type ('subtypes'), and to different types ('types') are given.

In a comparative phylogenetic analysis of available sequences, ranges of molecular evolutionary distances for different regions of the genome were calculated, based on 19,781 pairwise comparisons by means of the DNA DIST program of the phylogeny inference package PHYLIP version 3.5C (Felsenstein, 1993). The results are shown in Table 2 and indicate that although the majority of distances obtained in each region fit with classification of a certain isolate, only the ranges obtained in the 340 bp NS5B-region are non-overlapping and therefor conclusive. However, as was performed in the present invention, it is preferable to obtain sequence information from at least 2 regions before final classification of a given isolate.

Designation of a number to the different types of HCV and HCV types nomenclature is based on chronological discovery of the different types. The numbering system used in the present invention might still fluctuate according to international conventions or guidelines. For example, "type 4" might be changed into "type 5" or "type 6".

The term "subtype" corresponds to a group of HCV isolates of which the complete polyprotein shows a homology of more than 90% both at the nucleic acid and amino acid levels, or of which the NS5 region between nucleotide positions 7932 and 8271 shows a homology of more than 90% at the nucleic acid level to the corresponding parts of the genomes of the other isolates of the same group, with said numbering beginning with the adenine residue of the initiation codon of the HCV polyprotein. Isolates belonging to the same type but different subtypes of HCV show homologies of more than 74% at the nucleic acid level and of more than 78% at the amino acid level.

The term "BR36 subgroup" refers to a group of type 3a HCV isolates (BR36, BR33, BR34) that are 95%, preferably 95.5%, most preferably 96% homologous to the sequences as represented in SEQ ID NO 1, 3, 5, 7, 9, 11 in the NS-5b region from position 8023 to 8235.

It is to be understood that extremely variable regions like the E1, E2 and NS4 regions will exhibit lower homologies than the average homology of the complete genome of the polyprotein.

Using these criteria, HCV isolates can be classified into at least 6 types. Several subtypes can clearly be distinguished in types 1, 2, 3 and 4: 1a, 1b, 2a, 2b, 2c, 2d, 3a, 3b, 4a, 4b, 4c, 4d, 4e, 4f, 4g, 4h, 4i and 4j based on homologies of the 5' UR and coding regions including the part of NS5 between positions 7932 and 8271. An overview of most of the reported isolates and their proposed classification according to the typing system of the present invention as well as other proposed classifications is presented in Table 3.

TABLE 3

HCV CLASSIFICATION

|  | OKA-MOTO | MORI | NAKAO | CHA | PROTOTYPE |
|---|---|---|---|---|---|
| 1a | I | I | Pt | GI | HCV-1, HCV-H, HC-J1 |
| 1b | II | II | KI | GII | HCV-J, HCV-BK, HCV-T, HC-JK1, HC-J4, HCV-CHINA |
| 1c |  |  |  |  | HC-G9 |
| 2a | III | III | K2a | GIII | HC-J6 |
| 2b | IV | IV | K2b | GIII | HC-J8 |
| 2c |  |  |  |  | S83, ARG6, ARG8, I10, T983 |
| 2d |  |  |  |  | NE92 |
| 3a | V | V | K3 | GIV | E-b1, Ta, BR36, BR33, HD10, NZL1 |
| 3b |  | VI | K3 | GIV | HCV-TR, Tb |
| 3c |  |  |  |  | BE98 |
| 4a |  |  |  |  | Z4, GB809-4 |
| 4b |  |  |  |  | Z1 |
| 4c |  |  |  |  | GB116, GB358, GB215, Z6, Z7 |
| 44 |  |  |  |  | DK13 |
| 4e |  |  |  |  | GB809-2, CAM600, CAM736 |
| 4f |  |  |  |  | CAM622, CAM627 |
| 4g |  |  |  |  | GB549 |
| 4h |  |  |  |  | GB438 |
| 4i |  |  |  |  | CAR4/1205 |
| 4j |  |  |  |  | CAR1/501 |

TABLE 3-continued

HCV CLASSIFICATION

| OKA-MOTO | MORI | NAKA O | CHA | PROTOTYPE |
|---|---|---|---|---|
| 4k | | | | EG29 |
| 5a | | GV | | SA3, SA4, SA1, SA7, SA11, BE95 |
| 6a | | | | HK1, HK2, HK3, HK4 |

The term "complement" refers to a nucleotide sequence which is complementary to an indicated sequence and which is able to hybridize to the indicated sequences.

The composition of the invention can comprise many combinations. By way of example, the composition of the invention can comprise:
two (or more) nucleic acids from the same region or,
two nucleic acids (or more), respectively from different regions, for the same isolate or for different isolates,
or nucleic acids from the same regions and from at least two different regions (for the same isolate or for different isolates).

The present invention relates more particularly to a polynucleic acid composition as defined above, wherein said polynucleic acid corresponds to a nucleotide sequence selected from any of the following HCV type 3 genomic sequences:

an HCV genomic sequence having a homology of at least 67%, preferably more than 69%, more preferably 71%, even more preferably more than 73%, or most preferably more than 76% to any of the sequences as represented in SEQ ID NO 13, 15, 17, 19, 21, 23, 25 or 27 (HD10, BR36 or BR23 sequences) in the region spanning positions 417 to 957 of the Core/E1 region as shown in FIG. 4;

an HCV genomic sequence having a homology of at least 65%, preferably more than 67%, preferably more than 69%, even preferably more than 70%, most preferably more than 74% to any of the sequences as represented in SEQ ID NO 13, 15, 17, 19, 21, 23, 25 or 27 (HD10, BR36 or BR33 sequences) in the region spanning positions 574 to 957 of the E1 region as shown in FIG. 4;

an HCV genomic sequence as having a homology of at least 79%, more preferably at least 81%, most preferably more than 83% or more to any of the sequences as represented in SEQ ID NO 147 (representing positions 1 to 346 of the Core region of HVC type 3c, sequence BE98) in the region spanning positions 1 to 378 of the Core region as shown in FIG. 3;

an HCV genomic sequence of HVC type 3a having a homology of at least 74%, more preferably at least 76 most preferably more than 78% or more to any of the sequences as represented in SEQ ID NO 13, 15, 17, 19, 21, 23, 25 or 27 (HD10, BR36 or BR33 sequences) in the region spanning positions 417 to 957 in the Core/E1 region as shown in FIG. 4;

an HCV genomic sequence of HCV type 3a as having a homology of at least 74%, preferably more than 76%, most preferably 78% or more to any of the sequences as represented in SEQ ID NO 13, 15, 17, 19, 21, 23, 25 or 27 (HD10, BR36 or BR33 sequences) in the region spanning positions 574 to 957 in the E1 region as shown in FIG. 4;

an HCV genomic sequence as having a homology of more than 73.5%, preferably more than 74%, most preferably 75;% homology to the sequence as represented in SEQ ID NO 29 (HCC153 sequence) in the region spanning positions 4664 to 4730 of the NS3 region as shown in FIG. 6;

an HCV genomic sequence having a homology of more than 70%, preferably more than 72%, most preferably more than 74% homology to any of the sequences as represented in SEQ ID NO 29, 31, 33, 35, 37 or 39 (HCC153, HD10, BR36 sequences) in the region spanning positions 4892 to 5292 in the NS3/NS4 region as shown in FIG. 6 or 10;

an HCV genomic sequence of the BR36 subgroup of HCV type 3a as having a homology of more than 95%, preferably 95,5%, most preferably 96% homology to any of the sequences as represented in SEQ ID NO 5, 7, 1, 3, 9 or 11 (BR34, BR33, BR36 sequences) in the region spanning positions 8023 to 8235 of the NS5 region as shown in FIG. 1;

an HCV genomic sequence of the BR36 subgroup of HCV type 3a as having a homology of more than 96%, preferably 96.5%, most preferably 97% homology to any of the sequences as represented in SEQ ID NO 5, 7, 1, 3, 9 or 11 (BR34, BR33, BR36 sequences) in the region spanning positions 8023 to 8192 of the NS5B region as shown in FIG. 1;

an HCV genomic sequence of HCV type 3c being characterized as having a homology of more than 79%, more preferably more than 81%, and most preferably more than 83% to the sequence as represented in SEQ ID NO 149 (BE98 sequence) in the region spanning positions 7932 to 8271 in the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

an HCV genomic sequence being characterized as having a nucleotide distance of less than 0.44, preferably of less than 0.40, most preferably of less than 0.36 to any of the sequences as represented in SEQ ID NO 13, 15, 17, 19, 21, 23, 25 or 27 in the region spanning positions 417 to 957 of the Core/E1 region as shown in FIG. 4;

an HCV genomic sequence being characterized having a nucleotide distance of less than 0.53, preferably less than 0.49, most preferably of less than 0.45 to any of the sequences as represented in SEQ ID NO 19, 21, 23, 25 or 27 in the region spanning positions 574 to 957 of the E1 region as shown in FIG. 4;

an HCV genomic sequence characterized having a nucleotide distance of less than 0.15, preferably less than 0.13, and most preferably less than 0.11 to any of the sequences as represented in SEQ ID NO 147 in the region spanning positions 1 to 378 of the Core region as shown in FIG. 3;

an HCV genomic sequence of HVC type 3a being characterized as having a nucleotide distance of less than 0.3, preferably less than 0.26, most preferably of less than 0.22 to any of the sequences as represented in SEQ ID NO 13, 15, 17, 19, 21, 23, 25 or 27 in the region spanning positions 417 to 957 in the Core/E1 region as shown in FIG. 4;

an HCV genomic sequence of HCV type 3a being characterized as having a nucleotide distance of less than 0.35, preferably less than 0.31, most preferably of less than 0.27 to any of the sequences as represented in SEQ ID NO 13, 15, 17, 19, 21, 23, 25 or 27 in the region spanning positions 574 to 957 in the E1 region as shown in FIG. 4;

an HCV genomic sequence of the BR36 subgroup of HCV type 3a being characterized as having a nucleotide sequence of less than 0.0423, preferably less than 0.042, preferably less than 0.0362 to any of the sequences as represented in SEQ ID NO 5, 7, 1, 3, 9 or 11 in the region spanning positions 8023 to 8235 of the NS5 region as shown in FIG. 1;

an HCV genomic sequence of HCV type 3c being characterized as having a nucleotide distance of less than 0.255, preferably of less than 0.25, more preferably of less than 0.21, most preferably of less than 0.17 to the sequence as represented in SEQ ID NO 149 in the region spanning positions 7932 to 8271 in the NS5B region as shown in FIG. 1.

In the present application, the E1 sequences encoding the antigenic ectodomain of the E1 protein, which does not overlap the carboxyterminal signal-anchor sequences of E1 disclosed by Cha et al. (1992; WO 92/19743), in addition to the NS4 epitope region, and a part of the NS5 region are disclosed for 4 different isolates: BR33, BR34, BR36, HCC153 and HD10, all belonging to type 3a (SEQ ID NO 1, 3, 5, 7, 9, 11, 13, 15, 17, 19, 21, 23, 25, 27, 29, 31, 35, 37 or 39).

Also within the present invention are new subtype 3c sequences (SEQ ID NO 147, 149 of the isolate BE98 in the Core and NS5 regions (see FIGS. 3 and 1).

Finally the present invention also relates to a new subtype 3a sequence as represented in SEQ ID NO 217 (see FIG. 1).

Also included within the present invention are sequence variants of the polynucleic acids as selected from any of the nucleotide sequences as given in any of the above mentioned SEQ ID numbers, with said sequence variants containing either deletions and/or insertions of one or more nucleotides, mainly at the extremities of oligonucleotides (either 3' or 5'), or substitutions of some non-essential nucleotides by others (including modified nucleotides an/or inosine), for example, a type 1 or 2 sequence might be modified into a type 3 sequence by replacing some nucleotides of the type 1 or 2 sequence with type-specific nucleotides of type 3 as shown in FIG. 1 (NS5 region), FIG. 3 (Core region), FIG. 4 (Core/E1 region), FIG. 6 and 10 (NS3/NS4 region).

According to another embodiment, the present invention relates to a polynucleic acid composition as defined above, wherein said polynucleic acids correspond to a nucleotide sequence selected from any of the following HCV type 5 genomic sequences:

an HCV genomic sequence as having a homology of more than 85%, preferably more than 86%, most preferably more than 87% homology to any of the sequences as represented in SEQ ID NO 41, 43, 45, 47, 49, 51, 53 (PC sequences) or 151 (BE95 sequence) in the region spanning positions 1 to 573 of the Core region as shown in FIG. 9 and 3;

an HCV genomic sequence as having a homology of more than 61%, preferably more than 63%, more preferably more than 65% homology, even more preferably more than 66% homology and most preferably more than 67% homology (f.i. 69 and 71%) to any of the sequences as represented in SEQ ID NO 41, 43, 45, 47, 49, 51, 53 (PC sequences). 153 or 155 (BE95, BE100 sequences) in the region spanning positions 574 to 957 of the E1 region as shown in FIG. 4;

an HCV genomic sequence having a homology of more than 76.5%, preferably of more than 77%, most preferably of more than 78% homology with any of the sequences as represented in SEQ ID NO 55, 57, 197 or 199 (PC sequences) in the region spanning positions 3856 to 4209 of the NS3 region as shown in FIG. 6 or 10;

an HCV genomic sequence having a homology of more than 68%, preferably of more than 70%, most preferably of more than 72% homology with the sequence as represented in SEQ ID NO 157 (BE95 sequence) in the region spanning positions 980 to 1179 of the E1/E2 region as shown in FIG. 13;

an HCV genomic sequence having a homology of more than 57%, preferably more than 59%, most preferably more than 61% homology to any of the sequences as represented in SEQ ID NO 59 or 61 (PC sequences) in the region spanning positions 4936 to 5296 of the NS4 region as shown in FIG. 6 or 10;

an HCV genomic sequence as having a homology of more than 93%, preferably more than 93.5%, most preferably more than 94% homology to any of the sequences as represented in SEQ ID NO 159 or 161 (BE95 or BE96 sequences) in the region sparing positions 7932 to 8271 of the NS5B region as shown in FIG. 1.

Preferentially the above-mentioned genomic HCV sequences depict sequences from the coding regions of all the above-mentioned sequences.

According to the nucleotide distance classification system (with said nucleocide distances being calculated as explained above), said sequences of said composition are selected from:

a nucleotide distance of less than 0.53, preferably less than 0.51, more preferably less than 0.49 for the E1 region to the type 5 sequences depicted above;

a nucleotide distance of less than 0.3, preferably less than 0.28, more preferably of less than 0.26 for the Core region to the type 5 sequences depicted above;

a nucleotide distance of less than 0.072, preferably less than 0.071, more preferably less than 0.070 for the NS5B region to the type 5 sequences as depicted above.

Isolates with similar sequences in the 5' UR to a group of isolates including SA1, SA3, and SA7 described in the 5' UR by Bukh et al. (1992), have been reported and described in the 5' UR and NS5 region as group V by Cha et al. (1992; WO 92/19743). This group of isolates belongs to type 5a as described in the present invention (SEQ ID NO 41, 43, 45, 47, 49, 51, 53, 55, 57, 59, 61, 151, 153, 155, 157, 159, 161, 197 and 199).

Also included within the present invention are sequence variants of the polynucleic acids as selected from any of the nucleotide sequences as given in any of the above given SEQ ID numbers with said sequence variants containing either deletion and/or insertions of one or more nucleotides, mainly at the extremities of oligonucleotides (either 3' or 5'), or substitutions of some non-essential nucleotides (i.e. nucleotides not essential to discriminate between different genotypes of HCV) by others (including modified nucleotides an/or inosine), for example, a type 1 or 2 sequence might be modified into a type 5 sequence by replacing some nucleotides of the type 1 or 2 sequence with type-specific nucleotides of type 5 as shown in FIG. 3 (Core region), FIG. 4 (Core/E1 region), FIG. 10 (NS3/NS4 region), FIG. 14 (E1/E2 region).

Another group of isolates including BU74 and BU79 having similar sequences in the 5' UR to isolates including Z6 and Z7 as described in the 5' UR by Bukh et al. (1992), have been described in the 5' UR and classified as a new type 4 by the inventors of this application (Stuyver et al., 1993). Coding sequences, including core, E1 and NS5 sequences of several new Gabonese isolates belonging to this group, are disclosed in the present invention (SEQ ID NO 106, 108, 110, 112, 114, 116, 118, 120 and 122).

According to yet another embodiment, the present invention relates to a composition as defined above, wherein said polynucleic acids correspond to a nucleotide sequence selected from any of the following HCV type 4 genomic sequences:

- an HCV genomic sequence having a homology of more than 66%, preferably more than 68%, most preferably more than 70% homology in the E1 region spanning positions 574 to 957 to any of the sequences as represented in SEQ ID NO 118, 120 or 122 (GB358, GB549, GB809 sequences) as shown in FIG. 4;
- an HCV genomic sequence having a homology of more than 71%, preferably more than 72%, most preferably more than 74% homology to any of the sequences as represented in SEQ ID NO 118, 120 or 122 (GB358, GB549, GB809 sequences) in the region spanning positions 379 to 957 of the E1 region as shown in FIG. 4;
- an HCV genomic sequence having a homology of more than 92%, preferably more than 93%, most preferably more than 94% homology to any of the sequences as represented in SEQ ID NO 163 or 165 (GB809, CAM600 sequences) in the region spanning positions 1 to 378 of the Core/E1 region as shown in FIG. 4;
- an HCV genomic sequence (subtype 4c) having a homology of more than 85%, preferably more than 86%, more preferably more than 86.5% homology, most preferably more than 87, more than 88 or more than 89% homology to any of the sequences as represented in SEQ ID NO 183, 185 or 187 (GB116, GB215, GB809 sequences) in the region spanning positions 379 to 957 of the E1 region as shown in FIG. 4;
- an HCV genomic sequence (subtype 4a) having a homology of more than 81%, preferably more than 83%, most preferably more than 85% homology to the sequence as represented in SEQ ID NO 189 (GB908 sequence) in the region spanning positions 379 to 957 of the E1 region as shown in FIG. 4;
- an HCV genomic sequence (subtype 4e) having a homology of more than 85%, preferably more than 87%, most preferably more than 89% homology to any of the sequences as represented in SEQ ID NO 167 or 169 (CAM600, GB908 sequences) in the region spanning positions 379 to 957 of the E1 region as shown in FIG. 4;
- an HCV genomic sequence (subtype 4f) having a homology of more than 79%, preferably more than 81%, most preferably more than 83% homology to any of the sequences as represented in SEQ ID NO 171 or 173 (CAMG22, CAMG27 sequences) in the region spanning positions 379 to 957 of the E1 region as shown in FIG. 4;
- an HCV genomic sequence (subtype 4g) having a homology of more than 84%, preferably more than 86%, most preferably more than 88% homology to the sequence as represented in SEQ ID NO 175 (GB549 sequence) in the region spanning positions 379 to 957 of the E1 region as shown in FIG. 4;
- an HCV genomic sequence (subtype 4h) having a homology of more than 83%, preferably more than 85%, most preferably more than 87% homology to the sequence as represented in SEQ ID NO 177 (GB438 sequence) in the region spanning positions 379 to 957 of the E1 region as shown in FIG. 4;
- an HCV genomic sequence (subtype 4i) as having a homology of more than 76%, preferably more than 78%, most preferably more than 80% homology to the sequence as represented in SEQ ID NO 179 (CAR4/1205 sequence) in the region spanning positions 379 to 957 of the E1 region as shown in FIG. 4;
- an HCV genomic sequence (subtype 4j?) having a homology of more than 84%, preferably more than 86%, most preferably more than 88% homology to the sequence as represented in SEQ ID NO 181 (CAR4/901 sequence) in the region spanning positions 379 to 957 of the E1 region as shown in FIG. 4;
- an HCV genomic sequence as having a homology of more than 73%, preferably more than 75%, most preferably more than 77% homology to any of the sequences as represented in SEQ ID NO 106, 108, 110, 112, 114, or 116 (GB48, GB116, GB215, GB358, GB549, GB809 sequences) in the region spanning positions 7932 to 8271 of the NS5 region as shown in FIG. 1;
- an HCV genomic sequence (subtype 4c) having a homology of more than 88%, preferably more than 89%, most preferably more than 90% homology to any of the sequences as represented in SEQ ID NO 106, 108, 110, or 112 (GB48, GB116, GB215, GB358 sequences) in the region spanning positions 7932 to 8271 of the NS5 region as shown in FIG. 1;
- an HCV genomic sequence (subtype 4e) having a homology of more than 88%, preferably more than 89%, most preferably more than 90% homology to any of the sequences as represented in SEQ ID NO 116 or 201 (GB809 or CAM 600 sequences) in the region spanning positions 7932 to 8271 of the NS5 region as shown in FIG. 1;
- an HCV genomic sequence (subtype 4f) having a homology of more than 87%, preferably more than 89%, most preferably more than 90% homology to the sequence as represented in SEQ ID NO 203 (CAMG22 sequence) in the region spanning positions 7932 to 8271 of the NS5 region as shown in FIG. 1;
- an HCV genomic sequence (subtype 4g) as having a homology of more than 85%, preferably more than 87%, most preferably more than 89% homology to the sequence as represented in SEQ ID NO 114 (GB549 sequence) in the region spanning positions 7932 to 8271 of the NS5 region as shown in FIG. 1;
- an HCV genomic sequence (subtype 4h) as having a homology of more than 86%, preferably more than 87%, more preferably more than 88% homology, more preferably more than 89% homology to the sequence as represented in SEQ ID NO 207 (GB437 sequence) in the region spanning positions 7932 to 8271 of the NS5 region as shown in FIG. 1;
- an HCV genomic sequence (subtype 4i) having a homology of more than 81%, preferably more than 86%, most preferably more than 88% homology to the sequence as represented in SEQ ID NO 209 (CAR4/1205 sequence) in the region spanning positions 7932 to 8271 of the NS5 region as shown in FIG. 1;
- an HCV genomic sequence (subtype 4j) having a homology of more than 81%, preferably more than 83%, most preferably more than 85% homology to the sequence as represented in SEQ ID NO 211 (CAR1/501 sequence) in the region spanning positions 7932 to 8271 of the NS5 region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

an HCV genomic sequence (type 4) being characterized as having a nucleotide distance of less than 0.52, 0.50, 0.4880, 0.46, 0.44, 0.43 or most preferably less than 0.42 in the region spanning positions 574 to 957 to any of the sequences as represented in SEQ ID NO 118, 120 or 122 in the region spanning positions 1 to 957 of the Core/E1 region as shown in FIG. 4;

an HCV genomic sequence (type 4) being characterized as having a nucleotide distance of less than 0.39, 0.36 0.34 0.32 or most preferably less than 0.31 to any of the sequences as represented in SEQ ID NO 118, 120 or 122 in the region spanning positions 379 to 957 of the E1 region as shown in FIG. 4;

an HCV genomic sequence (subtype 4c) being characterized as having a nucleotide distance of less than 0.27, 0.26, 0.24, 0.22, 0.20, 0.18, 0.17, 0.162, 0.16 or most preferably less than 0.15 to any of the sequences as represented in SEQ ID NO 183, 185 or 187 in the region spanning positions 379 to 957 of the E1 region as shown in FIG. 4;

an HCV genomic sequence (subtype 4a) being characterized as having a nucleotide distance of less than 0.30, 0.28, 0.26, 0.24, 0.22, 0.21 or most preferably of less than 0.205 to the sequence as represented in SEQ ID NO 189 in the region spanning positions 379 to 957 of the E1 region as shown in FIG. 4;

an HCV genomic sequence (subtype 4e) being characterized as having a nucleotide distance of less than 0.26, 0.25, 0.23, 0.21, 0.19, 0.17, 0.165, most preferably less than 0.16 to any of the sequences as represented in SEQ ID NO 167 or 169 in the region spanning positions 379 to 957 of the E1 region as shown in FIG. 4;

an HCV genomic sequence (subtype 4f) being characterized as having a nucleotide distance of less than 0.26, 0.24, 0.22, 0.20, 0.18, 0.16, 0.15 or most preferably less than 0.14 to any of the sequences as represented in SEQ ID NO 171 or 173 in the region spanning positions 379 to 957 of the E1 region as shown in FIG. 4;

an HCV genomic sequence (subtype 4g) being characterized as having a nucleotide distance of less than 0.20, 0.19, 0.18, 0.17 or most preferably of less than 0.16 to the sequence as represented in SEQ ID NO 175 in the region spanning positions 379 to 957 of the E1 region as shown in FIG. 4;

an HCV genomic sequence (subtype 4h) being characterized as having a nucleotide distance of less than 0.20. 0.19, 0.18, 0.17 and most preferably less than 0.16 to the sequence as represented in SEQ ID NO 177 in the region spanning positions 379 to 957 of the E1 region as shown in FIG. 4;

an HCV genomic sequence (subtype 4i) being characterized as having a nucleotide distance of less than 0.27, 0.25, 0.23, 0.21 and preferably less than 0.16 to the sequence as represented in SEQ ID NO 179 in the region spanning positions 379 to 957 of the E1 region as shown in FIG. 4;

an HCV genomic sequence (subtype 4j?) being characterized as having a nucleotide distance of less than 0.19, 0.18, 0.17, 0.165 and most preferably less than 0.16 to the sequence as represented in SEQ ID NO 181 in the region spanning positions 379 to 957 of the E1 region as shown in FIG. 4;

an HCV genomic sequence (type 4) being characterized as having a nucleotide distance of less than 0.35, 0.34, 0.32 and most preferably of less then 0.30 to any of the sequences as represented in SEQ ID NO 106, 108, 110, 112, 114, or 116 in the region spanning positions 7932 to 8271 of the NS5 region as shown in FIG. 1;

an HCV genomic sequence (subtype 4c) being characterized as having a nucleotide distance of less than 0.18, 0.16, 0.14, 0.135, 0.13, 0.1275 or most preferably less than 0.125 to any of the sequences as represented in SEQ ID NO 106, 108, 110, or 112 in the region spanning positions 7932 to 8271 of the NS5 region as shown in FIG. 1;

an HCV genomic sequence (subtype 4e) being characterized as having a nucleotide distance of less than 0.15, 0.14, 0.135, 0.13 and most preferably of less than 0.125 to any of the sequences as represented in SEQ ID NO 116 or 201 in the region spanning positions 7932 to 8271 of the NS5 region as shown in FIG. 1;

an HCV genomic sequence (subtype 4t) being characterized as having a nucleotide distance of less than 0.15, 0.14, 0.135, 0.13 or most preferably less than 0.125 to the sequence as represented in SEQ ID NO 203 in the region spanning positions 7932 to 8271 of the NS5 region as shown in FIG. 1;

an HCV genomic sequence (subtype 4g) being characterized as having a nucleotide distance of less than 0.17, 0.16, 0.15, 0.14, 0.13 or most preferably less than 0.125 to the sequence as represented in SEQ ID NO 114 in the region spanning positions 7932 to 8271 of the NS5 region as shown in FIG. 1;

an HCV genomic sequence (subtype 4h) being characterized as having a nucleotide distance of less than 0.155, 0.15, 0.145, 0.14, 0.135, 0.13 or most preferably less than 0.125 to the sequence as represented in SEQ ID NO 207 in the region spanning positions 7932 to 8271 of the NS5 region as shown in FIG. 1;

an HCV genomic sequence (subtype4i) being characterized as having a nucleotide distance of less than 0.17, 0.16, 0.15, 0.14, 0.13 or most preferably of less than 0.125 to the sequence as represented in SEQ ID NO 209 in the region spanning positions 7932 to 8271 of the NS5 region as shown in FIG. 1;

an HCV genomic sequence (subtype 4j) being characterized as having a nucleotide distance of less than 0.21, 0.20, 0.19, 0.18, 0.17 0.16, 0.15, 0.14, 0.13 and most preferably of less than 0.125 to the sequence as represented in SEQ ID NO 211 in the region spanning positions 7932 to 8271 of the NS5 region as shown in FIG. 1.

Also included within the present invention are sequence variants of the polynucleic acids as selected from any of the nucleotide sequences as given in any of the above given SEQ ID numbers with said sequence variants containing either deletion and/or insertions of one or more nucleotides, mainly at the extremities of oligonucleotides (either 3' or 5'), or substitutions of some non-essential nucleotides (i.e. Nucleotides not essential to discriminate between different genotypes of HCV) by others (including modified nucleotides an/or inosine), for example, a type 1 or 2 sequence might be modified into a type 4 sequence by replacing some nucleotides of the type 1 or 2 sequence with type-specific nucleotides of type 4 as shown in FIG. 3 (Core region), FIG. 4 (Core/E1 region), FIG. 10 (NS3/NS4 region), FIG. 14 (E1/E2 region).

The present invention also relates to a sequence as represented in SEQ ID NO 193 (GB724 sequence).

After aligning NS5 or E1 sequences of GB48, GB, 116, GB215, GB358, GB549 and GB809, these isolates clearly segregated into 3 subtypes within pipe 4: GB48, GB116, GB215 and GB358 belong to the sybtype designated 4c, GB549 to subtype 4g and GB809 to subtype 4e. In NS5, GB809 (subtype 4e) showed a higher nucleic acids homology to subtype 4c isolates (85.6–86.8%) than to GB549 (subtype 4g, 79.7%), while GB549 showed similar homologies to both other subtypes (78.8 to 80% to subtype 4c and 79.7% to subtype 4e). In E1, subtype 4c showed equal nucleic acid homologies of 75.2% to subtypes 4g and 4e while 4g and 4e were 78.4% homologous. At the amino acid level however, subtype 4e showed a normal homology to subtype 4c (80.2%), while subtype 4g was more homologous to 4c (83.3%) and 4e (84.1%).

According to yet another embodiment, the present invention relates to a composition as defined above, wherein said polynucleic acids correspond to a nucleotide sequence selected from any of the following HCV type 2d genomic sequences:

an HCV genomic sequence as having a homology of more than 78%, preferably more than 80%, most preferably more than 82% homology to the sequence as represented in SEQ ID NO (NE92) 143 in the region spanning positions 379 to 957 of the Core/E1 region as shown in FIG. 4;

an HCV genomic sequence as having a homology of more than 74%, preferably more than 76%, most preferably more than 78% homology to the sequence as represented in SEQ ID NO 143 (NE92) in the region spanning positions 574 to 957 as shown in FIG. 4;

an HCV genomic sequence as having a homology of more than 87%, preferably more than 89%, most preferably more than 91% homology to the sequence as represented in SEQ ID NO 145 (NE92) in the region spanning positions 7932 to 8271 of the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

a nucleotide distance of less than 0.32, preferably less than 0.31, more preferably less than 0.30 for the E1 region (574 to 957) to any of the above specified sequences:

a nucleotide distance of less than 0.08, preferably less than 0.07, more preferably less than 0.06 for the Core region (1 to 378) to any of the above given sequences a nucleotide distance of less than 0.15, preferentially less than 0.13, more preferentially less than 0.12 for the NS5B region to any or the above-specified sequences.

Polynucleic acid sequences according to the present invention which are homologous to the sequences as represented by a SEQ ID NO can be characterized and isolated according to any of the techniques known in the art, such as amplification by means of type or subtype specific primers, hybridization with type or subtype specific probes under more or less stringent conditions, serological screening methods (see examples 4 and 11) or via the LiPA typing system.

Polynucleic acid sequences of the genomes indicated above from regions not yet depicted in the present examples, figures and sequence listing can be obtained by any of the techniques known in the art, such as amplification techniques using suitable primers from the type or subtype specific sequences of the present invention.

The present invention relates also to a composition as defined above, wherein said polynucleic acid is liable to act as a primer for amplifying the nucleic acid of a certain isolate belonging to the genotype from which the primer is derived.

An example of a primer according to this embodiment of the invention is HCPr 152 as shown in table 7 (SEQ ID NO 79).

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides. Specific length and sequence will depend on the complexity of the required DNA or RNA targets, as well as on the conditions of primer use such as temperature and ionic strength.

The fact that amplification primers do not have to match exactly with corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton. 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{32}P$, $^{35}S$, etc.) or non-isotopic (biotin, digoxigenin, etc.). The amplification reaction is repeated between 20 and 80 times. advantageously between 30 and 50 times.

The present invention also relates to a composition as defined above, wherein said polynucleic acid is able to act as a hybridization probe for specific detection and/or classification into types of a nucleic acid containing said nucleotide sequence, with said oligonucleotide being possibly labelled or attached to a solid substrate.

The term "probe" refers to single stranded sequence-specific oligonucleotides which have a sequence which is complementary to the target sequence of the HCV genotype(s) to be detected.

Preferably, these probes are about 5 to 50 nucleotides long, more preferably from about 10 to 25 nucleotides.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The present invention also relates to the use of a composition as defined above for detecting the presence of one or more HCV genotypes, more particularly for detecting the presence of a nucleic acid of any of the HCV genotypes having a nucleotide sequence as defined above, present in a biological sample liable to contain them, comprising at least the following steps:
(i) possibly extracting sample nucleic acid,
(ii) possibly amplifying the nucleic acid with at least one of the primers as defined above or any other HCV subtype 2d, HCV type 3, HCV type 4, HCV type 5 or universal HCV primer,
(iii) hybrizing the nucleic acids of the biological sample, possibly under denatured conditions, and with said nucleic acids being possibly labelled during or after amplification, at appropriate conditions with one or more probes as defined above, with said probes being preferably attached to a solid substrate,
(iv) washing at appropriate conditions,
(v) detecting the hybrids formed,
(vi) inferring the presence of one or more HCV genotypes present from the observed hybridization pattern.

Preferably, this technique could be performed in the Core or NS5B region.

The term "nucleic acid" can also be referred to as analyte strand and corresponds to a single- or double-stranded nucleic acid molecule. This analyte strand is preferentially positive-or negative stranded RNA, cDNA or amplified cDNA.

The term "biological sample" refers to any biological sample (tissue or fluid) containing HCV nucleic acid sequences and refers more particularly to blood serum or plasma samples.

The term "HCV subtype 2d primer" refers to a primer which specifically amplifies HCV subtype 2d sequences present in a sample (see Examples section and figures).

The term "HCV type 3 primer" refers to a primer which specifically amplifies HCV type 3 sequences present in a sample (see Examples section and figures).

The term "HCV type 4 primer" refers to a primer which specifically amplifies HCV type 4 genomes present in a sample.

The term "universal HCV primer" refers to oligonucleotide sequences complementary to any of the conserved regions of the HCV genome.

The term "HCV type 5 primer" refers to a primer which specifically amplifies HCV type 5 genomes present in a sample. The term "universal HCV primer" refers to oligonucleotide sequences complementary to any of the conserved regions of the HCV genome.

The expression "appropriate" hybridization and washing conditions are to be understood as stringent and are generally known in the art (e.g. Maniatis et al., Molecular Cloning: A Laboratory Manual, New York, Cold Spring Harbor Laboratory, 1982).

However, according to the hybridization solution (SSC, SSPE, etc.), these probes should be hybridized at their appropriate temperature in order to attain sufficient specificity.

The term "labelled" refers to the use of labelled nucleic acids. This may include the use of labelled nucleotides incorporated during the polymerase step of the amplification such as illustrated by Saiki et al. (1988) or Bej et al. (1990) or labelled primers, or by any other method known to the person skilled in the art.

The process of the invention comprises the steps of contacting any of the probes as defined above, with one of the following elements:
either a biological sample in which the nucleic acids are made available for hybridization,
or the purified nucleic acids contained in the biological sample
or a single copy derived from the purified nucleic acids,
or an amplified copy derived from the purified nucleic acids, with said elements or with said probes being attached to a solid substrate.

The expression "inferring the presence of one or more HCV genotypes present from the observed hybridization pattern" refers to the identification of the presence of HCV genomes in the sample by analyzing the pattern of binding of a panel of oligonucleotide probes. Single probes may provide useful information concerning the presence or absence of HCV genomes in a sample. On the other hand, the variation of the HCV genomes is dispersed in nature, so rarely is any one probe able to identify uniquely a specific HCV genome. Rather, the identity of an HCV genotype may be inferred from the pattern of binding of a panel of oligonucleotide probes, which are specific for (different) segments of the different HCV genomes. Depending on the choice of these oligonucleotide probes, each known HCV genotype will correspond to a specific hybridization pattern upon use of a specific combination of probes. Each HCV genotype will also be able to be discriminated from any other HCV genotype amplified with the same primers depending on the choice of the oligonucleotide probes. Comparison of the generated pattern of positively hybridizing probes for a sample containing one or more unknown HCV sequences to a scheme of expected hybridization patterns, allows one to clearly infer the HCV genotypes present in said sample.

The present invention thus relates to a method as defined above, wherein one or more hybridization probes are selected from any of SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, 106, 108, 110, 112, 114, 116, 118, 120, 122, 143, 145, 147, 149, 151, 153, 155, 157, 159, 161, 163, 165, 167, 169, 171, 173, 175, 177, 179, 181, 183, 185, 187, 198, 191, 193, 195, 197, 199, 201, 203, 205, 207, 209, 211, 213, 215, 217, 222, 269 or sequence variants thereof, with said sequence variants containing deletions and/or insertions of one or more nucleotides, mainly at their extremities (either 3' or 5'), or substitutions of some non-essential nucleotides (i.e. nucleotides not essential to discriminate between genotypes) by others (including modified nucleotides or inosine), or with said variants consisting of the complement of any of the above-mentioned oligonucleotide probes, or with said variants consisting of ribonucleotides instead of deoxyribonucleotides, all provided that said variant probes can be caused to hybridize with the same specificity as the oligonucleotide probes from which they are derived.

In order to distinguish the amplified HCV genomes from each other, the target polynucleic acids are hybridized to a set of sequence-specific DNA probes targetting HCV genotypic regions located in the HCV polynucleic acids.

Most of these probes target the most type-specific regions of HCV genotypes, but some can be caused to hybridize to more than one HCV genotype.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions (Jacobs et al., 1988).

Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the ample and the oligonucleotide probes according to the present invention may be used.

According to an advantageous embodiment, the process of detecting one or more HCV genotypes contained in a biological sample comprises the steps of contacting amplified HCV nucleic acid copies derived from the biological sample, with oligonucleotide probes which have been immobilized as parallel lines on a solid support.

According to this advantageous method, the probes are immobilized in a Line Probe Assay (LiPA) format. This is a reverse hybridization format (Saiki et al., 1989) using membrane strips onto which several oligonucleotide probes (including negative or positive control oligonucleotides) can be conveniently applied as parallel lines.

The invention thus also relates to a solid support, preferably a membrane strip, carrying on its surface, one or more probes as defined above, coupled to the support in the form of parallel lines.

The LiPA is a very rapid and user-friendly hybridization test. Results can be read 4 h. after the start of the amplification. After amplification during which usually a non-isotopic label is incorporated in the amplified product, and alkaline denaturation, the amplified product is contacted with the probes on the membrane and the hybridization is carried out for about 1 to 1,5 h hybridized polynucleic acid is detected. From the hybridization pattern generated, the HCV type can be deduced either visually, but preferably using dedicated software. The LiPA format is completely compatible with commercially available scanning devices, thus rendering automatic interpretation of the results very reliable. All those advantages make the LiPA format liable for the use of HCV detection in a routine setting. The LiPA format should be particularly advantageous for detecting the presence of different HCV genotypes.

The present invention also relates to a method for detecting and identifying novel HCV genotypes, different from the known HCV genomes, comprising the steps of:
  determining to which HCV genotype the nucleotides present in a biological sample belong, according to the process as defined above,
  in the case of observing a sample which does not generate a hybridization pattern compatible with those defined in Table 3, sequencing the portion of the HCV genome sequence corresponding to the aberrantly hybridizing probe of the new HCV genotype to be determined.

The present invention also relates to the use of a composition as defined above, for detecting one or more genotypes of HCV present in a biological sample liable to contain them, comprising the steps of:
  (i) possibly extracting sample nucleic acid,
  (ii) amplifying the nucleic acid with at least one of the primers as defined above,
  (iii) sequencing the amplified products
  (iv) inferring the HCV genotypes present from the determined sequences by comparison to all known HCV sequences.

The present invention also relates to a composition consisting of or comprising at least one peptide or polypeptide comprising a contiguous sequence of at least 5 amino acids corresponding to a contiguous amino acid sequence encoded by at least one of the HCV genomic sequences as defined above, having at least one amino acid differing from the corresponding region of known HCV (type 1 and/or type 2 and/or type 3) polyprotein sequences as shown in Table 3, or muteins thereof.

It is to be noted that, at the level of the amino acid sequence, an amino acid difference (with respect to known HCV amino acid sequences) is necessary, which means that the polypeptides of the invention correspond to polynucleic acids having a nucleotide difference (with known HCV polynucleic acid sequences) involving an amino acid difference.

The new amino acid sequences, as deduced from the disclosed nucleotide sequences (see SEQ ID NO 1 to 62 and 106 to 123 and 143 to 218, 223 and 270), show homologies of only 59.9 to 78% with prototype sequences of type 1 and 2 for the NS4 region, and of only 53.9 to 68.8% with prototype sequences of type 1 and 2 for the E1 region. As the NS4 region is known to contain several epitopes, for example characterized in patent application EP-A-0 489 968, and as the E1 protein is expected to be subject to immune attack as part of the viral envelope and expected to contain epitopes, the NS4 and E1 epitopes of the new type 3, 4 and 5 isolates will consistently differ from the epitopes present in type 1 and 2 isolates. This is exemplified by the type-specificity of NS4 synthetic peptides as presented in example 4, and the type-specificity of recombinant E1 proteins in example 11.

After aligning the new subtype 2d, type 3, 4 and 5 (see SEQ ID NO 1 to 62 and 106 to 123 and 143 to 218, 223 and 270) amino acid sequences with the prototype sequences of type 1a, 1b, 2a, and 2b, type- and subtype-specific variable regions can be delineated as presented in FIG. 5 and 7.

As to the muteins derived from the polypeptides of the invention, Table 4 gives an overview of the amino acid substitutions which could be the basis of some of the muteins as defined above.

The peptides according to the present invention contain preferably at least 5 contiguous HCV amino acids, preferably however at least 8 contiguous amino acids, at least 10 or at least 15 (for instance at least 9, 11, 12, 13, 14, 20 or 25 amino acids) of the new HCV sequences of the invention.

TABLE 4

| Amino acids | Synonymous groups |
|---|---|
| Ser (S) | Ser, Thr, Gly, Asn |
| Arg (R) | Arg, His, Lys, Glu, Gln |
| Leu (L) | Leu; Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Ile, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (ND | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

The polypeptides of the invention, and particularly the fragments, can be prepared by classical chemical synthesis.

The synthesis can be carried out in homogeneous solution or in solid phase.

For instance, the synthesis technique in homogeneous solution which can be used is the one described by Houbenweyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can be prepared by means of recombinant DNA techniques as described by Maniatis et al., Molecular Cloning: A Laboratory Manual, New York, Cold Spring Harbor Laboratory, 1982).

The present invention relates particularly to a polypeptide or peptide composition as defined above, wherein said contiguous sequence contains in its sequence at least one of the following amino acid residues: L7, Q43, M44, S60, R67, Q70, T71, A79, A87, N106, K115, A127, A190, S130, V134, G142, I144, E152, A157, V158, P165, S177 or Y177, I178, V180 or E180 or F182, R184, I186, H187, T189, A190, S191 or G191, Q192 or L192 or I192 or V192 or E192, N193 or H193 or P193, W194 or Y194, H195, A197 or I197 or V197 or T197, V202, I203 or L203, Q208, A210, V212, F214, T216, R217 or D217 or E217 or V217, H218 or N218, H219 or V219 or L219, L227 or I227, M231 or E231 or Q231, T232 or D232 or A232 or K232, Q235 or I235, A237 or T237, I242, I246, S247, S248, V249, S250 or Y250, I251 or V251 or M251 or F251, D252, T254 or V254, L255 or V255, E256 or A256, M258 or F258 or V258, A260 or Q260 or S260, A261, T264 or Y264, M265, I266 or A266, A267, G268 or T268, F271 or M271 or V271, I277, M280 or H280, I284 or A284 or L84, V274, V291, N292 or S292, R293 or I293 or Y293, Q294 or R294, L297 or I297 or Q297, A299 or K299 or Q299, N303 or T303, T308 or L308, T310 or F310 or A310 or D310 or V310, L313, G317 or Q317, L333, S351, A358, A359, A363, S364, A366, T369, L373, F376, Q386, I387, S392, I399, F402, I403, R405, D454, A461, A463, T464, K484, Q500, E501, S521, K522, H524, N528, S531, S532, V534, F536, F537, M539, I546, C1282, A1283, V1312, Q1321, P1368, V1372, V1373, K1405, Q1406, S1409, A1424, A1429, C1435, S1436, S1456, H1496, A1504, D1510, D1529, I1543, N1567, D1556, N1567, M1572, Q1579, L1581, S1583, F1585, V1595, E1606 or T1606, M1611, V1612 or L1612, P1630, C1636, P1651, T1656 or I1656, L1663, V1667, V1677, A1681, H1685, E1687, G1689, V1695, A1700, Q1704, Y1705, A1713, A1714or S1714, M1718, D1719, A1721 or T1721, R1722, A1723 or V1723, H1726 or G1726, E1730, V1732, F1735, I1736, S1737, R1738, T1739, G1740, Q1741, K1742, Q1743, A1744, T1745, L1746, E1747 or K1747, I1749, A1750, T1751 or A1751, V1753, N1755, K1756, A1757, P1758, A1759, H1762, T1763, Y1764, P2645, A2647, K2650, K2653 or L2653, S2664, N2673, F2680, K2681, L2686, H2692, Q2695 or L2695 or I2695, V2712, F2715, V2719 or Q2719, T2722, T2724, S2725, R2726, G2729, Y2735, H2739, I2748, G2746 or I2746, I2748, P2752 or K2752, P2754 or T2754, T2757 or P2757, with said notation being composed of a letter representing the amino acid residue by its one-letter code, and a number representing the amino acid numbering according to Kato et al., 1990 as shown in Table 1 (comparison with other isolates). See also the numbering in FIGS. 2, 5, 7, and 11 (alignment amino acid sequences).

Within the group of unique and new amino acid residues of the present invention, the following residues were found to be specific for the following types of HCV according to the HCV classification system used in the present invention:

- Q208, R217, E231, I235, I246, T264, I266, A267, F271, K299, L2686, Q2719 which are specific for the HCV subtype 2d sequences of the present invention as shown in FIG. 5 and 2;
- Q43, S60, R67, F182, I186, H187, A190, S191, L192, W194, V202, L203, V219, Q231, D232, A237, T254, M280, Q299, T303, L308, and/or L313 which are specific for the Core/E1 region of HCV type 3 of the invention as shown in FIG. 5;
- D1556, Q1579, L1581, S1584, F1585, E1606, V1612, P1630, C1636, T1656, L1663, H1685, E1687, G1689, V1695, Y1705, A1713, A1714, A1721, V1723, H1726, R1738, Q1743, A1744, E1747, I1749, A1751, A1759 and/or H1762 which are specific for the NS3/4 region of HCV type 3 sequences of the invention as shown in FIG. 7;
- K2665, D2666, R2670 which are specific for the NS5B region of HCV type 3 of the invention as shown in FIG. 2;
- L7, A79, A127, S130, E152, V158, S177 or Y177, V180 or E180, R184, T189, Q192 or E192 or I192, N193 or H193, I197 or V197, I203, A210, V212, E217, H218, H219, L227, A232, V249, I251 or M251, D252, L255 or V255, E256, M258 or V258 or F258, A260 or Q260, M265, T268, V271, V274, M280, I284, N292 or S292, Q294, L297 or I297, T308, A310 or D310 or V310 or T310, and G317 which are specific for the core/E1 region of HCV type 4 sequences of the present invention as shown in FIG. 5;
- P2645, K2650, K2653, G2656, V2658, T2668, N2673 or N2673, K2681, H2686, D2691, L2692, Q2695 or L2695 or I2695, Y2704, V2712, F2715, V2719, I2722, S2725, G2729, Y2735, G2746 or I2746, P2752 or K2752, Q2753, P2754 or T2754, T2757 or P2757 which are specific for the NS5B region of the HCV type 4 sequences of the present invention as shown in FIG. 2;
- M44, Q70, A87, N106, K115, V137, G142, P165, I178, F251, A299, N303, Q317 which are specific for the Core/E1 region of the HCV type 5 sequence of the present invention as shown in FIG. 5;

L333, S351, A358, A359, A363, S364, A366, T369, L373, F376, Q386, I387, S392, I399, F102, I403, R405, D454, A461, A463, T464, K484, Q500, E501, S521, K522, H524, N528, S532, V534, F537, M539, I546 which are specific for the E1/E2 region of the HCV type 5 sequences of the present invention as shown in FIG. 12;

C1282, A1283, V1312, Q1321, P1368, V1372, K1405, Q1406, S1409, A1424, A1429, C1435, S1436, S1456, H1496, A1504, D1510, D1529, I1543, N1567, M1572, V1595, T1606, M1611, L1612, I1656, V1667, A1681, A1700, A1713, S1714, M1718, D1719, T1721, R1722, A1723, G1726, F1735, I1736, S1737, T1739, G1740, K1742, T1745, L1746, K1747, A1750, V1753, N1755, A1757, D1758, T1763, and Y1764 which are specific for the NS3/NS4 region of HCV type 5 sequences of the invention as shown in FIG. 7;

A2647, L2653, S2674, F2680, T2724, R2726, Y2730, H2739 which are specific for the NS5B region of the HCV type 5 sequences of the present invention as shown in FIG. 2;

A256, P1631, V1677, Q1704, E1730, V1732, Q1741 and T1751 which are specific for the HCV type 3 and 5 sequences of the present invention as shown in FIG. 5 and 7;

T71, A157, I227, T237, T240, Y250, V251, S260, M271, T2673, T2722, I2748 which are specific for the HCV type 3 and 4 sequences of the present invention as shown in FIG. 5 and 2, V192, Y194, A197, P249, S250, R294 which are specific for the HCV type 4 and 5 sequences of the present invention as shown in FIG. 5;

I293 which is specific for the HCV type 4 and subtype 2d sequence of the present invention as shown in FIG. 5;

D217 and R294 which are specific for the HCV type 3, 4 and 5 sequences of the present invention as shown in FIG. 5;

L192 which is specific for the HCV type 3 and subtype 2d sequences of the present invention as shown in FIG. 5;

G191 and T197 which are specific for the HCV type 3, 4 and subtype 2d sequences of the present invention as shown in FIG. 5;

K232 which is specific for the HCV subtype 2d en type 5 sequences of the present invention as shown in FIG. 5.

and with said notation being composed of a letter, unambiguously representing the amino acid by its one-letter code, and a number representing the amino acid numbering according to Kato et al., 1990 (see also Table 1 for comparison with other isolates), as well as FIG. 2 (NS5 region), FIG. 5 (Core/E1 region), FIG. 7 (NS3/NS4 region), FIG. 12 (E1/E2 region). Some of the above-mentioned amino acids may be contained in type or subtype specific epitopes.

For example M231 (detected in type 5) refers to a methionine at position 231. A glutamine (Q) is present at the same position 231 in type 3 isolates, whereas this position is occupied by an arginine in type 1 isolates and by a lysine (K) or asparagine (N) in type 2 isolates (see FIG. 5).

The peptide or polypeptide according to this embodiment of the invention may be possibly labelled, or attached to a solid substrate, or coupled to a carrier molecule such as biotin, or mixed with a proper adjuvant.

The variable region in the core protein (V-CORE in FIG. 5) has been shown to be useful for serotyping (Machida et al., 1992). The sequence of the disclosed type 5 sequence in this region shows type-specific features. The peptide from amino acid 70 to 78 shows the following unique sequence for the sequences of the present inevntion (see FIG. 5):

QPTGRSWGQ (SEQ ID NO 93)
RSEGRTSWAQ (SEQ ID NO 220)
and RTEGRTSWAQ (SEQ ID NO 221)

Another preferred V-Core spanning region is the peptide spanning positions 60 to 78 of subtype 3c with sequence:

SRRQPIPRARRTEGRSWAQ (SEQ ID NO 268)

Five type-specific variable regions (V1 to V5) can be identified after aligning E1 amino acid sequences of the 4 genotypes, as shown in FIG. 5.

Region V1 encompasses amino acids 192 to 203, this is the amino-terminal 10 amino acids of the E1 protein. The following unique sequences as shown in FIG. 5 can be deduced:

| | |
|---|---|
| LEWRNTSGLYVL | (SEQ ID NO 83) |
| VNYRNASGIYHI | (SEQ ID NO 126) |
| QHYRNISGIYHV | (SEQ ID NO 127) |
| EHYRNASGIYHI | (SEQ ID NO 128) |
| IHYRNASGIYHI | (SEQ ID NO 224) |
| VPYRNASGIYHV | (SEQ ID NO 84) |
| VNYRNASGIYHI | (SEQ ID NO 225) |
| VNYRNASGVYHI | (SEQ ID NO 226) |
| VNYHNTSGIYHL | (SEQ ID NO 227) |
| QHYRNASGIYHV | (SEQ ID NO 228) |
| QHYRNVSGIYHV | (SEQ ID NO 229) |
| IHYRNASDGYYI | (SEQ ID NO 230) |
| LQVKNTSSSYMV | (SEQ ID NO 231) |

Region V2 encompasses amino acids 213 to 223. The following unique sequences can be found in the V2 region as shown in FIG. 5;

| | |
|---|---|
| VYEADDVILHT | (SEQ ID NO 85) |
| VYETEHHILHL | (SEQ ID NO 129) |
| VYEADHHIMHL | (SEQ ID NO 130) |
| VYETDHHILHL | (SEQ ID NO 131) |
| VYEADNLILHA | (SEQ ID NO 86) |
| VWQLRAIVLHV | (SEQ ID NO 232) |
| VYEADYHILHL | (SEQ ID NO 233) |
| VYETDNHILHL | (SEQ ID NO 234) |
| VYETENHILHL | (SEQ ID NO 235) |
| VFETVHHILHL | (SEQ ID NO 236) |
| VFETEHHILHL | (SEQ ID NO 237) |
| VFETDHHIMHL | (SEQ ID NO 238) |
| VYETENHILHL | (SEQ ID NO 239) |
| VYEADALILHA | (SEQ ID NO 240) |

Region V3 encompasses the amino acids 230 to 242. The following unique V3 region sequences can be deduced from FIG. 5;

```
VQDGNTSTCWTPV     (SEQ ID NO 87)
VQDGNTSACWTPV     (SEQ ID NO 241)
VRVGNQSRCWVAL     (SEQ ID NO 132)
VRTGNTSRCWVPL     (SEQ ID NO 133)
VRAGNVSRCWTPV     (SEQ ID NO 134)
EEKGNISRCWIPV     (SEQ ID NO 242)
VKTGNQSRCWVAL     (SEQ ID NO 243)
VRTGNQSRCWVAL     (SEQ ID NO 244)
VKTGNQSRCWIAL     (SEQ ID NO 245)
VKTGNVSRCWIPL     (SEQ ID NO 247)
VKTGNVSRCWISL     (SEQ ID NO 248)
VRKDNVSRCWVQI     (SEQ ID NO 249)
```

Region V4 encompasses the amino acids 248 to 257. The following unique V4 region sequences can be deduced from FIG. 5:

```
VRYVGATTAS        (SEQ ID NO 89)
APYIGAPLES        (SEQ ID NO 135)
APYVGAPLES        (SEQ ID NO 136)
AVSMDAPLES        (SEQ ID NO 137)
APSLGAVTAP        (SEQ ID NO 90)
APSFGAVTAP        (SEQ ID NO 250)
VSQPGALTKG        (SEQ ID NO 251)
VKYVGAYrAS        (SEQ ID NO 252)
APYIGAPVES        (SEQ ID NO 253)
AQHLNAPLES        (SEQ ID NO 254)
SPYVGAPLEP        (SEQ ID NO 255)
SPYAGAPLEP        (SEQ ID NO 256)
APYLGAPLEP        (SEQ ID NO 257)
APYLGAPLES        (SEQ ID NO 258)
APYVGAPLES        (SEQ ID NO 259)
VPYLGAPLTS        (SEQ ID NO 260)
APHLRAPLSS        (SEQ ID NO 261)
APYLGAPLTS        (SEQ ID NO 262)
```

Region V5 encompasses the amino acids 294 to 303. The following unique V5 region peptides can be deduced from FIG. 5:

```
RPRRHQTVQT        (SEQ ID NO 91)
QPRRHWYITQD       (SEQ ID NO 138)
```

-continued
```
RPRRHWTTQD        (SEQ ID NO 139)
RPRQHATVQN        (SEQ ID NO 92)
RPRQFIATVQD       (SEQ ID NO 263)
SPQHHKFVQD        (SEQ ID NO 264)
RPRRLWTTQE        (SEQ ID NO 265)
PPRIE-IETTQD      (SEQ ID NO 266)
```

The variable region in the E2 region (HVR-2) of type 5a as shown in FIG. 12 spanning amino acid positions 471 to 484 as also preferred peptide according to the present invention with the following sequence:

```
TISYANGSGPSDDK (SEQ ID NO 267)
```

The above given list of peptides are particularly suitable for vaccine and diagnostic development.

Also comprised in the present invention is any synthetic peptide or polypeptide containing at least 5 contiguous amino acids derived from the above-defined peptides in their peptidic chain.

According to a specific embodiment, the present invention relates to a composition as defined above, wherein said contiguous sequence is selected from any of the following HCV amino acid type 3 sequences:

a sequence having a homology of more than 72%, preferably more than 74%, more preferably more than 77% and most preferably more than 80 or 84% homology to any of the amino acid sequences as represented in SEQ ID NO 14, 16. 18, 20, 22, 24, 26 or 28 (HD10, BR36, BR33 sequences) in the region spanning positions 140 to 319 in the Core/E1 region as shown in FIG. 5;

a sequence having a homology of more than 70%, preferably more than 72%, more preferably more than 75% homology, most preferably more than 81% homology to any of the amino acid sequences as represented in SEQ ID NO 14, 16, 18, 20, 22, 24, 26 or 28 (HD10, BR36, BR33 sequences) in the E1 region spanning positions 192 to 319 as shown in FIG. 5;

a sequence having a homology of more than 86%, preferably more than 88%, and most preferably more than 90% homology to the amino acid sequences as represented in SEQ ID NO 148 (type 3c); BE98 in the region spanning positions 1 to 110 in the Core region as shown in FIG. 5;

a sequence having a homology of more than 76%, preferably more than 78%, most preferably more than 80% to any of the amino acid sequences as represented in SEQ ID NO 30, 32, 34, 36, 38 or 40 (HCC153, HD10, BR36 sequences) in the region spanning positions 1646 to 1764 in the NS3/NS4 region as shown in FIG. 7 and 11;

a sequence having a homology of more than 81%, preferably more than 83%, and most preferably more than 86% homology to any of the amino acid sequences as represented in SEQ ID NO 14, 16, 18, 20, 22, 24, 26 or 28 (HD10, BR36, BR33 sequences) in the region spanning positions 140 to 319 in the Core/E1 region as shown in FIG. 5;

a sequence having a homology of more than 81.5%, preferably more than 83%, and most preferably more than 86% homology to any of the amino acid sequences as represented in SEQ ID NO 14, 16, 18, 20, 22, 24, 26 or 28 (HD10, BR36, BR33 sequences) in the E1 region spanning positions 192 to 319 as shown in FIG. 5;

a sequence having a homology of more than 86%, preferably more than 88%, most preferably more than 90% to the amino acid sequence as represented in SEQ ID NO 150; (type 3c BE98) in the region spanning positions 2645 to 2757 in the NS5B region as shown in FIG. 2.

According to yet another embodiment, the present invention relates to a composition as defined above, wherein said contiguous sequence is selected from any of the following HCV amino acid type 4 sequences:

a sequence having a homology of more than 80%, preferably more than 82%, most preferably more than 84% homology to any of the amino acid sequences as represented in SEQ ID NO 119, 121, and 123 (GB358, GB549, GB809 sequences) in the region spanning positions 127 to 319 of the Core/E1 region as shown in FIG. 5;

a sequence having a homology of more than 73%, preferably more than 75%, most preferably more than 78% homology in the E1 region spanning positions 192 to 319 to any of the amino acid sequences as represented in SEQ ID NO 119, 121, and 123 (GB358, GB549, GB809 sequences) in the region spanning positions 140 to 319 of the Core/E1 region as shown in FIG. 5;

a sequence having more than 85%, preferably more than 86%, most preferably more than 87% homology to any of the amino acid sequences as represented in SEQ ID NO 119, 121 or 123 (GB358, GB549, GB809 sequences) in the region spanning positions 192 to 319 of E1 as shown in FIG. 5;

a sequence showing more than 73%, preferably more than 74%, most preferably more than 75% homology to any of the amino acid sequences as represented in SEQ ID NO 107, 109, 111, 113, 115 or 117 (GB48, GB116, GB215, GB358, GB549, GB809 sequences) in the region spanning positions 2645 to 2757 of the NS5B region as shown in FIG. 2;

a sequence having any of the sequences as represented in SEQ ID NO 164 or 166 (GB809 and CAM600 sequences) in the Core region as shown in FIG. 5;

a sequence having any of the sequences as represented in SEQ ID NO 168, 170, 172, 174, 176, 178, 180, 182, 184, 186, 188 or 190 (CAM600, GB809, CAMG22, CAMG27, GB549, GB438, CAR4/1205, CAR4/901, GB116, GB215, GB958, GB809-4 sequences) in the Core/E1 region as shown in FIG. 5;

a sequence having any of the sequences as represented in SEQ ID NO 194, 196, 202, 204, 206, 208, 210, 212 (GB724, BE100, PC, CAM600, CAMG22, etc.) in the NS5B region or SEQ ID NOs: 198, 200 in the NS3/4 region.

The above-mentioned type 4 peptides polypeptides comprise at least an amino acid sequence selected from any HCV type 4 polyprotein with the exception of core sequence as disclosed by Simmonds et al. (1993, EG-29, see FIG. 5).

According to yet another aspect, the present invention relates to a composition as defined above, wherein said contiguous sequence is selected from any of the following HCV amino acid type 5 sequences:

a sequence having more than 93%, preferably more than 94%, most preferably more than 95% homology in the region spanning Core positions 1 to 191 to any of the amino acid sequences as represented in SEQ ID NO 42, 44, 46, 48, 50, 52 or 54 (PC sequences) and SEQ ID NO 152 (BE95) as shown in FIG. 5;

a sequence having more than 73%, preferably more than 74% most preferably more than 76% homology in the region spanning E1 positions 192 to 319 to any of the amino acid sequences as represented in SEQ ID NO 42, 44, 46, 48, 50, 52 or 54 (PC sequences) as shown in FIG. 5;

a sequence having a more than 78%, preferably more than 80%, most preferably more than 83% homology to any of the amino acid sequences as represented in SEQ ID NO 42, 44, 46, 48, 50, 52, 54, 154, 156 (BE95, BE100) (PC sequences) in the region spanning positions 1 to 319 of the Core/ E1 region as shown in FIG. 5;

a sequence having more than 90%, preferably more than 91%, most preferably more than 92% homology to any of the amino acid sequences represented in SEQ ID NO 56 or 58 (PC sequences) in the region spanning positions 1286 to 1403 of the NS3 region as shown in FIG. 7 or 11;

a sequence having more than 66%, more particularly 68%, most particularly 70% or more homology to any of the amino acid sequences as represented in SEQ ID NO 60 or 62 (PC sequences) in the region spanning positions 1646 to 1764 of the NS3/4 region as shown in FIG. 7 or 11.

According to yet another embodiment, the present invention relates to a composition as defined above, wherein said contiguous sequence is selected from any of the following HCV amino acid type 2d sequences:

a sequence having more than 83%, preferably more than 85%, most preferably more than 87% homology to the amino acid sequence as represented in SEQ ID NO 144 (NE92) in the region spanning positions 1 to 319 of the Core/E1 region as shown in FIG. 5;

a sequence having more than 79%, preferably more than 81%, most preferably more than 84% homology in the region spanning E1 positions 192 to 319 to the amino acid sequence as represented in SEQ ID NO 144 (NE92) as shown in FIG. 12;

a sequence having more than 95%, more particularly 96%, most particularly 97% or more homology to the amino acid sequence as represented in SEQ ID NO 146 (NE92) in the region spanning positions 2645 to 2757 of the NS5B region as shown in FIG. 2.

The present invention also relates to a recombinant vector, particularly for cloning and/or expression, with said recombinant vector comprising a vector sequence, an appropriate prokaryotic, eukaryotic or viral promoter sequence followed by the nucleotide sequences as defined above, with said recombinant vector allowing the expression of any one of the HCV type 2 and/or HCV type 3 and/or type 4 and/or type 5 derived polypeptides as defined above in a prokaryotic, or eukaryotic host or in living mammals when injected as naked DNA, and more particularly a recombinant vector allowing the expression of any of the following HCV type 2d, type 3, type 4 or type 5 polypeptides spanning the following amino acid positions:

a polypeptide starting at position 1 and ending at any position in the region between positions 70 and 326, more particularly a polypeptide spanning positions 1 to 70, 1 to 85, positions 1 to 120, positions 1 to 150, positions 1 to 191, positions 1 to 200, for expression of the Core protein, and a polypeptide spanning positions 1 to 263, positions 1 to 326, for expression of the Core and E1 protein;

a polypeptide starting at any position in the region between positions 117 and 192, and ending at any position in the region between positions 263 and 326, for expression of E1, or forms that have the putative membrane anchor deleted (positions 264 to 293 plus or minus 8 amino acids);

a polypeptide starting at any position in the region between positions 1556 and 1688, and ending at any position in the region between positions 1739 and 1764, for expression of the NS4 regions, more particularly a polypeptide starting at position 1658 and ending at position 1711 for expression of the NS4a antigen, and more particularly, a polypeptide starting at position 1712 and ending between positions 1743 and 1972, for example 1712–1743, 1712–1764, 1712–1782, 1712–1972, 1712 to 1782 and 1902 to 1972 for expression of the NS4b protein or parts thereof.

The term "vector" may comprise a plasmid, a cosmid, a phage, or a virus.

In order to carry out the expression of the polypeptides of the invention in bacteria such as E. coli or in eukaryotic cells such as in S. cerevisiae, or in cultured vertebrate or invertebrate hosts such as insect cells, Chinese Hamster Ovary (CHO), COS, BHK, and MDCK cells, the following steps are carried out:

transformation of an appropriate cellular host with a recombinant vector, in which a nucleotide sequence coding for one of the polypeptides of the invention has been inserted under the control of the appropriate regulatory elements, particularly a promoter recognized by the polymerases of the cellular host and, in the case of a prokaryotic host, an appropriate ribosome binding site (RBS), enabling the expression in said cellular host of said nucleotide sequence. In the case of an eukaryotic host any artificial signal sequence or pre/pro sequence might be provided, or the natural HCV signal sequence might be employed, e.g. for expression of E1 the signal sequence starting between amino acid positions 117 and 170 and ending at amino acid position 191 can be used, for expression of NS4, the signal sequence starting between amino acid positions 1646 and 1659 can be used, culture of said transformed cellular host under conditions enabling the expression of said insert.

The present invention also relates to a composition as defined above, wherein said polypeptide is a recombinant polypeptide expressed by means of an expression vector as defined above.

The present invention also relates to a composition as defined above, for use in a method for immunizing a mammal, preferably humans, against HCV comprising administring a sufficient amount of the composition possibly accompanied by pharmaceutically acceptable adjuvants, to produce an immune response, more particularly a vaccine composition including HCV type 3 polypeptides derived from the Core, E1 or the NS4 region and/or HCV type 4 and/or HCV type 5 polypeptides and/or HCV type 2d polypeptides.

The present invention also relates to an antibody raised upon immunization with a composition as defined above by means of a process as defined above, with said antibody being reactive with any of the polypeptides as defined above, and with said antibody being preferably a monoclonal antibody.

The monoclonal antibodies of the invention can be produced by any hybridoma liable to be formed according to classical methods from splenic cells of an animal, particularly from a mouse or rat, immunized against the HCV polypeptides according to the invention, or muteins thereof, or fragments thereof as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains or from cDNA clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with type 3, type 4 or type 5 HCV, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al. 1991).

The invention also relates to the use of the proteins of the invention, muteins thereof, or peptides derived therefrom for the selection of recombinant antibodies by the process or repertoire cloning (Persson et al., 1991).

Antibodies directed to peptides derived from a certaing genotype may be used either for the detection of such HCV genotypes, or as therapeutic agents.

The present invention also relates to the use of a composition as defined above for incorporation into an immunoassay for detecting HCV, present in biological sample liable to contain it, comprising at least the following steps:

(i) contacting the biological sample to be analyzed for the presence of HCV antibodies with any of the compositions as defined above preferably in an immobilized form under appropriate conditions which allow the formation of an immune complex, wherein said polypeptide can be a biotinylated polypeptide which is covalently bound to a solid substrate by means of streptavidin or avidin complexes, (ii) removing unbound components, (iii) incubating the immune complexes formed with heterologous antibodies, which specifically bind to the antibodies present in the sample to be analyzed, with said heterologous antibodies having conjugated to a detectable label under appropriate conditions, (iv) detecting the presence of said immunecomplexes visually or by means of densitometry and inferring the HCV serotype present from the observed hybridization pattern.

The present invention also relates to the use of a composition as defined above, for incorporation into a serotyping assay for detecting one or more serological types of HCV present in a biological sample liable to contain it, more particularly for detecting E1 and N4 antigens or antibodies of the different types to be detected combined in one assay format, comprising at least the following steps:

(i) contacting the biological sample to be analyzed for the presence of HCV antibodies or antigens of one or more serological types, with at least one of the compositions as defied above, an immobilized form under appropriate conditions which allow the formation of an immunecomplex, (ii) removing unbound components, (iii) incubating the immunecomplexes formed with heterologous antibodies, which specifically bind to the antibodies present in the sample to be analyzed, with said heterologous antibodies having conjugated to a detectable label under appropriate conditions,
(iv) detecting the presence of said immunecomplexes visually or by means of densitometry and inferring the presence of one or more HCV serological types present from the observed binding pattern.

The present invention also relates to the use of a composition as defined above, for immobilization on a solid substrate and incorporation into a reversed phase hybridization assay, preferably for immobilization as parallel lines onto a solid support such as a membrane strip, for determining the presence or the genotype of HCV according to a method as defined above.

The present invention thus also relates to a kit for determining the presence of HCV genotypes as defined above present in a biological sample liable to contain them, comprising:
possibly at least one primer composition containing any primer selected from those defined above or any other HCV type 3 and/or HCV type 4, and/or HCV type 5, or universal HCV primers,
at least one probe composition as defined above, with said probes being preferentially immobilized on a solid substrate, and more preferentially on one and the same membrane strip,
a buffer or components necessary for producing the buffer enabling hybridization reaction between these probes and the possibly amplified products to be carried out,
means for detecting the hybrids resulting from the preceding hybriziation.
possibly also including an automated scanning and interpretation device for inferring the HCV genotypes present in the sample from the observed hybridization pattern.

The genotype may also be detected by means of a type-specific antibody as defined above, which is linked to any polynucleotide sequence that can afterwards be amplified by PCR to detect the immune complex formed (Immuno-PCR. Sano et al., 1992);

The present invention also relates to a kit for determining the presence of HCV antibodies as defined above present in a biological sample liable to contain them, comprising:
at least one polypeptide composition as defined above, preferentially in combination with other polypeptides or peptides from HCV type 1, HCV type 2 or other types of HCV, with said polypeptides being preferentially immobilized on a solid substrate, and more preferentially on one and the same membrane strip,
a buffer or components necessary for producing the buffer enabling binding reaction between these polypeptides and the antibodies against HCV present in the biological sample,
means for detecting the immunecomplexes formed in the preceding binding reaction,
possibly also including an automated scanning and interpretation device for inferring the HCV genotypes present in the sample from the observed binding pattern.

BRIEF DESCRIPTION OF THE DRAWINGS

FIG. 1 Alignment of consensus nucleotide sequences for each of the type 3a isolates BR34, BP36, and BR33, deduced from the clones with SEQ ID NO 1, 5, 9; type 4 isolates GB48, GB116, GB215, GB358, GB549, GB809, CAM600, CAM22, GB438, CAR4/1205, CAR1/501 (SEQ ID NO. 106, 108, 110, 112, 114, 116, 201, 203, 205, 207, 209 and 211); type 5a isolates BE95 and BE96 (SEQ ID NO 159 and 161) and type 2d isolate NE92 (SEQ ID NO 145) from the region between nucleotides 7932 and 8271, with known sequences from the corresponding region of isolates HCV-1, HCV-J, HC-J6, HC-J8, T1 and T9, and others as shown in Table 3.

FIG. 2 Alignment of amino acids sequences deduced from the nucleic acid sequences as represented in FIG. 1 from the subtype 3a clones BR34 (SEQ ID NO 2, 4), BR36 (SEQ ID NO 6, 8) and BR33 (SEQ ID NO 10, 12), the subtype 3c clone BE98 (SEQ ID NO 150), and the type 4 clones GB48 (SEQ ID NO 107), GB116 (SEQ ID NO 109), GB215 (SEQ ID NO 111), GB358 (SEQ ID NO 113), GB549 (SEQ ID NO 115) GB809 (SEQ ID NO 117); CAM600, CAMG22, GB438, CAR4/1205, CAR1/501 (SEQ ID NO 202, 204, 206, 208, 210, 212); the type 5a clones BE95 and BE96 (SEQ ID NO 160 and 162); as well as the subtype 2d isolate NE92 (SEQ ID NO 146) from the region between amino acids 2645 to 2757 with known sequences from the corresponding region of isolates HCV-I, HCV-J, HC-J6, and HC-J8, T1 and T9, and other sequences as shown in Table 3.

FIG. 3 Aligment of type 2d, 3c, 4 and 5a nucleotide sequences from isolates NE92, BE98, GB358, GB809, CAM600, GB724, BE95 (SEQ ID NO 143, 147, 191, 163, 165, 193 and 151) in the Core region between nucleotide positions 1 and 500, with known sequences from the corresponding region of type 1, type 2, type 3 and type 4 sequences.

FIG. 4 Alignment of nucleotide sequences for the subtype 2d isolate NE92 (SEQ ID NO 143), the type 4 isolates GB358 (SEQ ID NO 118 and 187), GB549 (SEQ ID NO 120 and 175), and GB809-2 (SEQ ID NO 122 and 169), GB 809-4, BG116, GB215, CAM600, CAMG22, CAMG27, GB438, CAR4/1205, CAR4/901 (SEQ ID NO 189, 183, 185, 167, 171, 173, 177, 179, 181), sequences for each of the subtype 3a isolates HD10, BR36, and BR33, (SEQ ID NO 13, 15, 17 (HD10), 19, 21 (BR36) and 23, 25 or 27 (BR23) and the subtype 5a isolates BE95 and BE100 (SEQ ID NO 143 and 195) from the region between nucleotides 379 and 957, with known sequences from the corresponding region of type 1 and 2 and 3.

FIG. 5 Alignment of amino acid sequences deduced from the new HCV nucleotide sequences of the Core/E1 region of isolates BR33, BR36, HD10, G358, GB549, and GB809, PC or BE95, CAM600, and GB724 (SEQ ID NO. 14, 20, 24, 119 or 192, 121, 123 or 164 , 54 or 152, 166 and 194) from the region between positions 1 and 319, with known sequences from type 1a (HCV-1), type 1b (HCV-J), type 2a (HC-JG), type 2b (HC-J8), NZL1, HCV-TR, positions 7–89 of type 3a (E-b1), and positions 8–88 of type 4a (EG-29). V-Core, variable region with type-specific features in the core protein, V1, variable region 1 of the E1 protein, V2, variable region 2 of the E1 protein, V3, variable region 3 of the E1 protein, V4, variable region 4 of the E1 protein, V5, variable region 5 of the E1 protein.

FIG. 6 Alignment of nucleotide sequences of isolates HCCL-3, HD10 and BR36, deduced from clones with SEQ ID NO 29, 31, 33, 35, 37 and 39, from the NS3/4 region between nucleotides 4664 to 5292, with known sequences from the corresponding region of isolates HCV-1, HCV-J, HC-J6, and HC-J8, EB1, EB2, EB6 and EB7.

FIG. 7 Alignment of amino acid sequences deduced from the new HCV nucleotide sequences of the NS3/NS4 region of isolate BR36 (SEQ ID NO 36, 38 and 40) and BE95 (SEQ ID NO 270). NS4-1, indicates the region that was synthesized as synthetic peptide 1 of the NS4 region, NS4-5, indicates the region that was synthesized as synthetic peptide 5 of the NS4 region; NS4-7, indicates the region that was synthesized as synthetic peptide 7 of the NS4 region.

FIG. 9 Nucleotide sequences of Core/E1 clones obtained from the PCR fragments PC-2, PC-3, and PC4, obtained from serum BE95 (PC-2-1 (SEQ ID NO 41), PC-2-6 (SEQ ID NO 43), PC-4-1 (SEQ ID NO 45), PC-4-6 (SEQ ID NO 47), PC-3-4 (SEQ ID NO 49), and PC-3-8 (SEQ ID NO 51)) of subtype 5a isolate BE95.

Figure 8:
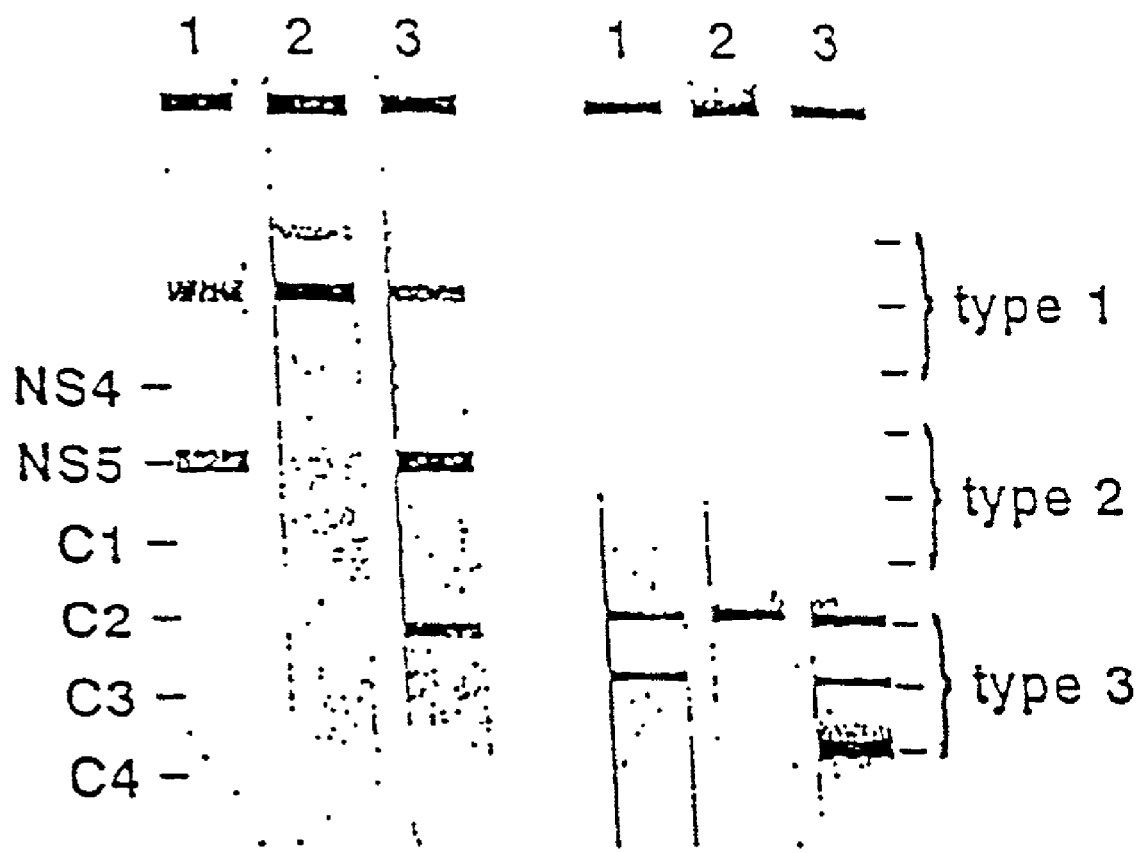
FIG. 8 Reactivity of the three LIPA-selected (Stuyver et al., 1993) type 3 sera on the Inno-LIA HCV Ab II assay (Innogenetics) (left), and on the NS4-LIA test. For the NS4-LIA test, NS4-1, NS4-5, and NS4-7 peptides were synthesized based on the type 1 (HCV-1), type 2 (HC-J6) and type 3 (BR36) prototype isolate sequences as shown in Table 4, and applied as parallel lines onto a membrane strip as indicated. 1, serum BR33, 2, serum HD10, 3, serum DKH.

A consensus sequence is shown for the Core and E1 region of isolate BE95, presented as PC C/E1 with SEQ ID NO 53. Y, C or T, R, A or G, S, C or G.

FIG. 10 Alignment of nucleotide sequences of clones with SEQ ID NO 197 and 199 (PC sequences, see also SEQ ID NO 55, 57, 59) and SEQ ID NO 35, 37 and 39 (BR36 sequences) from the NS3/4 region between nucleotides 3856 to 5292, with known sequences from the corresponding region of isolates HCV-1, HCV-J, HC-J6, and HC-J8.

FIG. 11 Alignment of amino acid sequences of subtype 5a BE95 isolate PC clones with SEQ ID NO 56 and 58, from the NS3/4 region between amino acids 1286 to 1764, with known sequences from the corresponding region of isolates HCV-1, HCV-J, HC-J6, and HC-J8.

FIG. 12 Aligment of amino acid sequences of subtype 5a isolate BE95 (SEQ ID NO 158) in the E1/E2 region spanning positions 328 to 546, with known sequnces from the corresponding region of isolates HCV-1, HCV-J, HC-J6, HC-J8, NZL1 and HCV-TR (see Table 3).

Figure 13:
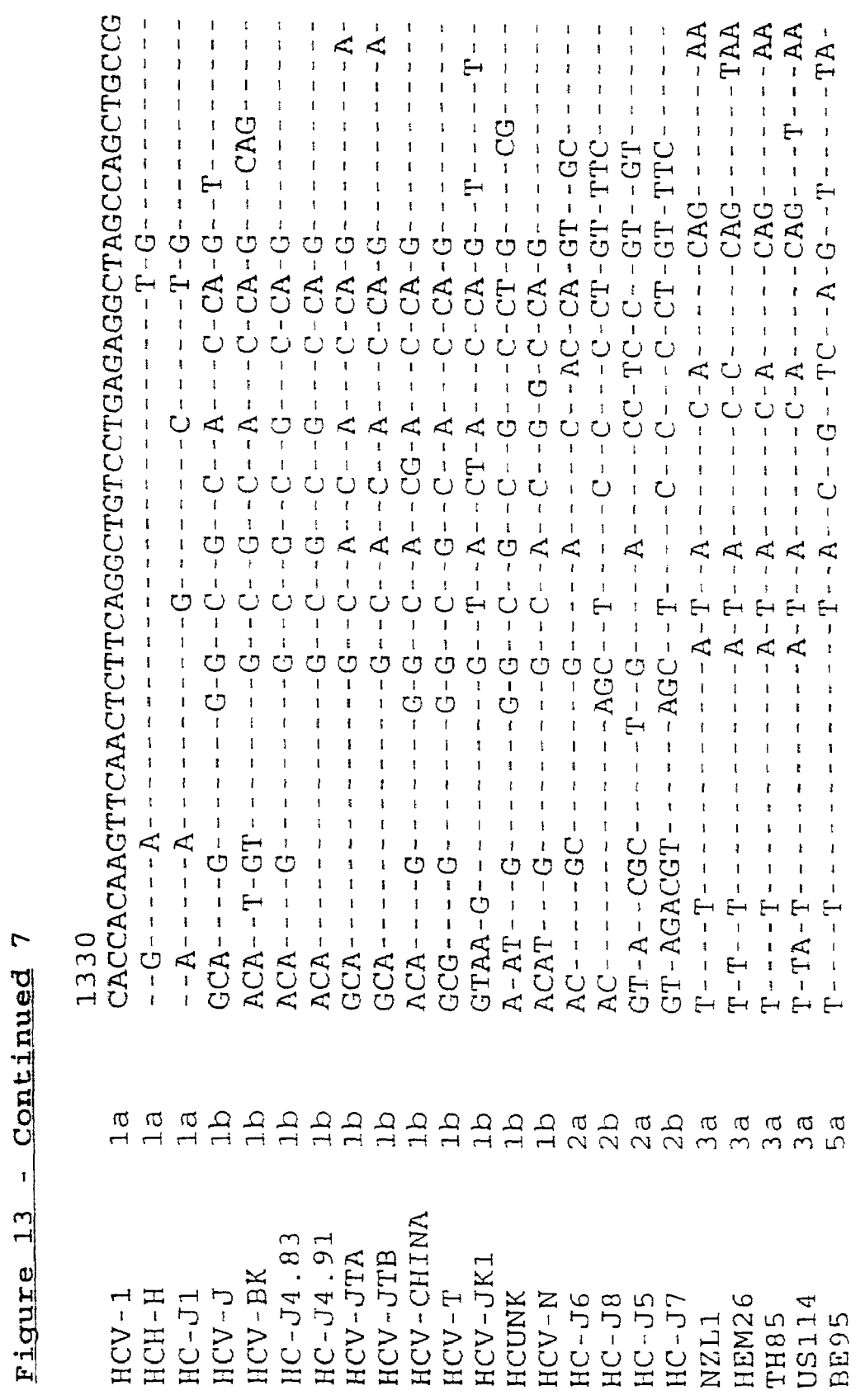

FIG. 13 Alignment of the nucleotide sequences of subtype 5a isolate BE95 (SEQ ID NO 157) in the E1/E2 region with known HCV sequences as shown in Table 3.

EXAMPLES

Example 1

The NS5b Region of HCV Type 3

Type 3 sera, selected by means of the INNO-LiPA HCV research kit (Stuyver et al., 1993) from a number of Brazilian blood donors, were positive in the HCV antibody ELISA (Innotest HCV Ab II; Innogenetics) and/or in the INNO-LIA HCV Ab II confirmation test (Innogenetics). Only those sera that were positive after the first round of PCR reactions (Stuyver et al., 1993) were retained for further study.

Reverse transcription and nested PCR: RNA was extracted from 50 µl serum and subjected to cDNA synthesis as described (Stuyver et al., 1993). This cDNA was used as template for PCR, for which the total volume was increased to 50 µl containing 10 pmoles of each primer, 3 µl of 10 µx Pfu buffer 2 (Stratagene) and 2.5 U of Pfu DNA polymerase (Stratagene). The cDNA was amplified over 45 cycles consisting of 1 min 94° C., 1 min 50° C. and 2 min 72° C. The amplified products were separated by electrophoresis, isolated, cloned and sequenced as described (Stuyver et al., 1993).

Type 3a and 3b-specific primers in the NS5 region were selected from the published sequences (Mori et al., 1992) as follows:

for type 3a:

```
HCPr161(+):
5'-ACCGGAGGCCAGGAGAGTGATCTCCTCC-3'    (SEQ ID NO 63)

and

HCPr162(-):
5'-GGGCTGCTCTATCCTCATCGACGCCATC-3';   (SEQ ID NO 64)
``` for type 3b:

```
HCPr163(+):
5'-GCCAGAGGCTCGGAAGGCGATCAGCGCT-3'    (SEQ ID NO 65)

and

HCPr164(-):
5'-GAGCTGCTCTGTCCTCCTCGACGCCGCA-3'    (SEQ ID NO 66)
```

Using the Line Probe Assay (LiPA) (Stuyver et al., 1993), seven high-titer type 3 sera were selected and subsequently analyzed with the primer sets HCPr161/162 for type 3a, and HCPr163/164 for type 3b. None of these sera was positive with the type 3b primers. NS5 PCR fragments obtained using the type 3a primers from serum BR36 (BR36-23), serum BR33 (BR33-2) and serum BR34 (BP34-4) were selected for cloning. The following sequences were obtained from the PCR fragments:

From fragment BR34-4:

| | |
|---|---|
| BR34-4-20, | (SEQ ID NO 1) |
| BR34-4-19 | (SEQ ID NO 3) |

From fragment BP36-23:

| | |
|---|---|
| BR36-23-18, | (SEQ ID NO 5) |
| BR36-23-20 | (SEQ ID NO 7) |

From fragment BR33-2:

| | |
|---|---|
| BR33-2-17, | (SEQ ID NO 9) |
| BR33-2-21 | (SEQ ID NO 11) |

Figure 1:
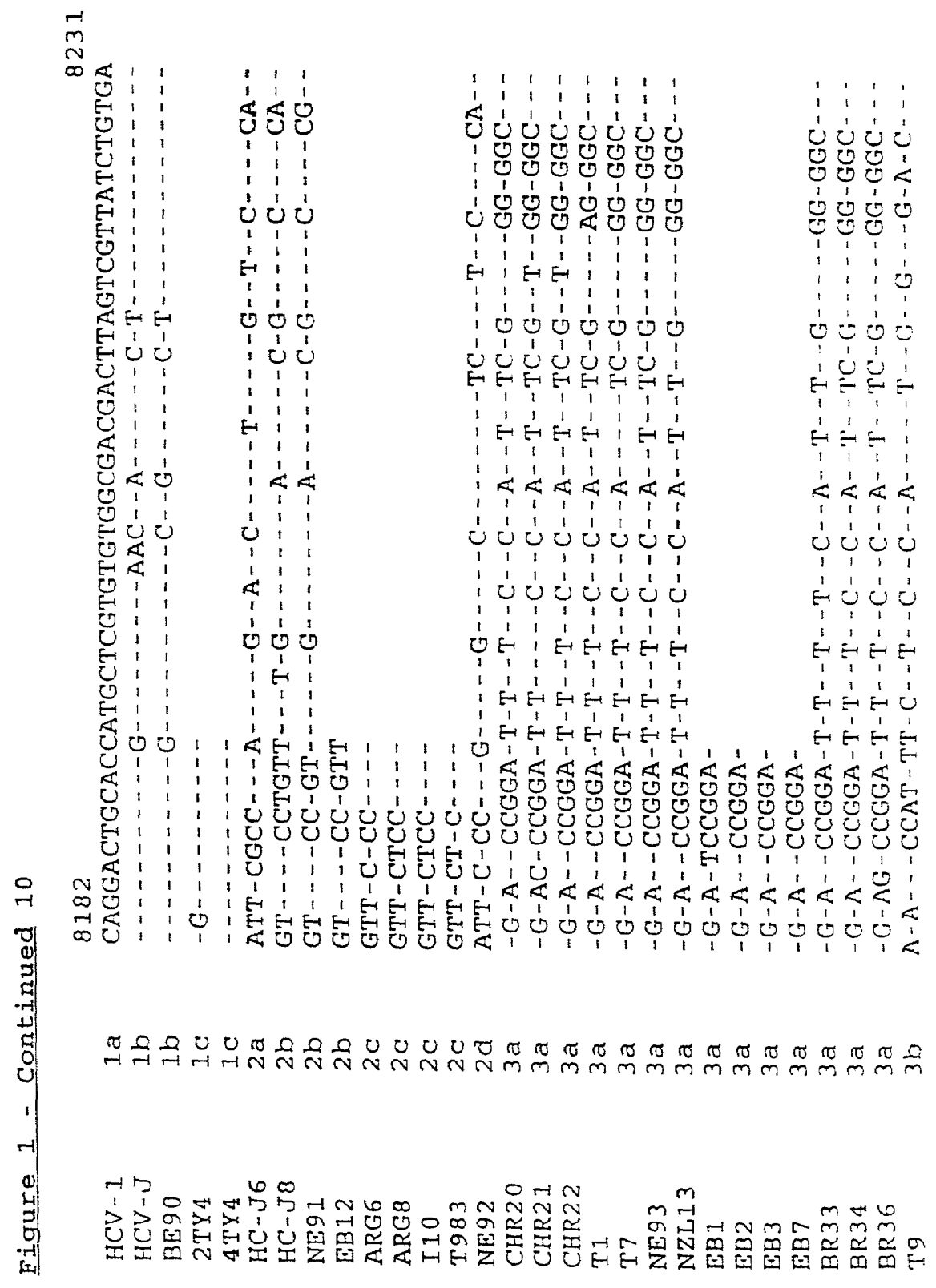

An alignment of sequences with SEQ ID NO 1, 5 and 9 with known sequences is given in FIG. 1. An alignment of the deduced amino acid sequences is shown in FIG. 2. The 3 isolates are very closely related to each other (mutual homologies of about 95%) and to the published sequences of type 3a (Mori et al., 1992), but are only distantly related to type 1 and type 2 sequences (Table 5). Therefore, it is clearly demonstrated that NS5 sequences from LiPA-selected type 3 sera are indeed derived from a type 3 genome. Moreover, by analyzing the NS5 region of serum BR34, for which no 5' UR sequences were determined as described in Stuyver et al. (1993), the excellent correlation between typing by means of the LiPA and genotyping as deduced from nucleotide sequencing was further proven.

Example 2

The Core/E1 Region of HCV Type 3

After aligning the sequences of HCV-1 (Choo et al., 1991), HCV-J (Kato et al., 1990), HC-J6 (Okamoto et al., 1991), and HC-J8 (Okamoto et al., 1992), PCR primers were chosen in those regions of little sequence variation. Primers HCPr23(+): 5'-CTCATGGGGTACATTCCGCT-3' (SEQ ID NO 67) and HCPr54(−): 5'-TATTACCAGTTCATCAT-CATATCCCA-3' (SEQ ID NO 68), were synthesized on a 392 DNA/RNA synthesizer (Applied Biosystems). This set of primers was selected to amplify the sequence from nucleotide 397 to 957, encoding amino acids 140 to 319 (Kato et al., 1990): 52 amino acids from the carboxyterminus of core and 128 amino acids of E1 (Kato et al., 1990). The amplification products BR36-9, BRR33-1, and HD10-2 were cloned as described (Stuyver et al., 1993). The following clones were obtained from the PCR fragments:

From fragment HD10-2:

| | |
|---|---|
| HD10-2-5, | (SEQ ID NO 13) |
| HD10-2-14, | (SEQ ID NO 15) |
| HD10-2-21, | (SEQ ID NO 17) |

From fragment BR36-9:

| | |
|---|---|
| BR36-9-13, | (SEQ ID NO 19) |
| BR36-9-20, | (SEQ ID NO 21) |

From fragment BR33-1:

| | |
|---|---|
| BR33-1-10, | (SEQ ID NO 23) |
| BR33-1-19, | (SEQ ID NO 25) |
| BR33-1-20, | (SEQ ID NO 27) |

Figure 4:
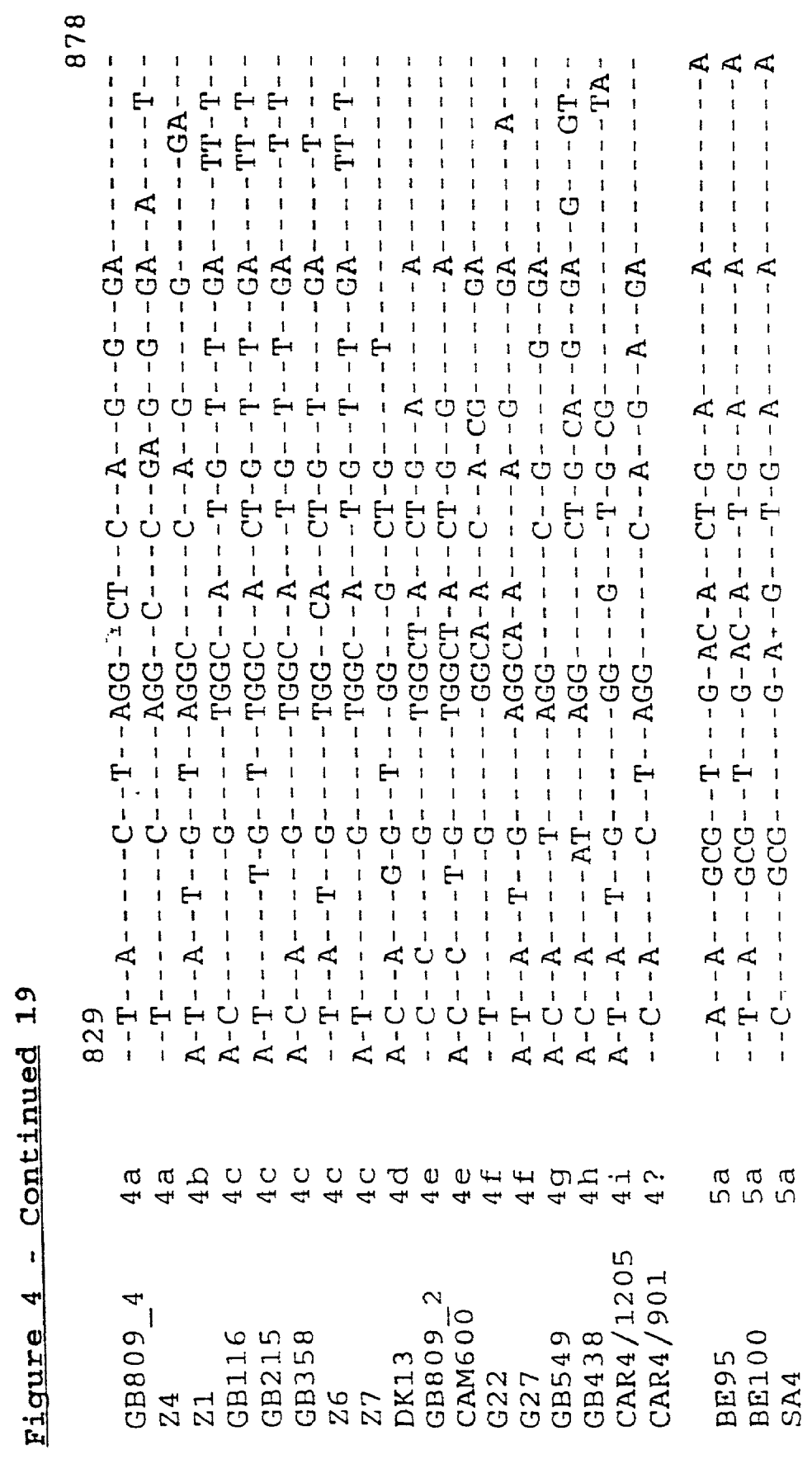

An alignment of the type 3 E1 nucleotide sequences (HD10, BR36, BR33) with SEQ ID NO 13, 19 and 23 with known E1 sequences is presented in FIG. 4. Four variations were detected in the E1 clones from serum HD10 and BR36, while only 2 were found in BR33. All are silent third letter variations, with the exception of mutations at position 40 (L to P) and 125 (M to I). The homologies of the type 3 E1 region (without core) with type 1 and 2 prototype sequences are depicted in Table 5.

In total, 8 clones covering the core/E1 region of 3 different isolates were sequenced and the E1 portion was compared with the known genotypes (Table 3) as shown in FIG. 5. After computer analysis of the deduced amino acid sequence, a signal-anchor sequence at the core carboxy terminus was detected which might, through analogy with type 1b (Hijikata et al., 1991), promote cleavage before the LEWRN sequence (position 192, FIG. 5; SEQ ID NO:271). The L-to-P mutation in one of the HD10-2 clones resides in this signal-anchor region and potentially impairs recognition by signal peptidase (computer prediction). Since no examples of such substitutions were found at this position in previously described sequences, this mutation might have resulted from reverse transcriptase or Pfu polymerase misincorporation. The 4 amino-terminal potential N-linked glycosylation sites, which are also present in HCV types 1a and 2, remain conserved in type 3. The N-glycosylation site in type 1b (aa 250. Kato et al., 1990) remains a unique feature of this subtype. All E1 cysteines, and the putative transmembrane region (aa 264 to 293, computer prediction) containing the aspartic acid at position 279, are conserved in all three HCV types. The following hypervariable regions can be delineated: V1 from aa 192 to 203 (numbering according to Kato et al., 1990), V2 (213–223), V3 (230–242), V4 (248–257), and V5 (294–303). Such hydrophilic regions are thought to be exposed to the host defense mechanisms. This variability might therefore have been induced by the host's immune response. Additional putative N-linked glycosylation sites in the V4 region in all type 1b isolates known today and in the V5 region of HC-J8 (type 2b) possibly further contribute to modulation of the immune response. Therefore analysis of this region, in the present invention, for type 3 and 4 sequences has been instrumental in the delineation of epitopes that reside in the V-regions of E1, which will be critical for future vaccine and diagnostics development.

Example 3

The NS3,N-S4 Region of HCV Type 3

For the NS3/NS4 border region, the following sets of primers were selected in the regions of little sequence variability after aligning the sequences of HCV-1 (Choo et al., 1991), HCV-J (Kato et al., 1990), HC-J6 (Okamoto et al., 1991), and HC-J8 (Okamoto et al., 1992) (smaller case lettering is used for nucleotides added for cloning purposes):

```
set A:
HCPr116(+): 5'-ttttAATACATCATGRCITGYATG-3'              (SEQ ID NO 69)

HCPr66 (-): 5'-ctattaTTGTATCCCRCTGATGAARTTCCACAT-3'     (SEQ ID NO 70)

set B:
HCPr116(+): 5'-ttttAAATACATCATGRCITGYATG-3'             (SEQ ID NO 69)

HCPr118(-): 5'-actagtcgactaYTGIATICCRCTIATRWARTTCCACAT-3' (SEQ ID NO 71)

set C:
HCPr117(+): 5'-ttttAAATACATCGCIRCITGCATGCA-3'           (SEQ ID NO 72)
```

-continued

```
HCPr66(-):   5'-ctattaTTGTATCCCRCTGATGAARTTCCACAT-3'       (SEQ ID NO 70)

set D:
HCPr117(+):  5'-ttttAAATACATCGCIRCITGCATGCA-3'            (SEQ ID NO 72)

HCPr118(-):  5'-actagtcgactaYTGIATICCRCTIATRWARTTCCACAT-3' (SEQ ID NO 71)

set E:
HCPr116(+):  5'-ttttAAATACATCATCGRCITGYATG-3'             (SEQ ID NO 69)

HCPr119(-):  actagtcgactaRTTIGCIATIAGCCG/TRTTCATCCAYTG-3' (SEQ ID NO 73)

set F:
HCPr117(+):  5'-ttttAAATACATCGCIRCITGCATGCA-3'            (SEQ ID NO 72)

HCPr119(-):  actagtcgactaRTTIGCIATIAGCCG/TRTTCATCCAYTG-3' (SEQ ID NO 73)

set G:
HCPr131(+):  5'-ggaattctagaCCITGGGAYGARAYITGGAARTG-3'     (SEQ ID NO 74)

HCPr66(-):   5'-ctattaTTGTATCCCRCTGATGAARTTCCACAT-3'      (SEQ ID NO 70)

set H:
HCPr130(+):  5'-ggaattctagACIGCITAYCARGCIACIGTITGYGC-3'   (SEQ ID NO 75)

HCPr66(-):   5'-ctattaTTGTATCCCRCTGATGAARTTCCACAT-3'      (SEQ ID NO 70)

set I:
HCPr134(+):  5'-CATATAGATGCCCACTTCCTATC-3'                (SEQ ID NO 76)

HCPr66(-):   5'-ctattaTTGTATCCCRCTGATGAARTTCCACAT-3'      (SEQ ID NO 70)

set J:
HCPr131(+):  5'-ggaattctagaCCITCITGGGAYGARAYITGGAARTG-3'  (SEQ ID NO 74)

HCPr118(-):  5'-actagtcgactaYTGIATICCRCTIATRWARTTCCACAT-3' (SEQ ID NO 71)

set K:
HCPr130(+):  5'-ggaattctagACIGCITAYCARGCIACIGTITGYGC-3'   (SEQ ID NO 75)

HCPr118(-):  5'-actagtcgactaYTGIATICCRCTIATRWARTTCCACAT-3' (SEQ ID NO 71)

set L:
HCPr134(+):  5'-CATATAGATGCCCACTTCCTATC-3'                (SEQ ID NO 76)

HCPr118(-):  5'-actagtcgactaYTGIATICCRCTIATRWARTTCCACAT-3' (SEQ ID NO 71)

set M:
HCPr3(+):    5'-GTGTGCCAGGACCATC-3' and                   (SEQ ID NO 77)

HCPr(-):     5'-GACATGCATGTCATGATGTA-3                    (SEQ ID NO 78)

set N:
HCPr3(+):    5'-GTGTGCCAGGACCATC-3' and                   (SEQ ID NO 77)

HCPr118(-):  5'-actagtcgactaYTGIATICCRCTIATRWARTTCCACAT-3' (SEQ ID NO 71)

set O:
HCPr3(+):    5'-GTGTGCCAGGACCATC-3' and                   (SEQ ID NO 77)

HCPr66(-):   5'-ctattaTTGTATCCCRCTGATGAARTTCCACAT-3'      (SEQ ID NO 70)
```

No PCR products could be obtained with the sets of primers A, B, C, D, E, F, G, H, I, J, K, L, M, and N, on random-primed cDNA obtained from type 3 sera. With the primer set O, no fragment could be amplified from type 3 sera. However, a smear containing a few weakly stainable bands was obtained from serum BR36. After sequence analysis of several DNA fragments, purified and cloned from the area around 300 bp on the agarose gel, only, one clone, HCC153 (SEQ ID NO 29), was shown to contain HCV information. This sequence was used to design primer HCPr152.

A new primer set P was subsequently tested on several sera.

set P:
HCPr152(+): 5'-TACGCCTCTTCTATATCGGTTGGGGCCTG-3' and (SEQ ID NO 79)

HCPr66(-): 5'-CTATTATTGTATCCCRCTGATGAARTTCCACAT-3' (SEQ ID NO 70)

The 464-bp HCPr152/66 fragment was obtained from serum BR36 (BR36-20) and serum HD10 (HD10-1). The following clones were obtained from these PCR products:
From fragment HD10-1:

|  |  |
|---|---|
| HD10-1-25, | (SEQ ID NO 31) |
| HD10-1-3, | (SEQ ID NO 33) |

From fragment BR36-20:

|  |  |
|---|---|
| BR36-20-164, | (SEQ ID NO 35) |
| BR36-20-165, | (SEQ ID NO 37) |
| BR36-20-166, | (SEQ ID NO 39) |

The nucleotide sequences obtained from clones with SEQ ID NO 29, 31, 33, 35, 37 or 39 are shown aligned with the sequences of prototype isolates of other types of HCV in FIG. 6. In addition to one silent 3rd letter variation, one 2nd letter mutation resulted in an E to G substitution at position 175 of the deduced amino acid sequence of BR-6 (FIG. 7). Serum HD10 clones were completely identical. The two type 3 isolates were nearly 94% homologous in this NS4 region. The homologies with other types are presented in Table 5.

Example 4

Analysis of the anti-NS4 Response to Type-specific Peptides

As the NS4 sequence contains the information for an important epitope cluster, and since antibodies towards this region seem to exhibit little cross-reactivity (Chan et al., 1991), it was worthwhile to investigate the type-specific antibody response to this region. For each of the 3 genotypes, HCV-1 (Choo et al., 1991). HC-J6 (Okamoto et al., 1991) and BR36 (present invention), three 20-mer peptides were synthesized covering the epitope region between amino acids 1688 and 1743 (as depicted in table 6). The synthetic peptides were applied as parallel lines onto membrane strips. Detection of anti-NS4 antibodies and color development was performed according to the procedure described for the INNO-LIA HCV Ab II kit (Innogenetics, Antwerp). Peptide synthesis was carried out on a 9050 PepSynthesizer (Millipore). After incubation with 15 LiPA-selected type 3 sera, 9 samples showed reactivity towards NS4 peptides of at least 2 different types, but a clearly positive reaction was observed for 3 sera (serum BR33. HD30 and DKH) on the type 3 peptides, while negative (serum BR33 and HD30) or indeterminate (serum DKH) on the type 1 and type 2 NS4 peptides; 3 sera tested negative for anti-NS4 antibodies (FIG. 8). Using the same membrane strips coated with the 9 peptides as indicated above and as shown in FIG. 8. 38 type 1 sera (10 type 1a and 28 type 1b), 11 type 2 sera (10 type 2a and 1 type 2b), 12 type 3a sera and 2 type 4 sera (as determined by the LiPA procedure) were also tested. As shown in Table 8, the sera reacted in a genotype-specific manner with the NS4 epitopes. These results demonstrate that type-specific anti-NS4 antibodies can be detected in the sera of some patients. Such genotype-specific synthetic peptides might be employed to develop serotyping assays, for example a mixture of the nine peptides as indicated above, or combined with the NS4 peptides from the HCV type 4 or 6 genotype or from new genotypes corresponding to the region between amino acids 1688 and 1743, or synthetic peptides of the NS4 region between amino acids 1688 and 1743 of at least one of the 6 genotypes, combined with the E1 protein or deletion mutants thereof, or synthetic E1 peptides of at least one of the genotypes. Such compositions could be further extended with type-specific peptides or proteins, including for example the region between amino acids 68 and 91 of the core protein, or more preferably the region between amino acids 68 and 78. Furthermore, such type-specific antigens may be advantageously used to improve current diagnostic screening and confirmation assays and/or HCV vaccines.

Example 5

The Core and E1 Reasons of HCV Type 5

Sample BE95 was selected from a group of sera that reacted positive in a prototype Line Probe Assay as described earlier (Stuyver et al., 1993), because a high-titer of HCV RNA could be detected, enabling cloning of fragments by a single round of PCR. As no sequences from any coding region of type 5 has been disclosed yet, synthetic oligonucleotides for PCR amplification were chosen in the regions of little sequence variation after aligning the sequences of HCV-1 (Choo et al., 1991), HCV-J (Kato et al., 1990), HC-J6 (Okamoto et al., 1991), HC-J8 (Okamoto et al., 1992), and the new type 3 sequences of the present invention HD10, BR33, and BR36 (see FIG. 5, Example 2). The following sets of primers were synthesized on a 392 DNA/RNA synthesizer (Applied Biosystems):

Set 1:
HCPr52(+): 5'-atgTTGGGTAAGGTCATCGATACCCT-3' (SEQ ID NO 80)
and

HCPr54(-): 5'-ctattaCCAGTTCATCATCATATCCCA-3' (SEQ ID NO 78)

Set 2:
HCPr41(+): 5'-CCCGGGAGGTCTCGTAGACCGTGCA-3' (SEQ ID NO 81)
and

```
HCPr40(-):  5'-ctattaAAGATAGAGAAAGAGCAACCGGG-3'   (SEQ ID NO 82)

Set 3:
HCPr41(+):  5'-CCCGGGAGGTCTCGTAGACCGTGCA-3'      (SEQ ID NO 81)
and

HCPr54(-):  5'-ccattaCCAGTTCATCATCATATCCCA-3'    (SEQ ID NO 78)
```

The three sets of primers were employed to amplify the regions of the type 5 isolate PC as described (Stuyver et al., 1993). Set 1 was used to amplify the E1 region and yielded fragment PC-4, set 2 was designed to yield the Core region and yielded fragment PC-2. Set 3 was used to amplify the Core and E1 region and yielded fragment PC-3. These fragments were cloned as described (Stuyver et al., 1993). The following clones were obtained from the PCR fragments:

From fragment PC-2:

```
PC-2-1 (SEQ ID NO 41), PC-2-6 (SEQ ID NO 43),
```

From fragment PC-4:

```
PC-4-1 (SEQ ID NO 45), PC-4-6 (SEQ ID NO 47),
```

From fragment PC-3:

```
PC-3-4 (SEQ ID NO 49), PC-3-8 (SEQ ID NO 51)
```

An alignment of sequences with SEQ ID NO 41, 43, 45, 47, 49 and 51, is given in FIG. 9. A consensus amino acid sequence (PC C/E1: SEQ ID NO 54) can be deduced from each of the 2 clones cloned from each of the three PCR fragments as depicted in FIG. 5, which overlaps the region between nucleotides 1 and 957 (.Kato et al., 1990). The 6 clones are very closely related to each other (mutual homologies of about 99.7%).

An alignment of nucleotide sequence with SEQ ID NO 53 or 151 (PC C/E1 from isolate BE95) with known nucleotide sequences from the Core/E1 region is given in FIG. 3. The clone is only distantly related to type 1, type 2, type 3 and type 4 sequences (Table 5).

Example 6

NS3/NS4 Region of HCV Type 5

Attempts were undertaken to clone the NS3/NS4 region of the isolate BE95, described in example 5. The following sets of primers were selected in the regions of little sequence variability after aligning the sequences of HCV-1 (Choo et al., 1991), HCV-J (Kato et al., 1991), HC-J6 (Okamoto et al., 1991), and HC-J8 (Okamoto et al., 1992) and of the sequences obtained from type 3 sera of the present invention (SEQ ID NO 31, 33, 35, 37 and 39); smaller case lettering is used for nucleotides added for cloning purposes:

```
set A:
HCPr116(+):  5'-ttttAAATACATCATGRCITGYATG-3'                    (SEQ ID NO 66)

HCPr66(-):   5'-ctattaTTGTATCCCRCTGATGAARTTCCACAT-3'            (SEQ ID NO 70)

set B:
HCPr116(+):  5'-ttttAAATACATCATGRCITGYATG-3'                    (SEQ ID NO 69)

HCPr118(-):  5'-actagtcgactaYTGIATICCRCTIATRWARTTCCACAT-3'      (SEQ ID NO 71)

set C:
HCPr117(+):  5'-ttttAAATACATCGCIRCITGCATGCA-3'                  (SEQ ID NO 72)

HCPr66(-):   5'-ctattaTTGTATCCCRCTGATGAARTTCCACAT-3'            (SEQ ID NO 70)

set D:
HCPr117(+):  5'-ttttAAATACATCGCIRCITGCATGCA-3'                  (SEQ ID NO 72)

HCPr118(-):  5'-actagtcgactaYTGIATICCRCTIATRWARTTCCACAT-3'      (SEQ ID NO 71)

set E:
HCPr116(+):  5'-ttttAAATACATCATGRCITGYATG-3'                    (SEQ ID NO 69)

HCPr119(-):  actagtcgactaRTTIGCIATIAGCCG/TRTTCATCCAYTG-3'       (SEQ ID NO 73)

set F:
HCPr117(+):  5'-ttttAAATACATCGCIRCITGCATGCA-3'                  (SEQ ID NO 72)

HCPr119(-):  actagtcgactaRTTIGCIATIAGCCG/TRTTCATCCAYTG-3'       (SEQ ID NO 73)

set G:
HCPr131(+):  5'-ggaattctagaCCITCITGGGAYGARAYITGGAARTG-3'        (SEQ ID NO 74)

HCPr66(-):   5'-ctattaTTGTATCCCRCTGATGAARTTCCACAT-3'            (SEQ ID NO 70)

set H:
```

-continued

```
HCPr130(+):  5'-ggaattctagACIGCITAYCARGCIACIGTITGYGC-3'         (SEQ ID NO 75)

HCPr66(-):   5'-ctattaTTGTATCCCRCTGATGAARTTCCACAT-3'            (SEQ ID NO 70)

set I:
HCPr134(+):  5'-CATATAGATGCCCACTTCCTATC-3'                      (SEQ ID NO 76)

HCPr66(-):   5'-ctattaTTGTATCCCRCTGATGAARTTCCACAT-3'            (SEQ ID NO 70)

set J:
HCPr131(+):  5'-ggaattctagaCCITCITGGGAYGARAYITGGAARTG-3'        (SEQ ID 74)

HCPr118(-):  5'-actagtcgactaYTGIATICCRCTIATRWARTTCCACAT-3'      (SEQ ID NO 71)

set K:
HCPr130(+):  5'-ggaattctagACIGCITAYCARGCIACIGTITGYGC-3'         (SEQ ID NO 75)

HCPr118(-):  5'-actagtcgactaYTGIATICCRCTIATRWARTTCCACAT-3'      (SEQ ID NO 71)

set L:
HCPr134(P30  5'-CATATAGATGCCCACTTCCTATC-3'                      (SEQ ID NO 76)
):

HCPr118(-):  5'-actagtcgactaYTGIATICCRCTIATRWARTTCCACAT-3'      (SEQ ID NO 71)

set M:
HCPr3(+):    5'-GTGTGCCAGGACCATC-3'                             (SEQ ID NO 77)
and HCPr4(-):    5'-GACATGCATGTCATGATGTA-3'                         (SEQ ID NO 78)

set N:
HCPr3(+):    5'-GTGTGCCAGGACCATC-3'                             (SEQ ID NO 77)
and HCPr118(-):  5'-actagtcgactaYTGIATICCRCTIATRWARTTCCACAT-3'      (SEQ ID NO 71)

set O:
HCPr3(+):    5'-GTGTGCCAGGACCATC-3'                             (SEQ ID NO 77)
and HCPr66(-):   5'-ctattaTTGTATCCCRCTGATGAARTTCCACAT-3'            (SEQ ID NO 70)
```

No PCR products could be obtained with the sets of primers A, B, C, D, E, F, G, H, I, J, K, L, M, and N, on random-primed cDNA obtained from type 3 sera. However, set O yielded what appeared to be a PCR artifact fragment estimated about 1450 base pairs, instead of the expected 628 base pairs. Although it is not expected that PCR artifact fragments contain information of the gene or genome that was targetted in the experiment, efforts were put in cloning of this artifact fragment, which was designated fragment PC-1. The following clones, were obtained from fragment PC-1:

PC-1-37 (SEQ ID NO 59 and SEQ ID NO 55), PC-1-48 (SEQ ID NO 61 and SEQ ID NO 57)

The sequences obtained from the 5' and 3' ends of the clones are given in SEQ ID NOS 55, 57, 59, and 61, and the complete sequences with SEQ ID NO 197 and 199 are shown aligned with the sequences of prototype isolates of other types of HCV in FIG. 10 and the alignment of the deduced amino acid sequences is shown in FIG. 11 and 7. Surprisingly, the PCR artifact clone contained HCV information. The positions of the sequences within the HCV genome are compatible with a contiguous HCV sequence of 1437 nucleotides, which was the estimated size of the cloned PCR artifact fragment. Primer HCPr66 primed correctly at the expected position in the HCV genome. Therefore, primer HCPr3 must have incidentally misprimed at a position 809 nucleotides upstream of its legitimate position in the HCV genome. This could not be expected since no sequence information was available from a coding region or type 5.

Example 7

The E2 Region of HCV Type 5

Serum BE95 was chosen for experiments aimed at amplifying a part of the E2 region of HCV type 5.

After aligning the sequences of HCV-1 (2), HCV-J(1), HC-J6 (3), and HC-J8 (4), PCR primers were chosen in those regions of little sequence variation.

Primers HCPr109(+): 5'-TGGGATATGATGAT-GAACTGGTC-3' (SEQ ID NO 141) and HCPr14(-): 5'-CCAGGTACAACCGAACCAATTGCC-3' (SEQ ID NO 142) were combined to amplify the aminoterminal region of the E2/NS1 region, and were synthesized on a 392 DNA/RNA synthesizer (Applied Biosystems). With primers HCPr109 and HCPr14, a PCR fragment of 661 bp was generated, containing 169 nucleodtides corresponding to the E1 carboxyterminus and 492 bases from the region encoding the E2 aminoterminus.

An alignment of the type 5 E1/E2 sequences with seq ID NO. 158 with known sequences is presented in FIG. 10. The deduced protein sequence was compared with the different genotypes (FIG. 12, amino acids 328–546). In the E1 region, there were no extra structural important motifs found. The aminoterminal part of E2 was hypervariable when compared with the other genotypes. All 6 N-glycosylation sites and all 7 cysteine residue's were conserved in this E2 region. To preserve alignment, it was necessary to introduce a gap between aa 474 and 475 as for type 3a, but not between aa 480 and 481, as for type 2.

Example 8

The NS5b Region of HCV Type 4

Type 4 sera GB48, GB116, GB215, and GB358, selected by means of the line probe assay (LiPA, Stuyver et al., 1993), as well as sera GB549 and GB809 that could not be typed by means of this LiPA (only hybridization was observed with the universal probes), were selected from Gabonese patients. All these sera were positive after the first round of PCR reactions for the 5' untranslated region (Stuyver et al., 1993) and were retained for further study.

RNA was isolated from the sera and cDNA synthesized as described in example 1. Universal primers in the NS5 region were selected after alignment of the published sequences as follows:

```
HCPr206(+): 5'-TGGGGATCCCGTATGATACCCGCTGCTTTGA-3'    (SEQ ID NO. 124)

and

HCPr207(-): 5'-GGCGGAATTCCTGGTCATAGCCTCCGTGAA-3'     (SEQ ID NO. 125);
``` and were synthesized on a 392 DNA/RNA synthesizer (Applied Biosystems). Using the Line Probe Assay (LiPA), four high-titer type 4 sera and 2 sera that could not be classified were selected and subsequently analyzed with the primer set HCPr206/207. NS5 PCR fragments obtained using these primers from serum GB48 (GB48-3), serum GB116 (GB116-3), serum GB215 (GB215-3), serum GB358 (GB358-3), serum GB549 (GB549-3), and serum GB809 (GB809-3), were selected for cloning. The following sequences were obtained from the PCR fragments:

```
From fragment GB48-3:  GB48-3-10 (SEQ ID NO. 106)

From fragment GB116-3: GB116-3-5 (SEQ ID NO. 108)

From fragment GB215-3: GB215-3-8 (SEQ ID NO. 110)

From fragment GB358-3: GB358-3-3 (SEQ ID NO. 112)

From fragment GB549-3: GB549-3-6 (SEQ ID NO. 114)

From fragment GB809-3: GB809-3-1 (SEQ ID NO. 116)
```

An alignment of nucleotide sequences with SEQ ID NO. 106, 108, 110, 112, 114, and 116 with known sequences is given in FIG. 1. An alignment of deduced amino acid sequences with SEQ ID NO. 107, 109, 111, 113, 1151, and 117 with known sequences is given in FIG. 2. The 4 isolates that had been typed as type 4 by means of LiPA are very closely related to each other (mutual homologies of about 95%), but are only distantly related to type 1, type 2, and type 3 sequences (e.g. GB358 shows homologies of 65.6 to 67.7% with other genotypes, Table 4). The sequence obtained from sera GB549 and GB809 also show similar homologies with genotypes 1, 2, and 3 (65.9 to 68.8% for GB549 and 65.0 to 68.5% for GB809, Table 4), but an intermediate homology of 79.7 to 86.8% (often observed between subtypes of the same type) exists between GB549 or GB809 with the group of isolates consisting of GB48, GB116, GB215, and GB358, or between GB549 and GB809. These data indicate the discovery of 3 new subtypes within the HCV genotype 4: in the present invention, these 3 subtypes are designated subtype 4c, represented by isolates GB48, GB 116, GB215, and GB358, subtype 4g, represented by isolate GB549, and subtype 4e, represented by isolate GB809. Although the homologies observed between subtypes in the NS5 region seem to indicate a closer relationship between subtypes 4c and 4e, the homologies observed in the E1 region indicate that subtypes 4g and 4e show the closest relation (see example 8).

Example 9

The Core/E1 Region of HCV Type 4

From each of the 3 new type 4 subtypes, one representative serum was selected for cloning experiments in the Core/E1 region. GB549 (subtype 4g) and GB809 (subtype 4e) were analyzed together with isolate GB358 that was chosen from the subtype 4c group.

Synthetic Oligonucleotides:

After aligning the sequences of HCV-1 (2), HCV-J(1), HC-J6 (3), and HC-J8 (4), PCR primers were chosen in those regions of little sequence variation. Primers HCPr52 (+): 5'-atgTTGGGTAAGGTCATCGATACCCT-3' (SEQ ID NO:80), HCPr23(+): 5'-CTCATGGGGTACATTCCGCT-3' (SEQ ID NO:67), and HCPr54(-): 5'-CTATTACCAGT-TCATCATCATATCCCA-3' (SEQ ID NO:68), were synthesized on a 392 DNA/RNA synthesizer (Applied Biosystems). The sets of primers HCPr23/54 and HCPr52/54 were used, but only with the primer set HCPr52/54, PCR fragments could be obtained. This set of primers amplified the sequence from nucleotide 379 to 957 encoding amino acids 127 to 319: 65 amino acids from the carboxyterminus of core and 128 amino acids of E1. The amplification products GB358-4, GB549-4, and GB809-4 were cloned as described in example 1. The following were obtained from the PCR fragments:

```
From fragment GB358-4: GB358-4-1 (SEQ ID NO 118)

From fragment GB549-4: GB549-4-3 (SEQ ID NO 120)

From fragment GB809-4: GB809-4-3 (SEQ ID NO 122)
```

An alignment of the type 4 Core/E1 nucleotide sequences with seq ID NO. 118, 120, and 122 with known sequences is presented in FIG. 4. The homologies of the type 4 E1 region (without core) with type 1, type 2, type 3, and type 5 prototype sequences are depicted in Table 4. Homologies of 53 to 66% are observed with representative isolates of non-type 4 genotypes. Observed homologies in the E1 region within type 4, between the different subtypes, ranges from 75.2 to 78.4%. The recently disclosed sequences of the core region of Egyptian type 4 isolates (for example EG-29 in FIG. 3) described by Simmonds et al. (1993) do not allow alignment with the Gabonese sequences (as described in the present invention) in the NSB region and may belong to different type 4 subtypes(s) as can be deduced from the core sequences. The deduced amino acid sequences with SEQ ID NO 119, 121, and 123 are aligned with other prototype sequences in FIG. 5. Again, type-specific variation mainly resides in the variable V regions, designated in the present invention, and therefore, type-4-specific amino acids or V regions will be instrumental in diagnosis and therapeutics for HCV type 4.

Example 10

The Core/E1 and NS5b Regions of New HCV Type 2, 3 and 4 Subtypes

Samples NE92 (subtype 2d), BE98 (subtype 3c), CAM600 and GB809 (subtype 4e), CAMG22 and CAMG27 (subtype 4f), GB438 (subtype 4h), CAR4/1205 subtype (4i), CAR1/501 (subtype 4j), CAR1/901 (subtype 4?), and GB724 (subtype 4?) were selected from a group of sera that reacted positive but aberrantly in a prototype Line Probe Assay as described earlier (Stuyver et al., 1993). Another type 5a isolate BE100 was also analyzed in the C/E1 region, and yet another type 5a isolate BE96 in the NS5b region. A high-titer of HCV RNA could be detected, enabling cloning of fragments by a single round of PCR. As no sequences from any coding region of these subtypes had been disclosed yet, synthetic oligonucleotides for PCR amplification were chosen in the regions of little sequence variation after aligning the sequences of HCV-1 (Choo et al., 1991), HCV-J(Kato et al., 1990), HC-J6 (Okamoto et al., 1991), HC-J8 (Okamoto et al., 1992), and the other new sequences of the present invention.

The above mentioned sets 1, 2 and 3 (see example 5) of primers were used, but only with set 1, PCR fragments could be obtained from all isolates (except for BE98, GB724, and CAR1/501). This set of primers amplified the sequence from nucleotide 379 to 957 encoding amino acids 127 to 319: 65 amino acids from the carboxyterminus of core and 128 amino acids of E1. With set 3, the core/E1 region from isolate NE92 and BE-98 could be amplified, and with set 2, the core region of GB358, GB724, GB809, and CAM600 could be amplified. The amplification products were cloned as described in example 1. The following clones were obtained from the PCR fragments:

From isolate GB724, the clone with SEQ ID NO 193 from the core region.
From isolate NE92, the clone with SEQ ID NO 143
From isolate BE98, the clone from the core/E1 region of which part of the sequence has been analyzed and is given in SEQ ID NO 147,
From isolate CAM600, the clone with SEQ ID NO 167 from the E1 region, or SEQ ID NO 165 from the Core/E1 region as shown in FIG. 3,
From isolate CAMG22, the clone with SEQ ID NO 171 from the E1 region as shown in FIG. 4,
from isolate GB358, the clone with SEQ ID NO 191 in the core region,
from isolate CAMG27, the clone with SEQ ID NO 173 from the core/E1 region,
from isolate GB438, the clone with SEQ ID NO 177 from the core/ E1 region,
from isolate CAR4/1205, the clone with SEQ ID NO 179 from the core/E1 region,
from isolate CAR1/901, the clone with SEQ ID NO 181 from the core/ E1 region,
from isolate GB809, the clone GB809-4 with SEQ ID NO 189 from the core/E1 region, clone GB809-2 with SEQ ID NO 169 from the core/E1 region and the clone with SEQ ID NO 163 from the core region,
and from isolate BE100, the clone with SEQ ID NO 155 from the Core/E1 region as shown in FIG. 4.

An alignment of these Core/E1 sequences with known Core/E1 sequences is presented in FIG. 4. The deduced amino acid sequences with SEQ ID NO 144, 148, 164, 168, 170, 172, 174, 178, 180, 182, 190, 192, 194, 156, 166 are aligned with other prototype sequences in FIG. 5. Again, type-specific variation mainly resides in the variable V regions, designated in the present invention, and therefore, type 2d, 3c and type 4-specific amino acids or V regions will be instrumental in diagnosis and therapeutics for HCV type (subtype) 2d, 3c or the different type 4 subtypes.

The NS5b region of isolates NE92, BE98, CAM600, CAMG22, GB438, CAR4/1205, CAR1/501, and BE96 was amplified with primers HCPr206 and HCPr207 (Table 7). The corresponding clones were cloned and sequenced as in example 1 and the corresponding sequences (of which BE98 was partly sequenced) received the following identification numbers:

| | |
|---|---|
| NE92: | SEQ ID NO 145 |
| BE98: | SEQ ID NO 149 |
| CAM600: | SEQ ID NO 201 |
| CAMG22: | SEQ ID NO 203 |
| GB438: | SEQ ID NO 207 |
| CAR4/1205: | SEQ ID NO 209 |
| CAR1/501: | SEQ ID NO 211 |
| BE95: | SEQ ID NO 159 |
| BE96: | SEQ ID NO 161 |

An alignment of these NS5b sequences with known NS5b sequences is presented in FIG. 1. The deduced amino acid sequences with SEQ ID NO 146, 150, 202, 204 206, 208, 210, 212, 160, 162 are aligned with other prototype sequences in FIG. 2. Again, subtype-specific variations can be observed, and therefore, type 2d, 3c and type 4-specific amino acids or V regions will be instrumental in diagnosis and therapeutics for HCV type (subtype) 2d, 3c or the different type 4 subtypes.

Example 11

Genotype-specific Reactivity of Anti-E1 Antibodies (Serotyping)

E1 proteins were expressed from vaccinia virus constructs containing a core/E1 region extending from nucleotide positions 355 to 978 (Core/E1 clones described in previous examples including the primers HCPr52 and HCPr54), and expressed proteins from L119 (after the initiator methionine) to W326 of the HCV polyprotein. The expressed protein was modified upon expression in the appropriate host cells (e.g. HeLa, RK13, HuTK-, HepG2) by cleavage between amino acids 191 and 192 of the HCV polyprotein and by the addition of high-mannose type carbohydrate motifs. Therefore, a 30 to 32 kDa glycoprotein could be observed on western blot by means of detection with serum from patients with hepatitis C.

As a reference, a genotype 1b clone obtained form the isolate HCV-B was also expressed in an identical way as described above, and was expressed from recombinant vaccinia virus vvHCV-11A.

A panel of 104 genotyped sera was first tested for reactivity with a cell lysate containing type 1b protein expressed from the recombinant vaccinia virus vvHCV-11A, and compared with cell lysate of RK13 cells infected with a wild type vaccinia virus ('E1WT'). The lysates were coated as a 1/20 dilution on a normal ELISA microtiter plate (Nunc maxisorb) and left to react with a 1/20 dilution of the respective sera. The panel consisted of 14 type 1a, 38 type 1b, 21 type 2, 21 type 3a, and 9 type 4 sera. Human antibodies were subsequently detected by a goat anti-human IgG conjugated with peroxidase and the enzyme activity was detected. The optical density values of the E1 and wild type lysates were divided and a factor 2 was taken as the cut-off. The results are given in the table A. Eleven out of 14 type 1a sera (79%), 25 out of 38 type 1b sera (66%), 6 out of 21 (29%), 5 out of 21 (24%), and none of the 9 type 4 or the type 5 serum reacted (0%). These experiments clearly show the high prevalence of anti-E1 antibodies reactive with the type 1 E1 protein in patients infected with type 1 (36/52 (69%)) (either type 1a or type 1b), but the low prevalence or absence in non-type sera (11/52 (21%)).

TABLE A

| serum | E1/WT |
|---|---|
| type 1a | |
| 3748 | 3.15 |
| 3807 | 3.51 |
| 5282 | 1.99 |
| 9321 | 3.12 |
| 9324 | 2.76 |
| 9325 | 6.12 |
| 9326 | 10.56 |
| 9356 | 1.79 |
| 9388 | 3.5 |
| 8366 | 10.72 |
| 8380 | 2.27 |
| 10925 | 4.02 |
| 10936 | 5.04 |
| 10938 | 1.36 |
| type 1b | |
| 5205 | 2.25 |
| 5222 | 1.33 |
| 5246 | 1.24 |
| 5250 | 13.58 |
| 5493 | 0.87 |
| 5573 | 1.75 |
| 8243 | 1.77 |
| 8244 | 2.05 |
| 8316 | 1.21 |

TABLE A-continued

| serum | E1/WT |
|---|---|
| 8358 | 5.04 |
| 9337 | 14.47 |
| 9410 | 5 |
| 9413 | 5.51 |
| 10905 | 1.26 |
| 10919 | 5.00 |
| 10928 | 8.72 |
| 10929 | 8.26 |
| 10931 | 2.3 |
| 10932 | 4.41 |
| 44 | 2.37 |
| 45 | 3.14 |
| 46 | 4.37 |
| 47 | 5.68 |
| 48 | 2.97 |
| 49 | 1.18 |
| 50 | 9.85 |
| 51 | 4.51 |
| 52 | 1.11 |
| 53 | 5.20 |
| 54 | 0.98 |
| 55 | 1.48 |
| 56 | 1.06 |
| 57 | 3.85 |
| 58 | 7.6 |
| 59 | 3.28 |
| 60 | 3.23 |
| 61 | 7.82 |
| 62 | 1.92 |
| type 2 | |
| 23 | 0.91 |
| 24 | 1.16 |
| 25 | 2.51 |
| 26 | 0.96 |
| 27 | 1.20 |
| 28 | 0.96 |
| 29 | 2.58 |
| 30 | 8.05 |
| 31 | 0.92 |
| 32 | 0.82 |
| 33 | 5.75 |
| 34 | 0.79 |
| 35 | 0.86 |
| 36 | 0.85 |
| 37 | 0.76 |
| 38 | 0.92 |
| 39 | 1.08 |
| 40 | 2.33 |
| 41 | 2.83 |
| 42 | 1.21 |
| 43 | 0.91 |
| type 3 | |
| 1 | 6.88 |
| 2 | 1.47 |
| 3 | 3.06 |
| 4 | 6.52 |
| 5 | 10.24 |
| 6 | 2.72 |
| 7 | 1.11 |
| 8 | 1.54 |
| 9 | 1.60 |
| 10 | 1.21 |
| 11 | 1.07 |
| 12 | 1.00 |
| 13 | 0.85 |
| 14 | 0.96 |
| 15 | 0.51 |
| 16 | 1.00 |
| 17 | 1.09 |
| 18 | 0.99 |
| 19 | 1.04 |
| 20 | 1.04 |
| 21 | 0.96 |

TABLE A-continued

| serum | E1/WT |
|---|---|
| type 4 | |
| 22 | 0.87 |
| GB48 | 0.49 |
| GB113 | 0.68 |
| GB116 | 0.73 |
| GB215 | 0.52 |
| GB358 | 0.56 |
| GB359 | 0.71 |
| GB438 | 1.08 |
| GB516 | 1.04 |
| type 5 | |
| BE95 | 0.86 |

Core/E1 clones of isolates BR136 (type 3a) and BE95 (type 5a) were subsequently recombined into the viruses vvHCV-62 and vvHCV-63, respectively,. A genotyped panel of sera was subsequently tested onto cell lysates obtained from RK13 cells infected with the recombinant viruses vvHCV-62 and vvHCV-63. Tests were carried out as described above and the results are given in the table given below (TABLE B). From these results, it can clearly be seen that, although some cross-reactivity occurs (especially between type 1 and 3), the obtained values of a given serum are usually higher on its homologous E1 protein than on an E1 protein of another genotype. For type 5 sera, none of the 5 sera were reactive on type 1 or 3 E1 proteins, while 3 out of 5 were shown to contain anti-E1 antibodies when tested on their homologous type 5 protein. Therefore, in this simple test system, a considerable number of sera can already be serotyped. Combined with the reactivity to type-specific $NS^4$ epitopes or epitopes derived from other type-specific parts of the HCV polyprotein, a serotyping assay may be developed for discriminating the major types of HCV. To overcome the problem of cross-reactivity, the position of cross-reactive epitopes may be determined by someone skilled in the art (e.g. by means of competition of the reactivity with synthetic peptides), and the epitopes evoking cross-reactivity may be left out of the composition to be included in the serotyping assay or may be included in sample diluent to outcompete cross-reactive antibodies.

TABLE B

| serum | $E1^{1b}$/WT | $E1^{3a}$/WT | $E1^{5a}$/WT |
|---|---|---|---|
| type 1b | | | |
| 8316 | 0.89 | 0.59 | 0.80 |
| 8358 | 2.22 | 2.65 | 1.96 |
| 9337 | 1.59 | 0.96 | 0.93 |
| 9410 | 16.32 | 9.60 | 3.62 |
| 9413 | 9.89 | 2.91 | 2.85 |
| 10905 | 1.04 | 0.96 | 1.05 |
| 10919 | 3.17 | 2.56 | 2.96 |
| 10928 | 4.39 | 2.28 | 2.07 |
| 10929 | 2.95 | 2.07 | 2.08 |
| 10931 | 3.11 | 1.49 | 2.11 |
| 5 | 0.86 | 0.86 | 0.96 |
| 6 | 3.48 | 1.32 | 1.32 |
| 7 | 6.76 | 4.00 | 3.77 |
| 8 | 10.88 | 3.44 | 4.04 |
| 9 | 1.76 | 1.88 | 1.58 |
| 10 | 9.88 | 7.48 | 7.20 |
| 11 | 8.48 | 8.99 | 8.45 |
| 12 | 0.76 | 0.72 | 0.76 |
| 13 | 5.04 | 5.67 | 5.37 |
| 14 | 10.48 | 10.54 | 11.22 |
| 15 | 5.18 | 1.62 | 1.65 |
| type 3 | | | |
| 8332 | 3.39 | 4.22 | 0.66 |
| 10907 | 3.24 | 4.39 | 0.96 |
| 10908 | 0.99 | 0.94 | 0.98 |
| 10934 | 0.86 | 0.90 | 0.90 |
| 10927 | 2.58 | 2.71 | 2.44 |
| 8210 | 0.82 | 0.80 | 0.86 |
| 8344 | 1.09 | 6.66 | 1.17 |
| 8351 | 1.21 | 1.29 | 1.22 |
| 30 | 0.85 | 4.11 | 0.98 |
| 32 | 0.85 | 2.16 | 1.04 |
| type 5 | | | |
| | 0.78 | 0.95 | 1.54 |
| BE110 | 0.79 | 1.01 | 4.95 |
| BE95 | 0.47 | 0.52 | 0.65 |
| BE111 | 0.71 | 0.75 | 8.33 |
| BE112 | 1.01 | 1.27 | 2.37 |
| BE113 | 1.11 | 1.35 | 1.60 |

TABLE 5

Homologies of new HCY sequences with other known HCV types

| Region | isolate | 1a | 1b | 2a | 2b | 3a | | 3b | |
|---|---|---|---|---|---|---|---|---|---|
| (nucleotides) | (type) | HCV-1 | HCV-J | HC-16 | HC-18 | T1 | T2 | T9 | T10 |
| Core (1–573) | PC (5) | 83.8 (91.6) | 84.8 (92.1) | 82.6 (90.1) | 82.4 (89.0) | | | | |
| E1 (574–957) | HD10 (3) | 61.5 (68.0) | 64.6 (68.8) | 57.8 (55.5) | 56.3 (59.4) | | | | |
| | BR36 (3) | 62.0 (66.4) | 62.5 (67.2) | 56.5 (53.9) | 55.2 (58.6) | | | | |

TABLE 5-continued Homologies of new HCY sequences with other known HCV types

| Region (nucleotides) | isolate (type) | 1a HCV-1 | 1b HCV-J | 2a HC-16 | 2b HC-18 | 3a T1 | 3a T2 | 3b T9 | 3b T10 |
|---|---|---|---|---|---|---|---|---|---|
| | BR33 (3) | 60.7 (67.2) | 63.3 (68.0) | 56.5 (54.7) | 56.0 (58.6) | | | | |
| | PC (5) | 61.4 (64.0) | 62.4 (64.8) | 54.1 (49.6) | 53.3 (47.2) | | | | |
| | GB358 (4a) | 62.5 (69.1) | 62.8 (65.9) | 59.4 (54.0) | 54.4 (54.0) | | | | |
| | GB549 (4b) | 66.0 (72.2) | 62.8 (69.8) | 59.1 (56.4) | 56.5 (54.0) | | | | |
| | GB809 (4c) | 63.3 (69.1) | 60.7 (64.3) | 56.7 (53.2) | 53.0 (51.6) | | | | |
| NS3 (3856–1209) | PC (5) | 74.7 (89) | 76.1 (86.4) | 76.1 (89.8) | 78.0 (89.0) | | | | |
| NS4 (4892–5292) | BR36 (3) | 6.78 (78.5) | 69.8 (75.1) | 62.0 (67.5) | 61.7 (66.0) | | | | |
| | HD 10 (3) | 69.8 (74.6) | 66.6 (69.7) | 57.8 (59.9) | 59.1 (59.9) | | | | |
| NS4 (4936–5292) | PC (5) | 61.3 (62.2) | 63.0 (65.5) | 52.9 (46.2) | 54.3 (43.7) | | | | |
| NS5b (8023–8235) | BR34 (3) | 65.7 | 66.7 | 63.9 | 64.3 | 94.8 | 93.9 | 75.6 | 77.0 |
| | BR36 (3) | 64.3 | 67.6 | 64.8 | 66.7 | 94.8 | 93.4 | 75.1 | 76.5 |
| | BR33 (3) | 65.7 | 67.1 | 64.3 | 64.8 | 94.8 | 93.9 | 76.0 | 77.5 |
| | GB358 (4a) | 67.7 (76.1) | 65.6 (77.0) | 66.5 (70.8) | 66.6 (71.7) | | | | |
| | GB549 (4b) | 68.8 (76.1) | 67.1 (77.0) | 65.9 (71.7) | 65.9 (74.4) | | | | |
| | GB809 (4c) | 68.5 (73.5) | 65.0 (73.5) | 67.7 (69.9) | 67.7 (73.5) | | | | |

Shown are the nucleotide homologies (the amino-acid homoloqy is given between brackets) for the region indicated in the left column.

TABLE 6

NS4 sequences of the different genotypes

| prototype | TYPE | SYNTHETIC PEPTIDE NS4-1 (NS4a) | | SYNTHETIC PEPTIDE NS4-5 (NS4b) | | SYNTHETIC PEPTDE NS4-7 (NS4b) | |
|---|---|---|---|---|---|---|---|
| position-> | | 169 | 170 | 172 | 173 | 173 | 174 |
| | | ** * ** ** | | * * * | | * * * * | |
| HCV-1 | 1a | LSG KPAIIPDREV LYREFDE (SEQ ID NO:272) | | SQHLPYIEQ GMMLAEQFKQ K (SEQ ID NO:273) | | LAEQFKQ KALGLLQTAS RQA (SEQ ID NO:274) | |
| HCV-J | 1b | LSG RPAVIPDREV LYQEFDE (SEQ ID NO:275) | | ASHLPYIEQ GMQLAEQFKQ K (SEQ ID NO:276) | | LAEQFKQ KALGLLQTAT KQA (SEQ ID NO:277) | |
| HC-J6 | 2a | VNQ RAVVAPDKEV LYEAFDE (SEQ ID NO:278) | | ASRAALIEE GQRIAEMLKS K (SEQ ID NO:279) | | IAEMLKS KIQGLLQQAS KQA (SEQ ID NO:280) | |
| HC-J8 | 2b | LND RVVVAPDKEI LYEAFDE (SEQ ID NO:281) | | ASKAALIEE GQRMAEMLKS K (SEQ ID NO:282) | | MAEMLKS KIQGLLQQAT RQA (SEQ ID NO:283) | |
| BR36 | 3a | LGG KPAIVPDKEV LYQQ YDE (SEQ ID NO:97) | | SQAAPYIEQ AQVIAHQFKE K (SEQ ID NO:99) | | IAHQFKE KVLGLLQRAT QQQ (SEQ ID NO:100) | |
| PC | 5 | LSG KPAIIPDREA LYQQ FDE<br>V<br>(SEQ ID NO:102 and SEQ ID NO:103, respectively) | | AASLPYMDE TRAIAGQFKE K (SEQ ID NO:284) | | IAGQFKE KVLGFISTTG QKA (SEQ ID NO:105) | |

* residues conserved in every genotype. Double underlined amino acids are type-specific, amino acids in italics are unique to type 3 and 5 sequences.

TABLE 7

| SEQ ID NO | Primer NO (polarity) | Sequence from 5' to 3' |
|---|---|---|
| 63 | HCPr161(-) | 5'-ACCGGAGGCCAGGAGAGTGATCTCCTCC-3' |
| 64 | HCPr162(-) | 5'-GGGCTGCTCTATCCTCATCGACGCCATC-3' |
| 65 | HCPr163(+) | 5'-GCCAGAGGCTCGGAAGGCGATCAGCGCT-3' |
| 66 | HCPr164(-) | 5'-GAGCTGCTCTGTCCTCCTCGACGCCGCA-3' |
| 67 | HCPr23(+) | 5'-CTCATGGGGTACATTCCGCT-3' |
| 68 | HCPr54(-) | 5'-CTATTACCAGTTCATCATCATATCCCA-3' |
| 69 | HCPr116(-) | 5'-ttttAAATACATCATGRCITGYATG-3' |
| 70 | HCPr66(-) | 5'-ctattaTTGTATCCCRCTGATGAARTTCCACAT-3' |
| 71 | HCPr118(-) | 5'actagtcgactaYTGIATICCRCTIATRWARTTCCACAT-3' |
| 72 | HCPr117(+) | 5'-ttttAAATACATCGCIRCITGCATGCA-3' |
| 73 | HCPr119(-) | 5'-actagtcgactaRTTIGCIATIAGCCKRTTCATCCAYTG-3' |
| 74 | HCPr131(-) | 5'-ggaattctagaCCITCITGGGAYGARAYITGGAARTG-3' |
| 75 | HCPr130(+) | 5'-ggaattctagACIGCITAYCARGCIACIGTITGYGC-3' |
| 76 | HCPr134(-) | 5'-CATATAGATGCCCACTTCCTATC-3' |
| 77 | HCPr3(-) | 5'-GTGTGCCAGGACCATC-3' |
| 78 | HCPr4(-) | 5'-GACATGCATGTCATGATGTA-3' |
| 79 | HCPr152(+) | 5'-TACGCCTCTTCTATATCGGTTGGGGCCTG-3' |
| 80 | HCPr52(-) | 5'-atgTTGGGTAAGGTCATCGATACCCT-3' |
| 81 | HCPr41(+) | 5'-CCCGGGAGGTCTCGTAGACCGTGCA-3' |
| 82 | HCPr40(-) | 5'-ctattaAAGATAGAGAAAGAGCAACCGGG-3' |
| 124 | HCPR206 | 5'-tggggatcccgtatgatacccgctgctttga-3' |
| 125 | HCPR207 | 5'-ggcggaattcctggtcatagcctccgtgaa-3' |
| 141 | HCPR109 | 5'-tgggatatgatgatgaactggtc-3' |
| 142 | HCPR14 | 5'-ccaggtacaaccgaaccaattgcc-3' |

TABLE 8

| | NS4 SEROTYPING | | | | | | | | |
|---|---|---|---|---|---|---|---|---|---|
| | Type 1 NS4 | | | Type 2 NS4 | | | Type 3 NS4 | | |
| serum | 1 | 5 | 7 | 1 | 5 | 7 | 1 | 5 | 7 |
| type 1a | | | | | | | | | |
| 101 | 3 | 3 | 3 | — | 1 | 3 | +/− | +/− | 3 |
| 102 | 1 | +/− | 2 | — | — | 2 | — | — | 1 |
| 103 | 1 | 3 | 3 | — | +/− | 3 | — | +/− | 3 |
| 104 | 3 | 3 | 3 | 2 | 2 | 3 | 3 | +/− | 2 |
| 105 | 3 | 3 | 3 | — | 2 | 2 | +/− | +/− | 2 |
| 106 | 3 | 1 | 1 | — | 1 | 2 | +/− | +/− | +/− |
| 107 | 3 | 3 | 3 | — | 2 | 2 | 2 | — | 1 |
| 108 | 3 | 3 | 3 | +/− | +/− | 2 | +/− | 1 | 2 |
| 109 | 3 | 3 | 3 | +/− | 2 | 3 | 1 | — | 3 |
| 110 | 3 | 3 | 3 | — | +/− | 1 | — | — | 3 |
| type 1b | | | | | | | | | |
| 111 | +/− | +/− | — | — | — | — | — | — | — |
| 112 | — | 2 | 3 | — | — | 2 | — | — | 3 |
| 113 | 2 | 3 | 3 | — | — | 1 | — | — | 3 |
| 114 | 2 | 3 | 3 | 1 | + | 2 | 1 | 1 | 3 |
| 115 | 3 | 3 | 3 | — | +/− | 1 | — | — | 3 |
| 116 | 3 | 3 | 3 | — | +/− | 1 | — | — | 1 |
| 117 | 3 | — | — | 3 | +/− | +/− | +/− | — | — |
| 118 | 1 | 2 | 3 | — | +/− | 2 | — | +/− | 3 |
| 119 | +/− | 2 | 2 | +/− | +/− | 2 | + | 1 | 2 |
| 120 | — | 3 | 3 | −3 | +/− | +/− | — | — | — |
| 121 | 3 | 3 | 3 | +/− | 2 | 2 | 2 | 2 | 3 |
| 122 | 3 | 3 | 1 | — | 1 | 2 | 2 | 1 | 1 |
| 123 | 3 | 3 | 2 | — | 1 | 2 | — | 1 | 1 |
| 124 | 3 | 3 | 3 | +/− | 2 | — | — | — | 2 |
| 125 | 3 | 3 | 3 | 1 | 1 | 3 | 2 | 1 | 3 |
| 126 | 1 | 2 | 2 | 1 | 1 | 1 | 1 | 1 | 1 |
| 127 | 3 | 2 | +/− | — | — | 1 | +/− | +/− | +/− |

TABLE 8-continued

NS4 SEROTYPING

| | Type 1 NS4 | | | Type 2 NS4 | | | Type 3 NS4 | | |
|---|---|---|---|---|---|---|---|---|---|
| serum | 1 | 5 | 7 | 1 | 5 | 7 | 1 | 5 | 7 |
| 128 | 3 | 3 | 3 | — | +/− | 1 | 2 | +/− | +/− |
| 129 | 2 | 3 | 3 | — | — | 3 | — | — | 3 |
| 130 | — | 2 | 1 | +/− | — | — | — | — | — |
| 131 | — | 1 | 1 | — | — | — | — | — | +/− |
| 132 | — | — | — | +/− | — | +/− | +/− | — | — |
| 133 | 3 | 3 | 3 | — | 1 | 3 | — | 1 | 3 |
| 134 | — | 2 | 2 | — | — | — | — | — | — |
| 135 | 3 | 3 | 3 | 1 | + | 2 | 2 | 1 | 3 |
| 136 | — | 3 | 3 | +/− | +/− | +/− | +/− | — | 3 |
| 137 | +/− | +/− | +/− | +/− | +/− | +/− | +/− | — | — |
| 138 | 3 | 3 | 3 | +/− | 2 | 2 | 1 | 1 | 3 | type 2a

| 139 | 3 | — | — | 3 | 3 | +/− | 1 | — | — |
|---|---|---|---|---|---|---|---|---|---|
| 140 | +/− | — | — | 3 | 3 | 3 | 3 | — | — |
| 141 | 2 | — | — | 2 | 1 | +/− | 2 | — | — |
| 142 | — | — | — | +/− | — | — | — | — | — |
| 143 | — | +/− | +/− | 1 | 2 | 1 | 1 | +/− | +/− |
| 144 | 1 | 1 | + | 1 | 3 | 2 | 1 | 1 | 2 |
| 145 | — | +/− | +/− | 3 | 1 | 2 | 2 | +/− | +/− |
| 146 | — | — | — | +/− | +/− | — | — | — | — |
| 147 | — | +/− | — | 3 | 1 | 3 | — | — | — |
| 148 | — | — | — | +/− | — | — | +/− | — | — | type 2b

| 149 | — | +/− | +/− | 3 | 3 | 1 | 2 | +/− | +/− |
|---|---|---|---|---|---|---|---|---|---| type 3

| 150 | +/− | +/− | +/− | +/− | +/− | +/− | 1 | 3 | 3 |
|---|---|---|---|---|---|---|---|---|---|
| 151 | — | — | — | — | — | — | 2 | — | 2 |
| 152 | +/− | — | — | — | — | — | 3 | — | — |
| 153 | — | — | — | — | — | — | 1 | — | — |
| 154 | +/− | 1 | 3 | — | +/− | 2 | 2 | 1 | 3 |
| 155 | — | 2 | 3 | — | 2 | 2 | 1 | 1 | 3 |
| 156 | — | — | — | — | — | — | — | — | — |
| 157 | — | — | — | +/− | +/− | — | +/− | 2 | 2 |
| 158 | 2 | — | — | — | 1 | 2 | 3 | 2 | 2 |
| 159 | — | — | — | — | +/− | +/− | — | 3 | 3 |
| 160 | — | — | — | — | +/− | — | — | 2 | 3 |
| 161 | — | — | — | — | 1 | 1 | +/− | 3 | 2 | type 4

| 162 | 1 | — | — | — | — | — | — | — | — |
|---|---|---|---|---|---|---|---|---|---|
| 163 | 2 | — | — | — | +/− | +/− | +/− | — | — |

REFERENCES

Barany F (1991). Genetic disease detection and DNA amplification using cloned thermostable ligase. Proc Natl Acad Sci USA 88: 189–193

Bej A, Mahbubani M, Miller R, Di Cesare J, Haff L, Atlas R (1990) Mutiplex PCR amplification and immobilized capture probes for detection of bacterial pathogens and indicators in water Mol Cell Probes 4.353–365.

Bukh J, Purcell R, Miller R (1992). Sequence analysis of the 5' noncoding region or hepatitis C virus. Proc Natl Acad Sci USA 89:4942–4946.

Bukh J, Purcell R, Miller R (1993). At least 12 genotypes PNAS 90,8231–823–8238

Cha T, Beal E, Irvine B, Kolberg J, Chien D, Kuo G, Urdea M (1992) At least five related, but distinct, hepatitis C viral genotypes exist, Proc Natl Acad Sci USA 89.7144–7148.

Chan S-W, Simmonds P, McOmish F, Yap P, Mitchell R, Dow B, Follett E (1991) Serological responses to infection with three different types of hepatitis C virus Lancet 338 1991.

Chan S-W, McOmish F, Holmes E, Dow B, Peutherer J, Follett E, Yap, P Simmonds P (1992) Analysis of a new hepatitis C virus type and its phylogenetic relationship to existing variants J Gen Virol 73:1131–1141

Chomczynski P, Sacchi N (1987) Single step method of RNA isolation by acid quanidinium thiocyanate-phenol-chloroform extraction. Anal Biochem 162:156–159.

Choo Q, Richman K, Han J, Berger K, Lee C, Dong C, Gallegos C, Coit D, Medina-Selby A, Barr P, Weiner A, Bradley D, Kuo G, Houghton M (1991) Genetic organization and diversity of the hepatitis C virus Proc Natl Acad Sci USA 88 2451–2455

Compton J (1991). Nucleic acid sequence-based amplification. Nature, 350: 91–92

Duchosal A, Eming S, Fisher P (1992) Immunization of hu-PBL-SCID mice and the resue of human monoclonal Fab fragments through combinatorial libraries. Nature 355.258–262.

Duck P (1990). Probe amplifier system based on chimeric cycling oligonucleotides. Biotechniques 9, 142–147.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878

Hijikata M, Kato N, Ootsuyama Y, Nakagawa M, Shimnotohmo K (1991) Gene mapping of the putative structural region of the hepatitis C virus genome by in vitro processing analysis Proc Natl Acad Sci USA 88, 554–5551.

Jacobs K. Rudersdorf R, Neill S, Dougherty J, Brown E, Fritsch E (1988) The thermal stability of oligonucleotide duplexes is sequence independent in tetraalkylammonium salt solutions: application to identifying recombinant DNA clones. Nucl Acids Res 16:4637–4650

Kato N, Hijikata M, Ootsuyama Y, Nakagawa M, Ohkoshi S, Sugimura T, Shimotohno K (1990) Molecular cloning of the human hepatitis C virus genome from Japanese patients with non-A, non-B hepatitis Proc Natl Acad Sci USA 87.9524–9528

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86 1173–1177

Kwok S, Kellogg D, McKinney N, Spasic D, Goda L, Levenson C, Sinisky J, (1990). Effects of primer-template mismatches on the polymerase chain reaction: Human immunodeficiency views type 1 model studies Nucl. Acids Res., 18 999

Landgren U, Kaiser R, Sanders J, Hood L (1988). A ligase-mediated gene detection technique Science 241:1077–1080.

Lizardi P, Guerra C, Lomeli H, Tussie-Luna I, Kramer F (1988) Exponential amplification of recombinant RNA hybridization probes. Bio/Technology 6:1197–1202.

Lomeli H, Tyagi S. Printchard C, Lisardi P, Kramer F (1989) Quantitative assays based on the use of replicatable hybridization probes. Clin Chem 35 1826–1831.

Machida A, Ohnuma H, Tsuda F, Munekata E, Tanaka T, Akahane Y, Okamoto H, Mishiro S (1992) Hepatology 16, 886–891.

Maniatis T, Fritsch E, Sambrook J (1982) Molecular cloning a laboratory manual. Cold Spring Harbor Laboratory Press, Cold Spring Harbor, N.Y.

Mori S, Kato N, Yagyu A, Tanaka T, Ikeda Y, Petchclai B, Chiewsilp P, Kurimura T, Shimotohno K (1992) A new type of hepatitis C virus in patients in Thailand Biochem Biophys Res Comm 183:334–342.

Okamoto H, Okada S, Sugiyama Y, Kurai K, Iizuka H, Machida A, Miyakawa Y, Mayumi M (1991) Nucleotide sequence of the genomic RNA of hepatitis C virus isolated from a human carrier: comparison with reported isolates for conserved and divergent regions J Gen Virol 72–9697–2704.

Okamoto H, Kurai K, Okada S, Yamamoto K, Lizuka H, Tanaka T, Fukuda S. Tsuda F, Mishiro S (1992) Full-length sequences of a hepatitis C virus genome having poor homology to reported isolates: comparative study of four distinct genotypes. Virology 188:331–341

Persson M, Caothien R, Burton D (1991) Generation of diverse high-affinity human monoclonal antibodies by repertoire cloning. Proc Natl Acad Sci USA 89:2432–2436

Saiki R, Gelfand D, Stoffel S, Scharf S, Higuchi R, Horn G, Mullis K, Erlich H (1988) Primer-directed enzymatic amplification of DNA with a thermostable DNA polymerase Science 239–487–491

Saiki R, Walsh P, Levenson C, Erlich H (1989) Genetic analysis of amplified DNA with immobilized sequence-specific oligonucleotide probes (1989) Proc Natl Acad Sci USA 86:6230–6234.

Sano T, Smith C, Cantor C (1992) Immuno-PCR: very sensitive antigen detection by means of specific antibody-DNA conjugates. Science 258:120–122.

Simmonds P, McOmsh F, Yap P. Chan S, Lin C, Dusheiko G, Saeed A, Holmes E (1993), Sequence variability in the 5' non-coding region of hepatitis C virus: identification of a new virus type and restrictions on sequence diversity. J Gen Virology, 74:661–668

Stuyver L, Rossau R, Wyseur A, Duhamel M, Vanderborght B, Van Heuverswyn H. Maertens G (1993) Typing of hepatitis C virus (HCV) isolates and characterization of new (sub)types using a Line Probe Assay. J Gen Virology, 74: 1093–1102

Walker G, Little M, Nadeau J, Shank D (1992). Isothermal in vitro amplification of DNA by a restriction enzyme/DNA polymerase system. Proc Natl Acad Sci USA 89–392–396

Wu D, Wallace B (1989). The ligation amplification reaction (LAR)—amplification of specific DNA sequences using sequential rounds of template-dependent ligation. Genomics 4:560–569

---

The invention claimed is:

1. An isolated Hepatitis C virus polynucleic acid selected from the group consisting of:
   (i) the nucleotide sequence of SEQ ID NO:147,
   (ii) at least 8 contiguous nucleotides of a nucleotide sequence having at least one genotype-specific nucleotide from the region spanning positions 1 to 346 of the Core-region of HCV subtype 3c, and, (iii) the complement of the nucleotide sequence of (i) or (ii).

2. A recombinant vector comprising a vector sequence and a prokaryotic, eukaryotic or viral promotor sequence operably linked to a polynucleic acid sequence of claim 1.

3. A method of detecting or screening for one or more HCV genotypes present in a biological sample, comprising the following steps:

(i) providing a sample nucleic acid, (ii) determining the presence of a polynucleic acid sequence according to claim 1, by means of a sequencing reaction, and, (iii) inferring from the presence of one or more of these HCV polynucleic acid sequences of step (ii) the genotype(s) present in said sample.

4. A method of detecting or screening for one or more HCV genotypes present in a biological sample, comprising the following steps:

(i) providing a sample nucleic acid, (ii) specifically amplifying a polynucleic acid sequence according to claim 1, and, (iii) inferring from the presence of one or more amplified HCV polynucleic acid sequences of step (ii) the genotype(s) present in said sample.

5. An isolated HCV polynucleic acid according to claim 1, wherein said polynucleic acid is capable of acting as a primer of a HCV subtype 3c nucleic acid sequence, and wherein said polynucleic acid comprises at least one HCV subtype 3c genotype specific nucleotide.

6. A kit for determining the presence of HCV genotypes comprising a solid support and a primer according to claim 5.

7. A method for determining the presence of HCV genotypes present in a biological sample comprising the steps of:

(i) providing a sample nucleic acid, (ii) amplifying the nucleic acid with at least one primer according to claim 5, (iii) detecting the amplified nucleic acids, (iv) inferring the presence of one or more genotypes of HCV present from the observed pattern of amplified fragments.

8. An isolated HCV polynucleic acid according to claim 1, wherein said polynucleic acid is capable of acting as a probe for specific hybridization to a HCV type or subtype-specific, and wherein said polynucleic acid consists of up to 50 contiguous nucleotides selected from said HCV subtype 3c genomic region.

9. A kit for determining the presence of HCV genotypes comprising a solid support and a probe according to claim 8.

10. A method for determining the presence of HCV genotypes present in a biological sample comprising the steps of:
    (i) providing a sample nucleic acid,
    (ii) optionally amplifying the nucleic acid with at least one primer,
    (iii) hybridizing the nucleic acids of the biological sample with one or more probes according to claim 8, with said probes being optionally attached to a solid substrate,
    (iv) optionally washing,
    (v) detecting the hybrids formed,
    (vi) inferring the presence of one or more genotypes of HCV present from the observed hybridization pattern.

11. An isolated HCV polynucleic acid according to claim 1, wherein said polynucleic acid is capable of acting as a probe for specific hybridization to a HCV subtype 3c nucleic acid sequence, and wherein said polynucleic acid comprises at least one HCV subtype 3c genotype specific nucleotide.

12. A kit for determining the presence of HCV genotypes comprising a solid support and a probe according to claim 11.

13. A method for determining the presence of HCV genotypes present in a biological sample comprising the steps of:
    (i) providing a sample nucleic acid,
    (ii) optionally amplifying the nucleic acid with at least one primer,
    (iii) hybridizing the nucleic acids of the biological sample with one or more probes according to claim 11, with said probes being optionally attached to a solid substrate,
    (iv) optionally washing,
    (v) detecting the hybrids formed,
    (vi) inferring the presence of one or more genotypes of HCV present from the observed hybridization pattern.

14. A kit for determining the presence of HCV genotypes comprising a solid support and a polynucleic acid sequence according to claim 1.

* * * * *

SEQUENCE LISTING (1) GENERAL INFORMATION:

(iii) NUMBER OF SEQUENCES: 270

(2) INFORMATION FOR SEQ ID NO: 1:

(i) SEQUENCE CHARACTERISTICS:
      (A) LENGTH: 213 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: BR34-4-20

(ix) FEATURE:
      (A) NAME/KEY: CDS
      (B) LOCATION: 1..213

(xi) SEQUENCE DESCRIPTION: SEQ ID NO: 1:

```
CTC ACG GAA CGG CTT TAC TGC GGG GGC CCT ATG TTC AAC AGC AAG GGG        48
Leu Thr Glu Arg Leu Tyr Cys Gly Gly Pro Met Phe Asn Ser Lys Gly
 1               5                  10                  15

GCC CAG TGT GGT TAT CGC CGC TGC CGT GCC AGT GGA GTT CTG CCT ACC        96
Ala Gln Cys Gly Tyr Arg Arg Cys Arg Ala Ser Gly Val Leu Pro Thr
             20                  25                  30

AGC TTC GGC AAC ACA ATC ACT TGC TAC ATC AAG GCC ACA GCG GCT GCA       144
Ser Phe Gly Asn Thr Ile Thr Cys Tyr Ile Lys Ala Thr Ala Ala Ala
         35                  40                  45

AGG GCC GCA GGC CTC CGG AAC CCG GAC TTT CTT GTC TGC GGA GAT GAT       192
```

```
Arg Ala Ala Gly Leu Arg Asn Pro Asp Phe Leu Val Cys Gly Asp Asp
    50                  55                  60

CTG GTC GTG GTG GCT GAG AGT                                         213
Leu Val Val Val Ala Glu Ser
65                  70

(2) INFORMATION FOR SEQ ID NO: 2:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 2:

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Arg Ala Ala Gly Leu Arg Asn Pro Asp Phe Leu Val Cys Gly Asp Asp
    50                  55                  60

Leu Val Val Val Ala Glu Ser
65                  70

(2) INFORMATION FOR SEQ ID NO: 3:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: BR36-23-18

(ix) FEATURE:
        (A) NAME/KEY: CDS
        (B) LOCATION: 1..213

(xi) SEQUENCE DESCRIPTION: SEQ ID NO: 3:

CTC ACG GAA CGG CTT TAC TGC GGG GGC CCT ATG TTC AAC AGC AAG GGG    48
Leu Thr Glu Arg Leu Tyr Cys Gly Gly Pro Met Phe Asn Ser Lys Gly
1               5                   10                  15

GCC CAG TGT GGT TAT CGC CGC TGC CGT GCC AGT GGA GTT CTG CCT ACC    96
Ala Gln Cys Gly Tyr Arg Arg Cys Arg Ala Ser Gly Val Leu Pro Thr
            20                  25                  30

AGC TTC GGC AAC ACA ATC ACT TGC TAC ATC AAG GCC ACA GCG GCT GCA    144
Ser Phe Gly Asn Thr Ile Thr Cys Tyr Ile Lys Ala Thr Ala Ala Ala
        35                  40                  45

AGG GCC GCA GGC CTC CGG AAC CCG GAC TTT CTT GTC TGC GGA GAT GAT    192
Arg Ala Ala Gly Leu Arg Asn Pro Asp Phe Leu Val Cys Gly Asp Asp
    50                  55                  60

CTG GTC GTG GTG GCT GAG AGT                                         213
Leu Val Val Val Ala Glu Ser
65                  70

(2) INFORMATION FOR SEQ ID NO: 4:
```

(i) SEQUENCE CHARACTERISTICS:
            (A) LENGTH: 71 amino acids
            (B) TYPE: amino acid
            (D) TOPOLOGY: linear (ii) MOLECULE TYPE: protein (xi) SEQUENCE DESCRIPTION: SEQ ID NO: 4:

Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
                20                  25                  30

Ser Phe Gly Asn Thr Ile Thr Cys Tyr Ile Lys Ala Thr Ala Ala Ala
            35                  40                  45

Arg Ala Ala Gly Leu Arg Asn Pro Asp Phe Leu Val Cys Gly Asp Asp
        50                  55                  60

Leu Val Val Val Ala Glu Ser
65                  70

(2) INFORMATION FOR SEQ ID NO: 5:

(i) SEQUENCE CHARACTERISTICS:
            (A) LENGTH: 213 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vii) IMMEDIATE SOURCE:
            (B) CLONE: BR36-23-18

(ix) FEATURE:
            (A) NAME/KEY: CDS
            (B) LOCATION: 1..213

(xi) SEQUENCE DESCRIPTION: SEQ ID NO: 5:

CTC ACG GAG CGG CTT TAC TGC GGG GGC CCT ATG TTT AAC AGC AAG GGG         48
Leu Thr Glu Arg Leu Tyr Cys Gly Gly Pro Met Phe Asn Ser Lys Gly
 1               5                  10                  15

GCC CAG TGT GGT TAT CGC CGT TGC CGT GCC AGT GGA GTT CTG CCT ACC         96
Ala Gln Cys Gly Tyr Arg Arg Cys Arg Ala Ser Gly Val Leu Pro Thr
                20                  25                  30

AGC TTC GGC AAC ACA ATC ACT TGT TAC ATC AAA GCC ACA GCG GCC GCA        144
Ser Phe Gly Asn Thr Ile Thr Cys Tyr Ile Lys Ala Thr Ala Ala Ala
            35                  40                  45

AAA GCC GCA GGC CTC CGG AGC CCG GAC TTT CTT GTC TGC GGA GAT GAT        192
Lys Ala Ala Gly Leu Arg Ser Pro Asp Phe Leu Val Cys Gly Asp Asp
        50                  55                  60

CTG GTC GTG GTG GCT GAG AGT                                            213
Leu Val Val Val Ala Glu Ser
65                  70

(2) INFORMATION FOR SEQ ID NO: 6:

(i) SEQUENCE CHARACTERISTICS:
            (A) LENGTH: 71 amino acids
            (B) TYPE: amino acid
            (D) TOPOLOGY: linear (ii) MOLECULE TYPE: protein (xi) SEQUENCE DESCRIPTION: SEQ ID NO: 6:

Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Ser Pro Asp Phe Leu Val Cys Gly Asp Asp
    50                  55                  60

Leu Val Val Val Ala Glu Ser
 65                  70

(2) INFORMATION FOR SEQ ID NO: 7:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR36-23-20

(ix) FEATURE:
        (A) NAME/KEY: CDS
        (B) LOCATION: 1..213

(xi) SEQUENCE DESCRIPTION: SEQ ID NO: 7:

CTC ACG GAG CGG CTT TAC TGC GGG GGC CCT ATG TTT AAC AGC AAA GGG      48
Leu Thr Glu Arg Leu Tyr Cys Gly Gly Pro Met Phe Asn Ser Lys Gly
 1               5                  10                  15

GCC CAG TGT GGT TAT CGC CGT TGC CGT GCC AGT GGA GTT CTG CCT ACC      96
Ala Gln Cys Gly Tyr Arg Arg Cys Arg Ala Ser Gly Val Leu Pro Thr
            20                  25                  30

AGC TTC GGC AAC ACA ATC ACT TGT TAC ATC AAA GCC ACA GCG GCC GCA     144
Ser Phe Gly Asn Thr Ile Thr Cys Tyr Ile Lys Ala Thr Ala Ala Ala
        35                  40                  45

AAA GCC GCA GGC CTC CGG AGC CCG GAC TTT CTT GTC TGC GGA GAT GAT     192
Lys Ala Ala Gly Leu Arg Ser Pro Asp Phe Leu Val Cys Gly Asp Asp
    50                  55                  60

CTG GTC GTG GTG GCT GAG AGT                                         213
Leu Val Val Val Ala Glu Ser
 65                  70

(2) INFORMATION FOR SEQ ID NO: 8:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 8:

Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
            20                  25                  30

```
Ser Phe Gly Asn Thr Ile Thr Cys Tyr Ile Lys Ala Thr Ala Ala Ala
         35                  40                  45

Lys Ala Ala Gly Leu Arg Ser Pro Asp Phe Leu Val Cys Gly Asp Asp
     50                  55                  60

Leu Val Val Val Ala Glu Ser
 65                  70
```

(2) INFORMATION FOR SEQ ID NO: 9:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR33-2-17

(ix) FEATURE:
        (A) NAME/KEY: CDS
        (B) LOCATION: 1..213

(xi) SEQUENCE DESCRIPTION: SEQ ID NO: 9:

```
CTC ACG GAG CGG CTT TAC TGC GGG GGC CCT ATG TTC AAC AGC AAG GGG    48
Leu Thr Glu Arg Leu Tyr Cys Gly Gly Pro Met Phe Asn Ser Lys Gly
 1               5                  10                  15

GCC CAG TGT GGT TAT CGC CGT TGT CGT GCC AGT GGA GTT CTG CCT ACC    96
Ala Gln Cys Gly Tyr Arg Arg Cys Arg Ala Ser Gly Val Leu Pro Thr
             20                  25                  30

AGT TTC GGC AAC ACA ATC ACT TGT TAC ATC AAG GCC ACA GCG GCT GCA   144
Ser Phe Gly Asn Thr Ile Thr Cys Tyr Ile Lys Ala Thr Ala Ala Ala
         35                  40                  45

AAA GCC GCA GGC CTC CGG AAC CCG GAC TTT CTT GTT TGC GGA GAT GAT   192
Lys Ala Ala Gly Leu Arg Asn Pro Asp Phe Leu Val Cys Gly Asp Asp
     50                  55                  60

TTG GTC GTG GTG GCT GAG AGT                                       213
Leu Val Val Val Ala Glu Ser
 65                  70
```

(2) INFORMATION FOR SEQ ID NO: 10:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 10:

```
Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
             20                  25                  30

Ser Phe Gly Asn Thr Ile Thr Cys Tyr Ile Lys Ala Thr Ala Ala Ala
         35                  40                  45

Lys Ala Ala Gly Leu Arg Asn Pro Asp Phe Leu Val Cys Gly Asp Asp
     50                  55                  60

Leu Val Val Val Ala Glu Ser
 65                  70
```

(2) INFORMATION FOR SEQ ID NO: 11:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR33-2-21

(ix) FEATURE:
        (A) NAME/KEY: CDS
        (B) LOCATION: 1..213

(xi) SEQUENCE DESCRIPTION: SEQ ID NO: 11:

```
CTC ACG GAG CGG CTT TAC TGC GGG GGC CCT ATG TTC AAC AGC AAG GGG        48
Leu Thr Glu Arg Leu Tyr Cys Gly Gly Pro Met Phe Asn Ser Lys Gly
 1               5                  10                  15

GCC CAG TGT GGT TAT CGC CGT TGT CGT GCC AGT GGA GTT CTG CCT ACC        96
Ala Gln Cys Gly Tyr Arg Arg Cys Arg Ala Ser Gly Val Leu Pro Thr
                 20                  25                  30

AGT TTC GGC AAC ACA ATC ACT TGT TAC ATC AAG GCC ACA GCG GCT GCA       144
Ser Phe Gly Asn Thr Ile Thr Cys Tyr Ile Lys Ala Thr Ala Ala Ala
             35                  40                  45

AAA GCC GCA GGC CTC CGG AAC CCG GAC TTT CTT GTT TGC GGA GAT GAT       192
Lys Ala Ala Gly Leu Arg Asn Pro Asp Phe Leu Val Cys Gly Asp Asp
     50                  55                  60

TTG GTC GTG GTG GCT GAG AGT                                           213
Leu Val Val Val Ala Glu Ser
 65                  70
```

(2) INFORMATION FOR SEQ ID NO: 12:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 12:

```
Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
                 20                  25                  30

Ser Phe Gly Asn Thr Ile Thr Cys Tyr Ile Lys Ala Thr Ala Ala Ala
             35                  40                  45

Lys Ala Ala Gly Leu Arg Asn Pro Asp Phe Leu Val Cys Gly Asp Asp
     50                  55                  60

Leu Val Val Val Ala Glu Ser
 65                  70
```

(2) INFORMATION FOR SEQ ID NO: 13:

(i) SEQUENCE CHARACTERISTICS:
        (A) LENGTH: 541 base pairs
        (B) TYPE: nucleic acid
        (C) STRANDEDNESS: single -continued (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: HD10-2-5

(ix) FEATURE:
      (A) NAME/KEY: CDS
      (B) LOCATION: 2..541

(xi) SEQUENCE DESCRIPTION: SEQ ID NO: 13:

```
C GTC GGC GCT CCT GTA GGA GGC GTC GCA AGA GCC CTT GCG CAT GGC          46
  Val Gly Ala Pro Val Gly Gly Val Ala Arg Ala Leu Ala His Gly
   1               5                  10                  15

GTG AGG GCC CTT GAA GAC GGG ATA AAT TTC GCA ACA GGG AAT TTG CCC        94
Val Arg Ala Leu Glu Asp Gly Ile Asn Phe Ala Thr Gly Asn Leu Pro
             20                  25                  30

GGT TGC TCC TTT TCT ATC TTC CTT CTT GCT CTG TTC TCT TGC TTA ATC       142
Gly Cys Ser Phe Ser Ile Phe Leu Leu Ala Leu Phe Ser Cys Leu Ile
                 35                  40                  45

CAT CCA GCA GCT AGT CTA GAG TGG CGG AAC ACG TCT GGC CTC TAT GTC       190
His Pro Ala Ala Ser Leu Glu Trp Arg Asn Thr Ser Gly Leu Tyr Val
             50                  55                  60

CTT ACC AAC GAC TGT TCC AAT AGC AGT ATT GTG TAT GAG GCC GAT GAC       238
Leu Thr Asn Asp Cys Ser Asn Ser Ser Ile Val Tyr Glu Ala Asp Asp
 65                  70                  75

GTT ATT CTG CAC ACA CCC GGC TGT GTA CCT TGT GTT CAG GAC GGT AAT       286
Val Ile Leu His Thr Pro Gly Cys Val Pro Cys Val Gln Asp Gly Asn
 80                  85                  90                  95

ACA TCT GCG TGC TGG ACC CCA GTG ACA CCT ACA GTG GCA GTC AGG TAC       334
Thr Ser Ala Cys Trp Thr Pro Val Thr Pro Thr Val Ala Val Arg Tyr
                100                 105                 110

GTC GGA GCA ACC ACC GCT TCG ATA CGC AGG CAT GTA GAC ATG TTG GTG       382
Val Gly Ala Thr Thr Ala Ser Ile Arg Arg His Val Asp Met Leu Val
                115                 120                 125

GGC GCG GCC ACG ATG TGC TCT GCT CTC TAC GTG GGT GAT ATG TGT GGG       430
Gly Ala Ala Thr Met Cys Ser Ala Leu Tyr Val Gly Asp Met Cys Gly
             130                 135                 140

GCC GTC TTC CTC GTG GGA CAA GCC TTC ACG TTC AGA CCT CGT CGC CAT       478
Ala Val Phe Leu Val Gly Gln Ala Phe Thr Phe Arg Pro Arg Arg His
 145                 150                 155

CAA ACG GTC CAG ACC TGT AAC TGC TCA CTG TAC CCA GGC CAT CTT TCA       526
Gln Thr Val Gln Thr Cys Asn Cys Ser Leu Tyr Pro Gly His Leu Ser
160                 165                 170                 175

GGA CAC CGA ATG GCT                                                   541
Gly His Arg Met Ala
                180
```

(2) INFORMATION FOR SEQ ID NO: 14:

(i) SEQUENCE CHARACTERISTICS:
      (A) LENGTH: 180 amino acids
      (B) TYPE: amino acid
      (D) TOPOLOGY: linear (ii) MOLECULE TYPE: protein (xi) SEQUENCE DESCRIPTION: SEQ ID NO: 14:

```
Val Gly Ala Pro Val Gly Gly Val Ala Arg Ala Leu Ala His Gly Val
 1               5                  10                  15
```

```
Arg Ala Leu Glu Asp Gly Ile Asn Phe Ala Thr Gly Asn Leu Pro Gly
            20                  25                  30

Cys Ser Phe Ser Ile Phe Leu Ala Leu Phe Ser Cys Leu Ile His
            35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Val
65                  70                  75                  80

Ile Leu His Thr Pro Gly Cys Val Pro Cys Val Gln Asp Gly Asn Thr
                85                  90                  95

Ser Ala Cys Trp Thr Pro Val Thr Pro Thr Val Ala Val Arg Tyr Val
            100                 105                 110

Gly Ala Thr Thr Ala Ser Ile Arg Arg His Val Asp Met Leu Val Gly
            115                 120                 125

Ala Ala Thr Met Cys Ser Ala Leu Tyr Val Gly Asp Met Cys Gly Ala
130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
        180

(2) INFORMATION FOR SEQ ID NO: 15:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: HD10-2-14

(ix) FEATURE:
        (A) NAME/KEY: CDS
        (B) LOCATION: 2..541

(xi) SEQUENCE DESCRIPTION: SEQ ID NO: 15:

C GTC GGC GCT CCT GTA GGA GGC GTC GCA AGA GCC CTT GCG CAT GGC        46
  Val Gly Ala Pro Val Gly Gly Val Ala Arg Ala Leu Ala His Gly
  1               5                   10                  15

GTG AGG GCC CTT GAA GAC GGG ATA AAT TTC GCA ACA GGG AAT TTG CCC      94
Val Arg Ala Leu Glu Asp Gly Ile Asn Phe Ala Thr Gly Asn Leu Pro
                20                  25                  30

GGT TGC TCC TTT TCT ATC TTC CTT CCT GCT CTG TTC TCT TGC TTA ATC     142
Gly Cys Ser Phe Ser Ile Phe Leu Pro Ala Leu Phe Ser Cys Leu Ile
            35                  40                  45

CAT CCA GCA GCT AGT CTA GAG TGG CGG AAC ACG TCT GGC CTC TAT GTC     190
His Pro Ala Ala Ser Leu Glu Trp Arg Asn Thr Ser Gly Leu Tyr Val
    50                  55                  60

CTT ACC AAC GAC TGT TCC AAT AGC AGT ATT GTG TAT GAG GCC GAT GAC     238
Leu Thr Asn Asp Cys Ser Asn Ser Ser Ile Val Tyr Glu Ala Asp Asp
65                  70                  75

GTT ATT CTG CAC ACA CCC GGC TGT GTA CCT TGT GTT CAG GAC GGT AAT     286
```

```
Val Ile Leu His Thr Pro Gly Cys Val Pro Cys Val Gln Asp Gly Asn
 80                  85                  90                  95

ACA TCT GCG TGC TGG ACC CCA GTG ACA CCT ACA GTG GCA GTC AGG TAC     334
Thr Ser Ala Cys Trp Thr Pro Val Thr Pro Thr Val Ala Val Arg Tyr
                100                 105                 110

GTC GGA GCA ACC ACC GCT TCG ATA CGC AGG CAT GTA GAC ATA TTG GTG     382
Val Gly Ala Thr Thr Ala Ser Ile Arg Arg His Val Asp Ile Leu Val
                115                 120                 125

GGC GCG GCC ACA ATG TGC TCT GCT CTC TAC GTG GGT GAT ATG TGT GGG     430
Gly Ala Ala Thr Met Cys Ser Ala Leu Tyr Val Gly Asp Met Cys Gly
                130                 135                 140

GCC GTC TTC CTC GTG GGA CAA GCC TTC ACG TTC AGA CCT CGT CGC CAT     478
Ala Val Phe Leu Val Gly Gln Ala Phe Thr Phe Arg Pro Arg Arg His
                145                 150                 155

CAA ACG GTC CAG ACC TGT AAC TGC TCA CTG TAC CCA GGC CAT CTT TCA     526
Gln Thr Val Gln Thr Cys Asn Cys Ser Leu Tyr Pro Gly His Leu Ser
160                 165                 170                 175

GGA CAC CGA ATG GCT                                                 541
Gly His Arg Met Ala
                180
```

(2) INFORMATION FOR SEQ ID NO: 16:

(i) SEQUENCE CHARACTERISTICS:
      (A) LENGTH: 180 amino acids
      (B) TYPE: amino acid
      (D) TOPOLOGY: linear (ii) MOLECULE TYPE: protein (xi) SEQUENCE DESCRIPTION: SEQ ID NO: 16:

```
Val Gly Ala Pro Val Gly Gly Val Ala Arg Ala Leu Ala His Gly Val
 1               5                  10                  15

Arg Ala Leu Glu Asp Gly Ile Asn Phe Ala Thr Gly Asn Leu Pro Gly
                20                  25                  30

Cys Ser Phe Ser Ile Phe Leu Pro Ala Leu Phe Ser Cys Leu Ile His
            35                  40                  45

Pro Ala Ala Ser Leu Glu Trp Arg Asn Thr Ser Gly Leu Tyr Val Leu
     50                  55                  60

Thr Asn Asp Cys Ser Asn Ser Ser Ile Val Tyr Glu Ala Asp Asp Val
 65                  70                  75                  80

Ile Leu His Thr Pro Gly Cys Val Pro Cys Val Gln Asp Gly Asn Thr
                 85                  90                  95

Ser Ala Cys Trp Thr Pro Val Thr Pro Thr Val Ala Val Arg Tyr Val
                100                 105                 110

Gly Ala Thr Thr Ala Ser Ile Arg Arg His Val Asp Ile Leu Val Gly
                115                 120                 125

Ala Ala Thr Met Cys Ser Ala Leu Tyr Val Gly Asp Met Cys Gly Ala
                130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

(2) INFORMATION FOR SEQ ID NO: 17 :

(i) SEQUENCE CHARACTERISTICS:

(A) LENGTH: 541 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vii) IMMEDIATE SOURCE:
(B) CLONE: HD10-2-21

(ix) FEATURE:
(A) NAME/KEY: CDS
(B) LOCATION: 2..541

(xi) SEQUENCE DESCRIPTION: SEQ ID NO: 17:

| | | | | | | | | | | | | | | | | |
|---|---|---|---|---|---|---|---|---|---|---|---|---|---|---|---|---|
| C | GTC | GGC | GCT | CCT | GTA | GGA | GGC | GTC | GCA | AGA | GCC | CTT | GCG | CAT | GGC | 46 |
| | Val | Gly | Ala | Pro | Val | Gly | Gly | Val | Ala | Arg | Ala | Leu | Ala | His | Gly | |
| | 1 | | | 5 | | | | 10 | | | | | 15 | | | |
| GTG | AGG | GCC | CTT | GAA | GAC | GGG | ATA | AAT | TTC | GCA | ACA | GGG | AAT | TTG | CCC | 94 |
| Val | Arg | Ala | Leu | Glu | Asp | Gly | Ile | Asn | Phe | Ala | Thr | Gly | Asn | Leu | Pro | |
| | | | 20 | | | | | 25 | | | | | 30 | | | |
| GGT | TGC | TCC | TTT | TCT | ATC | TTC | CTT | CTT | GCT | CTG | TTC | TCT | TGC | TTA | ATC | 142 |
| Gly | Cys | Ser | Phe | Ser | Ile | Phe | Leu | Leu | Ala | Leu | Phe | Ser | Cys | Leu | Ile | |
| | | | 35 | | | | | 40 | | | | | 45 | | | |
| CAT | CCA | GCA | GCT | AGT | CTA | GAG | TGG | CGG | AAC | ACG | TCT | GGC | CTC | TAC | GTC | 190 |
| His | Pro | Ala | Ala | Ser | Leu | Glu | Trp | Arg | Asn | Thr | Ser | Gly | Leu | Tyr | Val | |
| | | 50 | | | | | 55 | | | | | 60 | | | | |
| CTT | ACC | AAC | GAC | TGT | TCC | AAT | AGC | AGT | ATT | GTG | TAT | GAG | GCC | GAT | GAC | 238 |
| Leu | Thr | Asn | Asp | Cys | Ser | Asn | Ser | Ser | Ile | Val | Tyr | Glu | Ala | Asp | Asp | |
| | 65 | | | | | 70 | | | | | 75 | | | | | |
| GTT | ATT | CTG | CAC | ACA | CCC | GGC | TGT | GTA | CCT | TGT | GTT | CAG | GAC | GGT | AAT | 286 |
| Val | Ile | Leu | His | Thr | Pro | Gly | Cys | Val | Pro | Cys | Val | Gln | Asp | Gly | Asn | |
| 80 | | | | | 85 | | | | | 90 | | | | | 95 | |
| ACA | TCT | GCG | TGC | TGG | ACC | CCA | GTG | ACA | CCT | ACA | GTG | GCA | GTC | AGG | TAC | 334 |
| Thr | Ser | Ala | Cys | Trp | Thr | Pro | Val | Thr | Pro | Thr | Val | Ala | Val | Arg | Tyr | |
| | | | 100 | | | | | 105 | | | | | 110 | | | |
| GTC | GGA | GCA | ACC | ACC | GCT | TCG | ATA | CGC | AGG | CAT | GTA | GAC | ATA | TTG | GTG | 382 |
| Val | Gly | Ala | Thr | Thr | Ala | Ser | Ile | Arg | Arg | His | Val | Asp | Ile | Leu | Val | |
| | | | 115 | | | | | 120 | | | | | 125 | | | |
| GGC | GCG | GCC | ACG | ATG | TGC | TCT | GCT | CTC | TAC | GTG | GGT | GAT | ATG | TGT | GGG | 430 |
| Gly | Ala | Ala | Thr | Met | Cys | Ser | Ala | Leu | Tyr | Val | Gly | Asp | Met | Cys | Gly | |
| | | 130 | | | | | 135 | | | | | 140 | | | | |
| GCC | GTC | TTC | CTC | GTG | GGA | CAA | GCC | TTC | ACG | TTC | AGA | CCT | CGT | CGC | CAT | 478 |
| Ala | Val | Phe | Leu | Val | Gly | Gln | Ala | Phe | Thr | Phe | Arg | Pro | Arg | Arg | His | |
| | 145 | | | | | 150 | | | | | 155 | | | | | |
| CAA | ACG | GTC | CAG | ACC | TGT | AAC | TGC | TCA | CTG | TAC | CCA | GGC | CAT | CTT | TCA | 526 |
| Gln | Thr | Val | Gln | Thr | Cys | Asn | Cys | Ser | Leu | Tyr | Pro | Gly | His | Leu | Ser | |
| 160 | | | | | 165 | | | | | 170 | | | | | 175 | |
| GGA | CAC | CGA | ATG | GCT | | | | | | | | | | | | 541 |
| Gly | His | Arg | Met | Ala | | | | | | | | | | | | |
| | | | | 180 | | | | | | | | | | | | |

(2) INFORMATION FOR SEQ ID NO: 18:

(i) SEQUENCE CHARACTERISTICS:
(A) LENGTH: 180 amino acids
(B) TYPE: amino acid
(D) TOPOLOGY: linear (ii) MOLECULE TYPE: protein (xi) SEQUENCE DESCRIPTION: SEQ ID NO: 18:

```
Val Gly Ala Pro Val Gly Gly Val Ala Arg Ala Leu Ala His Gly Val
 1               5                  10                 15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Val Pro Cys Val Gln Asp Gly Asn Thr
                85                  90                  95

Ser Ala Cys Trp Thr Pro Val Thr Pro Thr Val Ala Val Arg Tyr Val
            100                 105                 110

Gly Ala Thr Thr Ala Ser Ile Arg Arg His Val Asp Ile Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

(2) INFORMATION FOR SEQ ID NO: 19:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR36-9-13

(ix) FEATURE:
        (A) NAME/KEY: CDS
        (B) LOCATION: 2..541

(xi) SEQUENCE DESCRIPTION: SEQ ID NO: 19:

C GTC GGC GCT CCC GTA GGA GGC GTC GCA AGA GCC CTT GCG CAT GGC        46
  Val Gly Ala Pro Val Gly Gly Val Ala Arg Ala Leu Ala His Gly
   1               5                  10                  15

GTG AGG GCC CTT GAA GAC GGG ATA AAT TTC GCA ACA GGG AAT TTG CCC      94
Val Arg Ala Leu Glu Asp Gly Ile Asn Phe Ala Thr Gly Asn Leu Pro
                20                  25                  30

GGT TGC TCC TTT TCT ATT TTC CTT CTT GCT CTG TTC TCT TGC TTA ATT      142
Gly Cys Ser Phe Ser Ile Phe Leu Leu Ala Leu Phe Ser Cys Leu Ile
            35                  40                  45

CAT CCA GCA GCT AGT CTA GAG TGG CGG AAT ACG TCT GGC CTC TAT GTC      190
His Pro Ala Ala Ser Leu Glu Trp Arg Asn Thr Ser Gly Leu Tyr Val
        50                  55                  60

CTT ACC AAC GAC TGT TCC AAT AGC AGT ATT GTG TAC GAG GCC GAT GAC      238
Leu Thr Asn Asp Cys Ser Asn Ser Ser Ile Val Tyr Glu Ala Asp Asp
```

```
                65                    70                    75
GTT ATT CTG CAC ACA CCC GGC TGC ATA CCT TGT GTC CAG GAC GGC AAT      286
Val Ile Leu His Thr Pro Gly Cys Ile Pro Cys Val Gln Asp Gly Asn
 80                      85                      90                      95

ACA TCC ACG TGC TGG ACC CCA GTG ACA CCT ACA GTG GCA GTC AAG TAC      334
Thr Ser Thr Cys Trp Thr Pro Val Thr Pro Thr Val Ala Val Lys Tyr
                        100                     105                     110

GTC GGA GCA ACC ACC GCT TCG ATA CGC AGT CAT GTG GAC CTA TTA GTG      382
Val Gly Ala Thr Thr Ala Ser Ile Arg Ser His Val Asp Leu Leu Val
                115                     120                     125

GGC GCG GCC ACG ATG TGC TCA GCG CTC TAC GTG GGT GAT ATG TGT GGG      430
Gly Ala Ala Thr Met Cys Ser Ala Leu Tyr Val Gly Asp Met Cys Gly
        130                     135                     140

GCC GTC TTC CTT GTG GGA CAA GCC TTC ACG TTC AGA CCT CGT CGC CAT      478
Ala Val Phe Leu Val Gly Gln Ala Phe Thr Phe Arg Pro Arg Arg His
        145                     150                     155

CAA ACG GTC CAG ACC TGT AAC TGC TCG CTG TAC CCA GGC CAT CTT TCA      526
Gln Thr Val Gln Thr Cys Asn Cys Ser Leu Tyr Pro Gly His Leu Ser
160                     165                     170                     175

GGA CAT CGA ATG GCT                                                  541
Gly His Arg Met Ala
                180
```

(2) INFORMATION FOR SEQ ID NO: 20:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 20:

```
Val Gly Ala Pro Val Gly Gly Val Ala Arg Ala Leu Ala His Gly Val
 1               5                  10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
            35                  40                  45

Pro Ala Ala Ser Leu Glu Trp Arg Asn Thr Ser Gly Leu Tyr Val Leu
     50                  55                  60

Thr Asn Asp Cys Ser Asn Ser Ser Ile Val Tyr Glu Ala Asp Asp Val
 65                  70                  75                  80

Ile Leu His Thr Pro Gly Cys Ile Pro Cys Val Gln Asp Gly Asn Thr
                85                  90                  95

Ser Thr Cys Trp Thr Pro Val Thr Pro Thr Val Ala Val Lys Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

(2) INFORMATION FOR SEQ ID NO: 21:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR36-9-20

(ix) FEATURE:
        (A) NAME/KEY: CDS
        (B) LOCATION: 2..541

(xi) SEQUENCE DESCRIPTION: SEQ ID NO: 21:

```
C GTC GGC GCT CCC GTA GGA GGC GTC GCA AGA GCC CTT GCG CAT GGC        46
  Val Gly Ala Pro Val Gly Gly Val Ala Arg Ala Leu Ala His Gly
   1               5                  10                  15

GTG AGG GCC CTT GAA GAC GGG ATA AAT TTC GCA ACA GGG AAT TTG CCC      94
Val Arg Ala Leu Glu Asp Gly Ile Asn Phe Ala Thr Gly Asn Leu Pro
                 20                  25                  30

GGT TGC TCC TTT TCT ATT TTC CTT CTT GCT CTG TTC TCT TGC TTA ATT     142
Gly Cys Ser Phe Ser Ile Phe Leu Leu Ala Leu Phe Ser Cys Leu Ile
                 35                  40                  45

CAT CCA GCA GCT AGT CTA GAG TGG CGG AAT ACG TCT GGC CTC TAT GTC     190
His Pro Ala Ala Ser Leu Glu Trp Arg Asn Thr Ser Gly Leu Tyr Val
         50                  55                  60

CTT ACC AAC GAC TGT TCC AAT AGC AGT ATT GTG TAC GAG GCC GAT GAC     238
Leu Thr Asn Asp Cys Ser Asn Ser Ser Ile Val Tyr Glu Ala Asp Asp
         65                  70                  75

GTT ATT CTG CAC ACA CCC GGC TGC ATA CCT TGT GTC CAG GAC GGC AAT     286
Val Ile Leu His Thr Pro Gly Cys Ile Pro Cys Val Gln Asp Gly Asn
 80                  85                  90                  95

ACA TCC ACG TGT TGG ACC CCA GTG ACA CCT ACA GTG GCA GTC AAG TAC     334
Thr Ser Thr Cys Trp Thr Pro Val Thr Pro Thr Val Ala Val Lys Tyr
                100                 105                 110

GTC GGA GCA ACC ACC GCT TCG ATA CGC AGT CAT GTG GAC CTA TTA GTG     382
Val Gly Ala Thr Thr Ala Ser Ile Arg Ser His Val Asp Leu Leu Val
                115                 120                 125

GGC GCG GCC ACG ATG TGC TCT GCG CTC TAC GTG GGT GAC ATG TGT GGG     430
Gly Ala Ala Thr Met Cys Ser Ala Leu Tyr Val Gly Asp Met Cys Gly
        130                 135                 140

GCT GTC TTC CTC GTG GGA CAA GCC TTC ACG TTC AGA CCT CGT CGC CAT     478
Ala Val Phe Leu Val Gly Gln Ala Phe Thr Phe Arg Pro Arg Arg His
        145                 150                 155

CAA ACG GTC CAG ACC TGT AAC TGC TCG CTG TAC CCA GGC CAT CTT TCA     526
Gln Thr Val Gln Thr Cys Asn Cys Ser Leu Tyr Pro Gly His Leu Ser
160                 165                 170                 175

GGA CAT CGA ATG GCT                                                 541
Gly His Arg Met Ala
                180
```

(2) INFORMATION FOR SEQ ID NO: 22:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 22:

```
Val Gly Ala Pro Val Gly Gly Val Ala Arg Ala Leu Ala His Gly Val
 1               5                  10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
            35                  40                  45

Pro Ala Ala Ser Leu Glu Trp Arg Asn Thr Ser Gly Leu Tyr Val Leu
        50                  55                  60

Thr Asn Asp Cys Ser Asn Ser Ser Ile Val Tyr Glu Ala Asp Asp Val
65                  70                  75                  80

Ile Leu His Thr Pro Gly Cys Ile Pro Cys Val Gln Asp Gly Asn Thr
                85                  90                  95

Ser Thr Cys Trp Thr Pro Val Thr Pro Thr Val Ala Val Lys Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

(2) INFORMATION FOR SEQ ID NO: 23:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR33-1-10

(ix) FEATURE:
        (A) NAME/KEY: CDS
        (B) LOCATION: 2..541

(xi) SEQUENCE DESCRIPTION: SEQ ID NO: 23:

```
C GTC GGC GCT CCC GTA GGA GGC GTC GCA AGA GCC CTT GCG CAT GGC         46
  Val Gly Ala Pro Val Gly Gly Val Ala Arg Ala Leu Ala His Gly
   1               5                  10                  15

GTG AGG GCC CTT GAG GAC GGG ATA AAC TTC GCA ACA GGG AAT TTG CCC        94
Val Arg Ala Leu Glu Asp Gly Ile Asn Phe Ala Thr Gly Asn Leu Pro
                20                  25                  30

GGT TGC TCC TTT TCT ATC TTC CTT CTT GCT CTG TTC TCT TGC TTA ATC       142
Gly Cys Ser Phe Ser Ile Phe Leu Leu Ala Leu Phe Ser Cys Leu Ile
            35                  40                  45

CAT CCA GCA GCT GGT CTA GAG TGG CGG AAT ACG TCT GGC CTC TAT GTC       190
His Pro Ala Ala Gly Leu Glu Trp Arg Asn Thr Ser Gly Leu Tyr Val
        50                  55                  60
```

```
CTT ACC AAC GAC TGT TCC AAT AGT AGT ATT GTG TAT GAG GCC GAT GAC      238
Leu Thr Asn Asp Cys Ser Asn Ser Ser Ile Val Tyr Glu Ala Asp Asp
    65                  70                  75

GTT ATT CTG CAC GCG CCC GGC TGT GTA CCT TGT GTC CAG GAC GGC AAT      286
Val Ile Leu His Ala Pro Gly Cys Val Pro Cys Val Gln Asp Gly Asn
80                  85                  90                  95

ACG TCT ACA TGC TGG ACC CCA GTA ACA CCT ACA GTG GCA GTC AGG TAC      334
Thr Ser Thr Cys Trp Thr Pro Val Thr Pro Thr Val Ala Val Arg Tyr
                100                 105                 110

GTC GGG GCA ACC ACC GCT TCG ATA CGC AGT CAT GTG GAC CTG TTA GTA      382
Val Gly Ala Thr Thr Ala Ser Ile Arg Ser His Val Asp Leu Leu Val
            115                 120                 125

GGC GCG GCC ACG ATG TGC TCT GCG CTT TAC GTG GGT GAT ATG TGT GGG      430
Gly Ala Ala Thr Met Cys Ser Ala Leu Tyr Val Gly Asp Met Cys Gly
        130                 135                 140

GCC GTC TTC CTC GTG GGA CAA GCC TTC ACG TTC AGA CCC CGC CGC CAT      478
Ala Val Phe Leu Val Gly Gln Ala Phe Thr Phe Arg Pro Arg Arg His
    145                 150                 155

CAA ACG GTC CAG ACC TGT AAC TGC TCG CTG TAC CCA GGC CAT CTT TCA      526
Gln Thr Val Gln Thr Cys Asn Cys Ser Leu Tyr Pro Gly His Leu Ser
160                 165                 170                 175

GGA CAT CGC ATG GCT                                                  541
Gly His Arg Met Ala
                180
```

(2) INFORMATION FOR SEQ ID NO: 24:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 24:

```
Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
            35                  40                  45

Pro Ala Ala Gly Leu Glu Trp Arg Asn Thr Ser Gly Leu Tyr Val Leu
        50                  55                  60

Thr Asn Asp Cys Ser Asn Ser Ser Ile Val Tyr Glu Ala Asp Asp Val
65                  70                  75                  80

Ile Leu His Ala Pro Gly Cys Val Pro Cys Val Gln Asp Gly Asn Thr
                85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
```

(2) INFORMATION FOR SEQ ID NO: 25:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR33-1-19

(ix) FEATURE:
        (A) NAME/KEY: CDS
        (B) LOCATION: 2..541

(xi) SEQUENCE DESCRIPTION: SEQ ID NO: 25:

```
C GTC GGC GCT CCC GTA GGA GGC GTC GCA AGA GCC CTT GCG CAT GGC        46
  Val Gly Ala Pro Val Gly Gly Val Ala Arg Ala Leu Ala His Gly
   1               5                  10                  15

GTG AGG GCC CTT GAG GAC GGG ATA AAC TTC GCA ACA GGG AAT TTG CCC       94
Val Arg Ala Leu Glu Asp Gly Ile Asn Phe Ala Thr Gly Asn Leu Pro
             20                  25                  30

GGT TGC TCT TTT TCT ATC TTC CTT CTT GCT CTG TTC TCT TGC TTA ATC      142
Gly Cys Ser Phe Ser Ile Phe Leu Leu Ala Leu Phe Ser Cys Leu Ile
                 35                  40                  45

CAT CCA GCA GCT GGT CTA GAG TGG CGG AAT ACG TCT GGC CTC TAT GTC      190
His Pro Ala Ala Gly Leu Glu Trp Arg Asn Thr Ser Gly Leu Tyr Val
             50                  55                  60

CTT ACC AAC GAC TGT TCC AAT AGT AGT ATT GTG TAT GAG GCC GAT GAC      238
Leu Thr Asn Asp Cys Ser Asn Ser Ser Ile Val Tyr Glu Ala Asp Asp
 65                  70                  75

GTT ATT CTG CAC GCG CCC GGC TGT GTA CCT TGT GTC CAG GAC GGC AAT      286
Val Ile Leu His Ala Pro Gly Cys Val Pro Cys Val Gln Asp Gly Asn
 80                  85                  90                  95

ACG TCT ACA TGC TGG ACC CCA GTA ACA CCT ACA GTG GCA GTC AGG TAC      334
Thr Ser Thr Cys Trp Thr Pro Val Thr Pro Thr Val Ala Val Arg Tyr
                100                 105                 110

GTC GGG GCA ACC ACC GCT TCG ATA CGC AGT CAT GTG GAC CTG TTA GTA      382
Val Gly Ala Thr Thr Ala Ser Ile Arg Ser His Val Asp Leu Leu Val
             115                 120                 125

GGC GCG GCC ACG ATG TGC TCT GCG CTT TAC GTG GGT GAT ATG TGT GGG      430
Gly Ala Ala Thr Met Cys Ser Ala Leu Tyr Val Gly Asp Met Cys Gly
             130                 135                 140

GCC GTC TTC CTC GTG GGA CAA GCC TTC ACG TTC AGA CCC CGC CGC CAT      478
Ala Val Phe Leu Val Gly Gln Ala Phe Thr Phe Arg Pro Arg Arg His
 145                 150                 155

CAA ACG GTC CAG ACC TGT AAC TGC TCG CTG TAC CCA GGC CAT CTT TCA      526
Gln Thr Val Gln Thr Cys Asn Cys Ser Leu Tyr Pro Gly His Leu Ser
160                 165                 170                 175

GGA CAT CGA ATG GCT                                                  541
Gly His Arg Met Ala
                180
```

(2) INFORMATION FOR SEQ ID NO: 26:

(i) SEQUENCE CHARACTERISTICS:
        (A) LENGTH: 180 amino acids (B) TYPE: amino acid
            (D) TOPOLOGY: linear (ii) MOLECULE TYPE: protein (xi) SEQUENCE DESCRIPTION: SEQ ID NO: 26:

Val Gly Ala Pro Val Gly Gly Val Ala Arg Ala Leu Ala His Gly Val
 1               5                  10                  15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
         35                  40                  45

Pro Ala Ala Gly Leu Glu Trp Arg Asn Thr Ser Gly Leu Tyr Val Leu
     50                  55                  60

Thr Asn Asp Cys Ser Asn Ser Ser Ile Val Tyr Glu Ala Asp Asp Val
 65                  70                  75                  80

Ile Leu His Ala Pro Gly Cys Val Pro Cys Val Gln Asp Gly Asn Thr
                 85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
        180

(2) INFORMATION FOR SEQ ID NO: 27:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR33-1-20

(ix) FEATURE:
        (A) NAME/KEY: CDS
        (B) LOCATION: 2..541

(xi) SEQUENCE DESCRIPTION: SEQ ID NO: 27:

C GTC GGC GCT CCC GTA GGA GGC GTC GCA AGA GCC CTT GCG CAT GGC         46
  Val Gly Ala Pro Val Gly Gly Val Ala Arg Ala Leu Ala His Gly
   1               5                  10                  15

GTG AGG GCC CTT GAG GAC GGG ATA AAC TTC GCA ACA GGG AAT TTG CCC       94
Val Arg Ala Leu Glu Asp Gly Ile Asn Phe Ala Thr Gly Asn Leu Pro
             20                  25                  30

GGT TGC TCT TTT TCT ATC TTC CTT CTT GCT CTG TTC TCT TGC TTA ATC      142
Gly Cys Ser Phe Ser Ile Phe Leu Leu Ala Leu Phe Ser Cys Leu Ile
             35                  40                  45

```
CAT CCA GCA GCT GGT CTA GAG TGG CGG AAT ACG TCT GGC CTC TAT GTC      190
His Pro Ala Ala Gly Leu Glu Trp Arg Asn Thr Ser Gly Leu Tyr Val
         50                  55                  60

CTT ACC AAC GAC TGT TCC AAT AGT AGT ATT GTG TAT GAG GCC GAT GAC      238
Leu Thr Asn Asp Cys Ser Asn Ser Ser Ile Val Tyr Glu Ala Asp Asp
         65                  70                  75

GTT ATT CTG CAC GCG CCC GGC TGT GTA CCT TGT GTC CAG GAC GGC AAT      286
Val Ile Leu His Ala Pro Gly Cys Val Pro Cys Val Gln Asp Gly Asn
80                   85                  90                  95

ACG TCT ACA TGC TGG ACC CCA GTA ACA CCT ACA GTG GCA GTC AGG TAC      334
Thr Ser Thr Cys Trp Thr Pro Val Thr Pro Thr Val Ala Val Arg Tyr
                    100                 105                 110

GTC GGG GCA ACC ACC GCT TCG ATA CGC AGT CAT GTG GAC CTG TTA GTA      382
Val Gly Ala Thr Thr Ala Ser Ile Arg Ser His Val Asp Leu Leu Val
                    115                 120                 125

GGC GCG GCC ACG ATG TGC TCT GCG CTT TAC GTG GGT GAT ATG TGT GGG      430
Gly Ala Ala Thr Met Cys Ser Ala Leu Tyr Val Gly Asp Met Cys Gly
        130                 135                 140

GCC GTC TTC CTC GTG GGA CAA GCC TTC ACG TTC AGA CCC CGC CGC CAT      478
Ala Val Phe Leu Val Gly Gln Ala Phe Thr Phe Arg Pro Arg Arg His
        145                 150                 155

CAA ACG GTC CAG ACC TGT AAC TGC TCG CTG TAC CCA GGC CAT CTT TCA      526
Gln Thr Val Gln Thr Cys Asn Cys Ser Leu Tyr Pro Gly His Leu Ser
160                 165                 170                 175

GGA CAT CGA ATG GCT                                                  541
Gly His Arg Met Ala
                180

(2) INFORMATION FOR SEQ ID NO: 28:

(i) SEQUENCE CHARACTERISTICS:
        (A) LENGTH: 180 amino acids
        (B) TYPE: amino acid
        (D) TOPOLOGY: linear (ii) MOLECULE TYPE: protein (xi) SEQUENCE DESCRIPTION: SEQ ID NO: 28:

Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
            35                  40                  45

Pro Ala Ala Gly Leu Glu Trp Arg Asn Thr Ser Gly Leu Tyr Val Leu
        50                  55                  60

Thr Asn Asp Cys Ser Asn Ser Ser Ile Val Tyr Glu Ala Asp Asp Val
65                  70                  75                  80

Ile Leu His Ala Pro Gly Cys Val Pro Cys Val Gln Asp Gly Asn Thr
                85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
```

165                 170                 175
His Arg Met Ala
        180

(2) INFORMATION FOR SEQ ID NO: 29:

(i) SEQUENCE CHARACTERISTICS:
        (A) LENGTH: 287 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: HCC1153

(ix) FEATURE:
        (A) NAME/KEY: CDS
        (B) LOCATION: 3..287

(xi) SEQUENCE DESCRIPTION: SEQ ID NO: 29:

```
TA GAC TTT TGG GAG AGC GTC TTC ACT GGA CTA ACT CAC ATA GAT GCC         47
   Asp Phe Trp Glu Ser Val Phe Thr Gly Leu Thr His Ile Asp Ala
   1               5                   10                  15

CAC TTT CTG TCA CAG ACT AAG CAG CAG GGA CTC AAC TTC TCG TTC CTG        95
His Phe Leu Ser Gln Thr Lys Gln Gln Gly Leu Asn Phe Ser Phe Leu
                20                  25                  30

ACT GCC TAC CAA GCC ACT GTG TGC GCT CGC GCG CAG GCT CCT CCC CCA       143
Thr Ala Tyr Gln Ala Thr Val Cys Ala Arg Ala Gln Ala Pro Pro Pro
            35                  40                  45

AGT TGG GAC GAG ATG TGG AAG TGT CTC GTA CGG CTT AAG CCA ACA CTA       191
Ser Trp Asp Glu Met Trp Lys Cys Leu Val Arg Leu Lys Pro Thr Leu
        50                  55                  60

CAT GGA CCT ACG CCT CTT CTA TAT CGG TTG GGG CCT GTC CAA AAT GAA       239
His Gly Pro Thr Pro Leu Leu Tyr Arg Leu Gly Pro Val Gln Asn Glu
65                  70                  75

ATC TGC TTG ACA CAC CCC ATC ACA AAA TAC ATC ATG GCA TGC ATG TCA       287
Ile Cys Leu Thr His Pro Ile Thr Lys Tyr Ile Met Ala Cys Met Ser
80                  85                  90                  95
```

(2) INFORMATION FOR SEQ ID NO: 30:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO: 30:

```
Asp Phe Trp Glu Ser Val Phe Thr Gly Leu Thr His Ile Asp Ala His
1               5                   10                  15

Phe Leu Ser Gln Thr Lys Gln Gln Gly Leu Asn Phe Ser Phe Leu Thr
            20                  25                  30

Ala Tyr Gln Ala Thr Val Cys Ala Arg Ala Gln Ala Pro Pro Pro Ser
        35                  40                  45

Trp Asp Glu Met Trp Lys Cys Leu Val Arg Leu Lys Pro Thr Leu His
    50                  55                  60

Gly Pro Thr Pro Leu Leu Tyr Arg Leu Gly Pro Val Gln Asn Glu Ile
65                  70                  75                  80
```

```
           Cys Leu Thr His Pro Ile Thr Lys Tyr Ile Met Ala Cys Met Ser
                        85                  90                  95

(2) INFORMATION FOR SEQ ID NO: 31:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: HD10-1-25

(ix) FEATURE:
        (A) NAME/KEY: CDS
        (B) LOCATION: 3..401

(xi) SEQUENCE DESCRIPTION: SEQ ID NO: 31:

TC CAA AAT GAA ATC TGC TTG ACA CAC CCC GTC ACA AAA TAC ATT ATG            47
   Gln Asn Glu Ile Cys Leu Thr His Pro Val Thr Lys Tyr Ile Met
    1               5                  10                  15

GCA TGC ATG TCA GCT GAT CTG GAA GTA ACC ACC AGC ACC TGG GTG TTG           95
Ala Cys Met Ser Ala Asp Leu Glu Val Thr Thr Ser Thr Trp Val Leu
                20                  25                  30

CTT GGA GGG GTC CTC GCG GCC CTA GCG GCC TAC TGC TTG TCA GTC GGC          143
Leu Gly Gly Val Leu Ala Ala Leu Ala Ala Tyr Cys Leu Ser Val Gly
            35                  40                  45

TGC GTT GTA ATC GTG GGT CAT ATC GAG CTG GGG GGC AAG CCG GCA CTC          191
Cys Val Val Ile Val Gly His Ile Glu Leu Gly Gly Lys Pro Ala Leu
        50                  55                  60

GTT CCA GAC AAG GAG GTG TTG TAT CAA CAG TAC GAT GAG ATG GAG GAG          239
Val Pro Asp Lys Glu Val Leu Tyr Gln Gln Tyr Asp Glu Met Glu Glu
    65                  70                  75

TGC TCG CAA GCC GCC CCA TAC ATC GAA CAA GCT CAG GTA ATA GCC CAC          287
Cys Ser Gln Ala Ala Pro Tyr Ile Glu Gln Ala Gln Val Ile Ala His
 80                  85                  90                  95

CAG TTC AAG GAG AAA ATC CTT GGA CTG CTG CAG CGA GCC ACC CAA CAA          335
Gln Phe Lys Glu Lys Ile Leu Gly Leu Leu Gln Arg Ala Thr Gln Gln
                100                 105                 110

CAA GCT GTC ATT GAG CCC GTA ATA GCT TCC AAC TGG CAA AAG CTT GAA          383
Gln Ala Val Ile Glu Pro Val Ile Ala Ser Asn Trp Gln Lys Leu Glu
            115                 120                 125

ACC TTC TGG CAC AAG CAT                                                  401
Thr Phe Trp His Lys His
        130

(2) INFORMATION FOR SEQ ID NO: 32:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO: 32:

Gln Asn Glu Ile Cys Leu Thr His Pro Val Thr Lys Tyr Ile Met Ala
 1               5                  10                  15
```

```
Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
            35                  40                  45

Val Val Ile Val Gly His Ile Glu Leu Gly Gly Lys Pro Ala Leu Val
            50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
            85                  90                  95

Phe Lys Glu Lys Ile Leu Gly Leu Leu Gln Arg Ala Thr Gln Gln Gln
            100                 105                 110

Ala Val Ile Glu Pro Val Ile Ala Ser Asn Trp Gln Lys Leu Glu Thr
            115                 120                 125

Phe Trp His Lys His
            130

(2) INFORMATION FOR SEQ ID NO: 33:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: HD10-1-3

(ix) FEATURE:
        (A) NAME/KEY: CDS
        (B) LOCATION: 3..401

(xi) SEQUENCE DESCRIPTION: SEQ ID NO: 33:

TC CAA AAT GAA ATC TGC TTG ACA CAC CCC GTC ACA AAA TAC ATT ATG           47
   Gln Asn Glu Ile Cys Leu Thr His Pro Val Thr Lys Tyr Ile Met
    1               5                  10                  15

GCA TGC ATG TCA GCT GAT CTG GAA GTA ACC ACC AGC ACC TGG GTG TTG          95
Ala Cys Met Ser Ala Asp Leu Glu Val Thr Thr Ser Thr Trp Val Leu
                20                  25                  30

CTT GGA GGG GTC CTC GCG GCC CTA GCG GCC TAC TGC TTG TCA GTC GGC         143
Leu Gly Gly Val Leu Ala Ala Leu Ala Ala Tyr Cys Leu Ser Val Gly
                35                  40                  45

TGC GTT GTA ATC GTG GGT CAT ATC GAG CTG GGG GGC AAG CCG GCA CTC         191
Cys Val Val Ile Val Gly His Ile Glu Leu Gly Gly Lys Pro Ala Leu
                50                  55                  60

GTT CCA GAC AAG GAG GTG TTG TAT CAA CAG TAC GAT GAG ATG GAG GAG         239
Val Pro Asp Lys Glu Val Leu Tyr Gln Gln Tyr Asp Glu Met Glu Glu
65                  70                  75

TGC TCG CAA GCC GCC CCA TAC ATC GAA CAA GCT CAG GTA ATA GCC CAC         287
Cys Ser Gln Ala Ala Pro Tyr Ile Glu Gln Ala Gln Val Ile Ala His
80                  85                  90                  95

CAG TTC AAG GAG AAA ATC CTT GGA CTG CTG CAG CGA GCC ACC CAA CAA         335
Gln Phe Lys Glu Lys Ile Leu Gly Leu Leu Gln Arg Ala Thr Gln Gln
                100                 105                 110

CAA GCT GTC ATT GAG CCC GTA ATA GCT TCC AAC TGG CAA AAG CTT GAA         383
Gln Ala Val Ile Glu Pro Val Ile Ala Ser Asn Trp Gln Lys Leu Glu
                115                 120                 125
```

```
ACC TTC TGG CAC AAG CAT                                              401
Thr Phe Trp His Lys His
        130

(2) INFORMATION FOR SEQ ID NO: 34:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO: 34:

Gln Asn Glu Ile Cys Leu Thr His Pro Val Thr Lys Tyr Ile Met Ala
 1               5                  10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Leu Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Ile Leu Gly Leu Leu Gln Arg Ala Thr Gln Gln Gln
            100                 105                 110

Ala Val Ile Glu Pro Val Ile Ala Ser Asn Trp Gln Lys Leu Glu Thr
        115                 120                 125

Phe Trp His Lys His
        130

(2) INFORMATION FOR SEQ ID NO: 35:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR36-20-164

(ix) FEATURE:
        (A) NAME/KEY: CDS
        (B) LOCATION: 3..401

(xi) SEQUENCE DESCRIPTION: SEQ ID NO: 35:

TC CAA AAT GAA ATC TGC TTG ACA CAC CCC ATC ACA AAA TAC ATC ATG        47
   Gln Asn Glu Ile Cys Leu Thr His Pro Ile Thr Lys Tyr Ile Met
    1               5                  10                  15

GCA TGC ATG TCA GCT GAT CTG GAA GTA ACC ACC AGC ACC TGG GTT TTG       95
Ala Cys Met Ser Ala Asp Leu Glu Val Thr Thr Ser Thr Trp Val Leu
            20                  25                  30

CTT GGA GGG GTC CTC GCG GCC CTA GCG GCC TAC TGC TTG TCA GTC GGT      143
Leu Gly Gly Val Leu Ala Ala Leu Ala Ala Tyr Cys Leu Ser Val Gly
        35                  40                  45
```

```
TGT GTT GTG ATT GTG GGT CAT ATC GAG CTG GGG GGC AAG CCG GCA ATC      191
Cys Val Val Ile Val Gly His Ile Glu Leu Gly Gly Lys Pro Ala Ile
        50                  55                  60

GTT CCA GAC AAA GAG GTG TTG TAT CAA CAA TAC GAT GAG ATG GAA GAG      239
Val Pro Asp Lys Glu Val Leu Tyr Gln Gln Tyr Asp Glu Met Glu Glu
65                  70                  75

TGC TCA CAA GCT GCC CCA TAT ATC GAA CAA GCT CAG GTA ATA GCT CAC      287
Cys Ser Gln Ala Ala Pro Tyr Ile Glu Gln Ala Gln Val Ile Ala His
80                  85                  90                  95

CAG TTC AAG GGA AAA GTC CTT GGA TTG CTG CAG CGA GCC ACC CAA CAA      335
Gln Phe Lys Gly Lys Val Leu Gly Leu Leu Gln Arg Ala Thr Gln Gln
                100                 105                 110

CAA GCT GTC ATT GAG CCC ATA GTA ACT ACC AAC TGG CAA AAG CTT GAG      383
Gln Ala Val Ile Glu Pro Ile Val Thr Thr Asn Trp Gln Lys Leu Glu
            115                 120                 125

GCC TTT TGG CAC AAG CAT                                              401
Ala Phe Trp His Lys His
        130
```

(2) INFORMATION FOR SEQ ID NO: 36:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO: 36:

```
Gln Asn Glu Ile Cys Leu Thr His Pro Ile Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Gly Lys Val Leu Gly Leu Leu Gln Arg Ala Thr Gln Gln Gln
            100                 105                 110

Ala Val Ile Glu Pro Ile Val Thr Thr Asn Trp Gln Lys Leu Glu Ala
        115                 120                 125

Phe Trp His Lys His
        130
```

(2) INFORMATION FOR SEQ ID NO: 37:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
    (B) CLONE: BR36-20-166

(ix) FEATURE:
    (A) NAME/KEY: CDS
    (B) LOCATION: 3..401

(xi) SEQUENCE DESCRIPTION: SEQ ID NO: 37:

```
TC CAA AAT GAA ATC TGC TTG ACA CAC CCC ATC ACA AAA TAC ATC ATG        47
   Gln Asn Glu Ile Cys Leu Thr His Pro Ile Thr Lys Tyr Ile Met
   1               5                  10                  15

GCA TGC ATG TCA GCT GAT CTG GAA GTA ACC ACC AGC ACC TGG GTT TTG       95
Ala Cys Met Ser Ala Asp Leu Glu Val Thr Thr Ser Thr Trp Val Leu
                20                  25                  30

CTT GGA GGG GTC CTC GCG GCC CTA GCG GCC TAC TGC TTG TCA GTC GGT      143
Leu Gly Gly Val Leu Ala Ala Leu Ala Ala Tyr Cys Leu Ser Val Gly
            35                  40                  45

TGT GTT GTG ATT GTG GGT CAT ATC GAG CTG GGG GGC AAG CCG GCA ATC      191
Cys Val Val Ile Val Gly His Ile Glu Leu Gly Gly Lys Pro Ala Ile
        50                  55                  60

GTT CCA GAC AAA GAG GTG TTG TAT CAA CAA TAC GAT GAG ATG GAA GAG      239
Val Pro Asp Lys Glu Val Leu Tyr Gln Gln Tyr Asp Glu Met Glu Glu
    65                  70                  75

TGC TCA CAA GCT GCC CCA TAT ATC GAA CAA GCT CAG GTG ATA GCT CAC      287
Cys Ser Gln Ala Ala Pro Tyr Ile Glu Gln Ala Gln Val Ile Ala His
80                  85                  90                  95

CAG TTC AAG GAA AAA GTC CTT GGA TTG CTG CAG CGA GCC ACC CAA CAA      335
Gln Phe Lys Glu Lys Val Leu Gly Leu Leu Gln Arg Ala Thr Gln Gln
                100                 105                 110

CAA GCT GTC ATT GAG CCC ATA GTA ACT ACC AAC TGG CAA AAG CTT GAG      383
Gln Ala Val Ile Glu Pro Ile Val Thr Thr Asn Trp Gln Lys Leu Glu
            115                 120                 125

GCC TTT TGG CAC AAG CAT                                              401
Ala Phe Trp His Lys His
        130
```

(2) INFORMATION FOR SEQ ID NO: 38:

(i) SEQUENCE CHARACTERISTICS:
       (A) LENGTH: 133 amino acids
       (B) TYPE: amino acid
       (D) TOPOLOGY: linear (ii) MOLECULE TYPE: protein (xi) SEQUENCE DESCRIPTION: SEQ ID NO: 38:

```
Gln Asn Glu Ile Cys Leu Thr His Pro Ile Thr Lys Tyr Ile Met Ala
1               5                  10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Val Leu Gly Leu Leu Gln Arg Ala Thr Gln Gln Gln
            100                 105                 110

Ala Val Ile Glu Pro Ile Val Thr Thr Asn Trp Gln Lys Leu Glu Ala
```

(2) INFORMATION FOR SEQ ID NO: 39:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: BR36-20-165

(ix) FEATURE:
        (A) NAME/KEY: CDS
        (B) LOCATION: 3..401

(xi) SEQUENCE DESCRIPTION: SEQ ID NO: 39:

```
TC CAA AAT GAA ATC TGC TTG ACA CAC CCC ATC ACA AAA TAC ATC ATG        47
   Gln Asn Glu Ile Cys Leu Thr His Pro Ile Thr Lys Tyr Ile Met
     1               5                  10                  15

GCA TGC ATG TCA GCT GAT CTG GAA GTA ACC ACC AGC ACC TGG GTT TTG        95
Ala Cys Met Ser Ala Asp Leu Glu Val Thr Thr Ser Thr Trp Val Leu
                20                  25                  30

CTT GGA GGG GTC CTC GCG GCC CTA GCG GCC TAC TGC TTG TCA GTC GGT       143
Leu Gly Gly Val Leu Ala Ala Leu Ala Ala Tyr Cys Leu Ser Val Gly
            35                  40                  45

TGT GTT GTG ATT GTG GGT CAT ATC GAG CTG GGG GGC AAG CCG GCA ATC       191
Cys Val Val Ile Val Gly His Ile Glu Leu Gly Gly Lys Pro Ala Ile
        50                  55                  60

GTT CCA GAC AAA GAG GTG TTG TAT CAA CAA TAC GAT GAG ATG GAA GAG       239
Val Pro Asp Lys Glu Val Leu Tyr Gln Gln Tyr Asp Glu Met Glu Glu
    65                  70                  75

TGC TCA CAA GCT GCC CCA TAT ATC GAA CAA GCT CAG GTA ATA GCT CAC       287
Cys Ser Gln Ala Ala Pro Tyr Ile Glu Gln Ala Gln Val Ile Ala His
 80                  85                  90                  95

CAG TTC AAG GAA AAA GTC CTT GGA TTG CTG CAG CGA GCC ACC CAA CAA       335
Gln Phe Lys Glu Lys Val Leu Gly Leu Leu Gln Arg Ala Thr Gln Gln
                100                 105                 110

CAA GCT GTC ATT GAG CCC ATA GTA ACT ACC AAC TGG CAA AAG CTT GAG       383
Gln Ala Val Ile Glu Pro Ile Val Thr Thr Asn Trp Gln Lys Leu Glu
            115                 120                 125

GCC TTT TGG CAC AAG CAT                                               401
Ala Phe Trp His Lys His
        130
```

(2) INFORMATION FOR SEQ ID NO: 40:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO: 40:

```
Gln Asn Glu Ile Cys Leu Thr His Pro Ile Thr Lys Tyr Ile Met Ala
  1               5                  10                  15
```

```
Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Val Leu Gly Leu Leu Gln Arg Ala Thr Gln Gln Gln
            100                 105                 110

Ala Val Ile Glu Pro Ile Val Thr Thr Asn Trp Gln Lys Leu Glu Ala
        115                 120                 125

Phe Trp His Lys His
    130
```

(2) INFORMATION FOR SEQ ID NO: 41:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-2-1

(ix) FEATURE:
        (A) NAME/KEY: CDS
        (B) LOCATION: 3..509

(xi) SEQUENCE DESCRIPTION: SEQ ID NO: 41:

```
CC ATG AGC ACG AAT CCT AAA CCT CAA AGA AAA ACC AAA AGA AAC ACC        47
   Met Ser Thr Asn Pro Lys Pro Gln Arg Lys Thr Lys Arg Asn Thr
   1               5                   10                  15

AAC CGT CGC CCA CAG GAC GTC AAG TTC CCG GGC GGT GGT CAG ATC GTT       95
Asn Arg Arg Pro Gln Asp Val Lys Phe Pro Gly Gly Gly Gln Ile Val
                20                  25                  30

GGC GGA GTT TAC TTG TTG CCG CGC AGG GGC CCT AGG ATG GGT GTG CGC      143
Gly Gly Val Tyr Leu Leu Pro Arg Arg Gly Pro Arg Met Gly Val Arg
            35                  40                  45

GCG ACT CGG AAG ACT TCG GAA CGG TCG CAA CCC CGT GGA CGG CGT CAG      191
Ala Thr Arg Lys Thr Ser Glu Arg Ser Gln Pro Arg Gly Arg Arg Gln
        50                  55                  60

CCT ATT CCC AAG GCG CGC CAG CCC ACG GGC CGG TCC TGG GGT CAA CCC      239
Pro Ile Pro Lys Ala Arg Gln Pro Thr Gly Arg Ser Trp Gly Gln Pro
65                  70                  75

GGG TAC CCT TGG CCC CTT TAC GCC AAT GAG GGC CTC GGG TGG GCA GGG      287
Gly Tyr Pro Trp Pro Leu Tyr Ala Asn Glu Gly Leu Gly Trp Ala Gly
80                  85                  90                  95

TGG CTG CTC TCC CCT CGA GGC TCT CGG CCT AAT TGG GGC CCC AAT GAC      335
Trp Leu Leu Ser Pro Arg Gly Ser Arg Pro Asn Trp Gly Pro Asn Asp
            100                 105                 110

CCC CGG CGA AAA TCG CGT AAT TTG GGT AAG GTC ATC GAT ACC CTA ACG      383
Pro Arg Arg Lys Ser Arg Asn Leu Gly Lys Val Ile Asp Thr Leu Thr
```

-continued

```
               115                 120                 125
TGC GGA TTC GCC GAT CTC ATG GGG TAT ATC CCG CTC GTA GGC GGC CCC        431
Cys Gly Phe Ala Asp Leu Met Gly Tyr Ile Pro Leu Val Gly Gly Pro
            130                 135                 140

ATT GGG GGC GTC GCA AGG GCT CTC GCA CAC GGT GTG AGG GTC CTT GAG        479
Ile Gly Gly Val Ala Arg Ala Leu Ala His Gly Val Arg Val Leu Glu
145                 150                 155

GAC GGG GTA AAC TAT GCA ACA GGG AAT TTA                                509
Asp Gly Val Asn Tyr Ala Thr Gly Asn Leu
160                 165
```

(2) INFORMATION FOR SEQ ID NO: 42:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO: 42:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Met Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Ile
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu
                165
```

(2) INFORMATION FOR SEQ ID NO: 43:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-2-6

(ix) FEATURE:
        (A) NAME/KEY: CDS (B) LOCATION: 3..509

(xi) SEQUENCE DESCRIPTION: SEQ ID NO: 43:

```
CC ATG AGC ACG AAT CCT AAA CCT CAA AGA AAA ACC AAA AGA AAC ACC         47
   Met Ser Thr Asn Pro Lys Pro Gln Arg Lys Thr Lys Arg Asn Thr
   1               5                   10                  15

AAC CGT CGC CCA CAG GAC GTC AAG TTC CCG GGC GGT GGT CAG ATC GTT        95
Asn Arg Arg Pro Gln Asp Val Lys Phe Pro Gly Gly Gly Gln Ile Val
                20                  25                  30

GGC GGA GTT TAC TTG TTG CCG CGC AGG GGC CCT AGG ATG GGT GTG CGC       143
Gly Gly Val Tyr Leu Leu Pro Arg Arg Gly Pro Arg Met Gly Val Arg
            35                  40                  45

GCG ACT CGG AAG ACT TCG GAA CGG TCG CAA CCC CGT GGA CGG CGT CAG       191
Ala Thr Arg Lys Thr Ser Glu Arg Ser Gln Pro Arg Gly Arg Arg Gln
        50                  55                  60

CCT ATT CCC AAG GCG CGC CAG CCC ACG GGC CGG TCC TGG GGT CAA CCC       239
Pro Ile Pro Lys Ala Arg Gln Pro Thr Gly Arg Ser Trp Gly Gln Pro
    65                  70                  75

GGG TAC CCT TGG CCC CTT TAC GCC AAT GAG GGC CTC GGG TGG GCA GGG       287
Gly Tyr Pro Trp Pro Leu Tyr Ala Asn Glu Gly Leu Gly Trp Ala Gly
80                  85                  90                  95

TGG CTG CTC TCC CCT CGA GGC TCT CGG CCT AAT TGG GGC CCC AAT GAC       335
Trp Leu Leu Ser Pro Arg Gly Ser Arg Pro Asn Trp Gly Pro Asn Asp
                100                 105                 110

CCC CGG CGA AAA TCG CGT AAT TTG GGT AAG GTC ATC GAT ACC CTA ACG       383
Pro Arg Arg Lys Ser Arg Asn Leu Gly Lys Val Ile Asp Thr Leu Thr
            115                 120                 125

TGC GGA TTC GCC GAT CTC ATG GGG TAT ATC CCG CTC GTA GGC GGC CCC       431
Cys Gly Phe Ala Asp Leu Met Gly Tyr Ile Pro Leu Val Gly Gly Pro
        130                 135                 140

ATT GGG GGC GTC GCA AGG GCT CTC GCA CAC GGT GTG AGG GTC CTT GAG       479
Ile Gly Gly Val Ala Arg Ala Leu Ala His Gly Val Arg Val Leu Glu
    145                 150                 155

GAC GGG GTA AAC TAT GCA ACA GGG AAT TTA                               509
Asp Gly Val Asn Tyr Ala Thr Gly Asn Leu
160                 165
```

(2) INFORMATION FOR SEQ ID NO: 44:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO: 44:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
```

```
            100                 105                 110
Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Ile
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu
                165

(2) INFORMATION FOR SEQ ID NO: 45:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-4-1

(ix) FEATURE:
        (A) NAME/KEY: CDS
        (B) LOCATION: 2..580

(xi) SEQUENCE DESCRIPTION: SEQ ID NO: 45:

A ACG TGC GGA TTC GCC GAT CTC ATG GGG TAT ATC CCG CTC GTA GGC      46
  Thr Cys Gly Phe Ala Asp Leu Met Gly Tyr Ile Pro Leu Val Gly
  1               5                  10                  15

GGC CCC ATT GGG GGC GTC GCA AGG GCT CTC GCA CAC GGT GTG AGG GTC    94
Gly Pro Ile Gly Gly Val Ala Arg Ala Leu Ala His Gly Val Arg Val
            20                  25                  30

CTT GAG GAC GGG GTA AAC TAT GCA ACA GGG AAT TTA CCC GGT TGC TCT   142
Leu Glu Asp Gly Val Asn Tyr Ala Thr Gly Asn Leu Pro Gly Cys Ser
                35                  40                  45

TTC TCT ATC TTT ATT CTT GCT CTT CTC TCG TGT CTG ACC GTT CCG GCC   190
Phe Ser Ile Phe Ile Leu Ala Leu Leu Ser Cys Leu Thr Val Pro Ala
        50                  55                  60

TCT GCA GTT CCC TAC CGA AAT GCC TCT GGG ATT TAT CAT GTT ACC AAT   238
Ser Ala Val Pro Tyr Arg Asn Ala Ser Gly Ile Tyr His Val Thr Asn
    65                  70                  75

GAT TGC CCA AAC TCT TCC ATA GTC TAT GAG GCA GAT AAC CTG ATC CTA   286
Asp Cys Pro Asn Ser Ser Ile Val Tyr Glu Ala Asp Asn Leu Ile Leu
80                  85                  90                  95

CAC GCA CCT GGT TGC GTG CCT TGT GTC ATG ACA GGT AAT GTG AGT AGA   334
His Ala Pro Gly Cys Val Pro Cys Val Met Thr Gly Asn Val Ser Arg
                100                 105                 110

TGC TGG GTC CAA ATT ACC CCT ACA CTG TCA GCC CCG AGC CTC GGA GCA   382
Cys Trp Val Gln Ile Thr Pro Thr Leu Ser Ala Pro Ser Leu Gly Ala
            115                 120                 125

GTC ACG GCT CCT CTT CGG AGA GCC GTT GAC TAC CTA GCG GGA GGG GCT   430
Val Thr Ala Pro Leu Arg Arg Ala Val Asp Tyr Leu Ala Gly Gly Ala
        130                 135                 140

GCC CTC TGC TCC GCG TTA TAC GTA GGA GAC GCG TGT GGG GCA CTA TTC   478
Ala Leu Cys Ser Ala Leu Tyr Val Gly Asp Ala Cys Gly Ala Leu Phe
    145                 150                 155

TTG GTA GGC CAA ATG TTC ACC TAT AGG CCT CGC CAG CAC GCT ACG GTG   526
```

```
Leu Val Gly Gln Met Phe Thr Tyr Arg Pro Arg Gln His Ala Thr Val
160                 165                 170                 175

CAG AAC TGC AAC TGT TCC ATT TAC AGT GGC CAT GTT ACC GGC CAC CGG    574
Gln Asn Cys Asn Cys Ser Ile Tyr Ser Gly His Val Thr Gly His Arg
                180                 185                 190

ATG GCA                                                              580
Met Ala
```

(2) INFORMATION FOR SEQ ID NO: 46:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 46:

```
Thr Cys Gly Phe Ala Asp Leu Met Gly Tyr Ile Pro Leu Val Gly Gly
  1               5                  10                  15

Pro Ile Gly Gly Val Ala Arg Ala Leu Ala His Gly Val Arg Val Leu
                 20                  25                  30

Glu Asp Gly Val Asn Tyr Ala Thr Gly Asn Leu Pro Gly Cys Ser Phe
             35                  40                  45

Ser Ile Phe Ile Leu Ala Leu Leu Ser Cys Leu Thr Val Pro Ala Ser
         50                  55                  60

Ala Val Pro Tyr Arg Asn Ala Ser Gly Ile Tyr His Val Thr Asn Asp
 65                  70                  75                  80

Cys Pro Asn Ser Ser Ile Val Tyr Glu Ala Asp Asn Leu Ile Leu His
                 85                  90                  95

Ala Pro Gly Cys Val Pro Cys Val Met Thr Gly Asn Val Ser Arg Cys
                100                 105                 110

Trp Val Gln Ile Thr Pro Thr Leu Ser Ala Pro Ser Leu Gly Ala Val
                115                 120                 125

Thr Ala Pro Leu Arg Arg Ala Val Asp Tyr Leu Ala Gly Gly Ala Ala
130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
                180                 185                 190

Ala
```

(2) INFORMATION FOR SEQ ID NO: 47:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-4-6

(ix) FEATURE:

```
          (A) NAME/KEY: CDS
          (B) LOCATION: 2..580

(xi) SEQUENCE DESCRIPTION: SEQ ID NO: 47:

A ACG TGC GGA TTC GCC GAT CTC ATG GGG TAT ATC CCG CTC GTA GGC        46
  Thr Cys Gly Phe Ala Asp Leu Met Gly Tyr Ile Pro Leu Val Gly
   1               5                  10                  15

GGC CCC ATT GGG GGC GTC GCA AGG GCT CTC GCA CAC GGT GTG AGG GTC      94
Gly Pro Ile Gly Gly Val Ala Arg Ala Leu Ala His Gly Val Arg Val
             20                  25                  30

CTT GAG GAC GGG GTA AAC TAT GCA ACA GGG AAT TTA CCC GGT TGC TCT     142
Leu Glu Asp Gly Val Asn Tyr Ala Thr Gly Asn Leu Pro Gly Cys Ser
             35                  40                  45

TTC TCT ATC TTT ATT CTT GCT CTT CTC TCG TGT CTG ACC GTT CCG GCC     190
Phe Ser Ile Phe Ile Leu Ala Leu Leu Ser Cys Leu Thr Val Pro Ala
         50                  55                  60

TCT GCA GTT CCC TAC CGA AAT GCC TCT GGG ATT TAT CAT GTT ACC AAT     238
Ser Ala Val Pro Tyr Arg Asn Ala Ser Gly Ile Tyr His Val Thr Asn
 65                  70                  75

GAT TGC CCA AAC TCT TCC ATA GTC TAT GAG GCA GAT AAC CTG ATC CTA     286
Asp Cys Pro Asn Ser Ser Ile Val Tyr Glu Ala Asp Asn Leu Ile Leu
 80                  85                  90                  95

CAC GCA CCT GGT TGC GTG CCT TGT GTC ATG ACA GGT AAT GTG AGT AGA     334
His Ala Pro Gly Cys Val Pro Cys Val Met Thr Gly Asn Val Ser Arg
                100                 105                 110

TGC TGG GTC CAA ATT ACC CCT ACA CTG TCA GCC CCG AGC CTC GGA GCA     382
Cys Trp Val Gln Ile Thr Pro Thr Leu Ser Ala Pro Ser Leu Gly Ala
            115                 120                 125

GTC ACG GCT CCT CTT CGG AGA GCC GTT GAC TAC CTA GCG GGA GGG GCT     430
Val Thr Ala Pro Leu Arg Arg Ala Val Asp Tyr Leu Ala Gly Gly Ala
            130                 135                 140

GCC CTC TGC TCC GCG TTA TAC GTA GGA GAC GCG TGT GGG GCA CTA TTC     478
Ala Leu Cys Ser Ala Leu Tyr Val Gly Asp Ala Cys Gly Ala Leu Phe
145                 150                 155

TTG GTA GGC CAA ATG TTC ACC TAT AGG CCT CGC CAG CAC GCT ACG GTG     526
Leu Val Gly Gln Met Phe Thr Tyr Arg Pro Arg Gln His Ala Thr Val
160                 165                 170                 175

CAG AAC TGC AAC TGT TCC ATT TAC AGT GGC CAT GTT ACC GGC CAC CGG     574
Gln Asn Cys Asn Cys Ser Ile Tyr Ser Gly His Val Thr Gly His Arg
                180                 185                 190

ATG GCA                                                              580
Met Ala (2) INFORMATION FOR SEQ ID NO: 48:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 48:

Thr Cys Gly Phe Ala Asp Leu Met Gly Tyr Ile Pro Leu Val Gly Gly
 1               5                  10                  15

Pro Ile Gly Gly Val Ala Arg Ala Leu Ala His Gly Val Arg Val Leu
             20                  25                  30

Glu Asp Gly Val Asn Tyr Ala Thr Gly Asn Leu Pro Gly Cys Ser Phe
             35                  40                  45

Ser Ile Phe Ile Leu Ala Leu Leu Ser Cys Leu Thr Val Pro Ala Ser
         50                  55                  60
```

```
Ala Val Pro Tyr Arg Asn Ala Ser Gly Ile Tyr His Val Thr Asn Asp
 65                  70                  75                  80

Cys Pro Asn Ser Ser Ile Val Tyr Glu Ala Asp Asn Leu Ile Leu His
                 85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
        115                 120                 125

Thr Ala Pro Leu Arg Arg Ala Val Asp Tyr Leu Ala Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
            180                 185                 190

Ala
```

(2) INFORMATION FOR SEQ ID NO: 49:

(i) SEQUENCE CHARACTERISTICS:
        (A) LENGTH: 959 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-3-4

(ix) FEATURE:
        (A) NAME/KEY: CDS
        (B) LOCATION: 3..959

(xi) SEQUENCE DESCRIPTION: SEQ ID NO: 49:

```
CC ATG AGC ACG AAT CCT AAA CCT CAA AGA AAA ACC AAA AGA AAC ACC          47
   Met Ser Thr Asn Pro Lys Pro Gln Arg Lys Thr Lys Arg Asn Thr
   1               5                   10                  15

AAC CGT CGC CCA CAG GAC GTC AAG TTC CCG GGC GGT GGT CAG ATC GTT         95
Asn Arg Arg Pro Gln Asp Val Lys Phe Pro Gly Gly Gly Gln Ile Val
                20                  25                  30

GGC GGA GTT TAC TTG TTG CCG CGC AGG GGC CCT AGG ATG GGT GTG CGC        143
Gly Gly Val Tyr Leu Leu Pro Arg Arg Gly Pro Arg Met Gly Val Arg
            35                  40                  45

GCG ACT CGG AAG ACT TCG GAA CGG TCG CAA CCC CGT GGA CGG CGT CAG        191
Ala Thr Arg Lys Thr Ser Glu Arg Ser Gln Pro Arg Gly Arg Arg Gln
        50                  55                  60

CCT ATT CCC AAG GCG CGC CAG CCC ACG GGC CGG TCC TGG GGT CAA CCC        239
Pro Ile Pro Lys Ala Arg Gln Pro Thr Gly Arg Ser Trp Gly Gln Pro
    65                  70                  75

GGG TAC CCT TGG CCC CTT TAC GCC AAT GAG GGC CTC GGG TGG CCA GGG        287
Gly Tyr Pro Trp Pro Leu Tyr Ala Asn Glu Gly Leu Gly Trp Ala Gly
80                  85                  90                  95

TGG CTG CTC TCC CCT CGA GGC TCT CGG CCT AAT TGG GGC CCC AAT GAC        335
Trp Leu Leu Ser Pro Arg Gly Ser Arg Pro Asn Trp Gly Pro Asn Asp
                100                 105                 110
```

```
CCC CGG CGA AAA TCG CGT AAT TTG GGT AAG GTC ATC GAT ACC CTA ACG      383
Pro Arg Arg Lys Ser Arg Asn Leu Gly Lys Val Ile Asp Thr Leu Thr
            115                 120                 125

TGC GGA TTC GCC GAT CTC ATG GGG TAT ATC CCG CTC GTA GGC GGC CCC      431
Cys Gly Phe Ala Asp Leu Met Gly Tyr Ile Pro Leu Val Gly Gly Pro
        130                 135                 140

ATT GGG GGC GTC GCA AGG GCT CTC GCA CAC GGT GTG AGG GTC CTT GAG      479
Ile Gly Gly Val Ala Arg Ala Leu Ala His Gly Val Arg Val Leu Glu
    145                 150                 155

GAC GGG GTA AAC TAT GCA ACA GGG AAT TTA CCC GGT TGC TCT TTC TCT      527
Asp Gly Val Asn Tyr Ala Thr Gly Asn Leu Pro Gly Cys Ser Phe Ser
160                 165                 170                 175

ATC TTT ATT CTT GCT CTT CTC TCG TGT CTG ACC GTT CCG GCC TCT GCA      575
Ile Phe Ile Leu Ala Leu Leu Ser Cys Leu Thr Val Pro Ala Ser Ala
                180                 185                 190

GTT CCC TAC CGA AAT GCC TCT GGG ATT TAT CAT GTT ACC AAT GAT TGC      623
Val Pro Tyr Arg Asn Ala Ser Gly Ile Tyr His Val Thr Asn Asp Cys
            195                 200                 205

CCA AAC TCT TCC ATA GTC TAT GAG GCA GAT AAC CTG ATC CTA CAC GCA      671
Pro Asn Ser Ser Ile Val Tyr Glu Ala Asp Asn Leu Ile Leu His Ala
        210                 215                 220

CCT GGT TGC GTG CCT TGT GTC ATG ACA GGT AAT GTG AGT AGA TGC TGG      719
Pro Gly Cys Val Pro Cys Val Met Thr Gly Asn Val Ser Arg Cys Trp
    225                 230                 235

GTC CAA ATT ACC CCT ACA CTG TCA GCC CCG AGC CTC GGA GCA GTC ACG      767
Val Gln Ile Thr Pro Thr Leu Ser Ala Pro Ser Leu Gly Ala Val Thr
240                 245                 250                 255

GCT CCT CTT CGG AGA GCC GTT GAC TAC CTA GCG GGA GGG GCT GCC CTC      815
Ala Pro Leu Arg Arg Ala Val Asp Tyr Leu Ala Gly Gly Ala Ala Leu
                260                 265                 270

TGC TCC GCG TTA TAC GTA GGA GAC GCG TGT GGG GCA CTA TTC TTG GTA      863
Cys Ser Ala Leu Tyr Val Gly Asp Ala Cys Gly Ala Leu Phe Leu Val
            275                 280                 285

GGC CAA ATG TTC ACC TAT AGG CCT CGC CAG CAC GCT ACG GTG CAG AAC      911
Gly Gln Met Phe Thr Tyr Arg Pro Arg Gln His Ala Thr Val Gln Asn
        290                 295                 300

TGC AAC TGT TCC ATT TAC AGT GGC CAT GTT ACC GGC CAC CGG ATG GCA      959
Cys Asn Cys Ser Ile Tyr Ser Gly His Val Thr Gly His Arg Met Ala
    305                 310                 315
```

(2) INFORMATION FOR SEQ ID NO: 50:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 50:

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Met Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80
```

```
Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
           100                 105                 110

Arg Arg Lys Ser Arg Asn Leu Gly Lys Val Ile Asp Thr Leu Thr Cys
           115                 120                 125

Gly Phe Ala Asp Leu Met Gly Tyr Ile Pro Leu Val Gly Gly Pro Ile
       130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
180                 185                 190

Pro Tyr Arg Asn Ala Ser Gly Ile Tyr His Val Thr Asn Asp Cys Pro
            195                 200                 205

Asn Ser Ser Ile Val Tyr Glu Ala Asp Asn Leu Ile Leu His Ala Pro
210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
            275                 280                 285

Gln Met Phe Thr Tyr Arg Pro Arg Gln His Ala Thr Val Gln Asn Cys
        290                 295                 300

Asn Cys Ser Ile Tyr Ser Gly His Val Thr Gly His Arg Met Ala
305                 310                 315
```

(2) INFORMATION FOR SEQ ID NO: 51:

(i) SEQUENCE CHARACTERISTICS:
        (A) LENGTH: 959 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-3-8

(ix) FEATURE:
        (A) NAME/KEY: CDS
        (B) LOCATION: 3..959

(xi) SEQUENCE DESCRIPTION: SEQ ID NO: 51:

```
CC ATG AGC ACG AAT CCT AAA CCT CAA AGA AAA ACC AAA AGA AAC ACC        47
   Met Ser Thr Asn Pro Lys Pro Gln Arg Lys Thr Lys Arg Asn Thr
    1               5                  10                  15

AAC CGT CGC CCA CAG GAC GTC AAG TTC CCG GGC GGT GGT CAG ATC GTT       95
Asn Arg Arg Pro Gln Asp Val Lys Phe Pro Gly Gly Gly Gln Ile Val
                 20                  25                  30

GGC GGA GTT TAC TTG TTG CCG CGC AGG GGC CCT AGG ATG GGT GTG CGC      143
Gly Gly Val Tyr Leu Leu Pro Arg Arg Gly Pro Arg Met Gly Val Arg
```

```
                  35                    40                    45
GCG ACT CGG AAG ACT TCG GAA CGG TCG CAA CCC CGT GGA CGG CGT CAG      191
Ala Thr Arg Lys Thr Ser Glu Arg Ser Gln Pro Arg Gly Arg Arg Gln
            50                    55                    60

CCT ATT CCC AAG GCG CGC CAG CCC ACG GGC CGG TCC TGG GGT CAA CCC      239
Pro Ile Pro Lys Ala Arg Gln Pro Thr Gly Arg Ser Trp Gly Gln Pro
        65                    70                    75

GGG TAC CCT TGG CCC CTT TAC GCC AAT GAG GGC CTC GGG TGG GCA GGG      287
Gly Tyr Pro Trp Pro Leu Tyr Ala Asn Glu Gly Leu Gly Trp Ala Gly
 80                    85                    90                    95

TGG CTG CTC TCC CCT CGA GGC TCT CGG CCT AAT TGG GGC CCC AAT GAC      335
Trp Leu Leu Ser Pro Arg Gly Ser Arg Pro Asn Trp Gly Pro Asn Asp
                100                   105                   110

CCC CGG CGA AAA TCG CGT AAT TTG GGT AAG GTC ATC GAT ACC CTA ACG      383
Pro Arg Arg Lys Ser Arg Asn Leu Gly Lys Val Ile Asp Thr Leu Thr
            115                   120                   125

TGC GGA TTC GCC GAT CTC ATG GGG TAC ATC CCG CTC GTA GGC GGC CCC      431
Cys Gly Phe Ala Asp Leu Met Gly Tyr Ile Pro Leu Val Gly Gly Pro
        130                   135                   140

GTT GGG GGC GTC GCA AGG GCT CTC GCA CAC GGT GTG AGG GTC CTT GAG      479
Val Gly Gly Val Ala Arg Ala Leu Ala His Gly Val Arg Val Leu Glu
145                   150                   155

GAC GGG GTA AAC TAT CCA ACA GGG AAT TTA CCC GGT TGC TCT TTC TCT      527
Asp Gly Val Asn Tyr Pro Thr Gly Asn Leu Pro Gly Cys Ser Phe Ser
160                   165                   170                   175

ATC TTT ATT CTT GCT CTT CTC TCG TGT CTG ACC GTT CCG GCC TCT GCA      575
Ile Phe Ile Leu Ala Leu Leu Ser Cys Leu Thr Val Pro Ala Ser Ala
                180                   185                   190

GTT CCC TAC CGA AAT GCC TCT GGG ATT TAT CAT GTT ACC AAT GAT TGC      623
Val Pro Tyr Arg Asn Ala Ser Gly Ile Tyr His Val Thr Asn Asp Cys
            195                   200                   205

CCA AAC TCT TCC ATA GTC TAT GAG GCA GAT AAC CTG ATC CTA CAC GCA      671
Pro Asn Ser Ser Ile Val Tyr Glu Ala Asp Asn Leu Ile Leu His Ala
        210                   215                   220

CCT GGT TGC GTG CCT TGT GTC ATG ACA GGT AAT GTG AGT AGA TGC TGG      719
Pro Gly Cys Val Pro Cys Val Met Thr Gly Asn Val Ser Arg Cys Trp
225                   230                   235

GTC CAA ATT ACC CCT ACA CTG TCA GCC CCG AGC CTC GGA GCA GTC ACG      767
Val Gln Ile Thr Pro Thr Leu Ser Ala Pro Ser Leu Gly Ala Val Thr
240                   245                   250                   255

GCT CCT CTT CGG AGA GCC GTT GAC TAC CTA GCG GGA GGG GCT GCC CTC      815
Ala Pro Leu Arg Arg Ala Val Asp Tyr Leu Ala Gly Gly Ala Ala Leu
                260                   265                   270

TGC TCC GCG TTA TAC GTA GGA GAC GCG TGT GGG GCA CTA TTC TTG GTA      863
Cys Ser Ala Leu Tyr Val Gly Asp Ala Cys Gly Ala Leu Phe Leu Val
            275                   280                   285

GGC CAA ATG TTC ACC TAT AGG CCT CGC CAG CAC GCT ACG GTG CAG AAC      911
Gly Gln Met Phe Thr Tyr Arg Pro Arg Gln His Ala Thr Val Gln Asn
        290                   295                   300

TGC AAC TGT TCC ATT TAC AGT GGC CAT GTT ACC GGC CAC CGG ATG GCA      959
Cys Asn Cys Ser Ile Tyr Ser Gly His Val Thr Gly His Arg Met Ala
305                   310                   315
```

(2) INFORMATION FOR SEQ ID NO: 52:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 52:

```
Met Ser Thr Asn Pro Lys Pro Gln Arg Lys Thr Lys Arg Asn Thr Asn
 1               5                  10                  15
Arg Arg Pro Gln Asp Val Lys Phe Pro Gly Gly Gln Ile Val Gly
            20                  25                  30
Gly Val Tyr Leu Leu Pro Arg Arg Gly Pro Arg Met Gly Val Arg Ala
            35                  40                  45
Thr Arg Lys Thr Ser Glu Arg Ser Gln Pro Arg Gly Arg Arg Gln Pro
 50                  55                  60
Ile Pro Lys Ala Arg Gln Pro Thr Gly Arg Ser Trp Gly Gln Pro Gly
 65                  70                  75                  80
Tyr Pro Trp Pro Leu Tyr Ala Asn Glu Gly Leu Gly Trp Ala Gly Trp
                85                  90                  95
Leu Leu Ser Pro Arg Gly Ser Arg Pro Asn Trp Gly Pro Asn Asp Pro
            100                 105                 110
Arg Arg Lys Ser Arg Asn Leu Gly Lys Val Ile Asp Thr Leu Thr Cys
            115                 120                 125
Gly Phe Ala Asp Leu Met Gly Tyr Ile Pro Leu Val Gly Gly Pro Val
 130                 135                 140
Gly Gly Val Ala Arg Ala Leu Ala His Gly Val Arg Val Leu Glu Asp
145                 150                 155                 160
Gly Val Asn Tyr Pro Thr Gly Asn Leu Pro Gly Cys Ser Phe Ser Ile
                165                 170                 175
Phe Ile Leu Ala Leu Leu Ser Cys Leu Thr Val Pro Ala Ser Ala Val
            180                 185                 190
Pro Tyr Arg Asn Ala Ser Gly Ile Tyr His Val Thr Asn Asp Cys Pro
            195                 200                 205
Asn Ser Ser Ile Val Tyr Glu Ala Asp Asn Leu Ile Leu His Ala Pro
210                 215                 220
Gly Cys Val Pro Cys Val Met Thr Gly Asn Val Ser Arg Cys Trp Val
225                 230                 235                 240
Gln Ile Thr Pro Thr Leu Ser Ala Pro Ser Leu Gly Ala Val Thr Ala
                245                 250                 255
Pro Leu Arg Arg Ala Val Asp Tyr Leu Ala Gly Gly Ala Ala Leu Cys
            260                 265                 270
Ser Ala Leu Tyr Val Gly Asp Ala Cys Gly Ala Leu Phe Leu Val Gly
            275                 280                 285
Gln Met Phe Thr Tyr Arg Pro Arg Gln His Ala Thr Val Gln Asn Cys
 290                 295                 300
Asn Cys Ser Ile Tyr Ser Gly His Val Thr Gly His Arg Met Ala
305                 310                 315
```

(2) INFORMATION FOR SEQ ID NO: 53:

(i) SEQUENCE CHARACTERISTICS:
        (A) LENGTH: 959 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:

(B) CLONE: PC C/E1

(ix) FEATURE:
   (A) NAME/KEY: CDS
   (B) LOCATION: 2..959

(xi) SEQUENCE DESCRIPTION: SEQ ID NO: 53:

```
CCATGAGCAC GAATCCTAAA CCTCAAAGAA AAACCAAAAG AAACACCAAC CGTCGCCCAC    60
AGGACGTCAA GTTCCCGGGC GGTGGTCAGA TCGTTGGCGG AGTTTACTTG TTGCCGCGCA   120
GGGGCCCTAG GATGGGTGTG CGCGCGACTC GGAAGACTTC GGAACGGTCG CAACCCCGTG   180
GACGGCGTCA GCCTATTCCC AAGGCGCGCC AGCCCACGGG CCGGTCCTGG GGTCAACCCG   240
GGTACCCTTG GCCCCTTTAC GCCAATGAGG GCCTCGGGTG GGCAGGGTGG CTGCTCTCCC   300
CTCGAGGCTC TCGGCCTAAT TGGGGCCCCA ATGACCCCCG GCGAAAATCG CGTAATTTGG   360
GTAAGGTCAT CGATACCCTA ACGTGCGGAT TCGCCGATCT CATGGGGTAY ATCCCGCTCG   420
TAGGCGGCCC CRTTGGGGGC GTCGCAAGGG CTCTCGCACA CGGTGTGAGG GTCCTTGAGG   480
ACGGGGTAAA CTATSCAACA GGGAATTTAC CCGGTTGCTC TTTCTCTATC TTTATTCTTG   540
CTCTTCTCTC GTGTCTGACC GTTCCGGCCT CTGCAGTTCC CTACCGAAAT GCCTCTGGGA   600
TTTATCATGT TACCAATGAT TGCCCAAACT CTTCCATAGT CTATGAGGCA GATAACCTGA   660
TCCTACACGC ACCTGGTTGC GTGCCTTGTG TCATGACAGG TAATGTGAGT AGATGCTGGG   720
TCCAAATTAC CCCTACACTG TCAGCCCCGA GCCTCGGAGC AGTCACGGCT CCTCTTCGGA   780
GAGCCGTTGA CTACCTAGCG GGAGGGGCTG CCCTCTGCTC CGCGTTATAC GTAGGAGACG   840
CGTGTGGGGC ACTATTCTTG GTAGGCCAAA TGTTCACCTA TAGGCCTCGC CAGCACGCTA   900
CGGTGCAGAA CTGCAACTGT TCCATTTACA GTGGCCATGT TACCGGCCAC CGGATGGCA    959
```

(2) INFORMATION FOR SEQ ID NO: 54:

(i) SEQUENCE CHARACTERISTICS:
      (A) LENGTH: 319 amino acids
      (B) TYPE: amino acid
      (D) TOPOLOGY: linear (ii) MOLECULE TYPE: protein (xi) SEQUENCE DESCRIPTION: SEQ ID NO: 54:

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140
```

```
Gly Gly Val Ala Arg Ala Leu Ala His Gly Val Arg Val Leu Glu Asp
145                 150                 155                 160

Gly Val Asn Tyr Pro Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205

Asn Ser Ser Ile Val Tyr Glu Ala Asp Asn Leu Ile Leu His Ala Pro
    210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
        275                 280                 285

Gln Met Phe Thr Tyr Arg Pro Arg Gln His Ala Thr Val Gln Asn Cys
    290                 295                 300

Asn Cys Ser Ile Tyr Ser Gly His Val Thr Gly His Arg Met Ala
305                 310                 315
```

(2) INFORMATION FOR SEQ ID NO: 55:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-1-37

(ix) FEATURE:
        (A) NAME/KEY: CDS
        (B) LOCATION: 1..354

(xi) SEQUENCE DESCRIPTION: SEQ ID NO: 55:

```
ACCACCGGAG CTTCTATCAC ATACTCCACT TACGGCAAGT TCCTTGCTGA TGGAGGGTGT      60

TCAGGCGGCG CGCATGACGT GATCATATGC GACGAGTGCC ATTCCCAGGA CGCCACCACC     120

ATTCTTGGGA TAGGCACTGT CCTTGACCAG GCAGAGACGG CTGGAGCTAG GCTCGTCGTC     180

TTGGCCACGG NCACCCCTCC CGGCAGTGTG ACAACGCCCC ACCCCAACAT CGAGGAAGTG     240

GCCCTGCCTC AGGAGGGGGA GGTTCCCTTC TACGGCAGAG CCATTCCCCT TGCTTTTATA     300

AAGGGTGGTA GGCATCTCAT CTTCTGCCAT TCCAAGAAAA ATTGTGATGA ACTC           354
```

(2) INFORMATION FOR SEQ ID NO: 56:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 56:

```
Thr Thr Gly Ala Ser Ile Thr Tyr Ser Thr Tyr Gly Lys Phe Leu Ala
1               5                   10                  15

Asp Gly Gly Cys Ser Gly Gly Ala His Asp Val Ile Ile Cys Asp Glu
            20                  25                  30

Cys His Ser Gln Asp Ala Thr Thr Ile Leu Gly Ile Gly Thr Val Leu
        35                  40                  45

Asp Gln Ala Glu Thr Ala Gly Ala Arg Leu Val Val Leu Ala Thr Xaa
    50                  55                  60

Thr Pro Pro Gly Ser Val Thr Thr Pro His Pro Asn Ile Glu Glu Val
65              70                  75                  80

Ala Leu Pro Gln Glu Gly Glu Val Pro Phe Tyr Gly Arg Ala Ile Pro
                85                  90                  95

Leu Ala Phe Ile Lys Gly Gly Arg His Leu Ile Phe Cys His Ser Lys
                100                 105                 110

Lys Asn Cys Asp Glu Leu
        115
```

(2) INFORMATION FOR SEQ ID NO: 57:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-1-48

(ix) FEATURE:
        (A) NAME/KEY: CDS
        (B) LOCATION: 1..354

(xi) SEQUENCE DESCRIPTION: SEQ ID NO: 57:

```
ACCACCGGAG CTTCTATCAC ATACTCCACT TACGGCAAGT TCCTTGCTGA TGGAGGGTGT      60
TCAGGCGGCG CGTATGACGT GATCATATGC GACGAGTGCC ATTCCCAGGA CGCCACCACC     120
ATTCTTGGGA TAGGCACTGT CCTTGACCAG GCAGAGACGG CTGGAGCTAG GCTCGTCGTC     180
TTGGNCACGG NCACCCCTCC CGGCAGTGTG ACAACGCCCC ACCCCAACAT CGAGGAAGTG     240
GCCCTGCCTC AGGAGGGGGA GGTTCCCTTC TACGGNAGAG CCATTCCCCT TGCTTTTATA     300
AAGGGTGGTA GGCATCTCAT CTTCTGCCAT TCCAAGAAAA AATGTGATGA ACTT           354
```

(2) INFORMATION FOR SEQ ID NO: 58:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 58:

```
Thr Thr Gly Ala Ser Ile Thr Tyr Ser Thr Tyr Gly Lys Phe Leu Ala
1               5                   10                  15
```

```
Asp Gly Gly Cys Ser Gly Gly Ala Tyr Asp Val Ile Ile Cys Asp Glu
            20                  25                  30

Cys His Ser Gln Asp Ala Thr Thr Ile Leu Gly Ile Gly Thr Val Leu
            35                  40                  45

Asp Gln Ala Glu Thr Ala Gly Ala Arg Leu Val Val Leu Xaa Thr Xaa
        50                  55                  60

Thr Pro Pro Gly Ser Val Thr Thr Pro His Pro Asn Ile Glu Glu Val
65                  70                  75                  80

Ala Leu Pro Gln Glu Gly Glu Val Pro Phe Tyr Xaa Arg Ala Ile Pro
                85                  90                  95

Leu Ala Phe Ile Lys Gly Gly Arg His Leu Ile Phe Cys His Ser Lys
            100                 105                 110

Lys Lys Cys Asp Glu Leu Arg Gln Ala Thr Asp Gln Pro Gly Arg Glu
            115                 120                 125

Arg Pro Trp Glu Tyr
    130
```

(2) INFORMATION FOR SEQ ID NO: 59:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-1-37

(ix) FEATURE:
        (A) NAME/KEY: CDS
        (B) LOCATION: 1..357

(xi) SEQUENCE DESCRIPTION: SEQ ID NO: 59:

```
ATGGCTTTCA TGTCTCCGGA CTTGGAGGTC ATTACCANCA CTTGGGTTCT GGTGGGGGGC    60
GTTGTGGCGA CCCTGNCGNC CTACTGCTTG ACGGTGGGTT CGGTAGCCAT AGTCGGTAGG   120
ATCATCCTCT CTGGGAAACC TGCCATCATT NCCGATAGGG AGGTATTATA CCAGCAATTT   180
GATGAGATGG AGGAGTGCTC GGCCTCGTTG CCCTATATGG ACGAAACACG TNCCATTGCC   240
GGACAATTCA AAGAGAAAGT GCTCGGCTTC ATCAGCACGA CCGGCCAGAA GGCTGAAACT   300
CTGAAGCCGG CAGCCACGTC TGTGTGGAAC AAGGCTGATC AGTTCTGGNC CACATAC      357
```

(2) INFORMATION FOR SEQ ID NO: 60:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 60:

```
Met Ala Phe Met Ser Pro Asp Leu Glu Val Ile Thr Xaa Thr Trp Val
1               5                   10                  15

Leu Val Gly Gly Val Val Ala Thr Leu Xaa Xaa Tyr Cys Leu Thr Val
            20                  25                  30
```

```
Gly Ser Val Ala Ile Val Gly Arg Ile Ile Leu Ser Gly Lys Pro Ala
        35                  40                  45

Ile Ile Xaa Asp Arg Glu Val Leu Tyr Gln Gln Phe Asp Glu Met Glu
 50                  55                  60

Glu Cys Ser Ala Ser Leu Pro Tyr Met Asp Thr Arg Xaa Ile Ala
 65              70                  75                  80

Gly Gln Phe Lys Glu Lys Val Leu Gly Phe Ile Ser Thr Thr Gly Gln
                85                  90                  95

Lys Ala Glu Thr Leu Lys Pro Ala Ala Thr Ser Val Trp Asn Lys Ala
                100                 105                 110

Asp Gln Phe Trp Xaa Thr Tyr Met Trp Asn Phe Ile Ser Gly Ile Gln
                115                 120                 125

(2) INFORMATION FOR SEQ ID NO: 61:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: PC-1-48

(ix) FEATURE:
        (A) NAME/KEY: CDS
        (B) LOCATION: 1..357

(xi) SEQUENCE DESCRIPTION: SEQ ID NO: 61:

ATGGCTTGCA TGTCTGCGGA CCTGGAGGTC ATTACCANCA CTTGGGTTCT GGTGGGGGGC    60

GTTGTGGCGN CCCTGGCGGC CTACTGCTTG ACGGTGGGTT CGGTAGCCAT AGTCGGTAGG   120

ATCATCCTCT CTGGGAAACC TGCCATCATT CCCGATAGGG AGGCATTATA CCANCAATTT   180

GATGAGATGG AGGAGTGCTC CGCCTCGTTG CCCTATATGG ACGAGACACG TGCCATTGCC   240

GGACAATTCA AGAGAAAGT GCTCGGCTTC ATCAGCACGA CCGGCCAGAA GGCTGAAACT   300

CTGAAGCCGG CAGCCACGTC TGTGTGGAAC AAGGCTGANC AGTTCTGGGC CACATAC    357

(2) INFORMATION FOR SEQ ID NO: 62:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 62:

Met Ala Cys Met Ser Ala Asp Leu Glu Val Ile Thr Xaa Thr Trp Val
  1               5                  10                  15

Leu Val Gly Gly Val Val Ala Xaa Leu Ala Ala Tyr Cys Leu Thr Val
                20                  25                  30

Gly Ser Val Ala Ile Val Gly Arg Ile Ile Leu Ser Gly Lys Pro Ala
                35                  40                  45

Ile Ile Pro Asp Arg Glu Ala Leu Tyr Xaa Gln Phe Asp Glu Met Glu
 50                  55                  60
```

```
Glu Cys Ser Ala Ser Leu Pro Tyr Met Asp Glu Thr Arg Ala Ile Ala
 65                  70                  75                  80

Gly Gln Phe Lys Glu Lys Val Leu Gly Phe Ile Ser Thr Thr Gly Gln
                 85                  90                  95

Lys Ala Glu Thr Leu Lys Pro Ala Ala Thr Ser Val Trp Asn Lys Ala
            100                 105                 110

Xaa Gln Phe Trp Ala Thr Tyr Met Trp Asn Phe Ile Ser Gly Ile Gln
        115                 120                 125
```

(2) INFORMATION FOR SEQ ID NO: 63:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (ix) FEATURE:
        (A) NAME/KEY: misc_feature
        (B) LOCATION: 1..28
        (D) OTHER INFORMATION: /standard_name= "HCV Primer
            HCPr161"

(xi) SEQUENCE DESCRIPTION: SEQ ID NO: 63:

ACCGGAGGCC AGGAGAGTGA TCTCCTCC                              28

(2) INFORMATION FOR SEQ ID NO: 64:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (ix) FEATURE:
        (A) NAME/KEY: misc_feature
        (B) LOCATION: 1..28
        (D) OTHER INFORMATION: /standard_name= "HCV Primer
            HCPr162"

(xi) SEQUENCE DESCRIPTION: SEQ ID NO: 64:

GGGCTGCTCT ATCCTCATCG ACGCCATC                              28

(2) INFORMATION FOR SEQ ID NO: 65:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (ix) FEATURE:
        (A) NAME/KEY: misc_feature (B) LOCATION: 1..28
          (D) OTHER INFORMATION: /standard_name= "HCV Primer
               HCPr163"

(xi) SEQUENCE DESCRIPTION: SEQ ID NO: 65:

GCCAGAGGCT CGGAAGGCGA TCAGCGCT                                           28

(2) INFORMATION FOR SEQ ID NO: 66:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (iv) ANTI-SENSE: YES (ix) FEATURE:
          (A) NAME/KEY: misc_feature
          (B) LOCATION: 1..28
          (D) OTHER INFORMATION: /standard_name= "HCV Primer
               HCPr164"

(xi) SEQUENCE DESCRIPTION: SEQ ID NO: 66:

GAGCTGCTCT GTCCTCCTCG ACGCCGCA                                           28

(2) INFORMATION FOR SEQ ID NO: 67:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (iv) ANTI-SENSE: NO (ix) FEATURE:
          (A) NAME/KEY: misc_feature
          (B) LOCATION: 1..28
          (D) OTHER INFORMATION: /standard_name= "HCV Primer
               HCPr23"

(xi) SEQUENCE DESCRIPTION: SEQ ID NO: 67:

CTCATGGGGT ACATTCCGCT                                                    20

(2) INFORMATION FOR SEQ ID NO: 68:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (iv) ANTI-SENSE: YES (ix) FEATURE:
          (A) NAME/KEY: misc_feature
          (B) LOCATION: 1..28
          (D) OTHER INFORMATION: /standard_name= "HCV Primer
               HCPr54"

```
        (xi) SEQUENCE DESCRIPTION: SEQ ID NO: 68:

CTATTACCAG TTCATCATCA TATCCCA                                          27

(2) INFORMATION FOR SEQ ID NO: 69:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: YES (iv) ANTI-SENSE: NO (ix) FEATURE:
           (A) NAME/KEY: misc_feature
           (B) LOCATION: 1..28
           (D) OTHER INFORMATION: /standard_name= "HCV Primer
               HCPr116"

(xi) SEQUENCE DESCRIPTION: SEQ ID NO: 69:

TTTTAAATAC ATCATGRCTG YATG                                             24

(2) INFORMATION FOR SEQ ID NO: 70:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: YES (iv) ANTI-SENSE: YES (ix) FEATURE:
           (A) NAME/KEY: misc_feature
           (B) LOCATION: 1..28
           (D) OTHER INFORMATION: /standard_name= "HCV Primer
               HCPr66"

(xi) SEQUENCE DESCRIPTION: SEQ ID NO: 70:

CTATTATTGT ATCCCRCTGA TGAARTTCCA CAT                                   33

(2) INFORMATION FOR SEQ ID NO: 71:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: YES (iv) ANTI-SENSE: YES (ix) FEATURE:
           (A) NAME/KEY: misc_feature
           (B) LOCATION: 1..28
           (D) OTHER INFORMATION: /standard_name= "HCV Primer
               HCPr118:

(xi) SEQUENCE DESCRIPTION: SEQ ID NO: 71:

ACTAGTCGAC TAYTGATCCR CTATRWARTT CCACAT                                36
```

(2) INFORMATION FOR SEQ ID NO: 72:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (ix) FEATURE:
        (A) NAME/KEY: misc_feature
        (B) LOCATION: 1..28
        (D) OTHER INFORMATION: /standard_name= "HCV Primer
            HCPr117:

(xi) SEQUENCE DESCRIPTION: SEQ ID NO: 72:

TTTTAAATAC ATCGCRCTGC ATGCA                                              25

(2) INFORMATION FOR SEQ ID NO: 73:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (ix) FEATURE:
        (A) NAME/KEY: misc_feature
        (B) LOCATION: 1..28
        (D) OTHER INFORMATION: /standard_name= "HCV Primer
            HCPr119:

(xi) SEQUENCE DESCRIPTION: SEQ ID NO: 73:

ACTAGTCGAC TARTTGCATA GCCKRTTCAT CCAYTG                                  36

(2) INFORMATION FOR SEQ ID NO: 74:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (ix) FEATURE:
        (A) NAME/KEY: misc_feature
        (B) LOCATION: 1..28
        (D) OTHER INFORMATION: /standard_name= "HCV Primer
            HCPr131:

(xi) SEQUENCE DESCRIPTION: SEQ ID NO: 74:

GGAATTCTAG ACCTCTGGGA YGARAYTGGA ARTG                                    34

(2) INFORMATION FOR SEQ ID NO: 75:

(i) SEQUENCE CHARACTERISTICS:

```
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: NO (ix) FEATURE:
            (A) NAME/KEY: misc_feature
            (B) LOCATION: 1..28
            (D) OTHER INFORMATION: /standard_name= "HCV Primer
                HCPr130:

(xi) SEQUENCE DESCRIPTION: SEQ ID NO: 75:

GGAATTCTAG ACGCTAYCAR GCACGTTGYG C                               31

(2) INFORMATION FOR SEQ ID NO: 76:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: NO (ix) FEATURE:
            (A) NAME/KEY: misc_feature
            (B) LOCATION: 1..28
            (D) OTHER INFORMATION: /standard_name= "HCV Primer
                HCPr134:

(xi) SEQUENCE DESCRIPTION: SEQ ID NO: 76:

CATATAGATG CCCACTTCCT ATC                                        23

(2) INFORMATION FOR SEQ ID NO: 77:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: YES (ix) FEATURE:
            (A) NAME/KEY: misc_feature
            (B) LOCATION: 1..28
            (D) OTHER INFORMATION: /standard_name= "HCV Primer
                HCPr3:

(xi) SEQUENCE DESCRIPTION: SEQ ID NO: 77:

GTGTGCCAGG ACCATC                                                16

(2) INFORMATION FOR SEQ ID NO: 78:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: YES (iv) ANTI-SENSE: YES (ix) FEATURE:
            (A) NAME/KEY: misc_feature
            (B) LOCATION: 1..28
            (D) OTHER INFORMATION: /standard_name= "HCV Primer
                HCPr4:

(xi) SEQUENCE DESCRIPTION: SEQ ID NO: 78:

GACATGCATG TCATGATGTA                                                         20

(2) INFORMATION FOR SEQ ID NO: 79:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: misc_feature
            (B) LOCATION: 1..28
            (D) OTHER INFORMATION: /standard_name= "HCV Primer
                HCPr152:

(xi) SEQUENCE DESCRIPTION: SEQ ID NO: 79:

TACGCCTCTT CTATATCGGT TGGGGCCTG                                               29

(2) INFORMATION FOR SEQ ID NO: 80:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: NO (ix) FEATURE:
            (A) NAME/KEY: misc_feature
            (B) LOCATION: 1..28
            (D) OTHER INFORMATION: /standard_name= "HCV Primer
                HCPr52:

(xi) SEQUENCE DESCRIPTION: SEQ ID NO: 80:

ATGTTGGGTA AGGTCATCGA TACCCT                                                  26

(2) INFORMATION FOR SEQ ID NO: 81:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: NO (ix) FEATURE:
            (A) NAME/KEY: misc_feature
            (B) LOCATION: 1..28
            (D) OTHER INFORMATION: /standard_name= "HCV Primer
                HCPr41:

(xi) SEQUENCE DESCRIPTION: SEQ ID NO: 81:

CCCGGGAGGT CTCGTAGACC GTGCA                                             25

(2) INFORMATION FOR SEQ ID NO: 82:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iv) ANTI-SENSE: YES (ix) FEATURE:
            (A) NAME/KEY: misc_feature
            (B) LOCATION: 1..28
            (D) OTHER INFORMATION: /standard_name= "HCV Primer
                HCPr40:

(xi) SEQUENCE DESCRIPTION: SEQ ID NO: 82:

CTATTAAAGA TAGAGAAAGA GCAACCGGG                                         29

(2) INFORMATION FOR SEQ ID NO: 83:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (viii) POSITION IN GENOME:
            (B) MAP POSITION: positions 192 to 203 of the V1 region of HCV
            type 3

(xi) SEQUENCE DESCRIPTION: SEQ ID NO: 83:

Leu Glu Trp Arg Asn Thr Ser Gly Leu Tyr Val Leu
1               5                   10

(2) INFORMATION FOR SEQ ID NO: 84:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (viii) POSITION IN GENOME:
            (B) MAP POSITION: positions 192 to 203 of the V1 region of HCV
            type 5

(xi) SEQUENCE DESCRIPTION: SEQ ID NO: 84:

-continued

```
Val Pro Tyr Arg Asn Ala Ser Gly Ile Tyr His Val
1               5                   10
```

(2) INFORMATION FOR SEQ ID NO: 85:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (B) MAP POSITION: positions 213 to 223 of the V2 region of HCV
        type 3

(xi) SEQUENCE DESCRIPTION: SEQ ID NO: 85:

```
Val Tyr Glu Ala Asp Asp Val Ile Leu His Thr
1               5                   10
```

(2) INFORMATION FOR SEQ ID NO: 86:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (B) MAP POSITION: positions 213 to 233 of the V2 region of HCV
        type 5

(xi) SEQUENCE DESCRIPTION: SEQ ID NO: 86:

```
Val Tyr Glu Ala Asp Asn Leu Ile Leu His Ala
1               5                   10
```

(2) INFORMATION FOR SEQ ID NO: 87:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (B) MAP POSITION: positions 230 to 242 of the V3 region of HCV
        type 3

(xi) SEQUENCE DESCRIPTION: SEQ ID NO: 87:

```
Val Gln Asp Gly Asn Thr Ser Thr Cys Trp Thr Pro Val
1               5                   10
```

(2) INFORMATION FOR SEQ ID NO: 88:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
           (B) MAP POSITION: positions 230 to 242 of the V3 region of HCV
           type 5

(xi) SEQUENCE DESCRIPTION: SEQ ID NO: 88:

Val Met Thr Gly Asn Val Ser Arg Cys Trp Val Gln Ile
1               5                   10

(2) INFORMATION FOR SEQ ID NO: 89:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (iii) HYPOTHETICAL: NO (viii) POSITION IN GENOME:
          (B) MAP POSITION: positions 248 to 257 of the V4 region of HCV
          type 3

(xi) SEQUENCE DESCRIPTION: SEQ ID NO: 89:

Val Arg Tyr Val Gly Ala Thr Thr Ala Ser
1               5                   10

(2) INFORMATION FOR SEQ ID NO: 90:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (iii) HYPOTHETICAL: NO (viii) POSITION IN GENOME:
          (B) MAP POSITION: positions 248 to 257 of the V4 region of HCV
          type 5

(xi) SEQUENCE DESCRIPTION: SEQ ID NO: 90:

Ala Pro Ser Leu Gly Ala Val Thr Ala Pro
1               5                   10

(2) INFORMATION FOR SEQ ID NO: 91:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (iii) HYPOTHETICAL: NO (viii) POSITION IN GENOME:
          (B) MAP POSITION: positions 294 to 303 of the V5 region of HCV
          type 3

(xi) SEQUENCE DESCRIPTION: SEQ ID NO: 91:

Arg Pro Arg Arg His Gln Thr Val Gln Thr
1               5                   10

(2) INFORMATION FOR SEQ ID NO: 92:

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (B) MAP POSITION: positions 294 to 303 of the V5 region of HCV
        type 5

(xi) SEQUENCE DESCRIPTION: SEQ ID NO: 92:

Arg Pro Arg Gln His Ala Thr Val Gln Asn
1               5                  10

(2) INFORMATION FOR SEQ ID NO: 93:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (B) MAP POSITION: positions 70 to 78 of HCV type 5

(xi) SEQUENCE DESCRIPTION: SEQ ID NO: 93:

Gln Pro Thr Gly Arg Ser Trp Gly Gln
1               5

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (C) INDIVIDUAL ISOLATE: BR33 and BR36

(viii) POSITION IN GENOME:
        (B) MAP POSITION: positions 230 to 237 of the V3 region of HCV
        type 3

(xi) SEQUENCE DESCRIPTION: SEQ ID NO: 94:

Val Gln Asp Gly Asn Thr Ser Thr
1               5

(2) INFORMATION FOR SEQ ID NO: 95:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO
```

```
     (vi) ORIGINAL SOURCE:
          (C) INDIVIDUAL ISOLATE: HD10

(viii) POSITION IN GENOME:
          (B) MAP POSITION: positions 230 to 237 of the V3 region of HCV
          type 3

(xi) SEQUENCE DESCRIPTION: SEQ ID NO: 95:

Val Gln Asp Gly Asn Thr Ser Ala
1               5

(2) INFORMATION FOR SEQ ID NO: 96:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (iii) HYPOTHETICAL: NO (vi) ORIGINAL SOURCE:
          (C) INDIVIDUAL ISOLATE: BR36

(viii) POSITION IN GENOME:
          (B) MAP POSITION: positions 248 to 257 of the V4 region of HCV
          type 3

(xi) SEQUENCE DESCRIPTION: SEQ ID NO: 96:

Val Lys Tyr Val Gly Ala Thr Thr Ala Ser
1               5                   10

(2) INFORMATION FOR SEQ ID NO: 97:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (vi) ORIGINAL SOURCE:
          (C) INDIVIDUAL ISOLATE: BR36

(viii) POSITION IN GENOME:
          (B) MAP POSITION: Positions 1688 to 1707 of HCV type 3

(xi) SEQUENCE DESCRIPTION: SEQ ID NO: 97:

Leu Gly Gly Lys Pro Ala Ile Val Pro Asp Lys Glu Val Leu Tyr Gln
1               5                   10                  15
Gln Tyr Asp Glu
            20

(2) INFORMATION FOR SEQ ID NO: 98:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (iii) HYPOTHETICAL: NO (vi) ORIGINAL SOURCE:
          (C) INDIVIDUAL ISOLATE: HD10
```

```
        (viii) POSITION IN GENOME:
              (B) MAP POSITION: positions 1688 to 1707 of HCV type 3

(xi) SEQUENCE DESCRIPTION: SEQ ID NO: 98:

Leu Gly Gly Lys Pro Ala Leu Val Pro Asp Lys Glu Val Leu Tyr Gln
 1               5                  10                  15

Gln Tyr Asp Glu
            20

(2) INFORMATION FOR SEQ ID NO: 99:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (viii) POSITION IN GENOME:
              (B) MAP POSITION: positions 1712 to 1731

(xi) SEQUENCE DESCRIPTION: SEQ ID NO: 99:

Ser Gln Ala Ala Pro Tyr Ile Glu Gln Ala Gln Val Ile Ala His Gln
 1               5                  10                  15

Phe Lys Glu Lys
            20

(2) INFORMATION FOR SEQ ID NO: 100:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (vi) ORIGINAL SOURCE:
              (C) INDIVIDUAL ISOLATE: BR36

(viii) POSITION IN GENOME:
              (B) MAP POSITION: positions 1724 to 1743 of HCV type 3

(xi) SEQUENCE DESCRIPTION: SEQ ID NO: 100:

Ile Ala His Gln Phe Lys Glu Lys Val Leu Gly Leu Leu Gln Arg Ala
 1               5                  10                  15

Thr Gln Gln Gln
            20

(2) INFORMATION FOR SEQ ID NO: 101:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (iii) HYPOTHETICAL: NO (vi) ORIGINAL SOURCE:
              (C) INDIVIDUAL ISOLATE: HD10
```

```
       (viii) POSITION IN GENOME:
            (B) MAP POSITION: positions 1724 to 1743 of HCV type 3

(xi) SEQUENCE DESCRIPTION: SEQ ID NO: 101:

Ile Ala His Gln Phe Lys Glu Lys Ile Leu Gly Leu Leu Gln Arg Ala
1               5                   10                  15

Thr Gln Gln Gln
            20

(2) INFORMATION FOR SEQ ID NO: 102:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (viii) POSITION IN GENOME:
            (B) MAP POSITION: positions 1688 to 1707 of HCV type 5

(xi) SEQUENCE DESCRIPTION: SEQ ID NO: 102:

Leu Ser Gly Lys Pro Ala Ile Ile Pro Asp Arg Glu Ala Leu Tyr Gln
1               5                   10                  15

Gln Phe Asp Glu
            20

(2) INFORMATION FOR SEQ ID NO: 103:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (viii) POSITION IN GENOME:
            (B) MAP POSITION: positions 1688 to 1707

(xi) SEQUENCE DESCRIPTION: SEQ ID NO: 103:

Leu Ser Gly Lys Pro Ala Ile Ile Pro Asp Arg Glu Val Leu Tyr Gln
1               5                   10                  15

Gln Phe Asp Glu
            20

(2) INFORMATION FOR SEQ ID NO: 104:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (viii) POSITION IN GENOME:
            (B) MAP POSITION: position 1712 to 1731 of HCV type 5

(xi) SEQUENCE DESCRIPTION: SEQ ID NO: 104:

Ser Ala Ser Leu Pro Tyr Met Asp Glu Thr Arg Ala Ile Ala Gly Gln
1               5                   10                  15
```

```
Phe Lys Glu Lys
        20

(2) INFORMATION FOR SEQ ID NO: 105:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (viii) POSITION IN GENOME:
        (B) MAP POSITION: positions 1724 to 1743 of HCV type 5

(xi) SEQUENCE DESCRIPTION: SEQ ID NO: 105:

Ile Ala Gly Gln Phe Lys Glu Lys Val Leu Gly Phe Ile Ser Thr Thr
1               5                   10                  15

Gly Gln Lys Ala
        20

(2) INFORMATION FOR SEQ ID NO: 106:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB48-3-10

(ix) FEATURE:
        (A) NAME/KEY: CDS
        (B) LOCATION: 2..340

(xi) SEQUENCE DESCRIPTION: SEQ ID NO: 106:

C TCC ACT GTA ACC GAA AAG GAC ATC AGG GTC GAG GAG GAG GTC TAT        46
  Ser Thr Val Thr Glu Lys Asp Ile Arg Val Glu Glu Glu Val Tyr
  1               5                   10                  15

CAG TGT TGT GAC CTG GAG CCC GAA GCC CGC AAG GCA ATT ACC GCC CTA      94
Gln Cys Cys Asp Leu Glu Pro Glu Ala Arg Lys Ala Ile Thr Ala Leu
                20                  25                  30

ACA GAG AGA CTC TAC GTG GGC GGT CCC ATG CAT AAC AGC AAG GGA GAC     142
Thr Glu Arg Leu Tyr Val Gly Gly Pro Met His Asn Ser Lys Gly Asp
            35                  40                  45

CTG TGC GGG TAT CGC AGA TGT CGC GCA AGC GGC GTC TAC ACC ACC AGC     190
Leu Cys Gly Tyr Arg Arg Cys Arg Ala Ser Gly Val Tyr Thr Thr Ser
        50                  55                  60

TTC GGG AAC ACA CTG ACG TGC TAC CTC AAA GCC TCA GCC GCT ATC AAA     238
Phe Gly Asn Thr Leu Thr Cys Tyr Leu Lys Ala Ser Ala Ala Ile Lys
    65                  70                  75

GCG GCG GGG CTG AGA GAC TGC ACC ATG TTG GTC TGT GGT GAT GAC CTG     286
Ala Ala Gly Leu Arg Asp Cys Thr Met Leu Val Cys Gly Asp Asp Leu
80                  85                  90                  95

GTT GTC ATC GCT GAG AGC GAT GGC GTA GAG GAG GAC AAA CGA CCC CTC     334
Val Val Ile Ala Glu Ser Asp Gly Val Glu Glu Asp Lys Arg Pro Leu
                100                 105                 110
```

```
GGA GCC                                                           340
Gly Ala (2) INFORMATION FOR SEQ ID NO: 107:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 107:

Ser Thr Val Thr Glu Lys Asp Ile Arg Val Glu Glu Val Tyr Gln
 1               5                  10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
    50                  55                  60

Gly Asn Thr Leu Thr Cys Tyr Leu Lys Ala Ser Ala Ala Ile Lys Ala
65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Pro Leu Gly
                100                 105                 110

Ala (2) INFORMATION FOR SEQ ID NO: 108:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB116-3-5

(ix) FEATURE:
        (A) NAME/KEY: CDS
        (B) LOCATION: 2..340

(xi) SEQUENCE DESCRIPTION: SEQ ID NO: 108:

C TCC ACT GTA ACC GAA AAG GAC ATC AGG GTC GAG GAG GAG GTA TAT        46
  Ser Thr Val Thr Glu Lys Asp Ile Arg Val Glu Glu Glu Val Tyr
   1               5                  10                  15

CAG TGT TGT GAC CTG GAG CCC GAG GCC CGC AGA GCA ATT ACC GCC CTA      94
Gln Cys Cys Asp Leu Glu Pro Glu Ala Arg Arg Ala Ile Thr Ala Leu
                20                  25                  30

ACA GAG AGA CTC TAC GTG GGC GGT CCC ATG CAT AAC AGC AGG GGA GAC     142
Thr Glu Arg Leu Tyr Val Gly Gly Pro Met His Asn Ser Arg Gly Asp
                35                  40                  45

CTG TGC GGG TAT CGC AGA TGC CGT GCG AGC GGC GTC TAC ACC ACC AGC     190
Leu Cys Gly Tyr Arg Arg Cys Arg Ala Ser Gly Val Tyr Thr Thr Ser
        50                  55                  60
```

-continued

```
TTC GGG AAC ACA CTG ACG TGC TAT CTC AAA GCC TCA GCC GCT ATC AGA        238
Phe Gly Asn Thr Leu Thr Cys Tyr Leu Lys Ala Ser Ala Ala Ile Arg
     65                  70                  75

GCG GCG GGG CTG AGA GAC TGC ACC ATG TTG GTC TGT GGT GAT GAC CTG        286
Ala Ala Gly Leu Arg Asp Cys Thr Met Leu Val Cys Gly Asp Asp Leu
 80                  85                  90                  95

GTC GTC ATT GCT GAA AGC GAT GGC GTA GAG GAG GAC AAA CGA GCC CTC        334
Val Val Ile Ala Glu Ser Asp Gly Val Glu Glu Asp Lys Arg Ala Leu
                100                 105                 110

GGA GCC                                                                340
Gly Ala
```

(2) INFORMATION FOR SEQ ID NO: 109:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 109:

```
Ser Thr Val Thr Glu Lys Asp Ile Arg Val Glu Glu Glu Val Tyr Gln
 1               5                  10                  15

Cys Cys Asp Leu Glu Pro Glu Ala Arg Arg Ala Ile Thr Ala Leu Thr
                20                  25                  30

Glu Arg Leu Tyr Val Gly Gly Pro Met His Asn Ser Arg Gly Asp Leu
             35                  40                  45

Cys Gly Tyr Arg Arg Cys Arg Ala Ser Gly Val Tyr Thr Thr Ser Phe
 50                  55                  60

Gly Asn Thr Leu Thr Cys Tyr Leu Lys Ala Ser Ala Ala Ile Arg Ala
 65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Ala Leu Gly
            100                 105                 110

Ala
```

(2) INFORMATION FOR SEQ ID NO: 110:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB215-3-8

(ix) FEATURE:
        (A) NAME/KEY: CDS
        (B) LOCATION: 2..340

(xi) SEQUENCE DESCRIPTION: SEQ ID NO: 110:

```
C TCC ACT GTA ACC GAA AAA GAC ATC AGG GTC GAG GAG GAG GTA TAT         46
  Ser Thr Val Thr Glu Lys Asp Ile Arg Val Glu Glu Glu Val Tyr
   1               5                  10                  15

CAG TGT TGT GAC CTG GAG CCC GAA GCC CGC AAG GTA ATT ACC GCC CTA        94
```

```
                                                                             Gln Cys Cys Asp Leu Glu Pro Glu Ala Arg Lys Val Ile Thr Ala Leu
                                                                                             20                  25                  30

ACA GAG AGA CTC TAT GTG GGC GGT CCC ATG CAT AAT AGC AAA GGA GAC              142
Thr Glu Arg Leu Tyr Val Gly Gly Pro Met His Asn Ser Lys Gly Asp
                35                  40                  45

CTG TGC GGG TAT CGC AGA TGC CGC GCA AGC GGC GTC TAC ACC ACC AGC              190
Leu Cys Gly Tyr Arg Arg Cys Arg Ala Ser Gly Val Tyr Thr Thr Ser
         50                  55                  60

TTC GGG AAC ACA CTG ACG TGC TAT CTC AAA GCC TCA GCC GCC ATC AGG              238
Phe Gly Asn Thr Leu Thr Cys Tyr Leu Lys Ala Ser Ala Ala Ile Arg
     65                  70                  75

GCG TCA GGG CTG AGA GAC TGC ACT ATG CTG GTC TAT GGT GAC GAC CTG              286
Ala Ser Gly Leu Arg Asp Cys Thr Met Leu Val Tyr Gly Asp Asp Leu
 80                  85                  90                  95

GTC GTC ATT GCC GAG AGC GAT GGC GTA GAG GAG GAC AAA CGA GCC CTC              334
Val Val Ile Ala Glu Ser Asp Gly Val Glu Glu Asp Lys Arg Ala Leu
                    100                 105                 110

GGA GTC                                                                      340
Gly Val
```

(2) INFORMATION FOR SEQ ID NO: 111:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 111:

```
Ser Thr Val Thr Glu Lys Asp Ile Arg Val Glu Glu Val Tyr Gln
 1               5                  10                  15

Cys Cys Asp Leu Glu Pro Glu Ala Arg Lys Val Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
 65                  70                  75                  80

Ser Gly Leu Arg Asp Cys Thr Met Leu Val Tyr Gly Asp Asp Leu Val
                85                  90                  95

Val Ile Ala Glu Ser Asp Gly Val Glu Glu Asp Lys Arg Ala Leu Gly
            100                 105                 110

Val
```

(2) INFORMATION FOR SEQ ID NO: 112:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB358-3-3

(ix) FEATURE:
    (A) NAME/KEY: CDS
    (B) LOCATION: 2..340

(xi) SEQUENCE DESCRIPTION: SEQ ID NO: 112:

```
C TCC ACT GTA ACC GAA AAG GAC ATC AGG GTC GAG GAG GAG GTG TAT      46
  Ser Thr Val Thr Glu Lys Asp Ile Arg Val Glu Glu Glu Val Tyr
   1               5                  10                  15

CAG TGT TGT GAC CTG GAG CCC GAG GCC CGC AAG GCA ATT ACT GCC CTA    94
Gln Cys Cys Asp Leu Glu Pro Glu Ala Arg Lys Ala Ile Thr Ala Leu
                20                  25                  30

ACA GAG AGA CTC TAT GTG GGC GGT CCC ATG CAT AAC AGC AAG GGA GAC   142
Thr Glu Arg Leu Tyr Val Gly Gly Pro Met His Asn Ser Lys Gly Asp
                    35                  40                  45

CTG TGT GGG TAT CGC AGA TGC CGC GCA AGC GGC GTC TAC ACC ACC AGC   190
Leu Cys Gly Tyr Arg Arg Cys Arg Ala Ser Gly Val Tyr Thr Thr Ser
                50                  55                  60

TTC GGG AAC ACA CTG ACG TGC TAC CTC AAA GCC TCA GCC GCT ATC AGA   238
Phe Gly Asn Thr Leu Thr Cys Tyr Leu Lys Ala Ser Ala Ala Ile Arg
             65                  70                  75

GCG GCG GGG CTG AGA GAC TGC ACC ATG TTG GTC TGT GGT GAT GAC CTG   286
Ala Ala Gly Leu Arg Asp Cys Thr Met Leu Val Cys Gly Asp Asp Leu
 80                  85                  90                  95

GTC GTC ATC GCT GAG AGC GAT GGC GTT GAG GAG GAC AAA CGA GCC CTC   334
Val Val Ile Ala Glu Ser Asp Gly Val Glu Glu Asp Lys Arg Ala Leu
                     100                 105                 110

GGA GCC                                                            340
Gly Ala
```

(2) INFORMATION FOR SEQ ID NO: 113:

(i) SEQUENCE CHARACTERISTICS:
       (A) LENGTH: 113 amino acids
       (B) TYPE: amino acid
       (D) TOPOLOGY: linear (ii) MOLECULE TYPE: protein (xi) SEQUENCE DESCRIPTION: SEQ ID NO: 113:

```
Ser Thr Val Thr Glu Lys Asp Ile Arg Val Glu Glu Val Tyr Gln
 1               5                  10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
                35                  40                  45

Cys Gly Tyr Arg Arg Cys Arg Ala Ser Gly Val Tyr Thr Thr Ser Phe
         50                  55                  60

Gly Asn Thr Leu Thr Cys Tyr Leu Lys Ala Ser Ala Ala Ile Arg Ala
 65                  70                  75                  80

Ala Gly Leu Arg Asp Cys Thr Met Leu Val Cys Gly Asp Asp Leu Val
                    85                  90                  95

Val Ile Ala Glu Ser Asp Gly Val Glu Glu Asp Lys Arg Ala Leu Gly
                 100                 105                 110

Ala
```

(2) INFORMATION FOR SEQ ID NO: 114:

(i) SEQUENCE CHARACTERISTICS:
       (A) LENGTH: 340 base pairs
       (B) TYPE: nucleic acid
       (C) STRANDEDNESS: single -continued

```
        (D) TOPOLOGY: linear (ii) MOLECULE TYPE: cDNA (iii) HYPOTHETICAL: NO (iv) ANTI-SENSE: NO (vii) IMMEDIATE SOURCE:
          (B) CLONE: GB549-3-6

(ix) FEATURE:
          (A) NAME/KEY: CDS
          (B) LOCATION: 2..340

(xi) SEQUENCE DESCRIPTION: SEQ ID NO: 114:

C TCC ACG GTG ACC GAA AGG GAT ATC AGG ACC GAG GAA GAG ATC TAC          46
  Ser Thr Val Thr Glu Arg Asp Ile Arg Thr Glu Glu Glu Ile Tyr
    1               5                  10                  15

CAG TGC TGC GAC CTG GAG CCC GAA GCC CGC AAG GTG ATA TCC GCC CTA        94
Gln Cys Cys Asp Leu Glu Pro Glu Ala Arg Lys Val Ile Ser Ala Leu
                 20                  25                  30

ACG GAA AGA CTC TAC GTG GGC GGT CCC ATG TAC AAC TCC AAG GGG GAC       142
Thr Glu Arg Leu Tyr Val Gly Gly Pro Met Tyr Asn Ser Lys Gly Asp
             35                  40                  45

CTA TGC GGG CAA CGG AGG TGC CGC GCA AGC GGG GTC TAC ACC ACC AGC       190
Leu Cys Gly Gln Arg Arg Cys Arg Ala Ser Gly Val Tyr Thr Thr Ser
         50                  55                  60

TTC GGG AAC ACT GTA ACG TGT TAT CTC AAG GCC GTT GCG GCT ACT AGG       238
Phe Gly Asn Thr Val Thr Cys Tyr Leu Lys Ala Val Ala Ala Thr Arg
     65                  70                  75

GCC GCA GGT CTG AAA GGT TGC AGC ATG CTG GTT TGT GGA GAC GAC TTA       286
Ala Ala Gly Leu Lys Gly Cys Ser Met Leu Val Cys Gly Asp Asp Leu
 80                  85                  90                  95

GTC GTC ATC TGC GAG AGC GGC GGC GTA GAG GAG GAT GCA AGA GCC CTC       334
Val Val Ile Cys Glu Ser Gly Gly Val Glu Glu Asp Ala Arg Ala Leu
                100                 105                 110

CGA GCC                                                               340
Arg Ala (2) INFORMATION FOR SEQ ID NO: 115:

(i) SEQUENCE CHARACTERISTICS:
          (A) LENGTH: 113 amino acids
          (B) TYPE: amino acid
          (D) TOPOLOGY: linear (ii) MOLECULE TYPE: protein (xi) SEQUENCE DESCRIPTION: SEQ ID NO: 115:

Ser Thr Val Thr Glu Arg Asp Ile Arg Thr Glu Glu Glu Ile Tyr Gln
  1               5                  10                  15

Cys Cys Asp Leu Glu Pro Glu Ala Arg Lys Val Ile Ser Ala Leu Thr
                 20                  25                  30

Glu Arg Leu Tyr Val Gly Gly Pro Met Tyr Asn Ser Lys Gly Asp Leu
             35                  40                  45

Cys Gly Gln Arg Arg Cys Arg Ala Ser Gly Val Tyr Thr Thr Ser Phe
         50                  55                  60

Gly Asn Thr Val Thr Cys Tyr Leu Lys Ala Val Ala Ala Thr Arg Ala
     65                  70                  75                  80

Ala Gly Leu Lys Gly Cys Ser Met Leu Val Cys Gly Asp Asp Leu Val
                 85                  90                  95

Val Ile Cys Glu Ser Gly Gly Val Glu Glu Asp Ala Arg Ala Leu Arg
```

```
                    100               105               110
Ala (2) INFORMATION FOR SEQ ID NO: 116:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: GB809-3-1

(ix) FEATURE:
         (A) NAME/KEY: CDS
         (B) LOCATION: 2..340

(xi) SEQUENCE DESCRIPTION: SEQ ID NO: 116:

C TCC ACT GTG ACT GAG AGA GAC ATC AAG GTC GAA GAA GAA GTC TAT           46
  Ser Thr Val Thr Glu Arg Asp Ile Lys Val Glu Glu Glu Val Tyr
  1               5                  10                  15

CAG TGT TGT GAT CTG GAG CCC GAG GCC CGC AAG GTA ATA GCC GCC CTC         94
Gln Cys Cys Asp Leu Glu Pro Glu Ala Arg Lys Val Ile Ala Ala Leu
                20                  25                  30

ACG GAG AGA CTC TAC GTG GGC GGC CCC ATG CAT AAC AGC AAG GGA GAC        142
Thr Glu Arg Leu Tyr Val Gly Gly Pro Met His Asn Ser Lys Gly Asp
                    35                  40                  45

CTT TGC GGG TAT CGT AGA TGC CGC GCG AGC GGC GTA TAC ACC ACC AGC        190
Leu Cys Gly Tyr Arg Arg Cys Arg Ala Ser Gly Val Tyr Thr Thr Ser
                50                  55                  60

TTC GGG AAC ACA ATG ACG TGC TAC CTT AAG GCC TCA GCA GCC ATC AGG        238
Phe Gly Asn Thr Met Thr Cys Tyr Leu Lys Ala Ser Ala Ala Ile Arg
65                  70                  75

GCT GCG GGG CTA AAG GAT TGC ACC ATG CTG GTT TGC GGT GAC GAC CTA        286
Ala Ala Gly Leu Lys Asp Cys Thr Met Leu Val Cys Gly Asp Asp Leu
80                  85                  90                  95

GTC GTG ATC GCC GAG AGC GGT GGC GTT GAG GAG GAC AAA CGA GCC CTC        334
Val Val Ile Ala Glu Ser Gly Gly Val Glu Glu Asp Lys Arg Ala Leu
                    100                 105                 110

GGA GCT                                                                 340
Gly Ala (2) INFORMATION FOR SEQ ID NO: 117:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 117:

Ser Thr Val Thr Glu Arg Asp Ile Lys Val Glu Glu Glu Val Tyr Gln
1               5                   10                  15

Cys Cys Asp Leu Glu Pro Glu Ala Arg Lys Val Ile Ala Ala Leu Thr
                20                  25                  30

Glu Arg Leu Tyr Val Gly Gly Pro Met His Asn Ser Lys Gly Asp Leu
                35                  40                  45
```

```
Cys Gly Tyr Arg Arg Cys Arg Ala Ser Gly Val Tyr Thr Thr Ser Phe
    50                  55                  60

Gly Asn Thr Met Thr Cys Tyr Leu Lys Ala Ser Ala Ala Ile Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Lys Arg Ala Leu Gly
            100                 105                 110

Ala
```

(2) INFORMATION FOR SEQ ID NO: 118:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB358-4-1

(ix) FEATURE:
        (A) NAME/KEY: CDS
        (B) LOCATION: 1..574

(xi) SEQUENCE DESCRIPTION: SEQ ID NO: 118:

```
ACT TGC GGC TTT GCC GAC CTC ATG GGA TAC ATC CCG CTC GTA GGC GCC      48
Thr Cys Gly Phe Ala Asp Leu Met Gly Tyr Ile Pro Leu Val Gly Ala
  1               5                  10                  15

CCT GTG GGT GGC GTC GCC AGG GCC CTG GCA CAC GGT GTT AGG GCT GTG      96
Pro Val Gly Gly Val Ala Arg Ala Leu Ala His Gly Val Arg Ala Val
                 20                  25                  30

GAG GAC GGG ATC AAT TAT GCG ACA GGG AAT CTT CCC GGT TGC TCT TTC     144
Glu Asp Gly Ile Asn Tyr Ala Thr Gly Asn Leu Pro Gly Cys Ser Phe
             35                  40                  45

TCT ATC TTC CTC TTG GCA CTT CTT TCG TGC CTG ACT GTT CCC ACC TCG     192
Ser Ile Phe Leu Leu Ala Leu Leu Ser Cys Leu Thr Val Pro Thr Ser
     50                  55                  60

GCC GTC AAC TAT CGC AAT GCC TCG GGC ATC TAT CAC ATC ACC AAT GAC     240
Ala Val Asn Tyr Arg Asn Ala Ser Gly Ile Tyr His Ile Thr Asn Asp
 65                  70                  75                  80

TGC CCG AAC TCG AGC ATA GTG TAC GAG ACC GAG CAC CAC ATC CTA CAC     288
Cys Pro Asn Ser Ser Ile Val Tyr Glu Thr Glu His His Ile Leu His
                 85                  90                  95

CTC CCA GGG TGT TTA CCC TGC GTG AGG GTT GGG AAT CAG TCA CGC TGC     336
Leu Pro Gly Cys Leu Pro Cys Val Arg Val Gly Asn Gln Ser Arg Cys
            100                 105                 110

TGG GTG GCC CTC ACT CCC ACC GTG GCG GCG CCT TAC ATC GGC GCT CCG     384
Trp Val Ala Leu Thr Pro Thr Val Ala Ala Pro Tyr Ile Gly Ala Pro
        115                 120                 125

CTT GAA TCC CTC CGG AGT CAT GTG GAT CTG ATG GTA GGT GCC GCT ACT     432
Leu Glu Ser Leu Arg Ser His Val Asp Leu Met Val Gly Ala Ala Thr
        130                 135                 140

GCG TGC TCC GCT CTT TAC ATC GGA GAC CTG TGC GGT GGC GTA TTC TTG     480
Ala Cys Ser Ala Leu Tyr Ile Gly Asp Leu Cys Gly Gly Val Phe Leu
145                 150                 155                 160
```

```
GTT GGT CAG ATG TTC TCT TTC CAG CCG CGG CGC CAC TGG ACT ACG CAG      528
Val Gly Gln Met Phe Ser Phe Gln Pro Arg Arg His Trp Thr Thr Gln
            165                 170                 175

GAC TGC AAT TGT TCC ATC TAC GCG GGG CAC GTT ACG GGC CAC AGG A        574
Asp Cys Asn Cys Ser Ile Tyr Ala Gly His Val Thr Gly His Arg
            180                 185                 190
```

(2) INFORMATION FOR SEQ ID NO: 119:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 119:

```
Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
 50                  55                  60

Ala Val Asn Tyr Arg Asn Ala Ser Gly Ile Tyr His Ile Thr Asn Asp
65                  70                  75                  80

Cys Pro Asn Ser Ser Ile Val Tyr Glu Thr His His Ile Leu His
            85                  90                  95

Leu Pro Gly Cys Leu Pro Cys Val Arg Val Gly Asn Gln Ser Arg Cys
            100                 105                 110

Trp Val Ala Leu Thr Pro Thr Val Ala Ala Pro Tyr Ile Gly Ala Pro
            115                 120                 125

Leu Glu Ser Leu Arg Ser His Val Asp Leu Met Val Gly Ala Ala Thr
            130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
            165                 170                 175

Asp Cys Asn Cys Ser Ile Tyr Ala Gly His Val Thr Gly His Arg
            180                 185                 190
```

(2) INFORMATION FOR SEQ ID NO: 120:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB549-4-3

(ix) FEATURE:
        (A) NAME/KEY: CDS
        (B) LOCATION: 1..574

(xi) SEQUENCE DESCRIPTION: SEQ ID NO: 120:

```
ACG TGC GGC TTT GCC GAC CTC ATG GGA TAC ATC CCG CTC GTG GGC GCC      48
Thr Cys Gly Phe Ala Asp Leu Met Gly Tyr Ile Pro Leu Val Gly Ala
 1               5                  10                  15

CCT GTG GGT GGC GTC GCC AGG GCC TTG GCA CAT GGT GTC AGG GCC GTG      96
Pro Val Gly Gly Val Ala Arg Ala Leu Ala His Gly Val Arg Ala Val
                20                  25                  30

GAG GAC GGG ATT AAC TAT GCA ACA GGG AAT CTT CCC GGT TGC TCC TTT     144
Glu Asp Gly Ile Asn Tyr Ala Thr Gly Asn Leu Pro Gly Cys Ser Phe
            35                  40                  45

TCT ATC TTC CTT CTA GCA CTT CTC TCG TGC TTG ACT GTC CCG GCC TCG     192
Ser Ile Phe Leu Leu Ala Leu Leu Ser Cys Leu Thr Val Pro Ala Ser
        50                  55                  60

GCG CAG CAC TAC CGG AAC ATC TCG GGC ATT TAT CAC GTC ACC AAT GAC     240
Ala Gln His Tyr Arg Asn Ile Ser Gly Ile Tyr His Val Thr Asn Asp
65                  70                  75                  80

TGC CCG AAC TCT AGT ATA GTG TAT GAA GCT GAC CAT CAT ATC ATG CAT     288
Cys Pro Asn Ser Ser Ile Val Tyr Glu Ala Asp His His Ile Met His
                85                  90                  95

CTA CCA GGG TGT GTG CCT TGC GTG AGA ACC GGG AAC ACC TCG CGC TGC     336
Leu Pro Gly Cys Val Pro Cys Val Arg Thr Gly Asn Thr Ser Arg Cys
            100                 105                 110

TGG GTT CCT TTA ACA CCC ACT GTG GCT GCC CCC TAT GTT GGC GCG CCG     384
Trp Val Pro Leu Thr Pro Thr Val Ala Ala Pro Tyr Val Gly Ala Pro
        115                 120                 125

CTC GAA TCC ATG CGG CGG CAC GTG GAC TTA ATG GTG GGT GCC GCC ACC     432
Leu Glu Ser Met Arg Arg His Val Asp Leu Met Val Gly Ala Ala Thr
    130                 135                 140

GTC TGC TCG GCC CTG TAC ATC GGA GAC CTT TGC GGA GGT GTC TTC CTG     480
Val Cys Ser Ala Leu Tyr Ile Gly Asp Leu Cys Gly Gly Val Phe Leu
145                 150                 155                 160

GTC GGG CAG ATG TTC ACC TTC CGG CCG CGC CGC CAT TGG ACT ACC CAG     528
Val Gly Gln Met Phe Thr Phe Arg Pro Arg Arg His Trp Thr Thr Gln
                165                 170                 175

GAC TGC AAC TGC TCT ATC TAT GAT GGC CAC ATC ACC GGC CAT AGA A       574
Asp Cys Asn Cys Ser Ile Tyr Asp Gly His Ile Thr Gly His Arg
            180                 185                 190

(2) INFORMATION FOR SEQ ID NO: 121:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 121:

Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
        50                  55                  60

Ala Gln His Tyr Arg Asn Ile Ser Gly Ile Tyr His Val Thr Asn Asp
65                  70                  75                  80

Cys Pro Asn Ser Ser Ile Val Tyr Glu Ala Asp His His Ile Met His
                85                  90                  95
```

```
Leu Pro Gly Cys Val Pro Cys Val Arg Thr Gly Asn Thr Ser Arg Cys
            100                 105                 110

Trp Val Pro Leu Thr Pro Thr Val Ala Ala Pro Tyr Val Gly Ala Pro
        115                 120                 125

Leu Glu Ser Met Arg Arg His Val Asp Leu Met Val Gly Ala Ala Thr
    130                 135                 140

Val Cys Ser Ala Leu Tyr Ile Gly Asp Leu Cys Gly Gly Val Phe Leu
145                 150                 155                 160

Val Gly Gln Met Phe Thr Phe Arg Pro Arg Arg His Trp Thr Thr Gln
                165                 170                 175

Asp Cys Asn Cys Ser Ile Tyr Asp Gly His Ile Thr Gly His Arg
            180                 185                 190

(2) INFORMATION FOR SEQ ID NO: 122:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: GB809-4-3

(ix) FEATURE:
        (A) NAME/KEY: CDS
        (B) LOCATION: 1..574

(xi) SEQUENCE DESCRIPTION: SEQ ID NO: 122:

ACG TGC GGC TTC GCC GAC CTC ATG GGA TAC ATC CCG CTC GTG GGC GCC      48
Thr Cys Gly Phe Ala Asp Leu Met Gly Tyr Ile Pro Leu Val Gly Ala
 1               5                  10                  15

CCC GTT GGG GGC GTC GCC AGG GCC CTG GCG CAT GGC GTC AGG GCT GTG      96
Pro Val Gly Gly Val Ala Arg Ala Leu Ala His Gly Val Arg Ala Val
                20                  25                  30

GAG GAC GGG ATT AAC TAT GCG ACA GGG AAT CTT CCC GGT TGC TCT TTC     144
Glu Asp Gly Ile Asn Tyr Ala Thr Gly Asn Leu Pro Gly Cys Ser Phe
            35                  40                  45

TCT ATC TTC CTC CTG GCA CTT CTT TCG TGC CTC ACT GTC CCA GCG TCA     192
Ser Ile Phe Leu Leu Ala Leu Leu Ser Cys Leu Thr Val Pro Ala Ser
         50                  55                  60

GCT GAG CAC TAC CGG AAT GCT TCG GGC ATC TAT CAC ATC ACC AAT GAC     240
Ala Glu His Tyr Arg Asn Ala Ser Gly Ile Tyr His Ile Thr Asn Asp
 65                  70                  75                  80

TGT CCG AAT TCC AGC GTA GTC TAT GAA ACT GAC CAC CAT ATA TTG CAC     288
Cys Pro Asn Ser Ser Val Val Tyr Glu Thr Asp His His Ile Leu His
                 85                  90                  95

TTG CCG GGG TGC GTA CCC TGC GTG AGG GCC GGG AAC GTG TCT CGT TGC     336
Leu Pro Gly Cys Val Pro Cys Val Arg Ala Gly Asn Val Ser Arg Cys
            100                 105                 110

TGG ACG CCG GTA ACA CCT ACG GTG GCT GCC GTA TCC ATG GAC GCT CCG     384
Trp Thr Pro Val Thr Pro Thr Val Ala Ala Val Ser Met Asp Ala Pro
        115                 120                 125

CTC GAG TCC TTC CGG CGG CAT GTG GAC CTA ATG GTA GGT GCG GCC ACC     432
Leu Glu Ser Phe Arg Arg His Val Asp Leu Met Val Gly Ala Ala Thr
    130                 135                 140

GTG TGT TCT GTC CTC TAT GTT GGA GAC CTC TGT GGA GGT GCT TTC CTA     480
Val Cys Ser Val Leu Tyr Val Gly Asp Leu Cys Gly Gly Ala Phe Leu
```

-continued

```
Val Cys Ser Val Leu Tyr Val Gly Asp Leu Cys Gly Ala Phe Leu
145                 150                 155                 160

GTG GGG CAG ATG TTC ACC TTC CAG CCG CGT CGC CAC TGG ACC ACG CAG        528
Val Gly Gln Met Phe Thr Phe Gln Pro Arg Arg His Trp Thr Thr Gln
                165                 170                 175

GAT TGT AAT TGC TCC ATC TAT ACT GGC CAT ATC ACC GGC CAC AGG A          574
Asp Cys Asn Cys Ser Ile Tyr Thr Gly His Ile Thr Gly His Arg
            180                 185                 190
```

(2) INFORMATION FOR SEQ ID NO: 123:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 123:

```
Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
        50                  55                  60

Ala Glu His Tyr Arg Asn Ala Ser Gly Ile Tyr His Ile Thr Asn Asp
65                  70                  75                  80

Cys Pro Asn Ser Ser Val Val Tyr Glu Thr Asp His His Ile Leu His
                85                  90                  95

Leu Pro Gly Cys Val Pro Cys Val Arg Ala Gly Asn Val Ser Arg Cys
            100                 105                 110

Trp Thr Pro Val Thr Pro Thr Val Ala Ala Val Ser Met Asp Ala Pro
        115                 120                 125

Leu Glu Ser Phe Arg Arg His Val Asp Leu Met Val Gly Ala Ala Thr
130                 135                 140

Val Cys Ser Val Leu Tyr Val Gly Asp Leu Cys Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg
            180                 185                 190
```

(2) INFORMATION FOR SEQ ID NO: 124:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..31
        (D) OTHER INFORMATION: /standard_name= "HCV Primer HCPr206"

(xi) SEQUENCE DESCRIPTION: SEQ ID NO: 124:

TGGGGATCCC GTATGATACC CGCTGCTTTG A                                              31

(2) INFORMATION FOR SEQ ID NO: 125:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: misc_feature
            (B) LOCATION: 1..30
            (D) OTHER INFORMATION: /standard_name= "HCV Primer HcPr207"

(xi) SEQUENCE DESCRIPTION: SEQ ID NO: 125:

GGCGGAATTC CTGGTCATAG CCTCCGTGAA                                                30

(2) INFORMATION FOR SEQ ID NO: 126:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (vi) ORIGINAL SOURCE:
            (A) ORGANISM: amino acid
            (C) INDIVIDUAL ISOLATE: GB358

(xi) SEQUENCE DESCRIPTION: SEQ ID NO: 126:

Val Asn Tyr Arg Asn Ala Ser Gly Ile Tyr His Ile
1               5                   10

(2) INFORMATION FOR SEQ ID NO: 127:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (vi) ORIGINAL SOURCE:
            (A) ORGANISM: Amino acid
            (C) INDIVIDUAL ISOLATE: GB549

(xi) SEQUENCE DESCRIPTION: SEQ ID NO: 127:

Gln His Tyr Arg Asn Ile Ser Gly Ile Tyr His Val
1               5                   10

(2) INFORMATION FOR SEQ ID NO: 128:

(i) SEQUENCE CHARACTERISTICS:
            (A) LENGTH: 12 amino acids
            (B) TYPE: amino acid
            (C) STRANDEDNESS: single

```
        (D) TOPOLOGY: linear (ii) MOLECULE TYPE: peptide (iii) HYPOTHETICAL: NO (vi) ORIGINAL SOURCE:
        (A) ORGANISM: Amino acid
        (C) INDIVIDUAL ISOLATE: GB809

(xi) SEQUENCE DESCRIPTION: SEQ ID NO: 128:

Glu His Tyr Arg Asn Ala Ser Gly Ile Tyr His Ile
1               5                  10

(2) INFORMATION FOR SEQ ID NO: 129:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB358

(xi) SEQUENCE DESCRIPTION: SEQ ID NO: 129:

Val Tyr Glu Thr Glu His His Ile Leu His Leu
1               5                  10

(2) INFORMATION FOR SEQ ID NO: 130:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB549

(xi) SEQUENCE DESCRIPTION: SEQ ID NO: 130:

Val Tyr Glu Ala Asp His His Ile Met His Leu
1               5                  10

(2) INFORMATION FOR SEQ ID NO: 131:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB809

(xi) SEQUENCE DESCRIPTION: SEQ ID NO: 131:

Val Tyr Glu Thr Asp His His Ile Leu His Leu
```

```
1               5              10
```

(2) INFORMATION FOR SEQ ID NO: 132:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB358

(xi) SEQUENCE DESCRIPTION: SEQ ID NO: 132:

```
Val Arg Val Gly Asn Gln Ser Arg Cys Trp Val Ala Leu
1               5              10
```

(2) INFORMATION FOR SEQ ID NO: 133:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB549

(xi) SEQUENCE DESCRIPTION: SEQ ID NO: 133:

```
Val Arg Thr Gly Asn Thr Ser Arg Cys Trp Val Pro Leu
1               5              10
```

(2) INFORMATION FOR SEQ ID NO: 134:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB809

(xi) SEQUENCE DESCRIPTION: SEQ ID NO: 134:

```
Val Arg Ala Gly Asn Val Ser Arg Cys Trp Thr Pro Val
1               5              10
```

(2) INFORMATION FOR SEQ ID NO: 135:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide

```
    (iii) HYPOTHETICAL: NO (vi) ORIGINAL SOURCE:
         (A) ORGANISM: amino acid
         (C) INDIVIDUAL ISOLATE: GB358

(xi) SEQUENCE DESCRIPTION: SEQ ID NO: 135:

Ala Pro Tyr Ile Gly Ala Pro Leu Glu Ser
1               5                   10

(2) INFORMATION FOR SEQ ID NO: 136:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
         (A) ORGANISM: amino acid
         (C) INDIVIDUAL ISOLATE: GB549

(xi) SEQUENCE DESCRIPTION: SEQ ID NO: 136:

Ala Pro Tyr Val Gly Ala Pro Leu Glu Ser
1               5                   10

(2) INFORMATION FOR SEQ ID NO: 137:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
         (A) ORGANISM: amino acid
         (C) INDIVIDUAL ISOLATE: GB809

(xi) SEQUENCE DESCRIPTION: SEQ ID NO: 137:

Ala Val Ser Met Asp Ala Pro Leu Glu Ser
1               5                   10

(2) INFORMATION FOR SEQ ID NO: 138:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
         (A) ORGANISM: amino acid
         (C) INDIVIDUAL ISOLATE: GB358 and GB809

(xi) SEQUENCE DESCRIPTION: SEQ ID NO: 138:

Gln Pro Arg Arg His Trp Thr Thr Gln Asp
1               5                   10

(2) INFORMATION FOR SEQ ID NO: 139:
```

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB549

(xi) SEQUENCE DESCRIPTION: SEQ ID NO: 139:

Arg Pro Arg Arg His Trp Thr Thr Gln Asp
1               5                   10

(2) INFORMATION FOR SEQ ID NO: 140:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (vi) ORIGINAL SOURCE:
        (A) ORGANISM: amino acid
        (C) INDIVIDUAL ISOLATE: GB549

(xi) SEQUENCE DESCRIPTION: SEQ ID NO: 140:

Arg Pro Arg Arg His Trp Thr Thr Gln Asp
1               5                   10

(2) INFORMATION FOR SEQ ID NO: 141:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 141:

TGGGATATGA TGATGAACTG GTC                                           23

(2) INFORMATION FOR SEQ ID NO: 142:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 142:

CCAGGTACAA CCGAACCAAT TGCC                                          24
```

(2) INFORMATION FOR SEQ ID NO: 143:

(i) SEQUENCE CHARACTERISTICS:
        (A) LENGTH: 957 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..957

(ix) FEATURE:
        (A) NAME/KEY: mat_peptide
        (B) LOCATION: 1..954

(xi) SEQUENCE DESCRIPTION: SEQ ID NO: 143:

```
ATG AGC ACA AAT CCT AAA CCT CAA AGA AAA ACC AAA AGA AAC ACT AAC         48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGC CAG ATC GTT GGT         96
Arg Arg Pro Gln Asp Val Lys Phe Pro Gly Gly Gly Gln Ile Val Gly
             20                  25                  30

GGA GTA TAC TTG TTG CCG CGC AGG GGC CCC CGG TTG GGT GTG CGC GCG        144
Gly Val Tyr Leu Leu Pro Arg Arg Gly Pro Arg Leu Gly Val Arg Ala
         35                  40                  45

ACG AGG AAA ACT TCC GAG CGG TCC CAG CCA CGT GGG AGG CGC CAG CCC        192
Thr Arg Lys Thr Ser Glu Arg Ser Gln Pro Arg Gly Arg Arg Gln Pro
     50                  55                  60

ATC CCC AAA GAT CGG CGC CCC ACT GGC AAG TCC TGG GGA AAA CCA GGA        240
Ile Pro Lys Asp Arg Arg Pro Thr Gly Lys Ser Trp Gly Lys Pro Gly
 65                  70                  75                  80

TAC CCT TGG CCC CTG TAC GGG AAT GAG GGC CTC GGC TGG GCA GGG TGG        288
Tyr Pro Trp Pro Leu Tyr Gly Asn Glu Gly Leu Gly Trp Ala Gly Trp
                 85                  90                  95

CTC CTG TCC CCC CGA GGG TCT CGC CCG TCA TGG GGC CCA ACT GAC CCC        336
Leu Leu Ser Pro Arg Gly Ser Arg Pro Ser Trp Gly Pro Thr Asp Pro
            100                 105                 110

CGG CAC AGG TCA CGC AAC TTG GGT AAG GTC ATC GAT ACC CTT ACG TGT        384
Arg His Arg Ser Arg Asn Leu Gly Lys Val Ile Asp Thr Leu Thr Cys
        115                 120                 125

GGC TTT GCC GAC CTC ATG GGG TAC ATC CCT GTC GTC GGC GCC CCA GTT        432
Gly Phe Ala Asp Leu Met Gly Tyr Ile Pro Val Val Gly Ala Pro Val
    130                 135                 140

GGT GGT GTC GCC AGA GCT CTC GCG CAT GGC GTG AGA GTT CTG GAA GAC        480
Gly Gly Val Ala Arg Ala Leu Ala His Gly Val Arg Val Leu Glu Asp
145                 150                 155                 160

GGG ATA AAC TAT GCA ACA GGG AAC TTG CCC GGT TGC TCC TTT TCT ATC        528
Gly Ile Asn Tyr Ala Thr Gly Asn Leu Pro Gly Cys Ser Phe Ser Ile
                165                 170                 175

TTC TTA TTG GCC CTG CTA TCT TGT ATC ACT GTG CCG GTC TCC GGC TTG        576
Phe Leu Leu Ala Leu Leu Ser Cys Ile Thr Val Pro Val Ser Gly Leu
            180                 185                 190

CAG GTC AAG AAC ACC AGC AGC TCT TAC ATG GTA ACC AAT GAC TGC CAG        624
Gln Val Lys Asn Thr Ser Ser Ser Tyr Met Val Thr Asn Asp Cys Gln
        195                 200                 205

AAC AGT AGC ATC GTC TGG CAG CTC AGG GAT GCT GTT CTT CAC GTC CCC        672
```

-continued

```
Asn Ser Ser Ile Val Trp Gln Leu Arg Asp Ala Val Leu His Val Pro
    210             215                 220

GGG TGT GTC CCT TGT GAG GAG AAG GGC AAC ATA TCC CGC TGT TGG ATA      720
Gly Cys Val Pro Cys Glu Glu Lys Gly Asn Ile Ser Arg Cys Trp Ile
225             230                 235                 240

CCG GTT TCG CCC AAT ATA GCT GTG AGC CAA CCT GGT GCG CTT ACC AAG      768
Pro Val Ser Pro Asn Ile Ala Val Ser Gln Pro Gly Ala Leu Thr Lys
                245                 250                 255

GGC CTG CGG ACG CAT ATT GAT ACC ATC ATT GCA TCC GCT ACG TTT TGC      816
Gly Leu Arg Thr His Ile Asp Thr Ile Ile Ala Ser Ala Thr Phe Cys
            260                 265                 270

TCT GCC CTG TAC ATA GGA GAC CTG TGT GGC GCG GTG ATG TTG GCT TCT      864
Ser Ala Leu Tyr Ile Gly Asp Leu Cys Gly Ala Val Met Leu Ala Ser
        275                 280                 285

CAA GTC TTC ATC ATC TCG CCC CAG CAT CAT AAG TTT GTC CAG GAC TGC      912
Gln Val Phe Ile Ile Ser Pro Gln His His Lys Phe Val Gln Asp Cys
    290                 295                 300

AAC TGT TCC ATA TAC CCA GGC CAC ATC ACT GGA CAT CGG ATG GCG          957
Asn Cys Ser Ile Tyr Pro Gly His Ile Thr Gly His Arg Met Ala
305                 310                 315
```

(2) INFORMATION FOR SEQ ID NO: 144:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 144:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Pro Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Val
        130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Gly Leu
            180                 185                 190

Gln Val Lys Asn Thr Ser Ser Tyr Met Val Thr Asn Asp Cys Gln
        195                 200                 205

Asn Ser Ser Ile Val Trp Gln Leu Arg Asp Ala Val Leu His Val Pro
```

```
               210                 215                 220
Gly Cys Val Pro Cys Glu Glu Lys Gly Asn Ile Ser Arg Cys Trp Ile
225                 230                 235                 240

Pro Val Ser Pro Asn Ile Ala Val Ser Gln Pro Gly Ala Leu Thr Lys
                245                 250                 255

Gly Leu Arg Thr His Ile Asp Thr Ile Ile Ala Ser Ala Thr Phe Cys
                260                 265                 270

Ser Ala Leu Tyr Ile Gly Asp Leu Cys Gly Ala Val Met Leu Ala Ser
                275                 280                 285

Gln Val Phe Ile Ile Ser Pro Gln His His Lys Phe Val Gln Asp Cys
    290                 295                 300

Asn Cys Ser Ile Tyr Pro Gly His Ile Thr Gly His Arg Met Ala
305                 310                 315
```

(2) INFORMATION FOR SEQ ID NO: 145:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: mat_peptide
        (B) LOCATION: 2..337

(ix) FEATURE:
        (A) NAME/KEY: CDS
        (B) LOCATION: 2..340

(xi) SEQUENCE DESCRIPTION: SEQ ID NO: 145:

```
C TCA ACG GTC ACG GAG AGG GAC ATC AGA ACT GAG GAG TCC ATA TAC        46
  Ser Thr Val Thr Glu Arg Asp Ile Arg Thr Glu Glu Ser Ile Tyr
   1               5                  10                  15

CTT GCT TGC TCT TTA CCC GAG CAG GCA CGG ACT GCC ATA CAC TCA CTG      94
Leu Ala Cys Ser Leu Pro Glu Gln Ala Arg Thr Ala Ile His Ser Leu
                  20                  25                  30

ACT GAG AGG CTT TAC GTG GGA GGG CCC ATG CTA AAC AGC AAA GGG CAA     142
Thr Glu Arg Leu Tyr Val Gly Gly Pro Met Leu Asn Ser Lys Gly Gln
                35                  40                  45

ACC TGC GGA TAC AGA CGC TGC CGC GCC AGC GGA GTG TTC ACC ACT AGC     190
Thr Cys Gly Tyr Arg Arg Cys Arg Ala Ser Gly Val Phe Thr Thr Ser
            50                  55                  60

ATG GGA AAT ACC ATC ACG TGC TAC GTG AAG GCA CAA GCA GCC TGT AAG     238
Met Gly Asn Thr Ile Thr Cys Tyr Val Lys Ala Gln Ala Ala Cys Lys
        65                  70                  75

GCT GCG GGC ATA ATT GCC CCC ACG ATG CTG GTG TGC GGC GAC GAT CTA     286
Ala Ala Gly Ile Ile Ala Pro Thr Met Leu Val Cys Gly Asp Asp Leu
    80                  85                  90                  95

GTT GTC ATC TCA GAG AGT CAG GGG ACC GAG GAG GAC GAG CGG AAC CTA     334
Val Val Ile Ser Glu Ser Gln Gly Thr Glu Glu Asp Glu Arg Asn Leu
                    100                 105                 110

CGA GCC                                                             340
Arg Ala
```

(2) INFORMATION FOR SEQ ID NO: 146:

(i) SEQUENCE CHARACTERISTICS:
    (A) LENGTH: 113 amino acids
    (B) TYPE: amino acid
    (D) TOPOLOGY: linear (ii) MOLECULE TYPE: protein (xi) SEQUENCE DESCRIPTION: SEQ ID NO: 146:

```
Ser Thr Val Thr Glu Arg Asp Ile Arg Thr Glu Glu Ser Ile Tyr Leu
 1               5                  10                  15

Ala Cys Ser Leu Pro Glu Gln Ala Arg Thr Ala Ile His Ser Leu Thr
            20                  25                  30

Glu Arg Leu Tyr Val Gly Gly Pro Met Leu Asn Ser Lys Gly Gln Thr
        35                  40                  45

Cys Gly Tyr Arg Arg Cys Arg Ala Ser Gly Val Phe Thr Thr Ser Met
50                  55                  60

Gly Asn Thr Ile Thr Cys Tyr Val Lys Ala Gln Ala Ala Cys Lys Ala
65                  70                  75                  80

Ala Gly Ile Ile Ala Pro Thr Met Leu Val Cys Gly Asp Asp Leu Val
                85                  90                  95

Val Ile Ser Glu Ser Gln Gly Thr Glu Glu Asp Glu Arg Asn Leu Arg
            100                 105                 110

Ala
```

(2) INFORMATION FOR SEQ ID NO: 147:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..345

(ix) FEATURE:
        (A) NAME/KEY: mat_peptide
        (B) LOCATION: 1..342

(xi) SEQUENCE DESCRIPTION: SEQ ID NO: 147:

```
ATG AGC ACA CTT CCT AAA CCA CAA AGA AAA ACC AAA AGA AAC ACC AAC      48
Met Ser Thr Leu Pro Lys Pro Gln Arg Lys Thr Lys Arg Asn Thr Asn
 1               5                  10                  15

CCC GGC CAC AGG ACG TTA AGT TCC CAG GCG GCG GTC AGA TCG TTG GTG      96
Pro Gly His Arg Thr Leu Ser Ser Gln Ala Ala Val Arg Ser Leu Val
            20                  25                  30

GAG TTT ACG TGC TAC CAC GCA GGG GCC CCC AGT TGG GTG TGC GTG CAG     144
Glu Phe Thr Cys Tyr His Ala Gly Ala Pro Ser Trp Val Cys Val Gln
        35                  40                  45

TGC GCA AGA CTT CCG AGC GGT CGC AAC CTC GCA GTA GGC GCC AAC CCA     192
Cys Ala Arg Leu Pro Ser Gly Arg Asn Leu Ala Val Gly Ala Asn Pro
50                  55                  60

TCC CCA GGG CGC GCC GAA CCG AGG GCA GGT CCT GGG CTC AGC CCG GGT     240
Ser Pro Gly Arg Ala Glu Pro Arg Ala Gly Pro Gly Leu Ser Pro Gly
65                  70                  75                  80

ACC CTT GGC CCC TAT ATG GGA ATG AGG GCT GCG GGT GGG CAG GGT GGC     288
Thr Leu Gly Pro Tyr Met Gly Met Arg Ala Ala Gly Gly Gln Gly Gly
```

```
                  85                  90                  95
TCC TGT CCC CGC GCG GCT CTC GCC CGT CGT GGG GCC CAA ATG ACC CCC       336
Ser Cys Pro Arg Ala Ala Leu Ala Arg Arg Gly Ala Gln Met Thr Pro
         100                 105                 110

GGC GCA GGA                                                           345
Gly Ala Gly
     115
```

(2) INFORMATION FOR SEQ ID NO: 148:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 148:

```
Met Ser Thr Leu Pro Lys Pro Gln Arg Lys Thr Lys Arg Asn Thr Asn
 1               5                  10                  15

Pro Gly His Arg Thr Leu Ser Ser Gln Ala Ala Val Arg Ser Leu Val
             20                  25                  30

Glu Phe Thr Cys Tyr His Ala Gly Ala Pro Ser Trp Val Cys Val Gln
         35                  40                  45

Cys Ala Arg Leu Pro Ser Gly Arg Asn Leu Ala Val Gly Ala Asn Pro
     50                  55                  60

Ser Pro Gly Arg Ala Glu Pro Arg Ala Gly Pro Gly Leu Ser Pro Gly
 65                  70                  75                  80

Thr Leu Gly Pro Tyr Met Gly Met Arg Ala Ala Gly Gly Gln Gly Gly
                 85                  90                  95

Ser Cys Pro Arg Ala Ala Leu Ala Arg Arg Gly Ala Gln Met Thr Pro
         100                 105                 110

Gly Ala Gly
     115
```

(2) INFORMATION FOR SEQ ID NO: 149:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..280

(ix) FEATURE:
        (A) NAME/KEY: mat_peptide
        (B) LOCATION: 2..277

(xi) SEQUENCE DESCRIPTION: SEQ ID NO: 149:

```
G GCC TGT GAC CTC AAG GAC GAG GCT AGG AGG GTG ATA ACT TCA CTC         46
  Ala Cys Asp Leu Lys Asp Glu Ala Arg Arg Val Ile Thr Ser Leu
   1               5                  10                  15

ACG GAG CGG CTT TAC TGT GGT GGT CCT ATG TTC AAC AGC AAG GGA CAA       94
Thr Glu Arg Leu Tyr Cys Gly Gly Pro Met Phe Asn Ser Lys Gly Gln
                 20                  25                  30

CAC TGC GGT TAC CGC CGC TGC CGT GCT AGT GGG GTG CTA CCC ACC AGC      142
His Cys Gly Tyr Arg Arg Cys Arg Ala Ser Gly Val Leu Pro Thr Ser
         35                  40                  45
```

```
TTC GGG AAC ACA ATC ACC TGT TAC ATC AAA GCA AAG GCA GCT ACC AAA      190
Phe Gly Asn Thr Ile Thr Cys Tyr Ile Lys Ala Lys Ala Ala Thr Lys
         50                  55                  60

GCT GCC GGA ATT AAA AAT CCA TCA TTC CTT GTC TGC GGA GAT GAC TTG      238
Ala Ala Gly Ile Lys Asn Pro Ser Phe Leu Val Cys Gly Asp Asp Leu
 65                  70                  75

GTC GTG ATT GCT GAG AGT GCA GGG ATC GAT GAG GAC AGA GCG              280
Val Val Ile Ala Glu Ser Ala Gly Ile Asp Glu Asp Arg Ala
 80                  85                  90
```

(2) INFORMATION FOR SEQ ID NO: 150:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO: 150:

```
Ala Cys Asp Leu Lys Asp Glu Ala Arg Arg Val Ile Thr Ser Leu Thr
 1                   5                  10                  15

Glu Arg Leu Tyr Cys Gly Gly Pro Met Phe Asn Ser Lys Gly Gln His
             20                  25                  30

Cys Gly Tyr Arg Arg Cys Arg Ala Ser Gly Val Leu Pro Thr Ser Phe
         35                  40                  45

Gly Asn Thr Ile Thr Cys Tyr Ile Lys Ala Lys Ala Ala Thr Lys Ala
     50                  55                  60

Ala Gly Ile Lys Asn Pro Ser Phe Leu Val Cys Gly Asp Asp Leu Val
 65                  70                  75                  80

Val Ile Ala Glu Ser Ala Gly Ile Asp Glu Asp Arg Ala
                 85                  90
```

(2) INFORMATION FOR SEQ ID NO: 151:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..499

(ix) FEATURE:
        (A) NAME/KEY: mat_peptide
        (B) LOCATION: 1..496

(xi) SEQUENCE DESCRIPTION: SEQ ID NO: 151:

```
ATG AGC ACG AAT CCT AAA CCT CAA AGA AAA ACC AAA AGA AAC ACC AAC       48
Met Ser Thr Asn Pro Lys Pro Gln Arg Lys Thr Lys Arg Asn Thr Asn
 1                   5                  10                  15

CGT CGC CCA CAG GAC GTC AAG TTC CCG GGC GGT GGT CAG ATC GTT GGC       96
Arg Arg Pro Gln Asp Val Lys Phe Pro Gly Gly Gly Gln Ile Val Gly
             20                  25                  30

GGA GTT TAC TTG TTG CCG CGC AGG GGC CCT AGG ATG GGT GTG CGC GCG      144
Gly Val Tyr Leu Leu Pro Arg Arg Gly Pro Arg Met Gly Val Arg Ala
         35                  40                  45
```

```
ACT CGG AAG ACT TCG GAA CGG TCG CAA CCC CGT GGA CGG CGT CAG CCT       192
Thr Arg Lys Thr Ser Glu Arg Ser Gln Pro Arg Gly Arg Arg Gln Pro
 50                  55                  60

ATT CCC AAG GCG CGC CAG CCC ACG GGC CGG TCC TGG GGT CAA CCC GGG       240
Ile Pro Lys Ala Arg Gln Pro Thr Gly Arg Ser Trp Gly Gln Pro Gly
 65                  70                  75                  80

TAC CCT TGG CCC CTT TAC GCC AAT GAG GGC CTC GGG TGG GCA GGG TGG       288
Tyr Pro Trp Pro Leu Tyr Ala Asn Glu Gly Leu Gly Trp Ala Gly Trp
                 85                  90                  95

CTG CTC TCC CCT CGA GGC TCT CGG CCT AAT TGG GGC CCC AAT GAC CCC       336
Leu Leu Ser Pro Arg Gly Ser Arg Pro Asn Trp Gly Pro Asn Asp Pro
            100                 105                 110

CGG CGA AAA TCG CGT AAT TTG GGT AAG GTC ATC GAT ACC CTA ACG TGC       384
Arg Arg Lys Ser Arg Asn Leu Gly Lys Val Ile Asp Thr Leu Thr Cys
        115                 120                 125

GGA TTC GCC GAT CTC ATG GGG TAT ATC CCG CTC GTA GGC GGC CCC ATT       432
Gly Phe Ala Asp Leu Met Gly Tyr Ile Pro Leu Val Gly Gly Pro Ile
130                 135                 140

GGG GGC GTC GCA AGG GCT CTC GCA CAC GGT GTG AGG GTC CTT GAG GAC       480
Gly Gly Val Ala Arg Ala Leu Ala His Gly Val Arg Val Leu Glu Asp
145                 150                 155                 160

GGG GTA AAC TAT GCA ACA G                                             499
Gly Val Asn Tyr Ala Thr
                165

(2) INFORMATION FOR SEQ ID NO: 152:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO: 152:

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Met Gly Val Arg Ala
             35                  40                  45

Thr Arg Lys Thr Ser Glu Arg Ser Gln Pro Arg Gly Arg Arg Gln Pro
         50                  55                  60

Ile Pro Lys Ala Arg Gln Pro Thr Gly Arg Ser Trp Gly Gln Pro Gly
 65                  70                  75                  80

Tyr Pro Trp Pro Leu Tyr Ala Asn Glu Gly Leu Gly Trp Ala Gly Trp
                 85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Ile
130                 135                 140

Gly Gly Val Ala Arg Ala Leu Ala His Gly Val Arg Val Leu Glu Asp
145                 150                 155                 160

Gly Val Asn Tyr Ala Thr
                165

(2) INFORMATION FOR SEQ ID NO: 153:
```

(i) SEQUENCE CHARACTERISTICS:
    (A) LENGTH: 579 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 1..579

(ix) FEATURE:
    (A) NAME/KEY: mat_peptide
    (B) LOCATION: 1..576

(xi) SEQUENCE DESCRIPTION: SEQ ID NO: 153:

| | | | | | | | | | | | | | | | | |
|---|---|---|---|---|---|---|---|---|---|---|---|---|---|---|---|---|
| ACG | TGC | GGA | TTC | GCC | GAT | CTC | ATG | GGG | TAC | ATC | CCG | CTC | GTA | GGC | GGC | 48 |
| Thr | Cys | Gly | Phe | Ala | Asp | Leu | Met | Gly | Tyr | Ile | Pro | Leu | Val | Gly | Gly | |
| 1 | | | | 5 | | | | | 10 | | | | | 15 | | |
| CCC | GTT | GGG | GGC | GTC | GCA | AGG | GCT | CTC | GCA | CAC | GGT | GTG | AGG | GTC | CTT | 96 |
| Pro | Val | Gly | Gly | Val | Ala | Arg | Ala | Leu | Ala | His | Gly | Val | Arg | Val | Leu | |
| | | | 20 | | | | | 25 | | | | | 30 | | | |
| GAG | GAC | GGG | GTA | AAC | TAT | CCA | ACA | GGG | AAT | TTA | CCC | GGT | TGC | TCT | TTC | 144 |
| Glu | Asp | Gly | Val | Asn | Tyr | Pro | Thr | Gly | Asn | Leu | Pro | Gly | Cys | Ser | Phe | |
| | | 35 | | | | | 40 | | | | | 45 | | | | |
| TCT | ATC | TTT | ATT | CTT | GCT | CTT | CTC | TCG | TGT | CTG | ACC | GTT | CCG | GCC | TCT | 192 |
| Ser | Ile | Phe | Ile | Leu | Ala | Leu | Leu | Ser | Cys | Leu | Thr | Val | Pro | Ala | Ser | |
| | 50 | | | | | 55 | | | | | 60 | | | | | |
| GCA | GTT | CCC | TAC | CGA | AAT | GCC | TCT | GGG | ATT | TAT | CAT | GTT | ACC | AAT | GAT | 240 |
| Ala | Val | Pro | Tyr | Arg | Asn | Ala | Ser | Gly | Ile | Tyr | His | Val | Thr | Asn | Asp | |
| 65 | | | | | 70 | | | | | 75 | | | | | 80 | |
| TGC | CCA | AAC | TCT | TCC | ATA | GTC | TAT | GAG | GCA | GAT | AAC | CTG | ATC | CTA | CAC | 288 |
| Cys | Pro | Asn | Ser | Ser | Ile | Val | Tyr | Glu | Ala | Asp | Asn | Leu | Ile | Leu | His | |
| | | | | 85 | | | | | 90 | | | | | 95 | | |
| GCA | CCT | GGT | TGC | GTG | CCT | TGT | GTC | ATG | ACA | GGT | AAT | GTG | AGT | AGA | TGC | 336 |
| Ala | Pro | Gly | Cys | Val | Pro | Cys | Val | Met | Thr | Gly | Asn | Val | Ser | Arg | Cys | |
| | | | 100 | | | | | 105 | | | | | 110 | | | |
| TGG | GTC | CAA | ATT | ACC | CCT | ACA | CTG | TCA | GCC | CCG | AGC | CTC | GGA | GCA | GTC | 384 |
| Trp | Val | Gln | Ile | Thr | Pro | Thr | Leu | Ser | Ala | Pro | Ser | Leu | Gly | Ala | Val | |
| | | 115 | | | | | 120 | | | | | 125 | | | | |
| ACG | GCT | CCT | CTT | CGG | AGA | GCC | GTT | GAC | TAC | CTA | GCG | GGA | GGG | GCT | GCC | 432 |
| Thr | Ala | Pro | Leu | Arg | Arg | Ala | Val | Asp | Tyr | Leu | Ala | Gly | Gly | Ala | Ala | |
| | 130 | | | | | 135 | | | | | 140 | | | | | |
| CTC | TGC | TCC | GCG | TTA | TAC | GTA | GGA | GAC | GCG | TGT | GGG | GCA | CTA | TTC | TTG | 480 |
| Leu | Cys | Ser | Ala | Leu | Tyr | Val | Gly | Asp | Ala | Cys | Gly | Ala | Leu | Phe | Leu | |
| 145 | | | | | 150 | | | | | 155 | | | | | 160 | |
| GTA | GGC | CAA | ATG | TTC | ACC | TAT | AGG | CCT | CGC | CAG | CAC | GCT | ACG | GTG | CAG | 528 |
| Val | Gly | Gln | Met | Phe | Thr | Tyr | Arg | Pro | Arg | Gln | His | Ala | Thr | Val | Gln | |
| | | | | 165 | | | | | 170 | | | | | 175 | | |
| AAC | TGC | AAC | TGT | TCC | ATT | TAC | AGT | GGC | CAT | GTT | ACC | GGC | CAC | CGG | ATG | 576 |
| Asn | Cys | Asn | Cys | Ser | Ile | Tyr | Ser | Gly | His | Val | Thr | Gly | His | Arg | Met | |
| | | | 180 | | | | | 185 | | | | | 190 | | | |
| GCG | | | | | | | | | | | | | | | | 579 |
| Ala | | | | | | | | | | | | | | | | |

(2) INFORMATION FOR SEQ ID NO: 154:

(i) SEQUENCE CHARACTERISTICS:
    (A) LENGTH: 193 amino acids (B) TYPE: amino acid
(D) TOPOLOGY: linear (ii) MOLECULE TYPE: protein (xi) SEQUENCE DESCRIPTION: SEQ ID NO: 154:

```
Thr Cys Gly Phe Ala Asp Leu Met Gly Tyr Ile Pro Leu Val Gly Gly
 1               5                  10                  15

Pro Val Gly Gly Val Ala Arg Ala Leu Ala His Gly Val Arg Val Leu
                20                  25                  30

Glu Asp Gly Val Asn Tyr Pro Thr Gly Asn Leu Pro Gly Cys Ser Phe
            35                  40                  45

Ser Ile Phe Ile Leu Ala Leu Leu Ser Cys Leu Thr Val Pro Ala Ser
        50                  55                  60

Ala Val Pro Tyr Arg Asn Ala Ser Gly Ile Tyr His Val Thr Asn Asp
 65                  70                  75                  80

Cys Pro Asn Ser Ser Ile Val Tyr Glu Ala Asp Asn Leu Ile Leu His
                85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
        115                 120                 125

Thr Ala Pro Leu Arg Arg Ala Val Asp Tyr Leu Ala Gly Gly Ala Ala
130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
            180                 185                 190

Ala
```

(2) INFORMATION FOR SEQ ID NO: 155:

(i) SEQUENCE CHARACTERISTICS:
(A) LENGTH: 579 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: CDS
(B) LOCATION: 1..579

(ix) FEATURE:
(A) NAME/KEY: mat_peptide
(B) LOCATION: 1..576

(xi) SEQUENCE DESCRIPTION: SEQ ID NO: 155:

```
ACG TGC GGA TTC GCC GAC CTC GTG GGG TAC ATC CCG CTC GTA GGC GGC      48
Thr Cys Gly Phe Ala Asp Leu Val Gly Tyr Ile Pro Leu Val Gly Gly
 1               5                  10                  15

CCC GTT GGG GGC GTC GCA AGG GCT CTC GCA CAT GGT GTG AGG GTT CTT      96
Pro Val Gly Gly Val Ala Arg Ala Leu Ala His Gly Val Arg Val Leu
                20                  25                  30

GAG GAC GGG GTG AAT TAT GCA ACA GGG AAT CTG CCT GGT TGC TCT TTC     144
```

-continued

```
Glu Asp Gly Val Asn Tyr Ala Thr Gly Asn Leu Pro Gly Cys Ser Phe
         35                  40                  45

TCT ATC TTC ATT CTT GCA CTT CTC TCG TGC CTC ACT GTC CCG GCC TCT      192
Ser Ile Phe Ile Leu Ala Leu Leu Ser Cys Leu Thr Val Pro Ala Ser
         50                  55                  60

GCA GTT CCC TAC CGA AAT GCC TCT GGG ATC TAT CAT GTC ACC AAT GAT      240
Ala Val Pro Tyr Arg Asn Ala Ser Gly Ile Tyr His Val Thr Asn Asp
 65              70                  75                  80

TGC CCA AAC TCT TCC ATA GTC TAT GAG GCA GAT GAT CTG ATC CTA CAC      288
Cys Pro Asn Ser Ser Ile Val Tyr Glu Ala Asp Asp Leu Ile Leu His
                 85                  90                  95

GCA CCT GGC TGC GTG CCT TGT GTC AGG AAA GAT AAT GTG AGT AGG TGC      336
Ala Pro Gly Cys Val Pro Cys Val Arg Lys Asp Asn Val Ser Arg Cys
                100                 105                 110

TGG GTC CAA ATT ACC CCC ACG CTG TCA GCC CCG AGC TTC GGA GCA GTC      384
Trp Val Gln Ile Thr Pro Thr Leu Ser Ala Pro Ser Phe Gly Ala Val
            115                 120                 125

ACG GCT CCC CTT CGG AGA GCC GTT GAT TAC TTG GTG GGA GGG GCT GCC      432
Thr Ala Pro Leu Arg Arg Ala Val Asp Tyr Leu Val Gly Gly Ala Ala
        130                 135                 140

CTC TGC TCC GCG TTA TAC GTT GGA GAC GCG TGT GGG GCA CTA TTT TTG      480
Leu Cys Ser Ala Leu Tyr Val Gly Asp Ala Cys Gly Ala Leu Phe Leu
145                 150                 155                 160

GTA GGC CAA ATG TTC ACC TAT AGG CCT CGC CAG CAT GCT ACG GTG CAG      528
Val Gly Gln Met Phe Thr Tyr Arg Pro Arg Gln His Ala Thr Val Gln
                165                 170                 175

GAC TGC AAC TGT TCC ATC TAC AGT GGC CAC GTC ACC GGC CAT CAG ATG      576
Asp Cys Asn Cys Ser Ile Tyr Ser Gly His Val Thr Gly His Gln Met
                180                 185                 190

GCA                                                                  579
Ala
```

(2) INFORMATION FOR SEQ ID NO: 156:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 156:

```
Thr Cys Gly Phe Ala Asp Leu Val Gly Tyr Ile Pro Leu Val Gly Gly
 1               5                  10                  15

Pro Val Gly Gly Val Ala Arg Ala Leu Ala His Gly Val Arg Val Leu
             20                  25                  30

Glu Asp Gly Val Asn Tyr Ala Thr Gly Asn Leu Pro Gly Cys Ser Phe
         35                  40                  45

Ser Ile Phe Ile Leu Ala Leu Leu Ser Cys Leu Thr Val Pro Ala Ser
         50                  55                  60

Ala Val Pro Tyr Arg Asn Ala Ser Gly Ile Tyr His Val Thr Asn Asp
 65              70                  75                  80

Cys Pro Asn Ser Ser Ile Val Tyr Glu Ala Asp Asp Leu Ile Leu His
                 85                  90                  95

Ala Pro Gly Cys Val Pro Cys Val Arg Lys Asp Asn Val Ser Arg Cys
                100                 105                 110

Trp Val Gln Ile Thr Pro Thr Leu Ser Ala Pro Ser Phe Gly Ala Val
            115                 120                 125

Thr Ala Pro Leu Arg Arg Ala Val Asp Tyr Leu Val Gly Gly Ala Ala
```

```
             130                 135                 140
Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asp Cys Asn Cys Ser Ile Tyr Ser Gly His Val Thr Gly His Gln Met
            180                 185                 190

Ala
```

(2) INFORMATION FOR SEQ ID NO: 157:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 3..530

(ix) FEATURE:
        (A) NAME/KEY: mat_peptide
        (B) LOCATION: 3..527

(xi) SEQUENCE DESCRIPTION: SEQ ID NO: 157:

```
CA CCT ACG ACA GCT CTG CTG GTG GCC CAG TTA CTG CGG ATT CCC CAA      47
   Pro Thr Thr Ala Leu Leu Val Ala Gln Leu Leu Arg Ile Pro Gln
    1               5                  10                  15

GTG GTC ATT GAC ATC ATC GCA GGG AGC CAC TGG GGG GTC TTG TTT GCC     95
Val Val Ile Asp Ile Ile Ala Gly Ser His Trp Gly Val Leu Phe Ala
                20                  25                  30

GCC GCA TAC TAT GCA TCG GTG GCT AAC TGG ACC AAG GTC GTG CTG GTC    143
Ala Ala Tyr Tyr Ala Ser Val Ala Asn Trp Thr Lys Val Val Leu Val
            35                  40                  45

TTG TTT CTG TTT GCA GGG GTT GAT GCT ACT ACC CAG ATT TCG GGC GGC    191
Leu Phe Leu Phe Ala Gly Val Asp Ala Thr Thr Gln Ile Ser Gly Gly
        50                  55                  60

TCC AGC GCC CAA ACG ACG TAT GGC ATC GCC TCA TTT ATC ACC CGC GGC    239
Ser Ser Ala Gln Thr Thr Tyr Gly Ile Ala Ser Phe Ile Thr Arg Gly
65                  70                  75

GCG CAG CAG AAA CTG CAG CTC ATA AAT ACC AAC GGA AGC TGG CAC ATC    287
Ala Gln Gln Lys Leu Gln Leu Ile Asn Thr Asn Gly Ser Trp His Ile
80                  85                  90                  95

AAC AGG ACC GCC CTT AAT TGT AAT GAC AGC CTC CAG ACT GGG TTC ATA    335
Asn Arg Thr Ala Leu Asn Cys Asn Asp Ser Leu Gln Thr Gly Phe Ile
                100                 105                 110

GCC GGC CTC TTC TAC TAC CAT AAG TTC AAC TCT TCT GGA TGC CCG GAT    383
Ala Gly Leu Phe Tyr Tyr His Lys Phe Asn Ser Ser Gly Cys Pro Asp
            115                 120                 125

CGG ATG GCT AGC TGT AGG GCC CTT GCC ACT TTT GAC CAG GGC TGG GGA    431
Arg Met Ala Ser Cys Arg Ala Leu Ala Thr Phe Asp Gln Gly Trp Gly
        130                 135                 140

ACT ATC AGC TAT GCC AAC ATA TCG GGT CCC AGT GAT GAC AAA CCA TAT    479
Thr Ile Ser Tyr Ala Asn Ile Ser Gly Pro Ser Asp Asp Lys Pro Tyr
145                 150                 155

TGC TGG CAC TAT CCC CCA CGG CCG TGC GGA GTG GTG CCA GCC CAA GAG    527
```

```
Cys Trp His Tyr Pro Pro Arg Pro Cys Gly Val Val Pro Ala Gln Glu
160                 165                 170                 175

GTC                                                                      530
Val (2) INFORMATION FOR SEQ ID NO: 158:

(i) SEQUENCE CHARACTERISTICS:
        (A) LENGTH: 176 amino acids
        (B) TYPE: amino acid
        (D) TOPOLOGY: linear (ii) MOLECULE TYPE: protein (xi) SEQUENCE DESCRIPTION: SEQ ID NO: 158:

Pro Thr Thr Ala Leu Leu Val Ala Gln Leu Leu Arg Ile Pro Gln Val
1               5                   10                  15

Val Ile Asp Ile Ile Ala Gly Ser His Trp Gly Val Leu Phe Ala Ala
                20                  25                  30

Ala Tyr Tyr Ala Ser Val Ala Asn Trp Thr Lys Val Val Leu Val Leu
            35                  40                  45

Phe Leu Phe Ala Gly Val Asp Ala Thr Thr Gln Ile Ser Gly Gly Ser
50                  55                  60

Ser Ala Gln Thr Thr Tyr Gly Ile Ala Ser Phe Ile Thr Arg Gly Ala
65                  70                  75                  80

Gln Gln Lys Leu Gln Leu Ile Asn Thr Asn Gly Ser Trp His Ile Asn
                85                  90                  95

Arg Thr Ala Leu Asn Cys Asn Asp Ser Leu Gln Thr Gly Phe Ile Ala
                100                 105                 110

Gly Leu Phe Tyr Tyr His Lys Phe Asn Ser Ser Gly Cys Pro Asp Arg
            115                 120                 125

Met Ala Ser Cys Arg Ala Leu Ala Thr Phe Asp Gln Gly Trp Gly Thr
130                 135                 140

Ile Ser Tyr Ala Asn Ile Ser Gly Pro Ser Asp Asp Lys Pro Tyr Cys
145                 150                 155                 160

Trp His Tyr Pro Pro Arg Pro Cys Gly Val Val Pro Ala Gln Glu Val
                165                 170                 175

(2) INFORMATION FOR SEQ ID NO: 159:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..337

(xi) SEQUENCE DESCRIPTION: SEQ ID NO: 159:

C TCG ACC GTT ACC GAA CAT GAC ATA ATG ACC GAA GAG TCC ATT TAC          46
  Ser Thr Val Thr Glu His Asp Ile Met Thr Glu Glu Ser Ile Tyr
  1               5                   10                  15
```

```
CAA TCA TGT GAC TTG CAG CCC GAG GCA CGC GCA GCA ATA CGG TCA CTC          94
Gln Ser Cys Asp Leu Gln Pro Glu Ala Arg Ala Ala Ile Arg Ser Leu
             20                  25                  30

ACC CAA CGC CTC TAC TGT GGA GGC CCC ATG TAC AAC AGC AAG GGG CAA         142
Thr Gln Arg Leu Tyr Cys Gly Gly Pro Met Tyr Asn Ser Lys Gly Gln
                 35                  40                  45

CAG TGT GGT TAT CGC AGA TGC CGC GCC AGC GGC GTT TTC ACC ACC AGT         190
Gln Cys Gly Tyr Arg Arg Cys Arg Ala Ser Gly Val Phe Thr Thr Ser
             50                  55                  60

ATG GGC AAC ACC ATG ACG TGC TAC ATC AAG GCT TTA GCC TCC TGT AGA         238
Met Gly Asn Thr Met Thr Cys Tyr Ile Lys Ala Leu Ala Ser Cys Arg
         65                  70                  75

GCC GCA AGG CTC CGG GAC TGC ACG CTC CTG GTG TGT GGT GAC GAT CTT         286
Ala Ala Arg Leu Arg Asp Cys Thr Leu Leu Val Cys Gly Asp Asp Leu
 80                  85                  90                  95

GTG GCC ATC TGC GAG AGC CAG GGG ACA CAC GAG GAT GAA GCA AGC CTG         334
Val Ala Ile Cys Glu Ser Gln Gly Thr His Glu Asp Glu Ala Ser Leu
                100                 105                 110

AGA GCC                                                                 340
Arg Ala (2) INFORMATION FOR SEQ ID NO: 160:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 160:

Ser Thr Val Thr Glu His Asp Ile Met Thr Glu Glu Ser Ile Tyr Gln
 1               5                  10                  15

Ser Cys Asp Leu Gln Pro Glu Ala Arg Ala Ala Ile Arg Ser Leu Thr
             20                  25                  30

Gln Arg Leu Tyr Cys Gly Gly Pro Met Tyr Asn Ser Lys Gly Gln Gln
         35                  40                  45

Cys Gly Tyr Arg Arg Cys Arg Ala Ser Gly Val Phe Thr Thr Ser Met
     50                  55                  60

Gly Asn Thr Met Thr Cys Tyr Ile Lys Ala Leu Ala Ser Cys Arg Ala
 65                  70                  75                  80

Ala Arg Leu Arg Asp Cys Thr Leu Leu Val Cys Gly Asp Asp Leu Val
                 85                  90                  95

Ala Ile Cys Glu Ser Gln Gly Thr His Glu Asp Glu Ala Ser Leu Arg
            100                 105                 110

Ala (2) INFORMATION FOR SEQ ID NO: 161:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
```

(A) NAME/KEY: CDS
            (B) LOCATION: 2..340

(ix) FEATURE:
            (A) NAME/KEY: mat_peptide
            (B) LOCATION: 2..337

(xi) SEQUENCE DESCRIPTION: SEQ ID NO: 161:

```
C TCA ACC GCC ACC GAA CAT GAC ATA TTG ACT GAA GAG TCC ATA TAC         46
  Ser Thr Ala Thr Glu His Asp Ile Leu Thr Glu Glu Ser Ile Tyr
   1               5                  10                  15

CAA TCA TGT GAC TCG CAG CCC GAC GCA CGC GCA GCA ATA CGG TCA CTC       94
Gln Ser Cys Asp Ser Gln Pro Asp Ala Arg Ala Ala Ile Arg Ser Leu
                 20                  25                  30

ACC CAA CGC TTG TTC TGT GGA GGC CCC ATG TAT AAC AGC AAG GGC CAA      142
Thr Gln Arg Leu Phe Cys Gly Gly Pro Met Tyr Asn Ser Lys Gly Gln
             35                  40                  45

CAA TGT GGT TAT CGC AGA TGC CGC GCC AGC GGC GTC TTC ACC ACC AGT      190
Gln Cys Gly Tyr Arg Arg Cys Arg Ala Ser Gly Val Phe Thr Thr Ser
         50                  55                  60

ATG GGC AAC ACC ATG ACG TGC TAC ATT AAG GCT TTA GCC TCC TGT AGA      238
Met Gly Asn Thr Met Thr Cys Tyr Ile Lys Ala Leu Ala Ser Cys Arg
     65                  70                  75

ACC GCT GGG CTC CGG GAC TAC ACG CTC CTG GTG TGT GGT GAC GAT CAT      286
Thr Ala Gly Leu Arg Asp Tyr Thr Leu Leu Val Cys Gly Asp Asp His
 80                  85                  90                  95

GTG GCC ATC TGC GAG AGC CAG GGG ACA CAC GAG GAT GAA GCG AAC CTG      334
Val Ala Ile Cys Glu Ser Gln Gly Thr His Glu Asp Glu Ala Asn Leu
                100                 105                 110

AGA GCC                                                              340
Arg Ala
```

(2) INFORMATION FOR SEQ ID NO: 162:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 162:

```
Ser Thr Ala Thr Glu His Asp Ile Leu Thr Glu Glu Ser Ile Tyr Gln
 1               5                  10                  15

Ser Cys Asp Ser Gln Pro Asp Ala Arg Ala Ala Ile Arg Ser Leu Thr
             20                  25                  30

Gln Arg Leu Phe Cys Gly Gly Pro Met Tyr Asn Ser Lys Gly Gln Gln
         35                  40                  45

Cys Gly Tyr Arg Arg Cys Arg Ala Ser Gly Val Phe Thr Thr Ser Met
     50                  55                  60

Gly Asn Thr Met Thr Cys Tyr Ile Lys Ala Leu Ala Ser Cys Arg Thr
 65                  70                  75                  80

Ala Gly Leu Arg Asp Tyr Thr Leu Leu Val Cys Gly Asp Asp His Val
                 85                  90                  95

Ala Ile Cys Glu Ser Gln Gly Thr His Glu Asp Glu Ala Asn Leu Arg
            100                 105                 110

Ala
```

(2) INFORMATION FOR SEQ ID NO: 163:

(i) SEQUENCE CHARACTERISTICS:

(A) LENGTH: 499 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..499

(ix) FEATURE:
        (A) NAME/KEY: mat_peptide
        (B) LOCATION: 1..496

(xi) SEQUENCE DESCRIPTION: SEQ ID NO: 163:

```
ATG AGC ACG AAT CCT AAA CTT CAA AGA AAA ACC AAA CGT AAC ACC AAC        48
Met Ser Thr Asn Pro Lys Leu Gln Arg Lys Thr Lys Arg Asn Thr Asn
 1               5                  10                  15

CGC CGC CCC ATG GAC GTT AAG TTC CCG GGT GGT GGC CAG ATC GTT GGC        96
Arg Arg Pro Met Asp Val Lys Phe Pro Gly Gly Gly Gln Ile Val Gly
                20                  25                  30

GGA GTT TAC TTG TTG CCG CGC AGG GGC CCT AGG TTG GGT GTG CGC GCG       144
Gly Val Tyr Leu Leu Pro Arg Arg Gly Pro Arg Leu Gly Val Arg Ala
            35                  40                  45

ACT CGG AAG ACT TCG GAG CGG TCG CAA CCT CGT GGG AGG CGC CAA CCT       192
Thr Arg Lys Thr Ser Glu Arg Ser Gln Pro Arg Gly Arg Arg Gln Pro
    50                  55                  60

ATC CCC AAG GCG CGC CGA TCC GAG GGC AGA TCC TGG GCG CAG CCC GGG       240
Ile Pro Lys Ala Arg Arg Ser Glu Gly Arg Ser Trp Ala Gln Pro Gly
 65                 70                  75                  80

TAT CCT TGG CCC CTT TAC GGC AAT GAG GGC TGT GGG TGG GCA GGG TGG       288
Tyr Pro Trp Pro Leu Tyr Gly Asn Glu Gly Cys Gly Trp Ala Gly Trp
                85                  90                  95

CTC CTG TCC CCT CGC GGG TCT CGG CCG TCT TGG GGC CCT AAT GAT CCC       336
Leu Leu Ser Pro Arg Gly Ser Arg Pro Ser Trp Gly Pro Asn Asp Pro
            100                 105                 110

CGG CGG AGG TCC CGC AAC CTG GGT AAG GTC ATC GAT ACC CTA ACA TGC       384
Arg Arg Arg Ser Arg Asn Leu Gly Lys Val Ile Asp Thr Leu Thr Cys
    115                 120                 125

GGC TTC GCC GAC CTC ATG GGA TAC ATC CCG CTT GTA GGC GCC CCC GTG       432
Gly Phe Ala Asp Leu Met Gly Tyr Ile Pro Leu Val Gly Ala Pro Val
130                 135                 140

GGT GGC GTC GCC AGA GCC CTG GCA CAC GGT GTT AGG GCT GTG GAA GAC       480
Gly Gly Val Ala Arg Ala Leu Ala His Gly Val Arg Ala Val Glu Asp
145                 150                 155                 160

GGG ATC AAC TAC GCA ACA G                                             499
Gly Ile Asn Tyr Ala Thr
                165
```

(2) INFORMATION FOR SEQ ID NO: 164:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO: 164:

```
Met Ser Thr Asn Pro Lys Leu Gln Arg Lys Thr Lys Arg Asn Thr Asn
 1               5                  10                  15
```

```
Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Val Glu Asp
145                 150                 155                 160

Gly Ile Asn Tyr Ala Thr
                165

(2) INFORMATION FOR SEQ ID NO: 165:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 165:

ATGAGCACGA ATCCTAAACC TCAAAGAAAA ACCAAACGTA ACACCAACCG CCGCCCTATG      60

GACGTTAAGT TCCCAGGCGG TGGTCAGATC GTTGGCGGAG TTTACTTGTT GCCGCGCAGG     120

GGCCCCAGGT TGGGTGTGCG CGCGACTCGG AAGACTTCGG AGCGGTCGCA ACCTCGTGGG     180

AGGCGCCAAC CTATCCCCAA GGCGCGCCGA ACCGAGGGCA GATCCTGGGC GCAGCCCGGG     240

TATCCTTGGC CCCTTTACGG CAATGAGGGC TGTGGGTGGG CAGGGTGGCT CCTGTCCCCT     300

CGCGGNTCTC GGNCGTCTTG GGCCCCAAT GATCCCCGGN GGAGATCCCG CAACTTGGGT      360

AAGGTCATCG ATACCCTAAC ATGCGGCTTC GCCGACCTCA TGGGATACAT CCCGCTTGTA     420

GGCGCCCCCG TGGGTGGCGT CGCCAGGGCC CTGGCACATG GTGTTAGGGC TGTGGAAGAC     480

GGGATCAATT ATGCAACAG                                                  499

(2) INFORMATION FOR SEQ ID NO: 166:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 166:
```

```
Met Ser Thr Asn Pro Lys Pro Gln Arg Lys Thr Lys Arg Asn Thr Asn
1               5                  10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                      55                      60

Ile Pro Lys Ala Arg Arg Thr Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Xaa Ser Arg Xaa Ser Trp Gly Pro Asn Asp Pro
                100                 105                 110

Arg Xaa Arg Ser Arg Asn Leu Gly Lys Val Ile Asp Thr Leu
        115                 120                 125
```

(2) INFORMATION FOR SEQ ID NO: 167:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..579

(xi) SEQUENCE DESCRIPTION: SEQ ID NO: 167:

```
ACA TGC GGC TTC GCC GAC CTC ATG GGA TAC ATC CCG CTT GTA GGC GCC      48
Thr Cys Gly Phe Ala Asp Leu Met Gly Tyr Ile Pro Leu Val Gly Ala
1               5                  10                  15

CCC GTG GGT GGC GTC GCC AGG GCC CTG GCA CAT GGT GTT AGG GCT GTG      96
Pro Val Gly Gly Val Ala Arg Ala Leu Ala His Gly Val Arg Ala Val
                20                  25                  30

GAA GAC GGG ATC AAT TAT GCA ACA GGG AAC TTT CCC GGT TGC TCC TTT     144
Glu Asp Gly Ile Asn Tyr Ala Thr Gly Asn Leu Pro Gly Cys Ser Phe
            35                  40                  45

TCT ATC TTC CTC TTG GCG CTC CTC TCG TGC CTG ACT GTT CCC ACA TCG     192
Ser Ile Phe Leu Leu Ala Leu Leu Ser Cys Leu Thr Val Pro Thr Ser
50                  55                  60

GCC GTT AAC TAT CGC AAT GCT TCG GGC ATT TAT CAC ATC ACC AAT GAC     240
Ala Val Asn Tyr Arg Asn Ala Ser Gly Ile Tyr His Ile Thr Asn Asp
65                  70                  75                  80

TGC CCG AAT GCA AGC ATA GTG TAC GAG ACC GAA AAT CAC ATC TTA CAC     288
Cys Pro Asn Ala Ser Ile Val Tyr Glu Thr Glu Asn His Ile Leu His
                85                  90                  95

CTC CCA GGG TGC GTA CCC TGT GTG AGG ACT GGG AAC CAG TCG CGG TGT     336
Leu Pro Gly Cys Val Pro Cys Val Arg Thr Gly Asn Gln Ser Arg Cys
            100                 105                 110

TGG GTG GCC CTC ACT CCC ACA GTA GCG TCG CCA TAC GCC GGT GCT CCG     384
Trp Val Ala Leu Thr Pro Thr Val Ala Ser Pro Tyr Ala Gly Ala Pro
```

```
                  115                 120                 125
CTT GAG CCC TTG CGG CGT CAT GTG GAC CTG ATG GTA GGT GCT GCC ACC    432
Leu Glu Pro Leu Arg Arg His Val Asp Leu Met Val Gly Ala Ala Thr
    130                 135                 140

ATG TGT TCC GCC CTC TAC ATC GGC GAC TTG TGC GGT GGC TTA TTC TTG    480
Met Cys Ser Ala Leu Tyr Ile Gly Asp Leu Cys Gly Gly Leu Phe Leu
145                 150                 155                 160

GTG GGC CAA ATG TTC ACC TTC CAA CCG CGA CGT CAC TGG ACC ACT CAG    528
Val Gly Gln Met Phe Thr Phe Gln Pro Arg Arg His Trp Thr Thr Gln
                    165                 170                 175

GAC TGC AAT TGT TCC ATC TAC ACG GGC CAC ATT ACG GGT CAT CGG ATG    576
Asp Cys Asn Cys Ser Ile Tyr Thr Gly His Ile Thr Gly His Arg Met
            180                 185                 190

GCA                                                                579
Ala
```

(2) INFORMATION FOR SEQ ID NO: 168:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 168:

```
Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
        50                  55                  60

Ala Val Asn Tyr Arg Asn Ala Ser Gly Ile Tyr His Ile Thr Asn Asp
 65                  70                  75                  80

Cys Pro Asn Ala Ser Ile Val Tyr Glu Thr Glu Asn His Ile Leu His
                 85                  90                  95

Leu Pro Gly Cys Val Pro Cys Val Arg Thr Gly Asn Gln Ser Arg Cys
            100                 105                 110

Trp Val Ala Leu Thr Pro Thr Val Ala Ser Pro Tyr Ala Gly Ala Pro
        115                 120                 125

Leu Glu Pro Leu Arg Arg His Val Asp Leu Met Val Gly Ala Ala Thr
    130                 135                 140

Met Cys Ser Ala Leu Tyr Ile Gly Asp Leu Cys Gly Gly Leu Phe Leu
145                 150                 155                 160

Val Gly Gln Met Phe Thr Phe Gln Pro Arg Arg His Trp Thr Thr Gln
                    165                 170                 175

Asp Cys Asn Cys Ser Ile Tyr Thr Gly His Ile Thr Gly His Arg Met
            180                 185                 190

Ala
```

(2) INFORMATION FOR SEQ ID NO: 169:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 1..579

(ix) FEATURE:
    (A) NAME/KEY: mat_peptide
    (B) LOCATION: 1..576

(xi) SEQUENCE DESCRIPTION: SEQ ID NO: 169:

```
ACA TGC GGC TTC GCC GAC CTC ATG GGA TAC ATC CCG CTT GTA GGC GCC      48
Thr Cys Gly Phe Ala Asp Leu Met Gly Tyr Ile Pro Leu Val Gly Ala
  1               5                  10                  15

CCC GTG GGT GGC GTC GCC AGA GCC CTG GCA CAC GGT GTT AGG GCT GTG      96
Pro Val Gly Gly Val Ala Arg Ala Leu Ala His Gly Val Arg Ala Val
             20                  25                  30

GAA GAC GGG ATC AAC TAC GCA ACA GGG AAT CTC CCC GGT TGC TCC TTT     144
Glu Asp Gly Ile Asn Tyr Ala Thr Gly Asn Leu Pro Gly Cys Ser Phe
         35                  40                  45

TCT ATC TTC CTC TTG GCA CTT CTC TCG TGC CTC ACT GTT CCC GCG TCG     192
Ser Ile Phe Leu Leu Ala Leu Leu Ser Cys Leu Thr Val Pro Ala Ser
     50                  55                  60

GGC GTT AAC TAT CGC AAT GCT TCG GGC GTT TAT CAC ATC ACC AAC GAC     240
Gly Val Asn Tyr Arg Asn Ala Ser Gly Val Tyr His Ile Thr Asn Asp
 65                  70                  75                  80

TGC CCG AAT GCG AGC ATA GTG TAC GAG ACC GAC AAT CAC ATC TTA CAC     288
Cys Pro Asn Ala Ser Ile Val Tyr Glu Thr Asp Asn His Ile Leu His
                 85                  90                  95

CTC CCA GGG TGC GTA CCC TGT GTG AAG ACC GGG AAC CAG TCG CGG TGT     336
Leu Pro Gly Cys Val Pro Cys Val Lys Thr Gly Asn Gln Ser Arg Cys
            100                 105                 110

TGG GTG GCC CTC ACT CCC ACA GTG GCG TCG CCT TAC GTC GGT GCT CCG     384
Trp Val Ala Leu Thr Pro Thr Val Ala Ser Pro Tyr Val Gly Ala Pro
        115                 120                 125

CTC GAG CCC TTG CGG CGC CAT GTG GAC CTG ATG GTA GGT GCT GCC ACC     432
Leu Glu Pro Leu Arg Arg His Val Asp Leu Met Val Gly Ala Ala Thr
    130                 135                 140

GTG TGC TCC GCC CTC TAC GTC GGC GAC CTG TGC GGT GGC TTA TTC TTG     480
Val Cys Ser Ala Leu Tyr Val Gly Asp Leu Cys Gly Gly Leu Phe Leu
145                 150                 155                 160

GTA GGC CAA ATG TTC ACC TTC CAA CCG CGA CGC CAC TGG ACG ACC CAG     528
Val Gly Gln Met Phe Thr Phe Gln Pro Arg Arg His Trp Thr Thr Gln
                165                 170                 175

GAC TGT AAT TGT TCC ATC TAC GCA GGG CAT ATT ACG GGC CAT CGG ATG     576
Asp Cys Asn Cys Ser Ile Tyr Ala Gly His Ile Thr Gly His Arg Met
            180                 185                 190

GCT                                                                 579
Ala
```

(2) INFORMATION FOR SEQ ID NO: 170:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 170:

-continued

```
Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
             20                  25                  30

Glu Asp Gly Ile Asn Tyr Ala Thr Gly Asn Leu Pro Gly Cys Ser Phe
         35                  40                  45

Ser Ile Phe Leu Leu Ala Leu Leu Ser Cys Leu Thr Val Pro Ala Ser
     50                  55                  60

Gly Val Asn Tyr Arg Asn Ala Ser Gly Val Tyr His Ile Thr Asn Asp
 65              70                  75                  80

Cys Pro Asn Ala Ser Ile Val Tyr Glu Thr Asp Asn His Ile Leu His
                 85                  90                  95

Leu Pro Gly Cys Val Pro Cys Val Lys Thr Gly Asn Gln Ser Arg Cys
                100                 105                 110

Trp Val Ala Leu Thr Pro Thr Val Ala Ser Pro Tyr Val Gly Ala Pro
                115                 120                 125

Leu Glu Pro Leu Arg Arg His Val Asp Leu Met Val Gly Ala Ala Thr
    130                 135                 140

Val Cys Ser Ala Leu Tyr Val Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Ala Gly His Ile Thr Gly His Arg Met
                180                 185                 190

Ala
```

(2) INFORMATION FOR SEQ ID NO: 171:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 171:

```
ACA TGC GGC TTC GCC GAC CTC ATG GGA TAC ATC CCG CTT GTG GGC GCC      48
Thr Cys Gly Phe Ala Asp Leu Met Gly Tyr Ile Pro Leu Val Gly Ala
  1               5                  10                  15

CCT GTT GGT GGC GTC GCC AGA GCC CTT GCG CAC GGC GTC AGG GCT GTG      96
Pro Val Gly Gly Val Ala Arg Ala Leu Ala His Gly Val Arg Ala Val
             20                  25                  30

GAA GAC GGG ATT AAC TAT GCA ACA GGG AAC CTT CCT GGT TGC TCC TTT     144
Glu Asp Gly Ile Asn Tyr Ala Thr Gly Asn Leu Pro Gly Cys Ser Phe
         35                  40                  45

TCT ATC TTC CTT CTG GCA CTT CTC TCG TGC CTG ACT GTC CCC GCC TCG     192
Ser Ile Phe Leu Leu Ala Leu Leu Ser Cys Leu Thr Val Pro Ala Ser
     50                  55                  60
```

```
GCT GTG CAT TAT CAC AAC ACC TCG GGC ATC TAC CAC CTC ACC AAT GAC    240
Ala Val His Tyr His Asn Thr Ser Gly Ile Tyr His Leu Thr Asn Asp
 65                  70                  75                  80

TGC CCT AAC TCT AGC ATA GTC TTT GAG GCA GTC CAT CAC ATC TTG CAC    288
Cys Pro Asn Ser Ser Ile Val Phe Glu Ala Val His His Ile Leu His
                 85                  90                  95

CTT CCA GGA TGC GTC CCT TGT GTA AGA ACT GGG AAC CAG TCT CGG TGC    336
Leu Pro Gly Cys Val Pro Cys Val Arg Thr Gly Asn Gln Ser Arg Cys
            100                 105                 110

TGG GTA GCC TTG ACC CCC ACG CTG GCC GCG CCA TAC CTT GGC GCT CCA    384
Trp Val Ala Leu Thr Pro Thr Leu Ala Ala Pro Tyr Leu Gly Ala Pro
        115                 120                 125

CTC GAG TCC ATG CGG CGT CAC GTG GAT TTG ATG GTG GGC ACT GCT ACA    432
Leu Glu Ser Met Arg Arg His Val Asp Leu Met Val Gly Thr Ala Thr
130                 135                 140

TTG TGC TCA GCA CTC TAC GTT GGG GAC CTG TGC GGG GGC ATA TTC CTA    480
Leu Cys Ser Ala Leu Tyr Val Gly Asp Leu Cys Gly Gly Ile Phe Leu
145                 150                 155                 160

GCG GGC CAG ATG TTC ACC TTC CGG CCC CGC CTC CAT TGG ACC ACC CAG    528
Ala Gly Gln Met Phe Thr Phe Arg Pro Arg Leu His Trp Thr Thr Gln
                165                 170                 175

GAG TGC AAT TGT TCC ACC TAT CCG GGC CAC ATC ACG GGT CAT AGA ATG    576
Glu Cys Asn Cys Ser Thr Tyr Pro Gly His Ile Thr Gly His Arg Met
            180                 185                 190

GCG                                                                579
Ala (2) INFORMATION FOR SEQ ID NO: 172:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 172:

Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
        50                  55                  60

Ala Val His Tyr His Asn Thr Ser Gly Ile Tyr His Leu Thr Asn Asp
 65                  70                  75                  80

Cys Pro Asn Ser Ser Ile Val Phe Glu Ala Val His His Ile Leu His
                 85                  90                  95

Leu Pro Gly Cys Val Pro Cys Val Arg Thr Gly Asn Gln Ser Arg Cys
            100                 105                 110

Trp Val Ala Leu Thr Pro Thr Leu Ala Ala Pro Tyr Leu Gly Ala Pro
        115                 120                 125

Leu Glu Ser Met Arg Arg His Val Asp Leu Met Val Gly Thr Ala Thr
130                 135                 140

Leu Cys Ser Ala Leu Tyr Val Gly Asp Leu Cys Gly Gly Ile Phe Leu
145                 150                 155                 160

Ala Gly Gln Met Phe Thr Phe Arg Pro Arg Leu His Trp Thr Thr Gln
```

```
                          165                 170                 175
Glu Cys Asn Cys Ser Thr Tyr Pro Gly His Ile Thr Gly His Arg Met
                180                 185                 190
Ala
```

(2) INFORMATION FOR SEQ ID NO: 173:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 173:

```
ACG TGC GGT TCC GCC GAC CTC ATG GGA TAC ATC CCG CTC GTA GGC GCC      48
Thr Cys Gly Ser Ala Asp Leu Met Gly Tyr Ile Pro Leu Val Gly Ala
 1               5                  10                  15

CCT GTG GGT GGC GTC GCC AGG GCC TTG GCG CAT GGC GTC AGG GCT GTG      96
Pro Val Gly Gly Val Ala Arg Ala Leu Ala His Gly Val Arg Ala Val
                20                  25                  30

GAG GAC GGG ATA AAC TAT GCA ACA GGG AAC CTT CCT GGT TGC TCT TTT     144
Glu Asp Gly Ile Asn Tyr Ala Thr Gly Asn Leu Pro Gly Cys Ser Phe
            35                  40                  45

TCT ATC TTC CTT CTG GCA CTT CTC TCG TGC CTG ACT GTC CCC GCC TCA     192
Ser Ile Phe Leu Leu Ala Leu Leu Ser Cys Leu Thr Val Pro Ala Ser
        50                  55                  60

GCT GTG CAT TAT CAC AAC ACC TCG GGC ATC TAT CAC ATC ACT AAT GAC     240
Ala Val His Tyr His Asn Thr Ser Gly Ile Tyr His Ile Thr Asn Asp
 65                 70                  75                  80

TGC CCT AAC TCT AGC ATA GTC TTT GAG GCA GAG CAT CAC ATC TTG CAT     288
Cys Pro Asn Ser Ser Ile Val Phe Glu Ala Glu His His Ile Leu His
                85                  90                  95

CTT CCA GGA TGC GTC CCC TGT GTG AGA ACT GGG AAC CAG TCA CGA TGC     336
Leu Pro Gly Cys Val Pro Cys Val Arg Thr Gly Asn Gln Ser Arg Cys
            100                 105                 110

TGG ATA GCC TTG ACC CCT ACG TTG GCC GCG CCA CAC ATT GGC GCT CCA     384
Trp Ile Ala Leu Thr Pro Thr Leu Ala Ala Pro His Ile Gly Ala Pro
        115                 120                 125

CTT GAG TCC ATG CGA CGT CAT GTG GAT TTG ATG GTA GGC ACT GCC ACA     432
Leu Glu Ser Met Arg Arg His Val Asp Leu Met Val Gly Thr Ala Thr
 130                135                 140

TTG TGC TCC GCA CTC TAC ATT GGA GAT CTG TGC GGA GGC ATA TTT CTA     480
Leu Cys Ser Ala Leu Tyr Ile Gly Asp Leu Cys Gly Gly Ile Phe Leu
145                 150                 155                 160

GTG GGC CAG ATG TTC AAC TTC AGG CCC CGC CTG CAC TGG ACC ACC CAG     528
Val Gly Gln Met Phe Asn Phe Arg Pro Arg Leu His Trp Thr Thr Gln
                165                 170                 175

GAG TGC AAT TGT TCC ATC TAT CCA GGC CAC ATC ACG GGT CAC AGA ATG     576
Glu Cys Asn Cys Ser Ile Tyr Pro Gly His Ile Thr Gly His Arg Met
            180                 185                 190
```

```
GCG                                                                579
Ala
```

(2) INFORMATION FOR SEQ ID NO: 174:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 174:

```
Thr Cys Gly Ser Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
             20                  25                  30

Glu Asp Gly Ile Asn Tyr Ala Thr Gly Asn Leu Pro Gly Cys Ser Phe
         35                  40                  45

Ser Ile Phe Leu Leu Ala Leu Leu Ser Cys Leu Thr Val Pro Ala Ser
     50                  55                  60

Ala Val His Tyr His Asn Thr Ser Gly Ile Tyr His Ile Thr Asn Asp
 65                  70                  75                  80

Cys Pro Asn Ser Ser Ile Val Phe Glu Ala Glu His His Ile Leu His
                 85                  90                  95

Leu Pro Gly Cys Val Pro Cys Val Arg Thr Gly Asn Gln Ser Arg Cys
                100                 105                 110

Trp Ile Ala Leu Thr Pro Thr Leu Ala Ala Pro His Ile Gly Ala Pro
            115                 120                 125

Leu Glu Ser Met Arg Arg His Val Asp Leu Met Val Gly Thr Ala Thr
        130                 135                 140

Leu Cys Ser Ala Leu Tyr Ile Gly Asp Leu Cys Gly Gly Ile Phe Leu
145                 150                 155                 160

Val Gly Gln Met Phe Asn Phe Arg Pro Arg Leu His Trp Thr Thr Gln
                165                 170                 175

Glu Cys Asn Cys Ser Ile Tyr Pro Gly His Ile Thr Gly His Arg Met
                180                 185                 190

Ala
```

(2) INFORMATION FOR SEQ ID NO: 175:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 175:

-continued

```
ACG TGC GGC TTT GCC GAC CTC ATG GGA TAC ATC CCG CTC GTG GGC GCC        48
Thr Cys Gly Phe Ala Asp Leu Met Gly Tyr Ile Pro Leu Val Gly Ala
  1               5                  10                  15

CCT GTG GGT GGC GTC GCC AGG GCC TTG GCA CAT GGT GTC AGG GCC GTG        96
Pro Val Gly Gly Val Ala Arg Ala Leu Ala His Gly Val Arg Ala Val
                 20                  25                  30

GAG GAC GGG ATT AAC TAT GCA ACA GGG AAT CTT CCC GGT TGC TCC TTT       144
Glu Asp Gly Ile Asn Tyr Ala Thr Gly Asn Leu Pro Gly Cys Ser Phe
             35                  40                  45

TCT ATC TTC CTT CTA GCA CTT CTC TCG TGC TTG ACT GTC CCG GCC TCG       192
Ser Ile Phe Leu Leu Ala Leu Leu Ser Cys Leu Thr Val Pro Ala Ser
     50                  55                  60

GCG CAG CAC TAC CGG AAC ATC TCG GGC ATT TAT CAC GTC ACC AAT GAC       240
Ala Gln His Tyr Arg Asn Ile Ser Gly Ile Tyr His Val Thr Asn Asp
 65                  70                  75                  80

TGC CCG AAC TCT AGT ATA GTG TAT GAA GCT GAC CAT CAT ATC ATG CAT       288
Cys Pro Asn Ser Ser Ile Val Tyr Glu Ala Asp His His Ile Met His
                 85                  90                  95

CTA CCA GGG TGT GTG CCT TGC GTG AGA ACC GGG AAC ACC TCG CGC TGC       336
Leu Pro Gly Cys Val Pro Cys Val Arg Thr Gly Asn Thr Ser Arg Cys
            100                 105                 110

TGG GTT CCT TTA ACA CCC ACT GTG GCT GCC CCC TAT GTT GGC GCG CCG       384
Trp Val Pro Leu Thr Pro Thr Val Ala Ala Pro Tyr Val Gly Ala Pro
            115                 120                 125

CTC GAA TCC ATG CGG CGG CAC GTG GAC TTA ATG GTG GGT GCC GCC ACC       432
Leu Glu Ser Met Arg Arg His Val Asp Leu Met Val Gly Ala Ala Thr
        130                 135                 140

GTC TGC TCG GCC CTG TAC ATC GGA GAC CTT TGC GGA GGT GTC TTC CTG       480
Val Cys Ser Ala Leu Tyr Ile Gly Asp Leu Cys Gly Gly Val Phe Leu
145                 150                 155                 160

GTC GGG CAG ATG TTC ACC TTC CGG CCG CGC CGC CAT TGG ACT ACC CAG       528
Val Gly Gln Met Phe Thr Phe Arg Pro Arg Arg His Trp Thr Thr Gln
                165                 170                 175

GAC TGC AAC TGC TCT ATC TAT GAT GGC CAC ATC ACC GGC CAT AGA ATG       576
Asp Cys Asn Cys Ser Ile Tyr Asp Gly His Ile Thr Gly His Arg Met
            180                 185                 190

GCT                                                                   579
Ala
```

(2) INFORMATION FOR SEQ ID NO: 176:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 176:

```
Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
             35                  40                  45

Ser Ile Phe Leu Leu Ala Leu Leu Ser Cys Leu Thr Val Pro Ala Ser
     50                  55                  60

Ala Gln His Tyr Arg Asn Ile Ser Gly Ile Tyr His Val Thr Asn Asp
 65                  70                  75                  80

Cys Pro Asn Ser Ser Ile Val Tyr Glu Ala Asp His His Ile Met His
```

-continued

```
              85                   90                   95
Leu Pro Gly Cys Val Pro Cys Val Arg Thr Gly Asn Thr Ser Arg Cys
            100                  105                  110

Trp Val Pro Leu Thr Pro Thr Val Ala Ala Pro Tyr Val Gly Ala Pro
        115                  120                  125

Leu Glu Ser Met Arg Arg His Val Asp Leu Met Val Gly Ala Ala Thr
    130                  135                  140

Val Cys Ser Ala Leu Tyr Ile Gly Asp Leu Cys Gly Val Phe Leu
145                  150                  155                  160

Val Gly Gln Met Phe Thr Phe Arg Pro Arg Arg His Trp Thr Thr Gln
            165                  170                  175

Asp Cys Asn Cys Ser Ile Tyr Asp Gly His Ile Thr Gly His Arg Met
        180                  185                  190

Ala
```

(2) INFORMATION FOR SEQ ID NO: 177:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 177:

```
ACG TGC GGG TTC GCC GAC CTC ATG GGA TAC ATC CCG CTC GTG GGC GCT        48
Thr Cys Gly Phe Ala Asp Leu Met Gly Tyr Ile Pro Leu Val Gly Ala
  1               5                  10                  15

CCA GTA GGA GGC GTC GCC AGA GCC TTG GCG CAT GGC GTC AGG GCT GTG        96
Pro Val Gly Gly Val Ala Arg Ala Leu Ala His Gly Val Arg Ala Val
             20                  25                  30

GAG GAC GGG ATC AAT TAC GCA ACA GGG AAC CTT CCC GGC TGC TCC TTT       144
Glu Asp Gly Ile Asn Tyr Ala Thr Gly Asn Leu Pro Gly Cys Ser Phe
         35                  40                  45

TCT ATC TTC CTC TTG GTA CTT CTC TCG CGC CTA ACT GTC CCA GCG TCT       192
Ser Ile Phe Leu Leu Val Leu Leu Ser Arg Leu Thr Val Pro Ala Ser
 50                  55                  60

GCT CAG CAC TAC CGG AAT GCA TCG GGC ATC TAC CAT GTC ACC AAC GAC       240
Ala Gln His Tyr Arg Asn Ala Ser Gly Ile Tyr His Val Thr Asn Asp
 65                  70                  75                  80

TGC CCG AAC TCC AGT ATT GTG TAT GAA GCC GAC CAT CAC ATC ATG CAC       288
Cys Pro Asn Ser Ser Ile Val Tyr Glu Ala Asp His His Ile Met His
             85                  90                  95

CTA CCC GGG TGT GTG CCC TGT GTA AGA ACT GGG AAT GTC TCG CGT TGC       336
Leu Pro Gly Cys Val Pro Cys Val Arg Thr Gly Asn Val Ser Arg Cys
            100                  105                  110

TGG ATT CCT TTA ACA CCC ACT GTA GCC GTC CCC TAC CTC GGG GCT CCA       384
Trp Ile Pro Leu Thr Pro Thr Val Ala Val Pro Tyr Leu Gly Ala Pro
        115                  120                  125
```

```
CTT ACG TCT GTA CGG CAG CAT GTG GAC CTG ATG GTG GGG GCG GCC ACC    432
Leu Thr Ser Val Arg Gln His Val Asp Leu Met Val Gly Ala Ala Thr
    130                 135                 140

TTA TGC TCT GCC CTC TAC ATC GGA GAC CAT TGC GGA GGT GTC TTC TTG    480
Leu Cys Ser Ala Leu Tyr Ile Gly Asp His Cys Gly Gly Val Phe Leu
145                 150                 155                 160

GCA GGG CAG ATG GTC AGT TTC CAA CCC CGG CGT CAT TGG ACT ACC CAG    528
Ala Gly Gln Met Val Ser Phe Gln Pro Arg Arg His Trp Thr Thr Gln
                165                 170                 175

GAT TGC AAC TGT TCC ATC TAT GTG GGC CAC ATC ACC GGC CAC AGG ATG    576
Asp Cys Asn Cys Ser Ile Tyr Val Gly His Ile Thr Gly His Arg Met
            180                 185                 190

GCC                                                                579
Ala
```

(2) INFORMATION FOR SEQ ID NO: 178:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 178:

```
Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Val Leu Leu Ser Arg Leu Thr Val Pro Ala Ser
        50                  55                  60

Ala Gln His Tyr Arg Asn Ala Ser Gly Ile Tyr His Val Thr Asn Asp
 65                 70                  75                  80

Cys Pro Asn Ser Ser Ile Val Tyr Glu Ala Asp His His Ile Met His
                85                  90                  95

Leu Pro Gly Cys Val Pro Cys Val Arg Thr Gly Asn Val Ser Arg Cys
                100                 105                 110

Trp Ile Pro Leu Thr Pro Thr Val Ala Val Pro Tyr Leu Gly Ala Pro
            115                 120                 125

Leu Thr Ser Val Arg Gln His Val Asp Leu Met Val Gly Ala Ala Thr
        130                 135                 140

Leu Cys Ser Ala Leu Tyr Ile Gly Asp His Cys Gly Gly Val Phe Leu
145                 150                 155                 160

Ala Gly Gln Met Val Ser Phe Gln Pro Arg Arg His Trp Thr Thr Gln
                165                 170                 175

Asp Cys Asn Cys Ser Ile Tyr Val Gly His Ile Thr Gly His Arg Met
            180                 185                 190

Ala
```

(2) INFORMATION FOR SEQ ID NO: 179:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(xi) SEQUENCE DESCRIPTION: SEQ ID NO: 179:

```
ACCTGCGGCT TCGCCGACCT CATGGGATAC ATCCCGCTCG TAGGCGCCCC CGTGGGAGGC    60

GTCGCCAGAR CTCTGGCGCA TGGCGTCAGG GCTCTGGAAG ACGGGATCAA TTATGCAACA   120

GGGAATCTTC CTGGTTGCTC TTTCTCTATC TCCCTTCTTG AACTTCTCTC GTGCCTGACT   180

GTTCCCGCCT CAGCCATCCA CTATCGCAAT GCTTCGGACG GTTATTATAT CACCAATGAT   240

TGCCCGAACT CTAGCATAGT GTATGAAGCC GAGAACCACA TCTTGCACCT TCCGGGGTGT   300

ATACCCTGTG TGAAGACCGG GAATCAGTCG CGGTGCTGGG TGGCTCTCAC CCCCACGCTG   360

GCGGCCCCAC ACCTACGTGC TCCGCTTTCG TCCTTACGGG CGCATGTGGA CCTAATGGTG   420

GGGGCCGCCA CGGCATGCTC CGCTTTTTAC ATTGGAGATC TGTGCGGGGG TGTGTTTTTG   480

GCGGGCCAAC TGTTCACTAT CCGGCCACGC ATTCATGAAA CCACTCAGGA CTGCAATTGC   540

TCCATCTACT CAGGGCACAT CACGGGTNNN NNNNNNNNN                          579
```

(2) INFORMATION FOR SEQ ID NO: 180:

(i) SEQUENCE CHARACTERISTICS:
        (A) LENGTH: 193 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 180:

```
Thr Cys Gly Phe Ala Asp Leu Met Gly Tyr Ile Pro Leu Val Gly Ala
 1               5                  10                  15

Pro Val Gly Gly Val Ala Arg Xaa Leu Ala His Gly Val Arg Ala Leu
            20                  25                  30

Glu Asp Gly Ile Asn Tyr Ala Thr Gly Asn Leu Pro Gly Cys Ser Phe
        35                  40                  45

Ser Ile Ser Leu Leu Glu Leu Leu Ser Cys Leu Thr Val Pro Ala Ser
    50                  55                  60

Ala Ile His Tyr Arg Asn Ala Ser Asp Gly Tyr Tyr Ile Thr Asn Asp
65                  70                  75                  80

Cys Pro Asn Ser Ser Ile Val Tyr Glu Ala Glu Asn His Ile Leu His
                85                  90                  95

Leu Pro Gly Cys Ile Pro Cys Val Lys Thr Gly Asn Gln Ser Arg Cys
            100                 105                 110

Trp Val Ala Leu Thr Pro Thr Leu Ala Ala Pro His Leu Arg Ala Pro
        115                 120                 125

Leu Ser Ser Leu Arg Ala His Val Asp Leu Met Val Gly Ala Ala Thr
    130                 135                 140

Ala Cys Ser Ala Phe Tyr Ile Gly Asp Leu Cys Gly Gly Val Phe Leu
145                 150                 155                 160

Ala Gly Gln Leu Phe Thr Ile Arg Pro Arg Ile His Glu Thr Thr Gln
                165                 170                 175

Asp Cys Asn Cys Ser Ile Tyr Ser Gly His Ile Thr Gly Xaa Xaa Xaa
            180                 185                 190
```

Xaa (2) INFORMATION FOR SEQ ID NO: 181:

(i) SEQUENCE CHARACTERISTICS:
       (A) LENGTH: 579 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (ix) FEATURE:
       (A) NAME/KEY: CDS
       (B) LOCATION: 1..578

(xi) SEQUENCE DESCRIPTION: SEQ ID NO: 181:

```
GCGTGCGGCT TCGCCGATCT CATGGGATAC ATCCCGCTCG TAGGCGCCCC CGTGGGTGGC    60
GTCGCCAGAG CCCTGGCGCA CGGTGTTAGG GCTGTGGAGG ACGGGATTAA CTACGCAACA   120
GGGAATCTTC CTGGTTGCTC TTTCTCTATC TNCCTTCTGG CACTTCTCTC GTGCCTGACT   180
GTCCCGGCCT CGGCTCAGCA CTACCGGAAT GTCTCGGGCA TCTACCACGT CACCAATGAT   240
TGCCCGAATT CCAGCATAGT GTATGAAGCC GATCACCACA TCATGCACTT ACCAGGGTGC   300
ATACCCTGCG TGAGGACCGG GAACGTTTCG CGCTGCTGGG TATCTCTGAC ACCTACTGTG   360
GCTGCTCCCT ACCTCGGGGC TCCGCTTACG TCGCTACGGC GGCATGTGGA TTTGATGGTG   420
GGTGCAGCCA CCCTTTGCTC TGCCCTCTAC GTCGGAGACC TCTGTGGAGG TGTCTTCCTA   480
GTGGGACAGA TGTTCACCTT CCAGCCGCGC CGCCACTGGA CCACTCAGGA CTGCAACTGC   540
TCCATTTACG TCGGCCACAT CACAGGCCAC AGAATGGCT                          579
```

(2) INFORMATION FOR SEQ ID NO: 182:

(i) SEQUENCE CHARACTERISTICS:
       (A) LENGTH: 193 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 182:

```
Ala Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Xaa Leu Leu Ala Leu Leu Ser Cys Leu Thr Val Pro Ala Ser
    50                  55                  60

Ala Gln His Tyr Arg Asn Val Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Cys Ile Pro Cys Val Arg Thr Gly Asn Val Ser Arg Cys
            100                 105                 110

Trp Val Ser Leu Thr Pro Thr Val Ala Ala Pro Tyr Leu Gly Ala Pro
```

```
              115                 120                 125
Leu Thr Ser Leu Arg Arg His Val Asp Leu Met Val Gly Ala Ala Thr
    130                 135                 140

Leu Cys Ser Ala Leu Tyr Val Gly Asp Leu Cys Gly Val Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Val Gly His Ile Thr Gly His Arg Met
            180                 185                 190

Ala (2) INFORMATION FOR SEQ ID NO: 183:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..579

(xi) SEQUENCE DESCRIPTION: SEQ ID NO: 183:

ACC TGC GGC TTT GCC GAC CTC ATG GGA TAC ATC CCG CTC GTA GGC GCC      48
Thr Cys Gly Phe Ala Asp Leu Met Gly Tyr Ile Pro Leu Val Gly Ala
 1               5                  10                  15

CCT GTG GGT GGC GTC GCC AGG GCC CTA GAA CAC GGT GTT AGG GCT GTG      96
Pro Val Gly Gly Val Ala Arg Ala Leu Glu His Gly Val Arg Ala Val
                20                  25                  30

GAG GAC GGT ATT AAT TAT GCA ACA GGG AAT CTC CCC GGT TGC TCT TTT     144
Glu Asp Gly Ile Asn Tyr Ala Thr Gly Asn Leu Pro Gly Cys Ser Phe
            35                  40                  45

TCT ATC TCC CTC TTG GCA CTT CTT TCG TGC CTG ACT GTT CCC ACC TCA     192
Ser Ile Ser Leu Leu Ala Leu Leu Ser Cys Leu Thr Val Pro Thr Ser
     50                  55                  60

GCC GTC AAC TAT CGC AAC GCC TCG GGC GTC TAT CAT ATC ACC AAT GAC     240
Ala Val Asn Tyr Arg Asn Ala Ser Gly Val Tyr His Ile Thr Asn Asp
 65                  70                  75                  80

TGC CCG AAT TCG AGC ATA GTG TAC GAG GCT GAC TAC CAC ATC CTA CAC     288
Cys Pro Asn Ser Ser Ile Val Tyr Glu Ala Asp Tyr His Ile Leu His
                85                  90                  95

CTC CCT GGG TGC TTA CCC TGC GTG AGG GTT GGG AAT CAG TCA CGC TGC     336
Leu Pro Gly Cys Leu Pro Cys Val Arg Val Gly Asn Gln Ser Arg Cys
            100                 105                 110

TGG GTG GCC CTT ACT CCC ACC GTG GCG GCG CCT TAC GTT GGT GCT CCG     384
Trp Val Ala Leu Thr Pro Thr Val Ala Ala Pro Tyr Val Gly Ala Pro
     115                 120                 125

CTA GAA TCC CTC CGG AGT CAT GTG GAT CTG ATG GTA GGT GCT GCT ACT     432
Leu Glu Ser Leu Arg Ser His Val Asp Leu Met Val Gly Ala Ala Thr
 130                 135                 140

GTG TGC TCC GCT CTT TAC ATC GGG GAC CTG TGC GGT GGC GTA TTT TTG     480
Val Cys Ser Ala Leu Tyr Ile Gly Asp Leu Cys Gly Gly Val Phe Leu
```

```
                145                 150                 155                 160
GTT GGT CAG ATG TTT TCT TTC CAG CCG CGA CGC CAC TGG ACC ACG CAG        528
Val Gly Gln Met Phe Ser Phe Gln Pro Arg Arg His Trp Thr Thr Gln
                    165                 170                 175

GAC TGC AAT TGT TCT ATC TAC GCG GGG CAC GTT ACG GGC CAC AGG ATG        576
Asp Cys Asn Cys Ser Ile Tyr Ala Gly His Val Thr Gly His Arg Met
                180                 185                 190

GCA                                                                    579
Ala
```

(2) INFORMATION FOR SEQ ID NO: 184:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 184:

```
Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
    50                  55                  60

Ala Val Asn Tyr Arg Asn Ala Ser Gly Ile Tyr His Ile Thr Asn Asp
65                  70                  75                  80

Cys Pro Asn Ala Ser Ile Val Tyr Glu Thr Glu Asn His Ile Leu His
                85                  90                  95

Leu Pro Gly Cys Val Pro Cys Val Arg Thr Gly Asn Gln Ser Arg Cys
            100                 105                 110

Trp Val Ala Leu Thr Pro Thr Val Ala Ser Pro Tyr Ala Gly Ala Pro
        115                 120                 125

Leu Glu Pro Leu Arg Arg His Val Asp Leu Met Val Gly Ala Ala Thr
    130                 135                 140

Met Cys Ser Ala Leu Tyr Ile Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
                180                 185                 190

Ala
```

(2) INFORMATION FOR SEQ ID NO: 185:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:

```
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 185:

ACT TGC GGC TTT GCC GAC CTC ATG GGA TAC ATC CCG CTC GTA GGC GCC        48
Thr Cys Gly Phe Ala Asp Leu Met Gly Tyr Ile Pro Leu Val Gly Ala
 1               5                  10                  15

CCC GTG GGT GGC GTC GCC AGA GCC CTG GAA CAT GGT GTT AGG GCT GTG        96
Pro Val Gly Gly Val Ala Arg Ala Leu Glu His Gly Val Arg Ala Val
                20                  25                  30

GAG GAC GGC ATC AAT TAT GCA ACA GGG AAT CTC CCC GGT TGC TCT TTC       144
Glu Asp Gly Ile Asn Tyr Ala Thr Gly Asn Leu Pro Gly Cys Ser Phe
            35                  40                  45

TCT ATC TAC CTC TTG GCA CTT CTC TCG TGC CTG ACT GTT CCC ACC TCG       192
Ser Ile Tyr Leu Leu Ala Leu Leu Ser Cys Leu Thr Val Pro Thr Ser
        50                  55                  60

GCC ATC CAC TAT CGC AAT GCC TCG GGC GTC TAC CAC GTC ACC AAT GAC       240
Ala Ile His Tyr Arg Asn Ala Ser Gly Val Tyr His Val Thr Asn Asp
65                  70                  75                  80

TGC CCG AAC TCG AGC ATA GTG TAC GAG GCC GAC CAC CAC ATC CTA CAC       288
Cys Pro Asn Ser Ser Ile Val Tyr Glu Ala Asp His His Ile Leu His
                85                  90                  95

CTT CCA GGG TGC TTA CCC TGT GTG AGG GTT GGG AAT CAG TCA CGT TGT       336
Leu Pro Gly Cys Leu Pro Cys Val Arg Val Gly Asn Gln Ser Arg Cys
            100                 105                 110

TGG GTG GCC CTC TCT CCC ACC GTG GCG GCG CCT TAC ATC GGT GCT CCA       384
Trp Val Ala Leu Ser Pro Thr Val Ala Ala Pro Tyr Ile Gly Ala Pro
        115                 120                 125

GTT GAA TCC TTC CGG AGA CAC GTG GAC ATG ATG GTG GGC GCT GCT ACT       432
Val Glu Ser Phe Arg Arg His Val Asp Met Met Val Gly Ala Ala Thr
    130                 135                 140

GTG TGC TCC GCT CTC TAT ATT GGG GAC TTG TGT GGT GGC GTA TTC TTG       480
Val Cys Ser Ala Leu Tyr Ile Gly Asp Leu Cys Gly Gly Val Phe Leu
145                 150                 155                 160

GTT GGT CAG ATG TTT TCT TTC CGG CCA CGA CGC CAC TGG ACT ACG CAG       528
Val Gly Gln Met Phe Ser Phe Arg Pro Arg Arg His Trp Thr Thr Gln
                165                 170                 175

GAC TGC AAT TGT TCC ATC TAC GCG GGG CAC ATC ACT GGC CAC GGA ATG       576
Asp Cys Asn Cys Ser Ile Tyr Ala Gly His Ile Thr Gly His Gly Met
            180                 185                 190

GCA                                                                   579
Ala (2) INFORMATION FOR SEQ ID NO: 186:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 186:

Thr Cys Gly Phe Ala Asp Leu Met Gly Tyr Ile Pro Leu Val Gly Ala
 1               5                  10                  15

Pro Val Gly Gly Val Ala Arg Ala Leu Glu His Gly Val Arg Ala Val
                20                  25                  30

Glu Asp Gly Ile Asn Tyr Ala Thr Gly Asn Leu Pro Gly Cys Ser Phe
```

```
                     35                  40                  45
Ser Ile Tyr Leu Leu Ala Leu Leu Ser Cys Leu Thr Val Pro Thr Ser
     50                  55                  60

Ala Ile His Tyr Arg Asn Ala Ser Gly Val Tyr His Val Thr Asn Asp
 65                  70                  75                  80

Cys Pro Asn Ser Ser Ile Val Tyr Glu Ala Asp His His Ile Leu His
                 85                  90                  95

Leu Pro Gly Cys Leu Pro Cys Val Arg Val Gly Asn Gln Ser Arg Cys
            100                 105                 110

Trp Val Ala Leu Ser Pro Thr Val Ala Ala Pro Tyr Ile Gly Ala Pro
        115                 120                 125

Val Glu Ser Phe Arg Arg His Val Asp Met Met Val Gly Ala Ala Thr
    130                 135                 140

Val Cys Ser Ala Leu Tyr Ile Gly Asp Leu Cys Gly Gly Val Phe Leu
145                 150                 155                 160

Val Gly Gln Met Phe Ser Phe Arg Pro Arg Arg His Trp Thr Thr Gln
                165                 170                 175

Asp Cys Asn Cys Ser Ile Tyr Ala Gly His Ile Thr Gly His Gly Met
            180                 185                 190

Ala (2) INFORMATION FOR SEQ ID NO: 187:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
         (A) NAME/KEY: CDS
         (B) LOCATION: 1..579

(ix) FEATURE:
         (A) NAME/KEY: mat_peptide
         (B) LOCATION: 1..576

(xi) SEQUENCE DESCRIPTION: SEQ ID NO: 187:

ACT TGC GGC TTT GCC GAC CTC ATG GGA TAC ATC CCG CTC GTA GGC GCC        48
Thr Cys Gly Phe Ala Asp Leu Met Gly Tyr Ile Pro Leu Val Gly Ala
 1               5                  10                  15

CCT GTG GGT GGC GTC GCC AGG GCC CTG GCA CAC GGT GTT AGG GCT GTG        96
Pro Val Gly Gly Val Ala Arg Ala Leu Ala His Gly Val Arg Ala Val
             20                  25                  30

GAG GAC GGG ATC AAT TAT GCG ACA GGG AAT CTT CCC GGT TGC TCT TTC       144
Glu Asp Gly Ile Asn Tyr Ala Thr Gly Asn Leu Pro Gly Cys Ser Phe
         35                  40                  45

TCT ATC TTC CTC TTG GCA CTT CTT TCG TGC CTG ACT GTT CCC ACC TCG       192
Ser Ile Phe Leu Leu Ala Leu Leu Ser Cys Leu Thr Val Pro Thr Ser
     50                  55                  60

GCC GTC AAC TAT CGC AAT GCC TCG GGC ATC TAT CAC ATC ACC AAT GAC       240
Ala Val Asn Tyr Arg Asn Ala Ser Gly Ile Tyr His Ile Thr Asn Asp
 65                  70                  75                  80

TGC CCG AAC TCG AGC ATA GTG TAC GAG ACC GAG CAC CAC ATC CTA CAC       288
Cys Pro Asn Ser Ser Ile Val Tyr Glu Thr Glu His His Ile Leu His
                 85                  90                  95
```

```
CTC CCA GGG TGT TTA CCC TGC GTG AGG GTT GGG AAT CAG TCA CGC TGC      336
Leu Pro Gly Cys Leu Pro Cys Val Arg Val Gly Asn Gln Ser Arg Cys
            100                 105                 110

TGG GTG GCC CTC ACT CCC ACC GTG GCG GCG CCT TAC ATC GGC GCT CCG      384
Trp Val Ala Leu Thr Pro Thr Val Ala Ala Pro Tyr Ile Gly Ala Pro
        115                 120                 125

CTT GAA TCC CTC CGG AGT CAT GTG GAT CTG ATG GTA GGT GCC GCT ACT      432
Leu Glu Ser Leu Arg Ser His Val Asp Leu Met Val Gly Ala Ala Thr
    130                 135                 140

GCG TGC TCC GCT CTT TAC ATC GGA GAC CTG TGT GGT GGC GTA TTT TTG      480
Ala Cys Ser Ala Leu Tyr Ile Gly Asp Leu Cys Gly Gly Val Phe Leu
145                 150                 155                 160

GTT GGT CAG ATG TTC TCT TTC CAG CCG CGG CGC CAC TGG ACT ACG CAG      528
Val Gly Gln Met Phe Ser Phe Gln Pro Arg Arg His Trp Thr Thr Gln
                165                 170                 175

GAC TGC AAT TGT TCC ATC TAC GCG GGG CAC GTT ACG GGC CAC AGG ATG      576
Asp Cys Asn Cys Ser Ile Tyr Ala Gly His Val Thr Gly His Arg Met
            180                 185                 190

GCA                                                                   579
Ala (2) INFORMATION FOR SEQ ID NO: 188:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 188:

Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
             35                  40                  45

Ser Ile Phe Leu Leu Ala Leu Leu Ser Cys Leu Thr Val Pro Thr Ser
         50                  55                  60

Ala Val Asn Tyr Arg Asn Ala Ser Gly Ile Tyr His Ile Thr Asn Asp
 65                  70                  75                  80

Cys Pro Asn Ser Ser Ile Val Tyr Glu Thr Glu His His Ile Leu His
                 85                  90                  95

Leu Pro Gly Cys Leu Pro Cys Val Arg Val Gly Asn Gln Ser Arg Cys
            100                 105                 110

Trp Val Ala Leu Thr Pro Thr Val Ala Ala Pro Tyr Ile Gly Ala Pro
        115                 120                 125

Leu Glu Ser Leu Arg Ser His Val Asp Leu Met Val Gly Ala Ala Thr
    130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg Met
            180                 185                 190

Ala
```

-continued (2) INFORMATION FOR SEQ ID NO: 189:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 189:

```
ACG TGC GGC TTC GCC GAC CTC ATG GGA TAC ATC CCG CTC GTG GGC GCC        48
Thr Cys Gly Phe Ala Asp Leu Met Gly Tyr Ile Pro Leu Val Gly Ala
 1               5                  10                  15

CCC GTT GGG GGC GTC GCC AGG GCC CTG GCG CAT GGC GTC AGG GCT GTG        96
Pro Val Gly Gly Val Ala Arg Ala Leu Ala His Gly Val Arg Ala Val
             20                  25                  30

GAG GAC GGG ATT AAC TAT GCG ACA GGG AAT CTT CCC GGT TGC TCT TTC       144
Glu Asp Gly Ile Asn Tyr Ala Thr Gly Asn Leu Pro Gly Cys Ser Phe
         35                  40                  45

TCT ATC TTC CTC CTG GCA CTT CTT TCG TGC CTC ACT GTC CCA GCG TCA       192
Ser Ile Phe Leu Leu Ala Leu Leu Ser Cys Leu Thr Val Pro Ala Ser
     50                  55                  60

GCT GAG CAC TAC CGG AAT GCT TCG GGC ATC TAT CAC ATC ACC AAT GAC       240
Ala Glu His Tyr Arg Asn Ala Ser Gly Ile Tyr His Ile Thr Asn Asp
 65                  70                  75                  80

TGT CCG AAT TCC AGC GTA GTC TAT GAA ACT GAC CAC CAT ATA TTG CAC       288
Cys Pro Asn Ser Ser Val Val Tyr Glu Thr Asp His His Ile Leu His
                 85                  90                  95

TTG CCG GGG TGC GTA CCC TGC GTG AGG GCC GGG AAC GTG TCT CGT TGC       336
Leu Pro Gly Cys Val Pro Cys Val Arg Ala Gly Asn Val Ser Arg Cys
            100                 105                 110

TGG ACG CCG GTA ACA CCT ACG GTG GCT GCC GTA TCC ATG GAC GCT CCG       384
Trp Thr Pro Val Thr Pro Thr Val Ala Ala Val Ser Met Asp Ala Pro
        115                 120                 125

CTC GAG TCC TTC CGG CGG CAT GTG GAC CTA ATG GTA GGT GCG GCC ACC       432
Leu Glu Ser Phe Arg Arg His Val Asp Leu Met Val Gly Ala Ala Thr
    130                 135                 140

GTG TGT TCT GTC CTC TAT GTT GGA GAC CTC TGT GGA GGT GCT TTC CTA       480
Val Cys Ser Val Leu Tyr Val Gly Asp Leu Cys Gly Gly Ala Phe Leu
145                 150                 155                 160

GTG GGG CAG ATG TTC ACC TTC CAG CCG CGT CGC CAC TGG ACC ACG CAG       528
Val Gly Gln Met Phe Thr Phe Gln Pro Arg Arg His Trp Thr Thr Gln
                165                 170                 175

GAT TGT AAT TGC TCC ATC TAT ACT GGC CAT ATC ACC GGC CAC AGG ATG       576
Asp Cys Asn Cys Ser Ile Tyr Thr Gly His Ile Thr Gly His Arg Met
            180                 185                 190

GCG                                                                   579
Ala
```

(2) INFORMATION FOR SEQ ID NO: 190:

(i) SEQUENCE CHARACTERISTICS:

(A) LENGTH: 193 amino acids
          (B) TYPE: amino acid
          (D) TOPOLOGY: linear (ii) MOLECULE TYPE: protein (xi) SEQUENCE DESCRIPTION: SEQ ID NO: 190:

Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
             35                  40                  45

Ser Ile Phe Leu Leu Ala Leu Leu Ser Cys Leu Thr Val Pro Ala Ser
         50                  55                  60

Ala Glu His Tyr Arg Asn Ala Ser Gly Ile Tyr His Ile Thr Asn Asp
 65                  70                  75                  80

Cys Pro Asn Ser Ser Val Val Tyr Glu Thr Asp His His Ile Leu His
                 85                  90                  95

Leu Pro Gly Cys Val Pro Cys Val Arg Ala Gly Asn Val Ser Arg Cys
                100                 105                 110

Trp Thr Pro Val Thr Pro Thr Val Ala Val Ser Met Asp Ala Pro
            115                 120                 125

Leu Glu Ser Phe Arg Arg His Val Asp Leu Met Val Gly Ala Ala Thr
            130                 135                 140

Val Cys Ser Val Leu Tyr Val Gly Asp Leu Cys Gly Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
                180                 185                 190

Ala (2) INFORMATION FOR SEQ ID NO: 191:

(i) SEQUENCE CHARACTERISTICS:
        (A) LENGTH: 289 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
         (A) NAME/KEY: CDS
         (B) LOCATION: 1..289

(ix) FEATURE:
         (A) NAME/KEY: mat_peptide
         (B) LOCATION: 1..286

(xi) SEQUENCE DESCRIPTION: SEQ ID NO: 191:

ATG AGC ACG AAT CCT AAA CCT CAA AGA AAA ACC AAA CGT AAC ACC AAC      48
Met Ser Thr Asn Pro Lys Pro Gln Arg Lys Thr Lys Arg Asn Thr Asn
  1               5                  10                  15

CGC CGC CCC ATG GAC GTT AAG TTC CCG GGC GGT GGC CAG ATC GTT GGT      96
Arg Arg Pro Met Asp Val Lys Phe Pro Gly Gly Gly Gln Ile Val Gly
                 20                  25                  30

-continued

```
GGA GTT TAC TTG TTG CCG CGC AGG GGC CCC AGG TTG GGT GTG CGC GCG        144
Gly Val Tyr Leu Leu Pro Arg Arg Gly Pro Arg Leu Gly Val Arg Ala
         35                  40                  45

ACT AGG AAG ACT TCG GAG CGG TCG CAA CCT CGT GGG AGA CGT CAG CCT        192
Thr Arg Lys Thr Ser Glu Arg Ser Gln Pro Arg Gly Arg Arg Gln Pro
 50                  55                  60

ATC CCC AAG GCA CGT CGA TCT GAG GGA AGG TCC TGG GCT CAG CCC GGG        240
Ile Pro Lys Ala Arg Arg Ser Glu Gly Arg Ser Trp Ala Gln Pro Gly
 65                  70                  75                  80

TAC CCA TGG CCT CTT TAC GGT AAT GAG GGT TGT GGG TGG GCA GGA TGG        289
Tyr Pro Trp Pro Leu Tyr Gly Asn Glu Gly Cys Gly Trp Ala Gly Trp
                 85                  90                  95
```

(2) INFORMATION FOR SEQ ID NO: 192:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO: 192:

```
Met Ser Thr Asn Pro Lys Pro Gln Arg Lys Thr Lys Arg Asn Thr Asn
 1                   5                  10                  15

Arg Arg Pro Met Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95
```

(2) INFORMATION FOR SEQ ID NO: 193:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..498

(ix) FEATURE:
        (A) NAME/KEY: mat_peptide
        (B) LOCATION: 1..495

(xi) SEQUENCE DESCRIPTION: SEQ ID NO: 193:

```
ATG AGC ACG AAT CCT AAA CCT CAA AGA AAA ACC AAA CGT AAC ACC AAC         48
Met Ser Thr Asn Pro Lys Pro Gln Arg Lys Thr Lys Arg Asn Thr Asn
 1                   5                  10                  15

CGC CGC CCT ATG GAC GTA AAG TTC CCG GGC GGT GGA CAG ATC GTT GGC         96
Arg Arg Pro Met Asp Val Lys Phe Pro Gly Gly Gly Gln Ile Val Gly
                 20                  25                  30
```

```
GGA GTT TAC TTG TTG CCG CGC AGG GGC CCC CGG TTG GGT GTG CGC GCG      144
Gly Val Tyr Leu Leu Pro Arg Arg Gly Pro Arg Leu Gly Val Arg Ala
        35                  40                  45

ACT CGG AAG ACT TCG GAG CGG TCG CAA CCT CGT GGC AGG CGT CAA CCT      192
Thr Arg Lys Thr Ser Glu Arg Ser Gln Pro Arg Gly Arg Arg Gln Pro
 50                  55                  60

ATC CCC AAG GCG CGC CGG TCC GAG GGC AGG TCC TGG GCG CAA GCC GGG      240
Ile Pro Lys Ala Arg Arg Ser Glu Gly Arg Ser Trp Ala Gln Ala Gly
 65                  70                  75                  80

TAC CCC TGG CCC CTC TAT GGC AAT GAG GGC TGT GGG TGG GCA GGG TGG      288
Tyr Pro Trp Pro Leu Tyr Gly Asn Glu Gly Cys Gly Trp Ala Gly Trp
                 85                  90                  95

CTC CTG TCT CCT CGC GGC TCT CGG CCA TCT TGG GGC CCA AAT GAT CCC      336
Leu Leu Ser Pro Arg Gly Ser Arg Pro Ser Trp Gly Pro Asn Asp Pro
             100                 105                 110

CGG CGG AGA TCG CGC AAT CTG GGT AAG GTC ATC GAT ACC CTG ACG TGC      384
Arg Arg Arg Ser Arg Asn Leu Gly Lys Val Ile Asp Thr Leu Thr Cys
             115                 120                 125

GGC TTC GCC GAC CTC ATG GGA TAC ATC CCG CTC GTG GGC GCC CCC GTC      432
Gly Phe Ala Asp Leu Met Gly Tyr Ile Pro Leu Val Gly Ala Pro Val
130                 135                 140

GGG GGC GTC GCC AGG GCC CTG GCG CAT GGC GTC AGG GCT GTG GAG GAC      480
Gly Gly Val Ala Arg Ala Leu Ala His Gly Val Arg Ala Val Glu Asp
145                 150                 155                 160

GGG ATT AAC TAT CGA CAG                                              498
Gly Ile Asn Tyr Arg Gln
                165
```

(2) INFORMATION FOR SEQ ID NO: 194:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO: 194:

```
Met Ser Thr Asn Pro Lys Pro Gln Arg Lys Thr Lys Arg Asn Thr Asn
 1               5                  10                  15

Arg Arg Pro Met Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Ser Glu Gly Arg Ser Trp Ala Gln Ala Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Val Glu Asp
145                 150                 155                 160

Gly Ile Asn Tyr Arg Gln
```

165

(2) INFORMATION FOR SEQ ID NO: 195:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..579

(ix) FEATURE:
        (A) NAME/KEY: mat_peptide
        (B) LOCATION: 1..576

(xi) SEQUENCE DESCRIPTION: SEQ ID NO: 195:

```
ACG TGC GGA TTC GCC GAC CTC GTG GGG TAC ATC CCG CTC GTA GGC GGC         48
Thr Cys Gly Phe Ala Asp Leu Val Gly Tyr Ile Pro Leu Val Gly Gly
 1               5                  10                  15

CCC GTT GGG GGC GTC GCA AGG GCT CTC GCA CAT GGT GTG AGG GTT CTT         96
Pro Val Gly Gly Val Ala Arg Ala Leu Ala His Gly Val Arg Val Leu
                20                  25                  30

GAG GAC GGG GTG AAT TAT GCA ACA GGG AAT CTG CCT GGT TGC TCT TTC        144
Glu Asp Gly Val Asn Tyr Ala Thr Gly Asn Leu Pro Gly Cys Ser Phe
            35                  40                  45

TCT ATC TTC ATT CTT GCA CTT CTC TCG TGC CTC ACT GTC CCG GCC TCT        192
Ser Ile Phe Ile Leu Ala Leu Leu Ser Cys Leu Thr Val Pro Ala Ser
        50                  55                  60

GCA GTT CCC TAC CGA AAT GCC TCT GGG ATC TAT CAT GTC ACC AAT GAT        240
Ala Val Pro Tyr Arg Asn Ala Ser Gly Ile Tyr His Val Thr Asn Asp
 65                 70                  75                  80

TGC CCA AAC TCT TCC ATA GTC TAT GAG GCA GAT GAT CTG ATC CTA CAC        288
Cys Pro Asn Ser Ser Ile Val Tyr Glu Ala Asp Asp Leu Ile Leu His
                85                  90                  95

GCA CCT GGC TGC GTG CCT TGT GTC AGG AAA GAT AAT GTG AGT AGG TGC        336
Ala Pro Gly Cys Val Pro Cys Val Arg Lys Asp Asn Val Ser Arg Cys
            100                 105                 110

TGG GTC CAA ATT ACC CCC ACG CTG TCA GCC CCG AGC TTC GGA GCA GTC        384
Trp Val Gln Ile Thr Pro Thr Leu Ser Ala Pro Ser Phe Gly Ala Val
        115                 120                 125

ACG GCT CCC CTT CGG AGA GCC GTT GAT TAC TTG GTG GGA GGG GCT GCC        432
Thr Ala Pro Leu Arg Arg Ala Val Asp Tyr Leu Val Gly Gly Ala Ala
    130                 135                 140

CTC TGC TCC GCG TTA TAC GTT GGA GAC GCG TGT GGG GCA CTA TTT TTG        480
Leu Cys Ser Ala Leu Tyr Val Gly Asp Ala Cys Gly Ala Leu Phe Leu
145                 150                 155                 160

GTA GGC CAA ATG TTC ACC TAT AGG CCT CGC CAG CAT GCT ACG GTG CAG        528
Val Gly Gln Met Phe Thr Tyr Arg Pro Arg Gln His Ala Thr Val Gln
                165                 170                 175

GAC TGC AAC TGT TCC ATC TAC AGT GGC CAC GTC ACC GGC CAT CAG ATG        576
Asp Cys Asn Cys Ser Ile Tyr Ser Gly His Val Thr Gly His Gln Met
            180                 185                 190

GCA                                                                    579
Ala
```

(2) INFORMATION FOR SEQ ID NO: 196:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 196:

```
Thr Cys Gly Phe Ala Asp Leu Val Gly Tyr Ile Pro Leu Val Gly Gly
  1               5                  10                  15

Pro Val Gly Gly Val Ala Arg Ala Leu Ala His Gly Val Arg Val Leu
             20                  25                  30

Glu Asp Gly Val Asn Tyr Ala Thr Gly Asn Leu Pro Gly Cys Ser Phe
         35                  40                  45

Ser Ile Phe Ile Leu Ala Leu Leu Ser Cys Leu Thr Val Pro Ala Ser
     50                  55                  60

Ala Val Pro Tyr Arg Asn Ala Ser Gly Ile Tyr His Val Thr Asn Asp
 65                  70                  75                  80

Cys Pro Asn Ser Ser Ile Val Tyr Glu Ala Asp Asp Leu Ile Leu His
                 85                  90                  95

Ala Pro Gly Cys Val Pro Cys Val Arg Lys Asp Asn Val Ser Arg Cys
            100                 105                 110

Trp Val Gln Ile Thr Pro Thr Leu Ser Ala Pro Ser Phe Gly Ala Val
            115                 120                 125

Thr Ala Pro Leu Arg Arg Ala Val Asp Tyr Leu Val Gly Gly Ala Ala
        130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asp Cys Asn Cys Ser Ile Tyr Ser Gly His Val Thr Gly His Gln Met
            180                 185                 190

Ala
```

(2) INFORMATION FOR SEQ ID NO: 197:

(i) SEQUENCE CHARACTERISTICS:
        (A) LENGTH: 1485 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1485

(xi) SEQUENCE DESCRIPTION: SEQ ID NO: 197:

```
TGTGCCAGGA CCATCACCAC CGGAGCTTCT ATCACATACT CCACTTACGG CAAGTTCCTT      60

GCTGATGGAG GGTGTTCAGG CGGCGCGCAT GACGTGATCA TATGCGACGA GTGCCATTCC     120

CAGGACGCCA CCACCATTCT TGGGATAGGC ACTGTCCTTG ACCAGGCAGA GACGGCTGGA     180

GCTAGGCTCG TCGTCTTGGC CACGGCCACC CCTCCCGGCA GTGTGACAAC GCCCCACCCC     240

AACATCGAGG AAGTGGCCCT GCCTCAGGAG GGGGAGGTTC CCTTCTACGG CAGAGCCATT     300

CCCCTTGCTT TTATAAAGGG TGGTAGGCAT CTCATCTTCT GCCATTCCAA GAAAAAATGT     360

GATGAACTCG CCAAGCAACT GACCAGCCTG GGCGTGAACG CCGTGGCATA TTATAGAGGT     420
```

-continued

```
CTAGACGTCG CCGTCATACC CACAACAGGA GACGTGGTCG TGTGCAGCAC CGACGCGCTC        480

ATGACGGGAT TCACCGGCGA CTTTGATTCT GTCATAGACT GCAACTCCGC CGTCACTCAG        540

ACGGTGGACT TCAGTCTGGA TCCCACTTTT ACCATTGAGA CTACCACAGT GCCCCAGGAC        600

GCAGTGTCCA GAAGCCAGCG TTGGGGCCGC ACGGGAGAG GTAGGCACGG CATATACCGG         660

TATGTCTCGG CTGGAGAGAG ACCGTCTGGC ATGTTCGACT CCGTGGTGCT CTGTGAGTGC        720

TACGATGCCG GATGTGCATG GTACGATCTG ACTCCTGCCG AGACTACCGT GAGGTTGCGC        780

GCTTACNTAA ACACCCCCGG GCTCCCTGTC TGTCAGGACC ATTTGGAATT CTGGGAGGGG        840

GTGTTCACGG GGCTCACTAA CATCGACGCT CACATGCTGT CACAGACCAA ACAGGGTGGG        900

GAGAATTTCC CATACCTTGT AGCGTACCAA GCAACAGTGT GTGTTCGCGC GAAAGCGCCC        960

CCCCCCAGCT GGGACACAAT GTGGAAATGC ATGCTCCGTC TCAAACCGAC NTTAACTGGC       1020

CCTACTCCCC TCTTGTACAG GCTGGGGCCC GTCCAGAATG AGATCACACT GACGCACCCC       1080

ATCACCAAGT ACATTATGGC TTGCATGTCT GCGGACTTGG AGGTCATTAC CAGCACTTGG       1140

GTTCTGGTGG GGGGCGTTGT GGCGGCCCTG GCGGCCTACT GCTTGACGGT GGGTTCGGTA       1200

GCCATAGTCG GTAGGATCAT CCTCTCTGGG AAACCTGCCA TCATTCCCGA TAGGGAGGTA       1260

TTATACCAGC AATTTGATGA GATGGAGGAG TGCTCGGCCT CGTTGCCCTA TATGGACGAA       1320

ACACGTGCCA TTGCCGGACA ATTCAAAGAG AAAGTGCTCG GCTTCATCAG CACGACCGGC       1380

CAGAAGGCTG AAACTCTGAA GCCGGCAGCC ACGTCTGTGT GGAACAAGGC TGAGCAGTTC       1440

TGGNCCACAT ACATGTGGAA CTTCATCAGT GGGATACAAT AATAG                       1485
```

(2) INFORMATION FOR SEQ ID NO: 198:

(i) SEQUENCE CHARACTERISTICS:
        (A) LENGTH: 484 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 198:

```
Cys Ala Arg Thr Ile Thr Thr Gly Ala Ser Ile Thr Tyr Ser Thr Tyr
 1               5                  10                  15

Gly Lys Phe Leu Ala Asp Gly Gly Cys Ser Gly Gly Ala His Asp Val
                20                  25                  30

Ile Ile Cys Asp Glu Cys His Ser Gln Asp Ala Thr Thr Ile Leu Gly
            35                  40                  45

Ile Gly Thr Val Leu Asp Gln Ala Glu Thr Ala Gly Ala Arg Leu Val
        50                  55                  60

Val Leu Ala Thr Ala Thr Pro Pro Gly Ser Val Thr Thr Pro His Pro
65                  70                  75                  80

Asn Ile Glu Glu Val Ala Leu Pro Gln Glu Gly Glu Val Pro Phe Tyr
                85                  90                  95

Gly Arg Ala Ile Pro Leu Ala Phe Ile Lys Gly Gly Arg His Leu Ile
                100                 105                 110

Phe Cys His Ser Lys Lys Lys Cys Asp Glu Leu Ala Lys Gln Leu Thr
            115                 120                 125

Ser Leu Gly Val Asn Ala Val Ala Tyr Tyr Arg Gly Leu Asp Val Ala
        130                 135                 140

Val Ile Pro Thr Thr Gly Asp Val Val Val Cys Ser Thr Asp Ala Leu
145                 150                 155                 160
```

```
Met Thr Gly Phe Thr Gly Asp Phe Asp Ser Val Ile Asp Cys Asn Ser
                165                 170                 175

Ala Val Thr Gln Thr Val Asp Phe Ser Leu Asp Pro Thr Phe Thr Ile
            180                 185                 190

Glu Thr Thr Thr Val Pro Gln Asp Ala Val Ser Arg Ser Gln Arg Trp
        195                 200                 205

Gly Arg Thr Gly Arg Gly Arg His Gly Ile Tyr Arg Tyr Val Ser Ala
    210                 215                 220

Gly Glu Arg Pro Ser Gly Met Phe Asp Ser Val Val Leu Cys Glu Cys
225                 230                 235                 240

Tyr Asp Ala Gly Cys Ala Trp Tyr Asp Leu Thr Pro Ala Glu Thr Thr
                245                 250                 255

Val Arg Leu Arg Ala Tyr Xaa Asn Thr Pro Gly Leu Pro Val Cys Gln
            260                 265                 270

Asp His Leu Glu Phe Trp Glu Gly Val Phe Thr Gly Leu Thr Asn Ile
        275                 280                 285

Asp Ala His Met Leu Ser Gln Thr Lys Gln Gly Gly Glu Asn Phe Pro
    290                 295                 300

Tyr Leu Val Ala Tyr Gln Ala Thr Val Cys Val Arg Ala Lys Ala Pro
305                 310                 315                 320

Pro Pro Ser Trp Asp Thr Met Trp Lys Cys Met Leu Arg Leu Lys Pro
                325                 330                 335

Xaa Leu Thr Gly Pro Thr Pro Leu Leu Tyr Arg Leu Gly Pro Val Gln
            340                 345                 350

Asn Glu Ile Thr Leu Thr His Pro Ile Thr Lys Tyr Ile Met Ala Cys
        355                 360                 365

Met Ser Ala Asp Leu Glu Val Ile Thr Ser Thr Trp Val Leu Val Gly
    370                 375                 380

Gly Val Val Ala Ala Leu Ala Ala Tyr Cys Leu Thr Val Gly Ser Val
385                 390                 395                 400

Ala Ile Val Gly Arg Ile Ile Leu Ser Gly Lys Pro Ala Ile Ile Pro
                405                 410                 415

Asp Arg Glu Val Leu Tyr Gln Gln Phe Asp Glu Met Glu Glu Cys Ser
            420                 425                 430

Ala Ser Leu Pro Tyr Met Asp Glu Thr Arg Ala Ile Ala Gly Gln Phe
        435                 440                 445

Lys Glu Lys Val Leu Gly Phe Ile Ser Thr Thr Gly Gln Lys Ala Glu
    450                 455                 460

Thr Leu Lys Pro Ala Ala Thr Ser Val Trp Asn Lys Ala Glu Gln Phe
465                 470                 475                 480

Trp Xaa Thr Tyr (2) INFORMATION FOR SEQ ID NO: 199:

(i) SEQUENCE CHARACTERISTICS:
        (A) LENGTH: 1485 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1485

(xi) SEQUENCE DESCRIPTION: SEQ ID NO: 199:
```

-continued

```
TGTGCCAGGA CCATCACCAC CGGAGCTTCT ATCACATACT CCACTTACGG CAAGTTCCTT      60

GCTGATGGAG GGTGTTCAGG CGGCGCGTAT GACGTGATCA TATGCGACGA GTGCCATTCC     120

CAGGACGCCA CCACCATTCT TGGGATAGGC ACTGTCCTTG ACCAGGCAGA GACGGCTGGA     180

GCTAGGCTCG TCGTCTTGGC CACGGCCACC CCTCCCGGCA GTGTGACAAC GCCCCACCCC     240

AACATCGAGG AAGTGGCCCT GCCTCAGGAG GGGGAGGTTC CCTTCTACGG CAGAGCCATT     300

CCCCTTGCTT TTATAAAGGG TGGTAGGCAT CTCATCTTCT GCCATTCCAA GAAAAAATGT     360

GATGAACTCG CCAAGCAACT GACCAGCCTG GGCGTGAACG CCGTGGCATA TTATAGAGGT     420

CTAGACGTCG CCGTCATCCC CACAGCAGGA GACGTGGTCG TGTGCAGCAC CGACGCGCTC     480

ATGACGGGAT TCACCGGCGA CTTTGATTCT GTCATAGACT GCAACTCCGC CGTCACTCAG     540

ACGGTGGACT TCAGTCTGGA TCCCACTTTT ACCATTGAGA CTACCACAGT GCCCCAGGAC     600

GCAGTGTCCA GAAGCCAGCG TAGGGGCCGA ACGGGGAGAG GTAGGCACGG CATATACCGG     660

TATGTCTCGG CTGGAGAGAG ACCNTCTGAC ATGTTCGACT CCGTGGTGCT CTGTGAGTGC     720

TACGATGCCG GATGTGCGTG GTATGATCTG ACTCCTGCCG AGACTACCGT GAGGTTGCGC     780

GCTTACATAA ACACCCCCGG GCTCCCTGTC TGTCAGGACC ATTTGGAATT CTGGGAGGGG     840

GTGTTCACGG GGCTCACTAA CATCGACGCT CACATGCTGT CACAGACCAA ACAGGGTGGG     900

GAGAATTTNC ATACCTTGT AGCGTACCAA GCAACAGTCT GTGTTCGCGC GAAAGCGCCC     960

CCCCCCAGCT GGGACACAAT GTGGAAATGC ATGCTCCGTC TCAAACCGAC TTTAACTGGC    1020

CCTACTCCCC TCTTGTACAG GCTGGGGCCC GTCCAGANTG AGATCACACT GACGCACCCC    1080

ATCACCAAGT ACATTATGGC TTGCATGTCT GCGGACTTGG AGGTCATTAC CANCACTTGG    1140

GTTCTGGTGG GGGGCGTTGT GGCGGCCCTG GCGGCCTACT GCTTGACGGT GGGTTCGGTA    1200

GCCATAGTCG GTAGGATCAT CCTCTCTGGG AAACCTGCCA TCATTCCCGA TAGGGAGGCA    1260

TTATACCAGC AATTTGATGA GATGGAGGAG TGCTCGGCCT CGTTGCCCTA TATGGACGAG    1320

ACACGTGCCA TTGCCGGACA ATTCAAAGAG AAAGTGCTCG GCTTCATCAG CACGACCGGC    1380

CAGAAGGCTG AAACTCTGAA GCCGGCAGCC ACGTCTGTGT GGAACAAGGC TGAGCAGTTC    1440

TGGGCCACAT ACATGTGGAA CTTCATCAGC GGGATACAAT AATAG                   1485
```

(2) INFORMATION FOR SEQ ID NO: 200:

(i) SEQUENCE CHARACTERISTICS:
        (A) LENGTH: 484 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 200:

```
Cys Ala Arg Thr Ile Thr Thr Gly Ala Ser Ile Thr Tyr Ser Thr Tyr
 1               5                  10                  15

Gly Lys Phe Leu Ala Asp Gly Gly Cys Ser Gly Gly Ala Tyr Asp Val
            20                  25                  30

Ile Ile Cys Asp Glu Cys His Ser Gln Asp Ala Thr Thr Ile Leu Gly
        35                  40                  45

Ile Gly Thr Val Leu Asp Gln Ala Glu Thr Ala Gly Ala Arg Leu Val
    50                  55                  60

Val Leu Ala Thr Ala Thr Pro Pro Gly Ser Val Thr Thr Pro His Pro
65                  70                  75                  80
```

-continued

```
Asn Ile Glu Glu Val Ala Leu Pro Gln Glu Gly Val Pro Phe Tyr
                 85                  90                  95

Gly Arg Ala Ile Pro Leu Ala Phe Ile Lys Gly Arg His Leu Ile
            100                 105                 110

Phe Cys His Ser Lys Lys Cys Asp Glu Leu Ala Lys Gln Leu Thr
            115                 120                 125

Ser Leu Gly Val Asn Ala Val Ala Tyr Tyr Arg Gly Leu Asp Val Ala
130                 135                 140

Val Ile Pro Thr Ala Gly Asp Val Val Cys Ser Thr Asp Ala Leu
145                 150                 155                 160

Met Thr Gly Phe Thr Gly Asp Phe Asp Ser Val Ile Asp Cys Asn Ser
                165                 170                 175

Ala Val Thr Gln Thr Val Asp Phe Ser Leu Asp Pro Thr Phe Thr Ile
                180                 185                 190

Glu Thr Thr Thr Val Pro Gln Asp Ala Val Ser Arg Ser Gln Arg Arg
                195                 200                 205

Gly Arg Thr Gly Arg Gly Arg His Gly Ile Tyr Arg Tyr Val Ser Ala
            210                 215                 220

Gly Glu Arg Xaa Ser Asp Met Phe Asp Ser Val Val Leu Cys Glu Cys
225                 230                 235                 240

Tyr Asp Ala Gly Cys Ala Trp Tyr Asp Leu Thr Pro Ala Glu Thr Thr
                245                 250                 255

Val Arg Leu Arg Ala Tyr Ile Asn Thr Pro Gly Leu Pro Val Cys Gln
            260                 265                 270

Asp His Leu Glu Phe Trp Glu Gly Val Phe Thr Gly Leu Thr Asn Ile
            275                 280                 285

Asp Ala His Met Leu Ser Gln Thr Lys Gln Gly Gly Glu Asn Xaa Pro
            290                 295                 300

Tyr Leu Val Ala Tyr Gln Ala Thr Val Cys Val Arg Ala Lys Ala Pro
305                 310                 315                 320

Pro Pro Ser Trp Asp Thr Met Trp Lys Cys Met Leu Arg Leu Lys Pro
                325                 330                 335

Thr Leu Thr Gly Pro Thr Pro Leu Leu Tyr Arg Leu Gly Pro Val Gln
                340                 345                 350

Xaa Glu Ile Thr Leu Thr His Pro Ile Thr Lys Tyr Ile Met Ala Cys
            355                 360                 365

Met Ser Ala Asp Leu Glu Val Ile Thr Xaa Thr Trp Val Leu Val Gly
370                 375                 380

Gly Val Val Ala Ala Leu Ala Ala Tyr Cys Leu Thr Val Gly Ser Val
385                 390                 395                 400

Ala Ile Val Gly Arg Ile Ile Leu Ser Gly Lys Pro Ala Ile Ile Pro
                405                 410                 415

Asp Arg Glu Ala Leu Tyr Gln Gln Phe Asp Glu Met Glu Glu Cys Ser
                420                 425                 430

Ala Ser Leu Pro Tyr Met Asp Glu Thr Arg Ala Ile Ala Gly Gln Phe
            435                 440                 445

Lys Glu Lys Val Leu Gly Phe Ile Ser Thr Thr Gly Gln Lys Ala Glu
            450                 455                 460

Thr Leu Lys Pro Ala Ala Thr Ser Val Trp Asn Lys Ala Glu Gln Phe
465                 470                 475                 480

Trp Ala Thr Tyr
```

(2) INFORMATION FOR SEQ ID NO: 201:

```
    (i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..337

(xi) SEQUENCE DESCRIPTION: SEQ ID NO: 201:

C TCC ACT GTG ACT GAG AGA GAC ATC AGG GTC GAA GAA GAA GTC TAT        46
  Ser Thr Val Thr Glu Arg Asp Ile Arg Val Glu Glu Glu Val Tyr
  1               5                  10                  15

CAG TGT TGT GAT CTG GAG CCC GAG GCC CGC AAG GTA ATA ACC GCC CTC      94
Gln Cys Cys Asp Leu Glu Pro Glu Ala Arg Lys Val Ile Thr Ala Leu
                 20                  25                  30

ACG GAG AGA CTC TAC GTG GGC GGC CCT ATG TAC AAT AGC AAG GGA GAC     142
Thr Glu Arg Leu Tyr Val Gly Gly Pro Met Tyr Asn Ser Lys Gly Asp
                 35                  40                  45

CTT TGC GGG TAT CGC AGG TGC CGC GCA AGC GGC GTA TAT ACC ACC AGC     190
Leu Cys Gly Tyr Arg Arg Cys Arg Ala Ser Gly Val Tyr Thr Thr Ser
         50                  55                  60

TTC GGG AAC ACA CTG ACG TGC TAC CTT AAA GCC TCA GCA GCC ATC AGG     238
Phe Gly Asn Thr Leu Thr Cys Tyr Leu Lys Ala Ser Ala Ala Ile Arg
    65                  70                  75

GCT GCG GGG CTG AAG GAC TGC ACC ATG CTG GTT TGC GGT GAC GAC TTA     286
Ala Ala Gly Leu Lys Asp Cys Thr Met Leu Val Cys Gly Asp Asp Leu
80                  85                  90                  95

GTC GTG ATC GCT GAA AGC GGT GGC GTC GAG GAG GAC AAG CGA GCC CTC     334
Val Val Ile Ala Glu Ser Gly Gly Val Glu Glu Asp Lys Arg Ala Leu
                100                 105                 110

GGA GCT                                                             340
Gly Ala (2) INFORMATION FOR SEQ ID NO: 202:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 202:

Ser Thr Val Thr Glu Arg Asp Ile Arg Val Glu Glu Glu Val Tyr Gln
1               5                  10                  15

Cys Cys Asp Leu Glu Pro Glu Ala Arg Lys Val Ile Thr Ala Leu Thr
                20                  25                  30

Glu Arg Leu Tyr Val Gly Gly Pro Met Tyr Asn Ser Lys Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
```

```
                65                  70                  75                  80
Ala Gly Leu Lys Asp Cys Thr Met Leu Val Cys Gly Asp Asp Leu Val
                    85                  90                  95

Val Ile Ala Glu Ser Gly Gly Val Glu Glu Asp Lys Arg Ala Leu Gly
                100                 105                 110

Ala (2) INFORMATION FOR SEQ ID NO: 203:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..337

(xi) SEQUENCE DESCRIPTION: SEQ ID NO: 203:

C TCC ACA GTG ACT GAA AGA GAC ATC AGG GTC GAG GAA GAG GTC TAC          46
  Ser Thr Val Thr Glu Arg Asp Ile Arg Val Glu Glu Glu Val Tyr
  1               5                  10                  15

CAG TGT TGT GAC CTG GAG CCT GAA ACC CGC AAG GTA ATA TCT GCC CTC        94
Gln Cys Cys Asp Leu Glu Pro Glu Thr Arg Lys Val Ile Ser Ala Leu
                20                  25                  30

ACT GAA AGA CTC TAT GTG GGC GGT CCC ATG CAC AAC AGC AGG GGA GAC       142
Thr Glu Arg Leu Tyr Val Gly Gly Pro Met His Asn Ser Arg Gly Asp
            35                  40                  45

CTA TGC GGG TAC CGT AGA TGC CGC GCG AGC GGC GTA TAC ACC ACA AGC       190
Leu Cys Gly Tyr Arg Arg Cys Arg Ala Ser Gly Val Tyr Thr Thr Ser
        50                  55                  60

TTC GGG AAC ACT CTG ACG TGC TTC CTC AAG GCC ACA GCG GCC ACC AAA       238
Phe Gly Asn Thr Leu Thr Cys Phe Leu Lys Ala Thr Ala Ala Thr Lys
    65                  70                  75

GCC GCT GGC CTA AAG GAC TGC ACC ATG TTG GTG TGT GGT GAC GAC TTA       286
Ala Ala Gly Leu Lys Asp Cys Thr Met Leu Val Cys Gly Asp Asp Leu
80                  85                  90                  95

GTC GTT ATC GCC GAA AGC GAT GGT GTC GAA GAG GAC CGC CGA GCC CTC       334
Val Val Ile Ala Glu Ser Asp Gly Val Glu Glu Asp Arg Arg Ala Leu
                    100                 105                 110

GGA GCT                                                               340
Gly Ala (2) INFORMATION FOR SEQ ID NO: 204:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 204:

Ser Thr Val Thr Glu Arg Asp Ile Arg Val Glu Glu Glu Val Tyr Gln
```

```
                    1               5              10              15
Cys Cys Asp Leu Glu Pro Glu Thr Arg Lys Val Ile Ser Ala Leu Thr
                  20                    25                  30

Glu Arg Leu Tyr Val Gly Gly Pro Met His Asn Ser Arg Gly Asp Leu
              35                      40                  45

Cys Gly Tyr Arg Arg Cys Arg Ala Ser Gly Val Tyr Thr Thr Ser Phe
          50                      55                  60

Gly Asn Thr Leu Thr Cys Phe Leu Lys Ala Thr Ala Ala Thr Lys Ala
 65                  70                  75                  80

Ala Gly Leu Lys Asp Cys Thr Met Leu Val Cys Gly Asp Asp Leu Val
              85                      90                  95

Val Ile Ala Glu Ser Asp Gly Val Glu Glu Asp Arg Arg Ala Leu Gly
          100                     105                     110

Ala
```

(2) INFORMATION FOR SEQ ID NO: 205:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..337

(xi) SEQUENCE DESCRIPTION: SEQ ID NO: 205:

```
C TCC ACG GTG ACC GAA AGG GAT ATC AGG ACC GAG GAA GAG ATC TAC        46
  Ser Thr Val Thr Glu Arg Asp Ile Arg Thr Glu Glu Glu Ile Tyr
   1               5                  10                  15

CAG TGC TGC GAC CTG GAG CCC GAA GCC CGC AAG GTG ATA TCC GCC CTA      94
Gln Cys Cys Asp Leu Glu Pro Glu Ala Arg Lys Val Ile Ser Ala Leu
                  20                  25                  30

ACG GAA AGA CTC TAC GTG GGC GGT CCC ATG TAC AAC TCC AAG GGG GAC     142
Thr Glu Arg Leu Tyr Val Gly Gly Pro Met Tyr Asn Ser Lys Gly Asp
              35                      40                  45

CTA TGC GGG CAA CGG AGG TGC CGC GCA AGC GGG GTC TAC ACC ACC AGC     190
Leu Cys Gly Gln Arg Arg Cys Arg Ala Ser Gly Val Tyr Thr Thr Ser
          50                      55                  60

TTC GGG AAC ACT GTA ACG TGT TAT CTC AAG GCC GTT GCG GCT ACT AGG     238
Phe Gly Asn Thr Val Thr Cys Tyr Leu Lys Ala Val Ala Ala Thr Arg
 65                  70                  75

GCC GCA GGT CTG AAA GGT TGC AGC ATG CTG GTT TGT GGA GAC GAC TTA     286
Ala Ala Gly Leu Lys Gly Cys Ser Met Leu Val Cys Gly Asp Asp Leu
 80                      85                  90                  95

GTC GTC ATC TGC GAG AGC GGC GGC GTA GAG GAG GAT GCA AGA GCC CTC     334
Val Val Ile Cys Glu Ser Gly Gly Val Glu Glu Asp Ala Arg Ala Leu
                 100                     105                     110

CGA GCC                                                              340
Arg Ala
```

(2) INFORMATION FOR SEQ ID NO: 206:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 206:

```
Ser Thr Val Thr Glu Arg Asp Ile Arg Thr Glu Glu Glu Ile Tyr Gln
 1               5                  10                  15

Cys Cys Asp Leu Glu Pro Glu Ala Arg Lys Val Ile Ser Ala Leu Thr
                20                  25                  30

Glu Arg Leu Tyr Val Gly Gly Pro Met Tyr Asn Ser Lys Gly Asp Leu
            35                  40                  45

Cys Gly Gln Arg Arg Cys Arg Ala Ser Gly Val Tyr Thr Thr Ser Phe
        50                  55                  60

Gly Asn Thr Val Thr Cys Tyr Leu Lys Ala Val Ala Ala Thr Arg Ala
 65                  70                  75                  80

Ala Gly Leu Lys Gly Cys Ser Met Leu Val Cys Gly Asp Asp Leu Val
                85                  90                  95

Val Ile Cys Glu Ser Gly Gly Val Glu Glu Asp Ala Arg Ala Leu Arg
            100                 105                 110

Ala
```

(2) INFORMATION FOR SEQ ID NO: 207:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..337

(xi) SEQUENCE DESCRIPTION: SEQ ID NO: 207:

```
C TCC ACG GTG ACT GAA AGG GAC ATT AGG GTC GAG GAA GAG ATC TAC         46
  Ser Thr Val Thr Glu Arg Asp Ile Arg Val Glu Glu Glu Ile Tyr
   1               5                  10                  15

CAG TGC TGT GAC CTG GAG CCC GAG GCA CGC AAG GTG ATA TCC GCT CTC       94
Gln Cys Cys Asp Leu Glu Pro Glu Ala Arg Lys Val Ile Ser Ala Leu
                20                  25                  30

ACA GAA AGA CTC TAC AAG GGC GGC CCC ATG TAT AAC AGC AAG GGG GAC      142
Thr Glu Arg Leu Tyr Lys Gly Gly Pro Met Tyr Asn Ser Lys Gly Asp
            35                  40                  45

CTA TGC GGG CTT CGG AGG TGC CGC GCA AGC GGG GTA TAC ACC ACA AGC      190
Leu Cys Gly Leu Arg Arg Cys Arg Ala Ser Gly Val Tyr Thr Thr Ser
        50                  55                  60

TTC GGG AAC ACG GTG ACA TGC TAC CTT AAA GCC ACA GCA GCC ACC AGG      238
Phe Gly Asn Thr Val Thr Cys Tyr Leu Lys Ala Thr Ala Ala Thr Arg
 65                  70                  75
```

```
GCT GCA GGG CTG AAA GAT TGC ACT ATG CTG GTA TGC GGT GAC GAC TTA      286
Ala Ala Gly Leu Lys Asp Cys Thr Met Leu Val Cys Gly Asp Asp Leu
 80              85                  90                  95

GTC GTT ATT GCC GAA AGC GGT GGC GTG GAG GAG GAC GCC CGA GCC CTC      334
Val Val Ile Ala Glu Ser Gly Gly Val Glu Glu Asp Ala Arg Ala Leu
                100                 105                 110

CGA GCC                                                              340
Arg Ala
```

(2) INFORMATION FOR SEQ ID NO: 208:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 208:

```
Ser Thr Val Thr Glu Arg Asp Ile Arg Val Glu Glu Glu Ile Tyr Gln
 1               5                  10                  15

Cys Cys Asp Leu Glu Pro Glu Ala Arg Lys Val Ile Ser Ala Leu Thr
                20                  25                  30

Glu Arg Leu Tyr Lys Gly Gly Pro Met Tyr Asn Ser Lys Gly Asp Leu
             35                  40                  45

Cys Gly Leu Arg Arg Cys Arg Ala Ser Gly Val Tyr Thr Thr Ser Phe
         50                  55                  60

Gly Asn Thr Val Thr Cys Tyr Leu Lys Ala Thr Ala Ala Thr Arg Ala
 65              70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Ala Arg Ala Leu Arg
                100                 105                 110

Ala
```

(2) INFORMATION FOR SEQ ID NO: 209:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..340

(xi) SEQUENCE DESCRIPTION: SEQ ID NO: 209:

```
CCCCACCGTG ACNGAGAGGG ACNTCAGGGT CGAGGAAGAG GTCTATCAGT GCTGTAATCT      60

GGAGNCCGAT GNCCGCAAGG TCATCAACGC CCTCACAGAG AGACTCTACG TGGGCGGCCC     120

TATGCACAAC AGCAAGGGAG ACCTGTGTGG CATCCGTAGA TGCCGCGCGA GCGGCGTTTA     180

CACCACGAGC TTCGGAAACA CGCTGACTTG CTACCTCAAA GCCACAGCGG CCACCAGGGC     240

CGCGGGCTTG AAGGATTGCA CCATGCTGGT CTGCGGNGAC GACCTGGTTG TCATTGCTGA     300

GAGCATTGGC ATAGACGAGG ACAAGCAAGC CCTCCGNACT                           340
```

(2) INFORMATION FOR SEQ ID NO: 210:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 210:

```
Pro Thr Val Thr Glu Arg Asp Xaa Arg Val Glu Glu Glu Val Tyr Gln
1               5                   10                  15

Cys Cys Asn Leu Glu Xaa Asp Xaa Arg Lys Val Ile Asn Ala Leu Thr
            20                  25                  30

Glu Arg Leu Tyr Val Gly Gly Pro Met His Asn Ser Lys Gly Asp Leu
        35                  40                  45

Cys Gly Ile Arg Arg Cys Arg Ala Ser Gly Val Tyr Thr Thr Ser Phe
50                      55                  60

Gly Asn Thr Leu Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Ile Gly Ile Asp Glu Asp Lys Gln Ala Leu Arg
            100                 105                 110

Thr
```

(2) INFORMATION FOR SEQ ID NO: 211:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..340

(xi) SEQUENCE DESCRIPTION: SEQ ID NO: 211:

```
CTCGACTGTG NCCGAGAGGG ACATCAGGAC AGAGGGAGAG GTCTATCAGT GTTGCGACCT      60

GGAACCGGAA GCCCGCAAGG TAATCACCGC CCTCACTGAG AGACTCTATG TGGGCGGACC     120

CATGTTCAAC AGCAAGGGAG ACCTGTGCGG ACAACGCCGG TGCCGCGCAA GCGGCGTGTT     180

CACCACCAGC TTCGGGAACA CACTGACGTG CTACCTTAAA GCCACAGCTG CTACTAGAGC     240

AGCCGGCTTA AAAGATTGCA CCATGCTGGT CTGCGGTGAC GACTTAGTCG TTATTTCCGA     300

GAGCGCCGGT GTGGAGGAGG ATCCCANAAC CCNNCGACCN                           340
```

(2) INFORMATION FOR SEQ ID NO: 212:

(i) SEQUENCE CHARACTERISTICS:
        (A) LENGTH: 113 amino acids
        (B) TYPE: amino acid (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 212:

Ser Thr Val Xaa Glu Arg Asp Ile Arg Thr Glu Gly Glu Val Tyr Gln
1               5                   10                  15

Cys Cys Asp Leu Glu Pro Glu Ala Arg Lys Val Ile Thr Ala Leu Thr
            20                  25                  30

Glu Arg Leu Tyr Val Gly Gly Pro Met Phe Asn Ser Lys Gly Asp Leu
        35                  40                  45

Cys Gly Gln Arg Arg Cys Arg Ala Ser Gly Val Phe Thr Thr Ser Phe
    50                  55                  60

Gly Asn Thr Leu Thr Cys Tyr Leu Lys Ala Thr Ala Thr Arg Ala
65                  70                  75                  80

Ala Gly Leu Lys Asp Cys Thr Met Leu Val Cys Gly Asp Asp Leu Val
            85                  90                  95

Val Ile Ser Glu Ser Ala Gly Val Glu Glu Asp Pro Xaa Thr Xaa Arg
            100                 105                 110

Pro (2) INFORMATION FOR SEQ ID NO: 213:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..337

(xi) SEQUENCE DESCRIPTION: SEQ ID NO: 213:

C TCA ACA GTC ACC GAG AAC GAC ATC CGT GTT GAG GAG TCA ATT TAC      46
  Ser Thr Val Thr Glu Asn Asp Ile Arg Val Glu Glu Ser Ile Tyr
  1               5                   10                  15

CAA TGT TGT GAC TTG GCC CCC GAG GCC AGA CAG GCC ATA AAG TCG CTC    94
Gln Cys Cys Asp Leu Ala Pro Glu Ala Arg Gln Ala Ile Lys Ser Leu
            20                  25                  30

ACA GAG CGG CTT TAT ATC GGG GGT CCC CTG ACT AAT TCA AAG GGG CAG   142
Thr Glu Arg Leu Tyr Ile Gly Gly Pro Leu Thr Asn Ser Lys Gly Gln
        35                  40                  45

AAC TGT GGC TAT CGC CGA TGC CGC GCA AGC GGC GTG CTG ACG ACC AGC   190
Asn Cys Gly Tyr Arg Arg Cys Arg Ala Ser Gly Val Leu Thr Thr Ser
    50                  55                  60

TGC GGT AAT ACC CTT ACA TGT TAC CTA AAG GCC TCT GCA GCC TGT CGA   238
Cys Gly Asn Thr Leu Thr Cys Tyr Leu Lys Ala Ser Ala Ala Cys Arg
65                  70                  75

```
GCT GCG AAG CTC CAG GAC TGC ACG ATG CTC GTG TGC GGG GAC GAC CTT        286
Ala Ala Lys Leu Gln Asp Cys Thr Met Leu Val Cys Gly Asp Asp Leu
 80              85                  90                  95

GTC GTT ATC TGT GAA AGC GCG GGA ACC CAA GAG GAC GCG GCG AGC CTA        334
Val Val Ile Cys Glu Ser Ala Gly Thr Gln Glu Asp Ala Ala Ser Leu
            100                 105                 110

CGA GTC                                                                340
Arg Val (2) INFORMATION FOR SEQ ID NO: 214:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 214:

Ser Thr Val Thr Glu Asn Asp Ile Arg Val Glu Glu Ser Ile Tyr Gln
 1               5                  10                  15

Cys Cys Asp Leu Ala Pro Glu Ala Arg Gln Ala Ile Lys Ser Leu Thr
             20                  25                  30

Glu Arg Leu Tyr Ile Gly Gly Pro Leu Thr Asn Ser Lys Gly Gln Asn
         35                  40                  45

Cys Gly Tyr Arg Arg Cys Arg Ala Ser Gly Val Leu Thr Thr Ser Cys
     50                  55                  60

Gly Asn Thr Leu Thr Cys Tyr Leu Lys Ala Ser Ala Ala Cys Arg Ala
 65                  70                  75                  80

Ala Lys Leu Gln Asp Cys Thr Met Leu Val Cys Gly Asp Asp Leu Val
             85                  90                  95

Val Ile Cys Glu Ser Ala Gly Thr Gln Glu Asp Ala Ala Ser Leu Arg
            100                 105                 110

Val (2) INFORMATION FOR SEQ ID NO: 215:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
        (B) LOCATION: 2..340

(xi) SEQUENCE DESCRIPTION: SEQ ID NO: 215:

C TCA ACC GTC ACG GAG AGG GAT ATA AGA ACA GAA GAA TCC ATA TAT          46
  Ser Thr Val Thr Glu Arg Asp Ile Arg Thr Glu Glu Ser Ile Tyr
   1               5                  10                  15

CAA GCT TGT TCC CTG CCC CAA GAG GCC AGA ACT GTC ATA CAC TCG CTC        94
Gln Ala Cys Ser Leu Pro Gln Glu Ala Arg Thr Val Ile His Ser Leu
             20                  25                  30
```

```
ACC GAG AGA CTC TAC GTG GGA GGG CCC ATG ATA AAC AGC AAA GGG CAA      142
Thr Glu Arg Leu Tyr Val Gly Gly Pro Met Ile Asn Ser Lys Gly Gln
             35                  40                  45

TCC TGC GGT TAC AGG CGT TGC CGC GCA AGC GGT GTT TTC ACC ACC AGC      190
Ser Cys Gly Tyr Arg Arg Cys Arg Ala Ser Gly Val Phe Thr Thr Ser
         50                  55                  60

ATG GGG AAT ACC ATG ACG TGT TAC ATC AAA GCC CTT GCA GCG TGT AAA      238
Met Gly Asn Thr Met Thr Cys Tyr Ile Lys Ala Leu Ala Ala Cys Lys
 65                  70                  75

GCC GCA GGG ATC GTG GAC CCC GTC ATG CTG GTG TGT GGA GAC GAC CTG      286
Ala Ala Gly Ile Val Asp Pro Val Met Leu Val Cys Gly Asp Asp Leu
 80                  85                  90                  95

GTC GTC ATC TCG GAG AGC CAG GGT AAC GAG GAG GAC GAG CGA AAC CTG      334
Val Val Ile Ser Glu Ser Gln Gly Asn Glu Glu Asp Glu Arg Asn Leu
                100                 105                 110

AGA GCT                                                              340
Arg Ala (2) INFORMATION FOR SEQ ID NO: 216:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 216:

Ser Thr Val Thr Glu Arg Asp Ile Arg Thr Glu Glu Ser Ile Tyr Gln
 1               5                  10                  15

Ala Cys Ser Leu Pro Gln Glu Ala Arg Thr Val Ile His Ser Leu Thr
             20                  25                  30

Glu Arg Leu Tyr Val Gly Gly Pro Met Ile Asn Ser Lys Gly Gln Ser
         35                  40                  45

Cys Gly Tyr Arg Arg Cys Arg Ala Ser Gly Val Phe Thr Thr Ser Met
     50                  55                  60

Gly Asn Thr Met Thr Cys Tyr Ile Lys Ala Leu Ala Ala Cys Lys Ala
 65                  70                  75                  80

Ala Gly Ile Val Asp Pro Val Met Leu Val Cys Gly Asp Asp Leu Val
             85                  90                  95

Val Ile Ser Glu Ser Gln Gly Asn Glu Glu Asp Glu Arg Asn Leu Arg
            100                 105                 110

Ala (2) INFORMATION FOR SEQ ID NO: 217:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..340

(ix) FEATURE:
        (A) NAME/KEY: mat_peptide
```

(B) LOCATION: 2..340

(xi) SEQUENCE DESCRIPTION: SEQ ID NO: 217:

```
C TCG ACT GTC ACT GAA CAG GAC ATC AGG GTG GAA GAG GAG ATA TAT        46
  Ser Thr Val Thr Glu Gln Asp Ile Arg Val Glu Glu Glu Ile Tyr
   1               5                  10                  15

CAA TGC TGC AAC CTT GAA CCG GAG GCC AGG AAA GTG ATC TCC TCC CTC      94
Gln Cys Cys Asn Leu Glu Pro Glu Ala Arg Lys Val Ile Ser Ser Leu
             20                  25                  30

ACG GAG CGG CTT TAC TGC GGA GGC CCT ATG TTT AAC AGC AAG GGG GCC     142
Thr Glu Arg Leu Tyr Cys Gly Gly Pro Met Phe Asn Ser Lys Gly Ala
                 35                  40                  45

CAG TGT GGT TAT CGC CGT TGC CGT GCC AGT GGA GTT CTG CCT ACC AGC     190
Gln Cys Gly Tyr Arg Arg Cys Arg Ala Ser Gly Val Leu Pro Thr Ser
         50                  55                  60

TTT GGC AAC ACA ATC ACT TGT TAC ATC AAG GCC ACA ACG GCC GCG AAG     238
Phe Gly Asn Thr Ile Thr Cys Tyr Ile Lys Ala Thr Thr Ala Ala Lys
     65                  70                  75

GCC GCA GGC CTC CGG AAC CCG GAC TTT CTT GTC TGC GGA GAT GAT CTG     286
Ala Ala Gly Leu Arg Asn Pro Asp Phe Leu Val Cys Gly Asp Asp Leu
 80                  85                  90                  95

GTC GTG GTG GCT GAG AGT GAT GGC GTC GAC GAG GAT AGA GCA GCC CTG     334
Val Val Val Ala Glu Ser Asp Gly Val Asp Glu Asp Arg Ala Ala Leu
                100                 105                 110

AGA GCC                                                              340
Arg Ala
```

(2) INFORMATION FOR SEQ ID NO: 218:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 218:

```
Ser Thr Val Thr Glu Gln Asp Ile Arg Val Glu Glu Glu Ile Tyr Gln
 1               5                  10                  15

Cys Cys Asn Leu Glu Pro Glu Ala Arg Lys Val Ile Ser Ser Leu Thr
             20                  25                  30

Glu Arg Leu Tyr Cys Gly Gly Pro Met Phe Asn Ser Lys Gly Ala Gln
         35                  40                  45

Cys Gly Tyr Arg Arg Cys Arg Ala Ser Gly Val Leu Pro Thr Ser Phe
     50                  55                  60

Gly Asn Thr Ile Thr Cys Tyr Ile Lys Ala Thr Thr Ala Ala Lys Ala
 65                  70                  75                  80

Ala Gly Leu Arg Asn Pro Asp Phe Leu Val Cys Gly Asp Asp Leu Val
                 85                  90                  95

Val Val Ala Glu Ser Asp Gly Val Asp Glu Asp Arg Ala Ala Leu Arg
            100                 105                 110

Ala
```

(2) INFORMATION FOR SEQ ID NO: 219:

(i) SEQUENCE CHARACTERISTICS:
        (A) LENGTH: 10 amino acids
        (B) TYPE: amino acid
        (C) STRANDEDNESS: single
        (D) TOPOLOGY: linear

```
       (ii) MOLECULE TYPE: peptide (xi) SEQUENCE DESCRIPTION: SEQ ID NO: 219:

Arg Ser Glu Gly Arg Thr Ser Trp Ala Gln
1               5                   10

(2) INFORMATION FOR SEQ ID NO: 220:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 220:

Arg Ser Glu Gly Arg Thr Ser Trp Ala Gln
1               5                   10

(2) INFORMATION FOR SEQ ID NO: 221:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 221:

Arg Thr Glu Gly Arg Thr Ser Trp Ala Gln
1               5                   10

(2) INFORMATION FOR SEQ ID NO: 222:

(i) SEQUENCE CHARACTERISTICS:
           (A) LENGTH: 629 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (ix) FEATURE:
           (A) NAME/KEY: CDS
           (B) LOCATION: 3..629

(ix) FEATURE:
           (A) NAME/KEY: mat_peptide
           (B) LOCATION: 3..629

(xi) SEQUENCE DESCRIPTION: SEQ ID NO: 222:

TA GAC TTT TGG GAG AGC GTC TTC ACT GGA CTA ACT CAC ATA GAT GCC        47
   Asp Phe Trp Glu Ser Val Phe Thr Gly Leu Thr His Ile Asp Ala
    1               5                   10                  15

CAC TTT CTG TCA CAG ACT AAG CAG CAG GGA CTC AAC TTC TCG TTC CTG       95
His Phe Leu Ser Gln Thr Lys Gln Gln Gly Leu Asn Phe Ser Phe Leu
                20                  25                  30

ACT GCC TAC CAA GCC ACT GTG TGC GCT CGC GCG CAG GCT CCT CCC CCA      143
Thr Ala Tyr Gln Ala Thr Val Cys Ala Arg Ala Gln Ala Pro Pro Pro
            35                  40                  45

AGT TGG GAC GAG ATG TGG AAG TGT CTC GTA CGG CTT AAG CCA ACA CTA      191
Ser Trp Asp Glu Met Trp Lys Cys Leu Val Arg Leu Lys Pro Thr Leu
        50                  55                  60
```

```
CAT GGA CCT ACG CCT CTT CTA TAT CGG TTG GGG CCT GTC CAA AAT GAA      239
His Gly Pro Thr Pro Leu Leu Tyr Arg Leu Gly Pro Val Gln Asn Glu
    65                  70                  75

ATC TGC TTG ACA CAC CCC ATC ACA AAA TAC ATC ATG GCA TGC ATG TCA      287
Ile Cys Leu Thr His Pro Ile Thr Lys Tyr Ile Met Ala Cys Met Ser
80              85                  90                  95

GCT GAT CTG GAA GTA ACC ACC AGC ACC TGG GTT TTG CTT GGA GGG GTC      335
Ala Asp Leu Glu Val Thr Thr Ser Thr Trp Val Leu Leu Gly Gly Val
                100                 105                 110

CTC GCG GCC CTA GCG GCC TAC TGC TTG TCA GTC GGT TGT GTT GTG ATT      383
Leu Ala Ala Leu Ala Ala Tyr Cys Leu Ser Val Gly Cys Val Val Ile
                115                 120                 125

GTG GGT CAT ATC GAG CTG GGG GGC AAG CCG GCA ATC GTT CCA GAC AAA      431
Val Gly His Ile Glu Leu Gly Gly Lys Pro Ala Ile Val Pro Asp Lys
        130                 135                 140

GAG GTG TTG TAT CAA CAA TAC GAT GAG ATG GAA GAG TGC TCA CAA GCT      479
Glu Val Leu Tyr Gln Gln Tyr Asp Glu Met Glu Glu Cys Ser Gln Ala
        145                 150                 155

GCC CCA TAT ATC GAA CAA GCT CAG GTA ATA GCT CAC CAG TTC AAG GAA      527
Ala Pro Tyr Ile Glu Gln Ala Gln Val Ile Ala His Gln Phe Lys Glu
160                 165                 170                 175

AAA GTC CTT GGA TTG CTG CAG CGA GCC ACC CAA CAA CAA GCT GTC ATT      575
Lys Val Leu Gly Leu Leu Gln Arg Ala Thr Gln Gln Gln Ala Val Ile
                180                 185                 190

GAG CCC ATA GTA ACT ACC AAC TGG CAA AAG CTT GAG GCC TTT TGG CAC      623
Glu Pro Ile Val Thr Thr Asn Trp Gln Lys Leu Glu Ala Phe Trp His
                195                 200                 205

AAG CAT                                                              629
Lys His (2) INFORMATION FOR SEQ ID NO: 223:

(i) SEQUENCE CHARACTERISTICS:
        (A) LENGTH: 209 amino acids
        (B) TYPE: amino acid
        (D) TOPOLOGY: linear (ii) MOLECULE TYPE: protein (xi) SEQUENCE DESCRIPTION: SEQ ID NO: 223:

Asp Phe Trp Glu Ser Val Phe Thr Gly Leu Thr His Ile Asp Ala His
1               5                   10                  15

Phe Leu Ser Gln Thr Lys Gln Gln Gly Leu Asn Phe Ser Phe Leu Thr
                20                  25                  30

Ala Tyr Gln Ala Thr Val Cys Ala Arg Ala Gln Ala Pro Pro Pro Ser
            35                  40                  45

Trp Asp Glu Met Trp Lys Cys Leu Val Arg Leu Lys Pro Thr Leu His
        50                  55                  60

Gly Pro Thr Pro Leu Leu Tyr Arg Leu Gly Pro Val Gln Asn Glu Ile
65                  70                  75                  80

Cys Leu Thr His Pro Ile Thr Lys Tyr Ile Met Ala Cys Met Ser Ala
                85                  90                  95

Asp Leu Glu Val Thr Thr Ser Thr Trp Val Leu Leu Gly Gly Val Leu
                100                 105                 110

Ala Ala Leu Ala Ala Tyr Cys Leu Ser Val Gly Cys Val Val Ile Val
            115                 120                 125

Gly His Ile Glu Leu Gly Gly Lys Pro Ala Ile Val Pro Asp Lys Glu
        130                 135                 140
```

```
Val Leu Tyr Gln Gln Tyr Asp Glu Met Glu Glu Cys Ser Gln Ala Ala
145                 150                 155                 160

Pro Tyr Ile Glu Gln Ala Gln Val Ile Ala His Gln Phe Lys Glu Lys
            165                 170                 175

Val Leu Gly Leu Leu Gln Arg Ala Thr Gln Gln Gln Ala Val Ile Glu
        180                 185                 190

Pro Ile Val Thr Thr Asn Trp Gln Lys Leu Glu Ala Phe Trp His Lys
        195                 200                 205

His
```

(2) INFORMATION FOR SEQ ID NO: 224:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 2..12

(xi) SEQUENCE DESCRIPTION: SEQ ID NO: 224:

```
Ile His Tyr Arg Asn Ala Ser Gly Ile Tyr His Ile
1               5                   10
```

(2) INFORMATION FOR SEQ ID NO: 225:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 225:

```
Val Asn Tyr Arg Asn Ala Ser Gly Ile Tyr His Ile
1               5                   10
```

(2) INFORMATION FOR SEQ ID NO: 226:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 226:

```
Val Asn Tyr Arg Asn Ala Ser Gly Val Tyr His Ile
1               5                   10
```

(2) INFORMATION FOR SEQ ID NO: 227:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 227:

-continued

```
Val Asn Tyr His Asn Thr Ser Gly Ile Tyr His Leu
1               5                   10
```

(2) INFORMATION FOR SEQ ID NO: 228:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 228:

```
Gln His Tyr Arg Asn Ala Ser Gly Ile Tyr His Val
1               5                   10
```

(2) INFORMATION FOR SEQ ID NO: 229:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 229:

```
Gln His Tyr Arg Asn Val Ser Gly Ile Tyr His Val
1               5                   10
```

(2) INFORMATION FOR SEQ ID NO: 230:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 230:

```
Ile His Tyr Arg Asn Ala Ser Asp Gly Tyr Tyr Ile
1               5                   10
```

(2) INFORMATION FOR SEQ ID NO: 231:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 231:

```
Leu Gln Val Lys Asn Thr Ser Ser Ser Tyr Met Val
1               5                   10
```

(2) INFORMATION FOR SEQ ID NO: 232:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 232:

```
Val Trp Gln Leu Arg Ala Ile Val Leu His Val
1               5                   10
```

(2) INFORMATION FOR SEQ ID NO: 233:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 233:

```
Val Tyr Glu Ala Asp Tyr His Ile Leu His Leu
1               5                   10
```

(2) INFORMATION FOR SEQ ID NO: 234:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 234:

```
Val Tyr Glu Thr Asp Asn His Ile Leu His Leu
1               5                   10
```

(2) INFORMATION FOR SEQ ID NO: 235:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 235:

```
Val Tyr Glu Thr Glu Asn His Ile Leu His Leu
1               5                   10
```

(2) INFORMATION FOR SEQ ID NO: 236:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 236:

```
Val Phe Glu Thr Val His His Ile Leu His Leu
1               5                   10
```

(2) INFORMATION FOR SEQ ID NO: 237:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 237:

Val Phe Glu Thr Glu His His Ile Leu His Leu
1               5                   10

(2) INFORMATION FOR SEQ ID NO: 238:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 238:

Val Phe Glu Thr Asp His His Ile Met His Leu
1               5                   10

(2) INFORMATION FOR SEQ ID NO: 239:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 239:

Val Tyr Glu Thr Glu Asn His Ile Leu His Leu
1               5                   10

(2) INFORMATION FOR SEQ ID NO: 240:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 240:

Val Tyr Glu Ala Asp Ala Leu Ile Leu His Ala
1               5                   10

(2) INFORMATION FOR SEQ ID NO: 241:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 241:

Val Gln Asp Gly Asn Thr Ser Ala Cys Trp Thr Pro Val
1               5                   10

(2) INFORMATION FOR SEQ ID NO: 242:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 242:

Val Lys Thr Gly Asn Gln Ser Arg Cys Trp Val Ala Leu
1               5                   10

(2) INFORMATION FOR SEQ ID NO: 243:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 243:

Val Lys Thr Gly Asn Gln Ser Arg Cys Trp Val Ala Leu
1               5                   10

(2) INFORMATION FOR SEQ ID NO: 244:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 244:

Val Arg Thr Gly Asn Gln Ser Arg Cys Trp Val Ala Leu
1               5                   10

(2) INFORMATION FOR SEQ ID NO: 245:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 245:

Val Lys Thr Gly Asn Gln Ser Arg Cys Trp Ile Ala Leu
1               5                   10

(2) INFORMATION FOR SEQ ID NO: 246:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 246:

Val Lys Thr Gly Asn Gln Ser Arg Cys Trp Ile Ala Leu
1               5                   10

(2) INFORMATION FOR SEQ ID NO: 247:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 247:

Val Lys Thr Gly Asn Ser Val Arg Cys Trp Ile Pro Leu
1               5                   10

(2) INFORMATION FOR SEQ ID NO: 248:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 248:

Val Lys Thr Gly Asn Val Ser Arg Cys Trp Ile Ser Leu
1               5                   10

(2) INFORMATION FOR SEQ ID NO: 249:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 249:

Val Arg Lys Asp Asn Val Ser Arg Cys Trp Val Gln Ile
1               5                   10

(2) INFORMATION FOR SEQ ID NO: 250:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 250:

Ala Pro Ser Phe Gly Ala Val Thr Ala Pro
1               5                   10

(2) INFORMATION FOR SEQ ID NO: 251:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 251:

Val Ser Gln Pro Gly Ala Leu Thr Lys Gly
1               5                   10

(2) INFORMATION FOR SEQ ID NO: 252:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 252:

Val Lys Tyr Val Gly Ala Thr Thr Ala Ser
1               5                   10

(2) INFORMATION FOR SEQ ID NO: 253:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 253:

Ala Pro Tyr Ile Gly Ala Pro Val Glu Ser
1               5                   10

(2) INFORMATION FOR SEQ ID NO: 254:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 254:

Ala Gln His Leu Asn Ala Pro Leu Glu Ser
1               5                   10

(2) INFORMATION FOR SEQ ID NO: 255:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 255:

Ser Pro Tyr Val Gly Ala Pro Leu Glu Pro
1               5                   10

(2) INFORMATION FOR SEQ ID NO: 256:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 256:

Ser Pro Tyr Ala Gly Ala Pro Leu Glu Pro
1               5                   10

(2) INFORMATION FOR SEQ ID NO: 257:

(i) SEQUENCE CHARACTERISTICS:
            (A) LENGTH: 10 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO: 257:

Ala Pro Tyr Leu Gly Ala Pro Leu Glu Ser
1               5                   10

(2) INFORMATION FOR SEQ ID NO: 258:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 258:

Ala Pro Tyr Leu Gly Ala Pro Leu Glu Ser
1               5                   10

(2) INFORMATION FOR SEQ ID NO: 259:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 259:

Ala Pro Tyr Val Gly Ala Pro Leu Glu Ser
1               5                   10

(2) INFORMATION FOR SEQ ID NO: 260:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 260:

Asn Val Pro Tyr Leu Gly Ala Pro Leu Thr Ser
1               5                   10

(2) INFORMATION FOR SEQ ID NO: 261:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 261:

Ala Pro His Leu Arg Ala Pro Leu Ser Ser
1               5                   10

(2) INFORMATION FOR SEQ ID NO: 262:

(i) SEQUENCE CHARACTERISTICS:
        (A) LENGTH: 10 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 262:

Ala Pro Tyr Leu Gly Ala Pro Leu Thr Ser
1               5                  10

(2) INFORMATION FOR SEQ ID NO: 263:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 263:

Arg Pro Arg Gln His Ala Thr Val Gln Asp
1               5                  10

(2) INFORMATION FOR SEQ ID NO: 264:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 264:

Ser Pro Gln His His Lys Phe Val Gln Asp
1               5                  10

(2) INFORMATION FOR SEQ ID NO: 265:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 265:

Arg Pro Arg Arg Leu Trp Thr Thr Gln Glu
1               5                  10

(2) INFORMATION FOR SEQ ID NO: 266:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 266:

Pro Pro Arg Ile His Glu Thr Thr Gln Asp
1               5                  10

(2) INFORMATION FOR SEQ ID NO: 267:

(i) SEQUENCE CHARACTERISTICS:
            (A) LENGTH: 14 amino acids
```

```
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 267:

Thr Ile Ser Tyr Ala Asn Gly Ser Gly Pro Ser Asp Asp Lys
1               5                   10

(2) INFORMATION FOR SEQ ID NO: 268:

(i) SEQUENCE CHARACTERISTICS:
                (A) LENGTH: 19 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 268:

Ser Arg Arg Gln Pro Ile Pro Arg Ala Arg Arg Thr Glu Gly Arg Se
1               5                   10                  15

Trp Ala Gln (2) INFORMATION FOR SEQ ID NO: 269:

(i) SEQUENCE CHARACTERISTICS:
                (A) LENGTH: 1443 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (ix) FEATURE:
                (A) NAME/KEY: CDS
                (B) LOCATION: 1..1443

(ix) FEATURE:
                (A) NAME/KEY: mat_peptide
                (B) LOCATION: 1..1443

(xi) SEQUENCE DESCRIPTION: SEQ ID NO: 269:

ACC ATC ACC ACC GGA GCT TCT ATC ACA TAC TCC ACT TAC GGC AAG TTC        48
Thr Ile Thr Thr Gly Ala Ser Ile Thr Tyr Ser Thr Tyr Gly Lys Phe
1               5                   10                  15

CTT GCT GAT GGA GGG TGT TCA GGC GGC GCG TAT GAC GTG ATC ATA TGC        96
Leu Ala Asp Gly Gly Cys Ser Gly Gly Ala Tyr Asp Val Ile Ile Cys
                20                  25                  30

GAC GAG TGC CAT TCC CAG GAC GCC ACC ACC ATT CTT GGG ATA GGC ACT       144
Asp Glu Cys His Ser Gln Asp Ala Thr Thr Ile Leu Gly Ile Gly Thr
            35                  40                  45

GTC CTT GAC CAG GCA GAG ACG GCT GGA GCT AGG CTC GTC GTC TTG GCC       192
Val Leu Asp Gln Ala Glu Thr Ala Gly Ala Arg Leu Val Val Leu Ala
        50                  55                  60

ACG GCC ACC CCT CCC GGC AGT GTG ACA ACG CCC CAC CCC AAC ATC GAG       240
Thr Ala Thr Pro Pro Gly Ser Val Thr Thr Pro His Pro Asn Ile Glu
65                  70                  75                  80

GAA GTG GCC CTG CCT CAG GAG GGG GAG GTT CCC TTC TAC GGC AGA GCC       288
Glu Val Ala Leu Pro Gln Glu Gly Glu Val Pro Phe Tyr Gly Arg Ala
                85                  90                  95

ATT CCC CTT GCT TTT ATA AAG GGT GGT AGG CAT CTC ATC TTC TGC CAT       336
```

```
                                              -continued

Ile Pro Leu Ala Phe Ile Lys Gly Gly Arg His Leu Ile Phe Cys His
            100                 105                 110

TCC AAG AAA AAA TGT GAT GAA CTC GCC AAG CAA CTG ACC AGC CTG GGC      384
Ser Lys Lys Lys Cys Asp Glu Leu Ala Lys Gln Leu Thr Ser Leu Gly
            115                 120                 125

GTG AAC GCC GTG GCA TAT TAT AGA GGT CTA GAC GTC GCC GTC ATC CCC      432
Val Asn Ala Val Ala Tyr Tyr Arg Gly Leu Asp Val Ala Val Ile Pro
        130                 135                 140

ACA GCA GGA GAC GTG GTC GTG TGC AGC ACC GAC GCG CTC ATG ACG GGA      480
Thr Ala Gly Asp Val Val Val Cys Ser Thr Asp Ala Leu Met Thr Gly
145                 150                 155                 160

TTC ACC GGC GAC TTT GAT TCT GTC ATA GAC TGC AAC TCC GCC GTC ACT      528
Phe Thr Gly Asp Phe Asp Ser Val Ile Asp Cys Asn Ser Ala Val Thr
                165                 170                 175

CAG ACG GTG GAC TTC AGT CTG GAT CCC ACT TTT ACC ATT GAG ACT ACC      576
Gln Thr Val Asp Phe Ser Leu Asp Pro Thr Phe Thr Ile Glu Thr Thr
            180                 185                 190

ACA GTG CCC CAG GAC GCA GTG TCC AGA AGC CAG CGT AGG GGC CGC ACG      624
Thr Val Pro Gln Asp Ala Val Ser Arg Ser Gln Arg Arg Gly Arg Thr
        195                 200                 205

GGG AGA GGT AGG CAC GGC ATA TAC CGG TAT GTC TCG GCT GGA GAG AGA      672
Gly Arg Gly Arg His Gly Ile Tyr Arg Tyr Val Ser Ala Gly Glu Arg
    210                 215                 220

CCG TCT GAC ATG TTC GAC TCC GTG GTG CTC TGT GAG TGC TAC GAT GCC      720
Pro Ser Asp Met Phe Asp Ser Val Val Leu Cys Glu Cys Tyr Asp Ala
225                 230                 235                 240

GGA TGT GCG TGG TAT GAT CTG ACT CCT GCC GAG ACT ACC GTG AGG TTG      768
Gly Cys Ala Trp Tyr Asp Leu Thr Pro Ala Glu Thr Thr Val Arg Leu
                245                 250                 255

CGC GCT TAC ATA AAC ACC CCC GGG CTC CCT GTC TGT CAG GAC CAT TTG      816
Arg Ala Tyr Ile Asn Thr Pro Gly Leu Pro Val Cys Gln Asp His Leu
            260                 265                 270

GAA TTC TGG GAG GGG GTG TTC ACG GGC CTC ACT AAC ATC GAC GCT CAC      864
Glu Phe Trp Glu Gly Val Phe Thr Gly Leu Thr Asn Ile Asp Ala His
        275                 280                 285

ATG CTG TCA CAG ACC AAA CAG GGT GGG GAG AAT TTC CCA TAC CTT GTA      912
Met Leu Ser Gln Thr Lys Gln Gly Gly Glu Asn Phe Pro Tyr Leu Val
    290                 295                 300

GCG TAC CAA GCA ACA GTC TGT GTT CGC GCG AAA GCG CCC CCC CCC AGC      960
Ala Tyr Gln Ala Thr Val Cys Val Arg Ala Lys Ala Pro Pro Pro Ser
305                 310                 315                 320

TGG GAC ACA ATG TGG AAA TGC ATG CTC CGT CTC AAA CCG ACT TTA ACT     1008
Trp Asp Thr Met Trp Lys Cys Met Leu Arg Leu Lys Pro Thr Leu Thr
                325                 330                 335

GGC CCT ACT CCC CTC TTG TAC AGG CTG GGG CCC GTC CAG AAT GAG ATC     1056
Gly Pro Thr Pro Leu Leu Tyr Arg Leu Gly Pro Val Gln Asn Glu Ile
            340                 345                 350

ACA CTG ACG CAC CCC ATC ACC AAG TAC ATT ATG GCT TGC ATG TCT GCG     1104
Thr Leu Thr His Pro Ile Thr Lys Tyr Ile Met Ala Cys Met Ser Ala
        355                 360                 365

GAC TTG GAG GTC ATT ACC AGC ACT TGG GTT CTG GTG GGG GGC GTT GTG     1152
Asp Leu Glu Val Ile Thr Ser Thr Trp Val Leu Val Gly Gly Val Val
    370                 375                 380

GCG GCC CTG GCG GCC TAC TGC TTG ACG GTG GGT TCG GTA GCC ATA GTC     1200
Ala Ala Leu Ala Ala Tyr Cys Leu Thr Val Gly Ser Val Ala Ile Val
385                 390                 395                 400

GGT AGG ATC ATC CTC TCT GGG AAA CCT GCC ATC ATT CCC GAT AGG GAG     1248
Gly Arg Ile Ile Leu Ser Gly Lys Pro Ala Ile Ile Pro Asp Arg Glu
                405                 410                 415
```

```
GCA TTA TAC CAG CAA TTT GAT GAG ATG GAG GAG TGC TCG GCC TCG TTG      1296
Ala Leu Tyr Gln Gln Phe Asp Glu Met Glu Glu Cys Ser Ala Ser Leu
            420                 425                 430

CCC TAT ATG GAC GAG ACA CGT GCC ATT GCC GGA CAA TTC AAA GAG AAA      1344
Pro Tyr Met Asp Glu Thr Arg Ala Ile Ala Gly Gln Phe Lys Glu Lys
            435                 440                 445

GTG CTC GGC TTC ATC AGC ACG ACC GGC CAG AAG GCT GAA ACT CTG AAG      1392
Val Leu Gly Phe Ile Ser Thr Thr Gly Gln Lys Ala Glu Thr Leu Lys
    450                 455                 460

CCG GCA GCC ACG TCT GTG TGG AAC AAG GCT GAG CAG TTC TGG GCC ACA      1440
Pro Ala Ala Thr Ser Val Trp Asn Lys Ala Glu Gln Phe Trp Ala Thr
465                 470                 475                 480

TAC                                                                   1443
Tyr (2) INFORMATION FOR SEQ ID NO: 270:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO: 270:

Thr Ile Thr Thr Gly Ala Ser Ile Thr Tyr Ser Thr Tyr Gly Lys Phe
 1               5                  10                  15

Leu Ala Asp Gly Gly Cys Ser Gly Gly Ala Tyr Asp Val Ile Ile Cys
                20                  25                  30

Asp Glu Cys His Ser Gln Asp Ala Thr Thr Ile Leu Gly Ile Gly Thr
                35                  40                  45

Val Leu Asp Gln Ala Glu Thr Ala Gly Ala Arg Leu Val Val Leu Ala
        50                  55                  60

Thr Ala Thr Pro Pro Gly Ser Val Thr Thr Pro His Pro Asn Ile Glu
65                  70                  75                  80

Glu Val Ala Leu Pro Gln Glu Gly Val Pro Phe Tyr Gly Arg Ala
                85                  90                  95

Ile Pro Leu Ala Phe Ile Lys Gly Gly Arg His Leu Ile Phe Cys His
                100                 105                 110

Ser Lys Lys Lys Cys Asp Glu Leu Ala Lys Gln Leu Thr Ser Leu Gly
            115                 120                 125

Val Asn Ala Val Ala Tyr Tyr Arg Gly Leu Asp Val Ala Val Ile Pro
        130                 135                 140

Thr Ala Gly Asp Val Val Cys Ser Thr Asp Ala Leu Met Thr Gly
145                 150                 155                 160

Phe Thr Gly Asp Phe Asp Ser Val Ile Asp Cys Asn Ser Ala Val Thr
                165                 170                 175

Gln Thr Val Asp Phe Ser Leu Asp Pro Thr Phe Thr Ile Glu Thr Thr
                180                 185                 190

Thr Val Pro Gln Asp Ala Val Ser Arg Ser Gln Arg Arg Gly Arg Thr
        195                 200                 205

Gly Arg Gly Arg His Gly Ile Tyr Arg Tyr Val Ser Ala Gly Glu Arg
    210                 215                 220

Pro Ser Asp Met Phe Asp Ser Val Val Leu Cys Glu Cys Tyr Asp Ala
225                 230                 235                 240

Gly Cys Ala Trp Tyr Asp Leu Thr Pro Ala Glu Thr Thr Val Arg Leu
                245                 250                 255
```

```
-continued

Arg Ala Tyr Ile Asn Thr Pro Gly Leu Pro Val Cys Gln Asp His Leu
            260                 265                 270

Glu Phe Trp Glu Gly Val Phe Thr Gly Leu Thr Asn Ile Asp Ala His
        275                 280                 285

Met Leu Ser Gln Thr Lys Gln Gly Gly Glu Asn Phe Pro Tyr Leu Val
    290                 295                 300

Ala Tyr Gln Ala Thr Val Cys Val Arg Ala Lys Ala Pro Pro Pro Ser
305                 310                 315                 320

Trp Asp Thr Met Trp Lys Cys Met Leu Arg Leu Lys Pro Thr Leu Thr
                325                 330                 335

Gly Pro Thr Pro Leu Leu Tyr Arg Leu Gly Pro Val Gln Asn Glu Ile
            340                 345                 350

Thr Leu Thr His Pro Ile Thr Lys Tyr Ile Met Ala Cys Met Ser Ala
            355                 360                 365

Asp Leu Glu Val Ile Thr Ser Thr Trp Val Leu Val Gly Gly Val Val
            370                 375                 380

Ala Ala Leu Ala Ala Tyr Cys Leu Thr Val Gly Ser Val Ala Ile Val
385                 390                 395                 400

Gly Arg Ile Ile Leu Ser Gly Lys Pro Ala Ile Ile Pro Asp Arg Glu
            405                 410                 415

Ala Leu Tyr Gln Gln Phe Asp Glu Met Glu Glu Cys Ser Ala Ser Leu
            420                 425                 430

Pro Tyr Met Asp Glu Thr Arg Ala Ile Ala Gly Gln Phe Lys Glu Lys
            435                 440                 445

Val Leu Gly Phe Ile Ser Thr Thr Gly Gln Lys Ala Glu Thr Leu Lys
    450                 455                 460

Pro Ala Ala Thr Ser Val Trp Asn Lys Ala Glu Gln Phe Trp Ala Thr
465                 470                 475                 480

Tyr
```